US012760321B2

(12) United States Patent
Bowen et al.

(10) Patent No.: US 12,760,321 B2
(45) Date of Patent: Oct. 13, 2026

(54) INSECT INHIBITORY PROTEINS

(71) Applicant: Monsanto Technology LLC, St. Louis, MO (US)

(72) Inventors: David J. Bowen, Wildwood, MO (US); Catherine A. Chay, Ballwin, MO (US); Todd A. Ciche, San Diego, CA (US); Stanislaw Flasinski, Ballwin, MO (US); Arlene R. Howe, Clarkson Valley, MO (US)

(73) Assignee: Monsanto Technology LLC, St. Louis, MO (US)

( * ) Notice: Subject to any disclaimer, the term of this patent is extended or adjusted under 35 U.S.C. 154(b) by 141 days.

(21) Appl. No.: 18/635,866

(22) Filed: Apr. 15, 2024

(65) Prior Publication Data

US 2024/0301441 A1 Sep. 12, 2024

Related U.S. Application Data

(62) Division of application No. 17/934,287, filed on Sep. 22, 2022, now Pat. No. 11,987,800, which is a division of application No. 16/580,583, filed on Sep. 24, 2019, now Pat. No. 11,512,324.

(60) Provisional application No. 62/736,236, filed on Sep. 25, 2018.

(51) Int. Cl.

| | |
|---|---|
| ***C12N 15/82*** | (2006.01) |
| ***A01N 63/50*** | (2020.01) |
| ***C07K 14/24*** | (2006.01) |

(52) U.S. Cl.
CPC ......... *C12N 15/8286* (2013.01); *A01N 63/50* (2020.01); *C07K 14/24* (2013.01)

(58) Field of Classification Search
None
See application file for complete search history.

(56) References Cited

U.S. PATENT DOCUMENTS

| | | | |
|---|---|---|---|
| 6,174,860 | B1 | 1/2001 | Kramer et al. |
| 6,277,823 | B1 | 8/2001 | Kramer et al. |
| 6,593,273 | B2 | 7/2003 | Asrar et al. |
| 9,469,880 | B2 | 10/2016 | Adams et al. |
| 2007/0020625 | A1 | 1/2007 | Duchaud et al. |
| 2012/0278954 | A1 | 11/2012 | Bowen et al. |
| 2013/0007923 | A1 | 1/2013 | Meade et al. |
| 2018/0208940 | A1 | 7/2018 | Bowen et al. |
| 2018/0346925 | A1 | 12/2018 | Bowen et al. |

FOREIGN PATENT DOCUMENTS

| | | |
|---|---|---|
| WO | 99/54472 | 10/1999 |
| WO | 2003087377 | 10/2003 |
| WO | 2016061377 | 4/2016 |
| WO | 2016061391 | 4/2016 |
| WO | 2017035364 | 3/2017 |
| WO | 2019211850 | 11/2019 |

OTHER PUBLICATIONS

GenBank Accession No. CDL79383 (2014, https:// www.ncbi.nlm.nih.gov/ protein/CDL79383).*
GenBank Accession No. OKP02680 (2017, https:// www.ncbi.nlm.nih.gov/protein/OKP02680).*
GenBank Accession No. PHM26048 (2017, https://www.ncbi.nlm.nih.gov/ protein/PHM26048).*
GenBank Accession No. WP_092549745, dated Jul. 29, 2017.
Blackburn et al., Remarkable Susceptibility of the Diamondback Moth (*Plutella xylostella*) to Ingestion of Pir Toxins from Photorhabdus Luminescens, Entomologia Experimentalis et Applicata, 2006, 31-37, 121-1.
Li et al., Photorhabdus Luminescens PirAB-Fusion Protein Exhibits Both Cytotoxicity and Insecticidal Activity, FEMS Microbiology Letters, 2014, 23-31, 356-1.
Waterfield et al. The Photorhabdus Pir Toxins are Similar to a Developmentally Regulated Insect Protein But Show No Juvenile Hormone Esterase Activity, FEMS Microbiology Letters, 2005, 47-52, 245-1.
Wu and Yi, Haemocoel Injection of PirA1B1 to Galleria Mellonella Larvae Leads to Disruption of the Haemocyte Immune Functions, Scientific Reports 6, Article No. 34996, 2016, 34996, 6.
Yang et al., PirAB Protein from Xenorhabdus Nematophila HB310 Exhibits a Binary Toxin with Insecticidal Activity and Cytotoxicity in Galleria Mellonella, Journal of Invertebrate Pathology, 2017, 43-50, 148.
Zhang et al., XaxAB-Like Binary Toxin From Photorhabdus Luminescens Exhibits Both Insecticidal Activity and Cytotoxicity, FEMS Microbiology Letters, 2014, 48-56, 350-1.
Invitation to Pay Additional Fees regarding PCT Application No. PCT/US2019/52782, mailed Nov. 27, 2019, 3 pages.
International Search Report and Written Opinion regarding PCT Application No. PCT/US2019/52782, mailed Jan. 31, 2020.
Guo et al., 2004, Proc. Natl. Acad. Sci. USA 101:9205-92-10.
Stilwell et al., 2018, mSphere 3:1-16 (e00530-17).
Cabi, https://www.cabi.org/isc/datasheet/51706, accessed Mar. 22, 2021.
NCBI Accession No. WP_092549743.1, dated Jul. 29, 2017.
GenBank CNG75815, 2015, https://www.ncbi.nim.nih.gov/protein/CNG75815.
GenBank CNG75798, 2015, https://www.ncbi.nim.nih.gov/protein/CNG75798.

(Continued)

*Primary Examiner* — Anne Kubelik
(74) *Attorney, Agent, or Firm* — Dentons US LLP; David Lanzotti

(57) ABSTRACT

A pesticidal protein class of PirA, PirB, and PirAB fusion proteins exhibiting toxic activity against Coleopteran, Lepidopteran, and Hemipteran pest species is disclosed. DNA constructs are provided which contain a recombinant nucleic acid sequence encoding the PirA, PirB, and PirAB fusion proteins. Transgenic plants, plant cells, seed, and plant parts resistant to Coleopteran, Lepidopteran, and Hemipteran infestation are provided which contain recombinant nucleic acid sequences encoding the PirA, PirB, and PirAB fusion proteins. Methods for detecting the presence of the recombinant nucleic acid sequences or the proteins of the present invention in a biological sample, and methods of controlling Coleopteran, Lepidopteran, and Hemipteran species pests using the PirA, PirB, and PirAB fusion proteins are also provided.

30 Claims, No Drawings

Specification includes a Sequence Listing.

(56) References Cited

OTHER PUBLICATIONS

Japanese Office Action regarding Japanese App. No. 2021-515455, dated Aug. 18, 2023.
Colombian Office Action regarding Colombian App. No. NC2023/0010856, dated Aug. 28, 2023.
GenBank Accession No. KG815221, dated Dec. 20, 2014.
GenBank Accession No. FI982754, dated May 22, 2010.
GenBank Accession No. BZ318215, dated Nov. 6, 2002.
GenBank Accession No. LN503569, dated Sep. 15, 2014.
GenBank Accession No. AC230033, dated Sep. 21, 2013.
GenBank Accession No. AAZ36638, dated Jun. 11, 2019.
Hernández-Rodríguez, et al, "Shared Midgut Binding Sites for Cry1A.105, Cry1Aa, Cry1Ab, Cry1Ac and Cry1Fa Proteins from Bacillus thuringiensis in Two Important Corn Pests, Ostrinia nubilalis and Spodoptera frugiperda", PLOS ONE, vol. 8, No. 7, (2013).
Wang et al, "Bacillus thuringiensis Cry1Da_7 and Cry1B.868 Protein Interactions with Novel Receptors Allow Control of Resistant Fall Armyworms, Spodoptera frugiperda (J.E. Smith).", Applied and Environmental Microbiology, vol. 85, No. 16, 2019.

* cited by examiner

INSECT INHIBITORY PROTEINS

REFERENCE TO RELATED APPLICATION

This application is a divisional of U.S. patent application Ser. No. 17/934,287, filed Sep. 22, 2022, which is a divisional of U.S. patent application Ser. No. 16/580,583, filed Sep. 24, 2019, now U.S. Pat. No. 11,512,324, which claims the benefit of U.S. Provisional Patent Application No. 62/736,236, filed Sep. 25, 2018, each of which is herein incorporated by reference in its entirety.

INCORPORATION OF SEQUENCE LISTING

The file named "MONS465USD2_ST26.xml" containing a computer-readable form of the Sequence Listing was created on Mar. 13, 2024. This file is 359,579 bytes (measured in MS-Windows®) is contemporaneously filed by electronic submission (using the United States Patent Office EFS-Web filing system), and is incorporated into this application by reference in its entirety.

FIELD OF THE INVENTION

The invention generally relates to the field of insect inhibitory proteins. A novel class of proteins exhibiting insect inhibitory activity against agriculturally-relevant pests of crop plants and seeds is disclosed. In particular, the disclosed proteins are insecticidally active against agriculturally-relevant pests of crop plants and seeds, particularly Coleopteran and Lepidopteran species of insect pests. Plants, plant parts, and seeds containing a recombinant polynucleotide construct encoding one or more of the disclosed toxin proteins are provided.

BACKGROUND OF THE INVENTION

Improving crop yield from agriculturally significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts of food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the Lepidoptera, Coleoptera, and Hemipteran orders, are considered a major cause of damage to field crops, thereby decreasing crop yields over infested areas. Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for pesticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of additional bacterial species, such as *Brevibacillus laterosporus, Lysinibacillus sphaericus* ("Ls" formerly known as *Bacillus sphaericus*), *Paenibacillus popilliae, Photorhabdus* and *Xenorhabdus.*

Crystalline and secreted soluble insecticidal toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal toxin proteins has been globally adapted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal toxin proteins used in these crops has created a selection pressure for existing insect alleles that impart resistance to the currently-utilized insecticidal proteins.

The development of resistance in target pests to insecticidal toxin proteins creates the continuing need for discovery and development of new forms of insecticidal toxin proteins that are useful for managing the increase in insect resistance to transgenic crops expressing insecticidal toxin proteins. New protein toxins with improved efficacy and which exhibit control over a broader spectrum of susceptible insect species will reduce the number of surviving insects which can develop resistance alleles. In addition, the use in one plant of two or more transgenic insecticidal toxin proteins toxic to the same insect pest and displaying different modes of action reduces the probability of resistance in any single target insect species.

Thus, the inventors herein disclose a protein toxin family from *Xenorhabdus* and *Photorhabdus* along with similar toxin proteins, variant proteins, and exemplary recombinant proteins that exhibit insecticidal activity against target Lepidopteran, Coleopteran, and Hemipteran pest species.

SUMMARY OF THE INVENTION

Disclosed herein is a group of pesticidal proteins with insect inhibitory activity (toxin proteins), referred to herein as PirAB (*Photorhabdus* insect related) protein toxins, which are shown to exhibit inhibitory activity against one or more pests of crop plants. The proteins in the PirAB protein toxin class can be used alone, or as fusions of a PirA protein and a PirB protein, or in combination with other insecticidal proteins and toxic agents in formulations and in planta, thus providing alternatives to insecticidal proteins and insecticide chemistries currently in use in agricultural systems.

In one embodiment, disclosed in this application is a recombinant nucleic acid molecule comprising a heterologous promoter operably linked to a polynucleotide segment encoding a pesticidal protein or fragment thereof, wherein: (a) said pesticidal protein comprises the amino acid sequence of SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or (b) said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143; or (c) said polynucleotide segment hybridizes to a polynucleotide having the nucleotide sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 52, 53, 54, 55, 56, 57, 59, 61, 63, 65, 67, 69, 71, 73, 75, 77, 79, 81, 83, 85, 87, 89, 91, 93, 95, 97, 99, 101, 103, 104, 106, 108, 110, 112, 114, 116, 118, 120, 122, 124, 126, 128, 130, 132, 134, 136, 138, 140, 142, 144, 146, 148, 150, 152, 154, 156, or 158; or (d) said recombinant nucleic acid molecule is in operable linkage with a vector, and said vector is selected from the group consisting of a plasmid, phagemid, bacmid, cosmid, and a bacterial or yeast artificial chromosome. The recombinant nucleic acid molecule can comprise a sequence that functions to express the pesticidal protein in a plant; or is expressed in a plant cell to produce a pesticidally effective amount of pesticidal protein.

In another embodiment of this application are host cells comprising a recombinant nucleic acid molecule of the application, wherein the host cell is selected from the group consisting of a bacterial and a plant cell. Contemplated host cells include *Agrobacterium, Rhizobium, Bacillus, Brevibacillus, Escherichia, Pseudomonas, Klebsiella, Pantoea*, and *Erwinia*. In certain embodiments said *Bacillus* species is *Bacillus cereus* or *Bacillus thuringiensis*, said *Brevibacillus* is *Brevibacillus laterosperus*, or said *Escherichia* is *Escherichia coli*. Contemplated plant host cells include a dicotyledonous cell and a monocotyledonous cell. Further contemplated plant host cells include an alfalfa, banana, barley, bean, broccoli, cabbage, *Brassica*, carrot, cassava, castor, cauliflower, celery, chickpea, Chinese cabbage, citrus, coconut, coffee, corn, clover, cotton (*Gossypium* sp.), a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

In yet another embodiment, the pesticidal protein exhibits activity against Coleopteran insect, including Western Corn Rootworm, Southern Corn Rootworm, Northern Corn Rootworm, Mexican Corn Rootworm, Brazilian Corn Rootworm, Colorado Potato Beetle, Brazilian Corn Rootworm complex consisting of *Diabrotica viridula* and *Diabrotica speciosa*, Crucifer Flea Beetle, Striped Flea Beetle, and Western Black Flea Beetle.

In another embodiment, the pesticidal protein exhibits activity against a Lepidopteran insect, including Black Cutworm, Corn Earworm, Diamondback Moth, European Corn Borer, Fall Armyworm, Southern Armyworm, Soybean Looper, Southwestern Corn Borer, Tobacco Budworm, Velvetbean Caterpillar, Sugarcane Borer, Lesser Cornstalk Borer, Black Armyworm, Beet Armyworm, Old World Bollworm, Oriental leaf Worm, or Pink Bollworm.

In yet another embodiment, the pesticidal protein exhibits activity against an insect species of the order of Hemiptera, including Southern Green Stinkbug, Neotropical Brown Stinkbug, Southern Green Stink Bug, Neotropical Brown Stink Bug, Redbanded Stink Bug, Black-Spined Green-Belly Stink Bug species, Brown-Winged Stink Bug, Brown Stink Bug, Green Stink Bug, Brown Marmorated Stink Bug, Western Tarnished Plant Bug, or Tarnished Plant Bug.

Also contemplated in this application are plants comprising a recombinant nucleic acid molecule comprising a heterologous promoter operably linked to a polynucleotide segment encoding a pesticidal protein or fragment thereof, wherein: (a said pesticidal protein comprises the amino acid sequence of SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or (b) said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143; or (c) said polynucleotide segment hybridizes under stringent hybridization conditions to the compliment of the nucleotide sequence of to SEQ ID NOs: 49, 51, 52, 53, 54, 55, 56, 146, 148, 150, 152, 154, 156, or 158; or (d) said plant exhibits a detectable amount of said pesticidal protein. In certain embodiments the pesticidal protein comprises SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157. In one embodiment, the plant is either a monocot or a dicot. In another embodiment, the plant is selected from the group consisting of an alfalfa, banana, barley, bean, broccoli, cabbage, *Brassica*, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

In further embodiments, seeds comprising the recombinant nucleic acid molecules are disclosed.

In another embodiment, an insect inhibitory composition comprising the recombinant nucleic acid molecules disclosed in this application are contemplated. The insect inhibitory composition can further comprise a nucleotide sequence encoding at least one other pesticidal agent that is different from said pesticidal protein. The at least one other pesticidal agent is selected from the group consisting of an insect inhibitory protein, an insect inhibitory dsRNA molecule, and an ancillary protein. The at least one other pesticidal agent in the insect inhibitory composition exhibits activity against one or more pest species of the orders Lepidoptera, Coleoptera, or Hemiptera. The at least one other pesticidal agent in the insect inhibitory composition is in one embodiment selected from the group consisting of: a Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-AXMI-, AXMI-88, AXMI-97, AXMI-102, AXMI-112, AXMI-117, AXMI-100, AXMI-115, AXMI-113, and AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z and AXMI-225z, AXMI-238, AXMI-270, AXMI-279, AXMI-345, AXMI-335, AXMI-R1 and variants thereof, IP3 and variants thereof, DIG-3, DIG-5, DIG-10, DIG-657 DIG-11, Cry71Aa1, Cry72Aa1, PHI-4 variants, PIP-72 variants, PIP-45 variants, PIP-64 variants, PIP-74 variants, PIP-75 variants, PIP-77 variants, Axmi422, Dig-305, Axmi440, PIP-47 variants, Axmi281, BT-009, BT-0012, BT-0013, BT-0023, BT0067, BT-0044, BT-0051, BT-0068, BT-0128, DIG-17, DIG-90, DIG-79, Cry1JP578V, Cry1JPS1, and Cry1 JPS1P578V.

Commodity products comprising a detectable amount of the recombinant nucleic acid molecules disclosed in this application are contemplated. Such commodity products include commodity corn bagged by a grain handler, corn flakes, corn cakes, corn flour, corn meal, corn syrup, corn oil, corn silage, corn starch, corn cereal, and the like, and corresponding cotton commodity products such as whole or processed cotton seed, cotton oil, lint, seeds and plant parts processed for feed or food, fiber, paper, biomasses, and fuel products such as fuel derived from cotton oil or pellets derived from cotton gin waste, and corresponding soybean commodity products such as whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts, and corresponding rice, wheat, sorghum, pigeon pea, peanut, fruit, melon, and vegetable commodity products including where applicable, juices, concentrates, jams, jellies, marmalades, and other edible forms of such commodity products containing a detectable amount of such polynucleotides and or polypeptides of this application.

Also contemplated in this application is a method of producing seed comprising the recombinant nucleic acid molecules disclosed in this application. The method comprises planting at least one of the seed comprising the recombinant nucleic acid molecules disclosed in this application; growing plant from the seed; and harvesting seed from the plants, wherein the harvested seed comprises the recombinant nucleic acid molecules in this application.

In another illustrative embodiment, a plant resistant to insect infestation is provided, wherein the cells of said plant comprise: (a) a recombinant nucleic acid molecule encoding an insecticidally effective amount of a pesticidal protein as set forth in SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or (b) said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143.

Also disclosed in this application are methods for controlling a Coleopteran or Lepidopteran species pest, and controlling a Coleopteran or Lepidopteran species pest infestation of a plant, particularly a crop plant. The method comprises, in one embodiment, (a) contacting the pest with an insecticidally effective amount of one or more pesticidal proteins as set forth in SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or (b) said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143.

Further provided herein is a method of detecting the presence of a recombinant nucleic acid molecule comprising a polynucleotide segment encoding a pesticidal protein or fragment thereof, wherein: (a) said pesticidal protein comprises the amino acid sequence of SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or (b) said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143; or (c) said polynucleotide segment hybridizes to a polynucleotide having the nucleotide sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 52, 53, 54, 55, 56, 57, 59, 61, 63, 65, 67, 69, 71, 73, 75, 77, 79, 81, 83, 85, 87, 89, 91, 93, 95, 97, 99, 101, 103, 104, 106, 108, 110, 112, 114, 116, 118, 120, 122, 124, 126, 128, 130, 132, 134, 136, 138, 140, 142, 144, 146, 148, 150, 152, 154, 156, or 158. In one embodiment of the invention, the method comprises contacting a sample of nucleic acids with a nucleic acid probe that hybridizes under stringent hybridization conditions with genomic DNA from a plant comprising a polynucleotide segment encoding a pesticidal protein or fragment thereof provided herein, and does not hybridize under such hybridization conditions with genomic DNA from an otherwise isogenic plant that does not comprise the segment, wherein the probe is homologous or complementary to SEQ ID NOs: 49, 51, 52, 53, 54, 55, 56, 146, 148, 150, 152, 154, 156, or 158, or a sequence that encodes a pesticidal protein comprising an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143. The method may further comprise (a) subjecting the sample and probe to stringent hybridization conditions; and (b) detecting hybridization of the probe with DNA of the sample.

Also provided by the invention are methods of detecting the presence of a pesticidal protein or fragment thereof in a sample comprising protein, wherein said pesticidal protein comprises the amino acid sequence of SEQ ID NOs:2, 4, 6, 8, 10, 12, 14, 16, 18, 20, 22, 24, 26, 28, 30, 32, 34, 36, 38, 40, 42, 44, 46, 48, 50, 58, 60, 62, 64, 66, 68, 70, 72, 74, 76, 78, 80, 82, 84, 86, 88, 90, 92, 94, 96, 98, 100, 102, 105, 107, 109, 111, 113, 115, 117, 119, 121, 123, 125, 127, 129, 131, 133, 135, 137, 139, 141, 143, 145, 147, 149, 151, 153, 155, or 157; or said pesticidal protein comprises an amino acid sequence having: (i) at least 65% identity to SEQ ID NOs:44, 46, 48, 123, 127, 129, 131, 133, and 145; or (ii) at least 70% identity to SEQ ID NOs:109, 121, and 125; or (iii) at least 80% identity to SEQ ID NOs: 12, 18, 24, 36, 42, 62, 68, 74, 80, 86, 98, 113, 117, 119, 147, 149, 153, 155, and 157; or (iv) at least 82% identity to SEQ ID NOs:30, 92, 111, 115, and 151; or (v) at least 86% identity to SEQ ID NOs:6 and 50; or (vi) at least 94% identity to SEQ ID NOs:137 and 141; or (vii) at least 97% identity to SEQ ID NOs:4, 26, and 32; or (viii) at least 98% identity to SEQ ID NOs:2, 28, 34, 102, and 102; or (ix) at least 99% identity to SEQ ID NO:135; or (x) 100% identity to SEQ ID NOs:8, 10, 14, 16, 20, 22, 38, 40, 58, 60, 64, 66, 70, 72, 76, 78, 82, 84, 88, 90, 94, 96, 100, 105, 107, 139, and 143. In one embodiment, the method comprises: (a) contacting a sample with an immunoreactive antibody; and (b) detecting binding of the antibody with the pesticidal protein or fragment thereof, wherein binding indicates the presence of the protein. In some embodiments, the step of detecting comprises an ELISA, or a Western blot.

BRIEF DESCRIPTION OF THE SEQUENCES

SEQ ID NO:1 is a nucleic acid sequence obtained from *Xenorhabdus nematophila* strain ISB000002 encoding a TIC4771 PirA pesticidal protein sequence.

SEQ ID NO:2 is the amino acid sequence of the TIC4771 PirA protein.

SEQ ID NO:3 is a nucleic acid sequence obtained from *Xenorhabdus nematophila* strain ISB000002 encoding a TIC4772 PirB pesticidal protein sequence.

SEQ ID NO:4 is the amino acid sequence of the TIC4772 PirB protein.

SEQ ID NO:5 is a nucleic acid sequence encoding a PirAB fusion protein, TIC6880 comprised of the TIC4771 and TIC4772 coding sequences in operable linkage and in frame.

SEQ ID NO:6 is the amino acid sequence of the TIC6880 PirAB fusion protein.

SEQ ID NO:7 is a nucleic acid sequence obtained from *Xenorhabdus ehlersii* strain 85823 encoding a TIC7575 PirA pesticidal protein sequence.

SEQ ID NO:8 is the amino acid sequence of the TIC7575 PirA protein.

SEQ ID NO:9 is a nucleic acid sequence obtained from *Xenorhabdus ehlersii* strain 85823 encoding a TIC7576 PirB pesticidal protein sequence.

SEQ ID NO:10 is the amino acid sequence of the TIC7576 PirB protein.

SEQ ID NO:11 is a nucleic acid sequence encoding a PirAB fusion protein, TIC9316 comprised of the TIC7575 and TIC7576 coding sequences in operable linkage and in frame.

SEQ ID NO:12 is the amino acid sequence of the TIC9316 PirAB fusion protein.

SEQ ID NO:13 is a nucleic acid sequence obtained from *Xenorhabdus cabanillasii* strain 85908 encoding a TIC7660 PirA pesticidal protein sequence.

SEQ ID NO:14 is the amino acid sequence of the TIC7660 PirA protein.

SEQ ID NO:15 is a nucleic acid sequence obtained from *Xenorhabdus cabanillasii* strain 85908 encoding a TIC7661 PirB pesticidal protein sequence.

SEQ ID NO:16 is the amino acid sequence of the TIC7661 PirB protein.

SEQ ID NO:17 is a nucleic acid sequence encoding a PirAB fusion protein, TIC9317 comprised of the TIC7660 and TIC7661 coding sequences in operable linkage and in frame.

SEQ ID NO:18 is the amino acid sequence of the TIC9317 PirAB fusion protein.

SEQ ID NO:19 is a nucleic acid sequence obtained from *Xenorhabdus ehlersii* strain 85887 encoding a TIC7662 PirA pesticidal protein sequence.

SEQ ID NO:20 is the amino acid sequence of the TIC7662 PirA protein.

SEQ ID NO:21 is a nucleic acid sequence obtained from *Xenorhabdus ehlersii* strain 85887 encoding a TIC7663 PirB pesticidal protein sequence.

SEQ ID NO:22 is the amino acid sequence of the TIC7663 PirB protein.

SEQ ID NO:23 is a nucleic acid sequence encoding a PirAB fusion protein, TIC9318 comprised of the TIC7662 and TIC7663 coding sequences in operable linkage and in frame.

SEQ ID NO:24 is the amino acid sequence of the TIC9318 PirAB fusion protein.

SEQ ID NO:25 is a nucleic acid sequence obtained from *Xenorhabdus poinarii* strain 86198 encoding a TIC7664 PirA pesticidal protein sequence.

SEQ ID NO:26 is the amino acid sequence of the TIC7664 PirA protein.

SEQ ID NO:27 is a nucleic acid sequence obtained from *Xenorhabdus poinarii* strain 86198 encoding a TIC7665 PirB pesticidal protein sequence.

SEQ ID NO:28 is the amino acid sequence of the TIC7665 PirB protein.

SEQ ID NO:29 is a nucleic acid sequence encoding a PirAB fusion protein, TIC9319 comprised of the TIC7664 and TIC7665 coding sequences in operable linkage and in frame.

SEQ ID NO:30 is the amino acid sequence of the TIC9319 PirAB fusion protein.

SEQ ID NO:31 is a nucleic acid sequence obtained from *Photorhabdus luminescens* strain 86197 encoding a TIC7666 PirA pesticidal protein sequence.

SEQ ID NO:32 is the amino acid sequence of the TIC7666 PirA protein.

SEQ ID NO:33 is a nucleic acid sequence obtained from *Photorhabdus luminescens* strain 86197 encoding a TIC7667 pesticidal PirB protein sequence.

SEQ ID NO:34 is the amino acid sequence of the TIC7667 PirB protein.

SEQ ID NO:35 is a nucleic acid sequence encoding a PirAB fusion protein, TIC9322 comprised of the TIC7666 and TIC7667 coding sequences in operable linkage and in frame.

SEQ ID NO:36 is the amino acid sequence of the TIC9322 PirAB fusion protein.

SEQ ID NO:37 is a nucleic acid sequence obtained from *Photorhabdus luminescens* strain 86194 encoding a TIC7668 PirA pesticidal protein sequence.

SEQ ID NO:38 is the amino acid sequence of the TIC7668 PirA protein.

SEQ ID NO:39 is a nucleic acid sequence obtained from *Photorhabdus luminescens* strain 86194 encoding a TIC7669 PirB pesticidal protein sequence.

SEQ ID NO:40 is the amino acid sequence of the TIC7669 PirB protein.

SEQ ID NO:41 is a nucleic acid sequence encoding a PirAB fusion protein, TIC9320 comprised of the TIC7668 and TIC7669 coding sequences in operable linkage and in frame.

SEQ ID NO:42 is the amino acid sequence of the TIC9320 PirAB fusion protein.

SEQ ID NO:43 is a nucleic acid sequence obtained from an unknown bacterial strain comprised within a microbiome encoding a TIC7939 pesticidal PirA protein sequence.

SEQ ID NO: 44 is the amino acid sequence of the TIC7939 PirA protein.

SEQ ID NO:45 is a nucleic acid sequence obtained from an unknown bacterial strain comprised within a microbiome encoding a TIC7940 PirB pesticidal protein sequence.

SEQ ID NO:46 is the amino acid sequence of the TIC7940 PirB protein.

SEQ ID NO:47 is a nucleic acid sequence encoding a PirAB fusion protein, TIC9321 comprised of the TIC7939 and TIC7940 coding sequences in operable linkage and in frame.

SEQ ID NO:48 is the amino acid sequence of the TIC9321 PirAB fusion protein.

SEQ ID NO:49 is a synthetic coding sequence used for expression in plant cells encoding a TIC6880PL PirAB fusion protein wherein an additional alanine codon is inserted immediately following the initiating methionine codon of the TIC4771 protein encoding fragment.

SEQ ID NO:50 is the amino acid sequence of the TIC6880PL PirAB fusion protein.

SEQ ID NO:51 is a synthetic coding sequence used for expression in plant cells encoding a TIC9316 PirAB fusion protein.

SEQ ID NO:52 is a synthetic coding sequence used for expression in plant cells encoding a TIC9317 PirAB fusion protein.

SEQ ID NO:53 is a synthetic coding sequence used for expression in plant cells encoding a TIC9318 PirAB fusion protein.

SEQ ID NO:54 is a synthetic coding sequence used for expression in plant cells encoding a TIC9319 PirAB fusion protein.

SEQ ID NO:55 is a synthetic coding sequence used for expression in plant cells encoding a TIC9320 PirAB fusion protein.

SEQ ID NO:56 is a synthetic coding sequence used for expression in plant cells encoding a TIC9322 PirAB fusion protein.

SEQ ID NO:57 is a nucleic acid sequence obtained from *Shewanella violacea* strain DSS12 encoding a TIC10357 pesticidal PirA protein sequence.

SEQ ID NO:58 is the amino acid sequence of the TIC10357 PirA protein.

SEQ ID NO:59 is a nucleic acid sequence obtained from *Shewanella violacea* strain DSS12 encoding a TIC10366 pesticidal PirB protein sequence.

SEQ ID NO:60 is the amino acid sequence of the TIC10366 PirB protein.

SEQ ID NO:61 is a nucleic acid sequence encoding a PirAB fusion protein, TIC10375 comprised of the TIC10357 and TIC10366 coding sequences in operable linkage and in frame.

SEQ ID NO:62 is the amino acid sequence of the TIC10375 PirAB fusion protein.

SEQ ID NO:63 is a nucleic acid sequence obtained from *Photorhabdus luminescens* strain laumondii TTO1 encoding a TIC10358 pesticidal PirA protein sequence.

SEQ ID NO:64 is the amino acid sequence of the TIC10358 PirA protein.

SEQ ID NO:65 is a nucleic acid sequence obtained from *Photorhabdus luminescens* strain laumondii TTO1 encoding a TIC10367 pesticidal PirB protein sequence.

SEQ ID NO:66 is the amino acid sequence of the TIC10367 PirB protein.

SEQ ID NO:67 is a nucleic acid sequence encoding a PirAB fusion protein, TIC10376 comprised of the TIC10358 and TIC10367 coding sequences in operable linkage and in frame.

SEQ ID NO:68 is the amino acid sequence of the TIC10376 PirAB fusion protein.

SEQ ID NO:69 is a nucleic acid sequence obtained from *Photorhabdus asymbiotica* encoding a TIC10360 pesticidal PirA protein sequence.

SEQ ID NO:70 is the amino acid sequence of the TIC10360 PirA protein.

SEQ ID NO:71 is a nucleic acid sequence obtained from *Photorhabdus asymbiotica* encoding a TIC10369 pesticidal PirB protein sequence.

SEQ ID NO:72 is the amino acid sequence of the TIC10369 PirB protein.

SEQ ID NO:73 is a nucleic acid sequence encoding a PirAB fusion protein, TIC10377 comprised of the TIC10360 and TIC10369 coding sequences in operable linkage and in frame.

SEQ ID NO:74 is the amino acid sequence of the TIC10377 PirAB fusion protein.

SEQ ID NO:75 is a nucleic acid sequence obtained from *Xenorhabdus* sp. strain NBAII XenSa04 encoding a TIC10361 pesticidal PirA protein sequence.

SEQ ID NO:76 is the amino acid sequence of the TIC10361 PirA protein.

SEQ ID NO:77 is a nucleic acid sequence obtained from *Xenorhabdus* sp. strain NBAII XenSa04 encoding a TIC10370 pesticidal PirB protein sequence.

SEQ ID NO:78 is the amino acid sequence of the TIC10370 PirB protein.

SEQ ID NO:79 is a nucleic acid sequence encoding a PirAB fusion protein, TIC10378 comprised of the TIC10361 and TIC10370 coding sequences in operable linkage and in frame.

SEQ ID NO:80 is the amino acid sequence of the TIC10378 PirAB fusion protein.

SEQ ID NO:81 is a nucleic acid sequence obtained from *Yersinia aldovae* strain 670-83 encoding a TIC10362 pesticidal PirA protein sequence.

SEQ ID NO:82 is the amino acid sequence of the TIC10362 PirA protein.

SEQ ID NO:83 is a nucleic acid sequence obtained from *Yersinia aldovae* strain 670-83 encoding a TIC10371 pesticidal PirB protein sequence.

SEQ ID NO:84 is the amino acid sequence of the TIC10371 PirB protein.

SEQ ID NO:85 is a nucleic acid sequence encoding a PirAB fusion protein, TIC10379 comprised of the TIC10362 and TIC10371 coding sequences in operable linkage and in frame.

SEQ ID NO:86 is the amino acid sequence of the TIC10379 PirAB fusion protein.

SEQ ID NO:87 is a nucleic acid sequence obtained from *Xenorhabdus doucetiae* strain FRM16 encoding a TIC10363 pesticidal PirA protein sequence.

SEQ ID NO:88 is the amino acid sequence of the TIC10363 PirA protein.

SEQ ID NO:89 is a nucleic acid sequence obtained from *Xenorhabdus doucetiae* strain FRM16 encoding a TIC10372 pesticidal PirB protein sequence.

SEQ ID NO:90 is the amino acid sequence of the TIC10372 PirB protein.

SEQ ID NO:91 is a nucleic acid sequence encoding a PirAB fusion protein, TIC10380 comprised of the TIC10363 and TIC10372 coding sequences in operable linkage and in frame.

SEQ ID NO:92 is the amino acid sequence of the TIC10380 PirAB fusion protein.

SEQ ID NO:93 is a nucleic acid sequence obtained from *Xenorhabdus griffiniae* strain BMMCB encoding a TIC10364 pesticidal PirA protein sequence.

SEQ ID NO:94 is the amino acid sequence of the TIC10364 PirA protein.

SEQ ID NO:95 is a nucleic acid sequence obtained from *Xenorhabdus griffiniae* strain BMMCB encoding a TIC10373 pesticidal PirB protein sequence.

SEQ ID NO:96 is the amino acid sequence of the TIC10373 PirB protein.

SEQ ID NO:97 is a nucleic acid sequence encoding a PirAB fusion protein, TIC10381 comprised of the TIC10364 and TIC10364 coding sequences in operable linkage and in frame.

SEQ ID NO:98 is the amino acid sequence of the TIC10381 PirAB fusion protein.

SEQ ID NO:99 is a nucleic acid sequence obtained from *Xenorhabdus nematophila* encoding a TIC10359 pesticidal PirA protein sequence.

SEQ ID NO:100 is the amino acid sequence of the TIC10359 PirA protein.

SEQ ID NO:101 is a nucleic acid sequence obtained from *Xenorhabdus nematophila* encoding a TIC10368 pesticidal PirB protein sequence.

SEQ ID NO:102 is the amino acid sequence of the TIC10368 PirB protein.

SEQ ID NO:103 is a nucleic acid sequence encoding an operon comprised of the coding sequences TIC10359 and TIC10368.

SEQ ID NO:104 is a nucleic acid sequence obtained from *Photorhabdus luminescens* strain Hm encoding a PirA_ABE68878 pesticidal PirA protein sequence.

SEQ ID NO:105 is the amino acid sequence of the PirA_ABE68878 PirA protein.

SEQ ID NO:106 is a nucleic acid sequence obtained from *Photorhabdus luminescens* strain Hm encoding a PirB-_ABE68879 pesticidal PirB protein sequence.

SEQ ID NO:107 is the amino acid sequence of the PirB_ABE68879 PirB protein.

SEQ ID NO:108 is a nucleic acid sequence encoding a PirAB fusion protein, TIC10434 comprised of the PirA_ABE68878 and PirB_ABE68879 coding sequences in operable linkage and in frame.

SEQ ID NO:109 is the amino acid sequence of the TIC10434 PirAB fusion protein.

SEQ ID NO:110 is a nucleic acid sequence encoding a PirAB fusion protein, TIC11210 comprised of the TIC7575 and TIC7665 coding sequences in operable linkage and in frame.

SEQ ID NO:111 is the amino acid sequence of the TIC11210 PirAB fusion protein.

SEQ ID NO:112 is a nucleic acid sequence encoding a PirAB fusion protein, TIC11211 comprised of the TIC7575 and TIC7667 coding sequences in operable linkage and in frame.

SEQ ID NO:113 is the amino acid sequence of the TIC11211 PirAB fusion protein.

SEQ ID NO:114 is a nucleic acid sequence encoding a PirAB fusion protein, TIC11212 comprised of the TIC7662 and TIC7665 coding sequences in operable linkage and in frame.

SEQ ID NO:115 is the amino acid sequence of the TIC11212 PirAB fusion protein.

SEQ ID NO:116 is a nucleic acid sequence encoding a PirAB fusion protein, TIC11301 comprised of the TIC7575 and TIC7661 coding sequences in operable linkage and in frame.

SEQ ID NO:117 is the amino acid sequence of the TIC11301 PirAB fusion protein.

SEQ ID NO:118 is a nucleic acid sequence encoding a f PirAB fusion protein, TIC11302 comprised of the TIC7660 and TIC7576 coding sequences in operable linkage and in frame.

SEQ ID NO:119 is the amino acid sequence of the TIC11302 f PirAB fusion protein.

SEQ ID NO:120 is a nucleic acid sequence encoding a PirAB fusion protein, TIC11440 comprised of the TIC4771, TIC4771, and TIC4772 coding sequences in operable linkage and in frame.

SEQ ID NO:121 is the amino acid sequence of the TIC11440 PirAB fusion protein.

SEQ ID NO:122 is a nucleic acid sequence encoding a PirAB fusion protein, TIC11441 comprised of the TIC7575, TIC7575, and TIC7576 coding sequences in operable linkage and in frame.

SEQ ID NO:123 is the amino acid sequence of the TIC11441 f PirAB fusion protein.

SEQ ID NO:124 is a nucleic acid sequence encoding a PirAB fusion protein, TIC11442 comprised of the TIC7575, TIC4771, and TIC4772 coding sequences in operable linkage and in frame.

SEQ ID NO:125 is the amino acid sequence of the TIC11442 PirAB fusion protein.

SEQ ID NO:126 is a nucleic acid sequence encoding a PirAB fusion protein, TIC11443 comprised of the TIC7660, TIC7575, and TIC7576 coding sequences in operable linkage and in frame.

SEQ ID NO:127 is the amino acid sequence of the TIC11443 PirAB fusion protein.

SEQ ID NO:128 is a nucleic acid sequence encoding a PirAB fusion protein, TIC11444 comprised of the TIC7660 and TIC7576 coding sequences in operable linkage and in frame.

SEQ ID NO:129 is the amino acid sequence of the TIC11444 PirAB fusion protein.

SEQ ID NO:130 is a nucleic acid sequence encoding a PirAB fusion protein, TIC11445 comprised of the TIC7660, TIC7662, and TIC7663 coding sequences in operable linkage and in frame.

SEQ ID NO:131 is the amino acid sequence of the TIC11445 PirAB fusion protein.

SEQ ID NO:132 is a nucleic acid sequence encoding a fusion protein, TIC11446 comprised of the TIC7662, TIC7660, and TIC7661 coding sequences in operable linkage and in frame.

SEQ ID NO:133 is the amino acid sequence of the TIC11446 PirAB fusion protein.

SEQ ID NO:134 is a nucleic acid sequence obtained from *Xenorhabdus nematophila* strain MDI-0035777 encoding a TIC11505 pesticidal PirB protein sequence.

SEQ ID NO:135 is the amino acid sequence of the TIC11505 PirB protein.

SEQ ID NO:136 is a nucleic acid sequence encoding a PirAB fusion protein, TIC11506 comprised of the TIC10364 and TIC11505 coding sequences in operable linkage and in frame.

SEQ ID NO:137 is the amino acid sequence of the TIC11506 PirAB fusion protein.

SEQ ID NO:138 is a nucleic acid sequence obtained from *Xenorhabdus bovienii* strain MDI-0035808 encoding a TIC11510 pesticidal PirB protein sequence.

SEQ ID NO:139 is the amino acid sequence of the TIC11510 PirB protein.

SEQ ID NO:140 is a nucleic acid sequence encoding a PirAB fusion protein, TIC11512 comprised of the TIC10364 and TIC11510 coding sequences in operable linkage and in frame.

SEQ ID NO:141 is the amino acid sequence of the TIC11512 PirAB fusion protein.

SEQ ID NO:142 is a nucleic acid sequence obtained from *Xenorhabdus nematophila* strain AN6/1 encoding a TIC11511 pesticidal PirB protein sequence.

SEQ ID NO:143 is the amino acid sequence of the TIC11511 PirB protein.

SEQ ID NO:144 is a nucleic acid sequence encoding a PirAB fusion protein, TIC11513 comprised of the TIC10364 and TIC11511 coding sequences in operable linkage and in frame.

SEQ ID NO:145 is the amino acid sequence of the TIC11513 PirAB fusion protein.

SEQ ID NO:146 is a synthetic coding sequence used for expression in plant cells encoding a TIC10376PL PirAB fusion protein wherein an additional alanine codon is inserted immediately following the initiating methionine codon of the TIC10358 protein encoding fragment.

SEQ ID NO:147 is the amino acid sequence of the TIC10376PL PirAB fusion protein.

SEQ ID NO:148 is a synthetic coding sequence used for expression in plant cells encoding a TIC10378PL PirAB fusion protein wherein an additional alanine codon is inserted immediately following the initiating methionine codon of the TIC10361 protein encoding fragment.

SEQ ID NO:149 is the amino acid sequence of the TIC10378PL PirAB fusion protein.

SEQ ID NO:150 is a synthetic coding sequence used for expression in plant cells encoding a TIC10380PL PirAB fusion protein wherein an additional alanine codon is inserted immediately following the initiating methionine codon of the TIC10363 protein encoding fragment.

SEQ ID NO:151 is the amino acid sequence of the TIC10380PL PirAB fusion protein.

SEQ ID NO:152 is a synthetic coding sequence used for expression in plant cells encoding a TIC10381PL PirAB fusion protein wherein an additional alanine codon is inserted immediately following the initiating methionine codon of the TIC10364 protein encoding fragment.

SEQ ID NO:153 is the amino acid sequence of the TIC10381PL PirAB fusion protein.

SEQ ID NO:154 is a synthetic coding sequence used for expression in plant cells encoding a TIC11103 PirAB fusion protein comprised of the TIC7661 and TIC7660 coding sequences operably linked.

SEQ ID NO:155 is the amino acid sequence of the TIC11103 PirAB fusion protein.

SEQ ID NO:156 is a synthetic coding sequence used for expression in plant cells encoding a TIC11104 PirAB fusion protein comprised of the TIC7663 and TIC7662 coding sequences operably linked.

SEQ ID NO:157 is the amino acid sequence of the TIC11104 PirAB fusion protein.

SEQ ID NO:158 is a synthetic coding sequence used for expression in plant cells encoding a TIC11302 PirAB fusion protein.

SEQ ID NO:159 is a synthetic coding sequence encoding a Histidine tag that is operably linked to coding sequences expressed in *Escherichia coli* and used for protein purification.

SEQ ID NO:160 is the amino acid sequence of the Histidine tag.

DETAILED DESCRIPTION OF THE INVENTION

A problem in the art of agricultural pest control can be characterized as a need for new toxin proteins that are efficacious against target pests, exhibit broad spectrum toxicity against target pest species, are capable of being expressed in plants without causing undesirable agronomic issues, and provide an alternative mode of action compared to current toxins that are used commercially in plants.

Disclosed herein are novel PirAB pesticidal protein classes, exemplified by the PirA proteins TIC4771, TIC7575, TIC7660, TIC7662, TIC7664, TIC7666, TIC7668, TIC7939, TIC10357, TIC10358, TIC10360, TIC10361, TIC10362, TIC10363, TIC10364, TIC10359, and PirA_ABE68878 (collectively, "The PirA Proteins"); the PirB proteins TIC4772, TIC7576, TIC7661, TIC7663, TIC7665, TIC7667, TIC7669, TIC7940, TIC10366, TIC10367, TIC10369, TIC10370, TIC10371, TIC10372, TIC10373, TIC10368, PirB_ABE68879, TIC11505, TIC11510, and TIC11511 (collectively, "The PirB Proteins"); and the PirAB fusion proteins, TIC6880, TIC9316, TIC9317, TIC9318, TIC9319, TIC9322, TIC9320, TIC9321, TIC6880PL, TIC10375, TIC10376, TIC10377, TIC10378, TIC10379, TIC10380, TIC10381, TIC10434, TIC11210, TIC11211, TIC11212, TIC11301, TIC11302, TIC11440, TIC11441, TIC11442, TIC11443, TIC11444, TIC11445, TIC11446, TIC11506, TIC11512, TIC11513, TIC10376PL, TIC10378PL, TIC10380PL, TIC10381PL, TIC11103, and TIC11104 (collectively, "The PirAB Fusion Protein") which provide resistance against Coleopteran, Hemipteran, and Lepidopteran insect pests.

Also disclosed are synthetic coding sequences designed for expression in a plant cell that encode the PirAB fusion proteins, TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302. Further disclosed are recombinant nucleic acid molecules comprising a promoter in operable linkage to a coding sequence encoding one or more of The PirA Proteins, The PirB Proteins, or The PirAB Fusion Proteins.

Reference in this application to "PirA proteins", "PirA protein toxin", "PirA toxin protein", "PirA pesticidal protein", "PirA-related toxins", or "PirA-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC4771 (SEQ ID NO:2), TIC7575 (SEQ ID NO:8), TIC7660 (SEQ ID NO:14), TIC7662 (SEQ ID NO:20), TIC7664 (SEQ ID NO:26), TIC7666 (SEQ ID NO:32), TIC7668 (SEQ ID NO:38), TIC7939 (SEQ ID NO:44), TIC10357 (SEQ ID NO:58), TIC10358 (SEQ ID NO:64), TIC10360 (SEQ ID NO:70), TIC10361 (SEQ ID NO:76), TIC10362 (SEQ ID NO:82), TIC10363 (SEQ ID NO:88), TIC10364 (SEQ ID NO:94), TIC10359 (SEQ ID NO:100), and PirA_ABE68878 (SEQ ID NO:105) and pesticidal or insect inhibitory segments thereof, or combinations thereof, that confer activity against Coleopteran pests, Hemipteran pests, and Lepidopteran pests, including any protein exhibiting pesticidal or insect inhibitory activity if alignment of such protein with any of the PirA proteins results in amino acid sequence identity of any fraction percentage from about 20 to about 100 percent.

Reference in this application to "PirB proteins", "PirB protein toxin", "PirB toxin protein", "PirB pesticidal protein", "PirB-related toxins", or "PirB-related toxin protein", and the like, refer to any novel pesticidal protein or insect inhibitory protein, that comprises, that consists of, that is substantially homologous to, that is similar to, or that is derived from any pesticidal protein or insect inhibitory protein sequence of TIC4772 (SEQ ID NO:4), TIC7576 (SEQ ID NO:10), TIC7661 (SEQ ID NO:16), TIC7663 (SEQ ID NO:22), TIC7665 (SEQ ID NO:28), TIC7667 (SEQ ID NO:34), TIC7669 (SEQ ID NO:40), TIC7940 (SEQ ID NO:46), TIC10366 (SEQ ID NO:60), TIC10367 (SEQ ID NO:66), TIC10369 (SEQ ID NO:72), TIC10370 (SEQ ID NO:78), TIC10371 (SEQ ID NO:84), TIC10372 (SEQ ID NO:90), TIC10373 (SEQ ID NO:96), TIC10368 (SEQ ID NO:102), PirB_ABE68879 (SEQ ID NO:107), TIC11505 (SEQ ID NO:135), TIC11510 (SEQ ID NO:139), and TIC11511 (SEQ ID NO:143) and pesticidal or insect inhibitory segments thereof, or combinations thereof, that confer activity against Coleopteran pests, Hemipteran pests, and Lepidopteran pests, including any protein exhibiting pesticidal or insect inhibitory activity if alignment of such protein with and of the PirB proteins results in amino acid sequence identity of any fraction percentage from about 24 to about 100 percent.

The term "PirAB fusion protein" is used in this application to describe a protein that comprises both a PirA protein contiguous with a PirB protein. The DNA sequence encoding the PirAB fusion protein can comprise a coding sequence encoding a PirA protein operably linked and in frame with a coding sequence encoding a PirB protein such that when it is expressed in a cell produces a fusion protein comprising both a PirA protein and PirB protein. The PirA protein can be comprised of a PirA protein and a PirB protein derived from the same bacterial operon, or alternatively, can be comprised of a PirA protein and a PirB protein derived from different bacterial operons. Exemplary PirAB fusion proteins wherein the PirA protein is contiguous with a PirB protein are provided in Table 1.

TABLE 1

Exemplary PirAB fusion proteins comprised of a PirA protein contiguous with a PirB protein and the corresponding PirA and PirB proteins comprised within.

| PirA Protein | | PirB Protein | | PirAB Fusion Protein | |
|---|---|---|---|---|---|
| Toxin | Protein SEQ ID NO: | Toxin | Protein SEQ ID NO: | Toxin | Protein SEQ ID NO: |
| TIC4771 | 2 | TIC4772 | 4 | TIC6880 | 6 |
| TIC7575 | 8 | TIC7576 | 10 | TIC9316 | 12 |
| TIC7660 | 14 | TIC7661 | 16 | TIC9317 | 18 |
| TIC7662 | 20 | TIC7663 | 22 | TIC9318 | 24 |
| TIC7664 | 26 | TIC7665 | 28 | TIC9319 | 30 |
| TIC7666 | 32 | TIC7667 | 34 | TIC9322 | 36 |
| TIC7668 | 38 | TIC7669 | 40 | TIC9320 | 42 |
| TIC7939 | 44 | TIC7940 | 46 | TIC9321 | 48 |
| TIC4771* | 2 | TIC4772 | 4 | TIC6880PL* | 6 |
| TIC10357 | 58 | TIC10366 | 60 | TIC10375 | 62 |
| TIC10358 | 64 | TIC10367 | 66 | TIC10376 | 68 |
| TIC10360 | 70 | TIC10369 | 72 | TIC10377 | 74 |
| TIC10361 | 76 | TIC10370 | 78 | TIC10378 | 80 |
| TIC10362 | 82 | TIC10371 | 84 | TIC10379 | 86 |
| TIC10363 | 88 | TIC10372 | 90 | TIC10380 | 92 |
| TIC10364 | 94 | TIC10373 | 96 | TIC10381 | 98 |
| PirA_ABE68878 | 105 | PirB_ABE68879 | 107 | TIC10434 | 109 |
| TIC10358* | 64 | TIC10367 | 66 | TIC10376PL* | 147 |
| TIC10361* | 76 | TIC10370 | 78 | TIC10378PL* | 149 |
| TIC10363* | 88 | TIC10372 | 90 | TIC10380PL* | 151 |
| TIC10364* | 94 | TIC10373 | 96 | TIC10381PL* | 153 |
| TIC7575 | 8 | TIC7665 | 28 | TIC11210 | 111 |
| TIC7575 | 8 | TIC7667 | 34 | TIC11211 | 113 |
| TIC7662 | 20 | TIC7665 | 28 | TIC11212 | 115 |
| TIC7575 | 8 | TIC7661 | 16 | TIC11301 | 117 |
| TIC7660 | 14 | TIC7576 | 10 | TIC11302 | 119 |
| TIC10364 | 94 | TIC11505 | 135 | TIC11506 | 137 |
| TIC10364 | 94 | TIC11510 | 139 | TIC11512 | 141 |
| TIC10364 | 94 | TIC11511 | 143 | TIC11513 | 145 |

*comprises an additional alanine residue immediately following the initiating methionine residue.

The term “PirAB fusion protein” is also used in this application to describe a protein that comprises a PirB protein contiguous with a PirA protein. The DNA sequence encoding the PirAB fusion protein of this type can comprise a coding sequence encoding a PirB protein operably linked and in frame with a coding sequence encoding a PirA protein such that when it is expressed in a cell it produces a fusion protein comprising both a PirB protein and PirA protein. The PirB protein can be comprised of a PirB protein and a PirA protein derived from the same bacterial operon, or alternatively, can be comprised of a PirB protein and a PirA protein derived from different operons. Exemplary proteins wherein a PirB protein is contiguous with a PirA protein are provided in Table 2.

TABLE 2

Exemplary PirAB fusion proteins comprised of a PirB protein contiguous with a PirA protein and the corresponding PirB and PirA proteins comprised within.

| PirB Protein | | PirA Protein | | PirAB Fusion Protein | |
|---|---|---|---|---|---|
| Toxin | Protein SEQ ID NO: | Toxin | Protein SEQ ID NO: | Toxin | Protein SEQ ID NO: |
| TIC7661 | 16 | TIC7660 | 14 | TIC11103 | 155 |
| TIC7663 | 22 | TIC7662 | 20 | TIC11104 | 157 |

The term “PirAB fusion protein” is also used in this application to describe a protein that comprises two PirA proteins contiguous with a PirB protein. The DNA sequence encoding the PirAB fusion protein of this type can comprise a coding sequence encoding a PirA protein, operably linked to a coding sequence encoding the same PirA protein or a different PirA protein, operably linked to a coding sequence encoding a PirB protein such that when it is expressed in a cell it produces a fusion protein comprising a PirA protein, another PirA protein, and a PirB protein. Exemplary PirAB fusion proteins comprising two PirA proteins contiguous with a PirB protein are provided in Table 3.

another. The multiple PirA and/or PirB proteins can be duplicated PirA or PirB proteins, or can be different PirA or PirB proteins. The combination of multiple PirA and/or PirB proteins as a fusion protein can increase activity against a specific target pest species or may increase the range of pest species in which activity is present.

The term “segment” or “fragment” is used in this application to describe consecutive amino acid or nucleic acid sequences that are shorter than the complete amino acid or nucleic acid sequence describing one of The PirA Proteins, The PirB Proteins, or The PirAB Proteins. A segment or fragment exhibiting insect inhibitory activity is also disclosed in this application if alignment of such segment or fragment, with the corresponding section of the PirA proteins set forth in SEQ ID NOs:2, 8, 14, 20, 26, 32, 38, 44, 58, 64, 70, 76, 82, 88, 94, 100, or 105; the PirB proteins set forth in SEQ ID NOs:4, 10, 16, 22, 28, 34, 40, 46, 60, 66, 72, 78, 84, 90, 96, 102, 107, 135, 139, or 143; or the PirAB fusion proteins set forth in SEQ ID NOs:6, 12, 18, 24, 30, 36, 42, 48, 50, 62, 68, 74, 80, 86, 92, 98, 109, 111, 113, 115, 117, 119, 121, 123, 125, 127, 129, 131, 133, 137, 141, 145, 147, 149, 151, 153, 155, or 157, or related family member insecticidal protein results in an alignment from about 65 to about 100 percent identity between the segment or fragment and the corresponding section of the aligned protein. A segment or fragments of one of The PirA Proteins, The PirB Proteins, or The PirAB Proteins described herein may comprise at least about 50 contiguous amino acids, at least about 75 contiguous amino acids, at least about 100 contiguous amino acids, at least about 125 contiguous amino acids, at least about 150 contiguous amino acids, at least about 200 contiguous amino acids, at least about 250 contiguous amino acids, at least about 300 contiguous amino acids, at least about 350 contiguous amino acids, at least about 400 contiguous amino acids, at least about 450 contiguous amino acids, at least about 500 contiguous amino acids, at least about 550 contiguous amino acids, or at least about 600 contiguous amino acids of one of The PirA Proteins, The PirB Proteins, or The PirAB Proteins. A segment or fragment of one of The PirA Proteins, The PirB Proteins, or The PirAB Proteins described herein may exhibit the activity of the base sequence.

TABLE 3

Exemplary PirAB fusion proteins comprised of a PirA protein contiguous with another PirA protein, and contiguous with a PirB protein, and the corresponding PirA and PirB proteins comprised within.

| PirA Protein | | PirA Protein | | PirB Protein | | PirAB Fusion Protein | |
|---|---|---|---|---|---|---|---|
| Toxin | Protein SEQ ID NO: | Toxin | Protein SEQ ID NO: | Toxin | Protein SEQ ID NO: | Toxin | Protein SEQ ID NO: |
| TIC4771 | 2 | TIC4771 | 2 | TIC4772 | 4 | TIC11440 | 121 |
| TIC7575 | 8 | TIC7575 | 8 | TIC7576 | 10 | TIC11441 | 123 |
| TIC7575 | 8 | TIC4771 | 2 | TIC4772 | 4 | TIC11442 | 125 |
| TIC7660 | 14 | TIC7575 | 8 | TIC7576 | 10 | TIC11443 | 127 |
| TIC7575 | 8 | TIC7660 | 14 | TIC7661 | 16 | TIC11444 | 129 |
| TIC7660 | 14 | TIC7662 | 20 | TIC7663 | 22 | TIC11445 | 131 |
| TIC7662 | 20 | TIC7660 | 14 | TIC7661 | 16 | TIC11446 | 133 |

The term “PirAB fusion protein” is also used in this application to describe a protein that comprises multiple PirA and/or multiple PirB proteins contiguous with one Reference in this application to the terms “active” or “activity”, “pesticidal activity” or “pesticidal” or “insecticidal activity”, “insect inhibitory” or “insecticidal” refer to efficacy of a toxic agent, such as a protein toxin, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of one or more of The PirA Proteins, The PirB Proteins or The PirAB Fusion Proteins. These terms are intended to include the result of providing a pesticidally effective amount of a toxic protein to a pest where the exposure of the pest to the toxic protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the toxic protein in or on the plant. In general, pesticidal activity refers to the ability of a toxic protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera, Coleoptera or Hemiptera. The toxic protein can be produced by the plant or can be applied to the plant or to the environment within the location where the plant is located. The terms "bioactivity", "effective", "efficacious" or variations thereof are also terms interchangeably utilized in this application to describe the effects of proteins of the present invention on target insect pests.

A pesticidally effective amount of a toxic agent, when provided in the diet of a target pest, exhibits pesticidal activity when the toxic agent contacts the pest. A toxic agent can be a pesticidal protein or one or more chemical agents known in the art. Pesticidal or insecticidal chemical agents and pesticidal or insecticidal protein agents can be used alone or in combinations with each other. Chemical agents include, but are not limited to, dsRNA molecules targeting specific genes for suppression in a target pest, organochlorides, organophosphates, carbamates, pyrethroids, neonicotinoids, and ryanoids. Pesticidal or insecticidal protein agents include the protein toxins set forth in this application, as well as other proteinaceous toxic agents including those that target Coleopteran, Lepidopteran, Hemipteran, Thysanopteran, or Dipteran pest species.

The "*Photorhabdus* insect-related" proteins, or PirAB proteins, are binary toxins with pesticidal activity against some insects. Some PirAB proteins have been shown to have Lepidopteran activity when injected into the insect hemocoel. However, when presented in the insect diet, the oral application of the PirAB proteins have shown little to no activity (see, for example, Yang et al. (2017) PirAB protein from *Xenorhabdus nematophila* HB310 exhibits a binary toxin with insecticidal activity and cytotoxicity in *Galleria mellonella*. J. Invertebr Pathol, 148: 43-50; Li et al. (2014) *Photorhabdus luminescens* PirAB-fusion protein exhibits both cytotoxicity and insecticidal activity. FEMS Microbial Lett, 356: 23-31; Wu and Yunhong (2016) Scientific Reports 6, Article number: 34996; doi:10.1038/srep34996; and Zhang et al. (2013) XaxAB-like binary toxin from *Photorhabdus luminescens* exhibits both insecticidal activity and cytotoxicity. FEMS Microbiol Lett 350: 48-56). Oral activity of the PirAB proteins against Lepidotera have been reported but those studies have relied on the insect ingesting a diet comprising *E. coli* bacteria expressing the PirAB proteins and not purified toxin provided in the insect diet (see, for example, Waterfield et al. (2005) The *Photorhabdus* Pir toxins are similar to a developmentally regulated insect protein but show no juvenile hormone esterase activity. FEMS Microbiol Lett, 245: 47-52 and Blackburn et al. (2006) Remarkable susceptibility of the diamondback moth (*Plutella xylostella*) to ingestion of Pir toxins from *Photorhabdus luminescens*. Entomologia Experimentalis et Applicata, 121: 31-37). In stark contrast, herein, as described in the Examples, protein preparations of The PirA Proteins, The PirB Proteins, and The PirAB Fusion Proteins were provided in the insect diet bioassays. Oral activity against Lepidopteran, Coleopteran, and Hemipteran insect pests was observed and is presented in the Examples. In addition, leaf discs derived from plants expressing the PirAB fusion proteins, TIC9316, TIC9317, and TIC9318 were used in oral insect feeding studies which demonstrated activity against the Lepidopteran insect pest species European corn borer and Southwestern corn borer (SWCB). Further, leaf discs derived from plants expressing TIC10376, TIC10378, TIC10380, and TIC10381 demonstrated activity against SWCB. Also, as described in the Examples, TIC9315 and TIC11302 demonstrated activity against Western Corn Rootworm pests in stably transformed plants.

It is intended that reference to a pest, particularly a pest of a crop plant, means insect pests of crop plants, particularly those that are controlled by at least one of The PirA Proteins, The PirB Protein, and The PirAB Proteins, a related family member insecticidal protein, or a segment or fragment thereof.

As described in the Examples, one or more of The PirA Proteins, The PirB Proteins, or The PirAB Proteins exhibits insecticidal activity towards insect pests from the Coleopteran, Hemipteran, and Lepidopteran insect pest species, including adults, pupae, larvae, and neonates.

The insects of the order Lepidoptera include, but are not limited to, armyworms, cutworms, loopers, and heliothines in the Family Noctuidae, e.g., fall armyworm (*Spodoptera frugiperda*), Beet armyworm (*Spodoptera exigua*), Black armyworm (*Spodoptera exempta*), Bertha armyworm (*Mamestra configurata*), Southern armyworm (*Spodoptera eridania*), Black cutworm (*Agrotis ipsilon*), Cabbage looper (*Trichoplusia ni*), Soybean looper (*Pseudoplusia includens*), Velvetbean caterpillar (*Anticarsia gemmatalis*), Green cloverworm (*Hypena scabra*), Tobacco budworm (*Heliothis virescens*), Granulate cutworm (*Agrotis subterranea*), Armyworm (Pseudaletia *unipuncta*), Western cutworm (*Agrotis orthogonia*); borers, casebearers, webworms, coneworms, cabbageworms and skeletonizers from the Family Pyralidae, e.g., European corn borer (*Ostrinia nubilalis*), Navel orangeworm (*Amyelois transitella*), Corn root webworm (*Crambus caliginosellus*), Sod webworm (*Herpetogramma licarsisalis*), Sunflower moth (*Homoeosoma electellum*), Lesser cornstalk borer (*Elasmopalpus lignosellus*); leafrollers, budworms, seed worms, and fruit worms in the Family Tortricidae, e.g., Codling moth (*Cydia pomonella*), Grape berry moth (*Endopiza viteana*), Oriental fruit moth (*Grapholita molesta*), Sunflower bud moth (*Suleima helianthana*); and many other economically important Lepidoptera, e.g., Diamondback moth (*Plutella xylostella*), Pink bollworm (*Pectinophora gossypiella*) and Gypsy moth (*Lymantria dispar*). Other insect pests of order Lepidoptera include, e.g., Cotton leaf worm (*Alabama argillacea*), Fruit tree leaf roller (*Archips argyrospila*), European leafroller (*Archips rosana*) and other *Archips* species, (*Chilo suppressalis*, Asiatic rice borer, or rice stem borer), Rice leaf roller (Cnaphalocrocis *medinalis*), Corn root webworm (*Crambus caliginosellus*), Bluegrass webworm (*Crambus teterrellus*), Southwestern corn borer (*Diatraea grandiosella*), Surgarcane borer (*Diatraea* saccharalis), Spiny bollworm (*Earias insulana*), Spotted bollworm (*Earias vittella*), Old World bollworm (*Helicoverpa armigera*), Corn earworm (*Helicoverpa zea*, also known as soybean podworm and cotton bollworm), Tobacco budworm (*Heliothis virescens*), Sod webworm (*Herpetogramma licarsisalis*), Western bean cutworm (*Striacosta albicosta*), European grape vine moth (*Lobesia botrana*), Citrus leafminer (*Phyllocnistis citrella*), large white butterfly (*Pieris brassicae*), small white butterfly (*Pieris rapae*, also known as imported cabbageworm), Tobacco cutworm (*Spodoptera litura*, also known as cluster caterpillar), and Tomato leafminer (*Tuta absoluta*).

The insects of the order Coleoptera include, but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp, particularly when the pest is Western Corn Rootworm (*Diabrotica virgifera*, WCR), Northern Corn Rootworm (*Diabrotica barberi*, NCR), Mexican Corn Rootworm (*Diabrotica virgifera zeae*, MCR), Brazilian Corn Rootworm (*Diabrotica balteata*, BZR), Southern Corn Rootworm (*Diabrotica undecimpunctata howardii*, SCR), Colorado potato beetle (*Leptinotarsa decemlineata*, CPB), a Brazilian Corn Rootworm complex (BCR, consisting of *Diabrotica viridula* and *Diabrotica speciosa*), Crucifer Flea Beetle (*Phyllotreta cruciferae*), Striped Flea Beetle (*Phyllotreta striolata*), and Western Black Flea Beetle (*Phyllotreta pusilla*).

The insects of the order Hemiptera include, but are not limited to, Stink Bugs of the family Pentatomidae: Green Stink Bugs from the genus *Chinavia* (*Chinavia hilaris, Chinavia marginata*, and *Chinavia pensylvanica*), Stink bugs of the genus *Chlorochroa* (*Chlorochroa granulose, Chlorochroa* kanei, *Chlorochroa ligata, Chlorochroa lineate, Chlorochroa opuntiae, Chlorochroa persimilis, Chlorochroa rossiana, Chlorochroa sayi, Chlorochroa uhleri, Chlorochroa belfragii, Chlorochroa faceta, Chlorochroa osborni, Chlorochroa saucia*, and *Chlorochroa senilis*), Southern Green Stink Bug (*Nezara viridula*), Stink Bugs from the genus *Edessa* (*Edessa meditabunda, Edessa bifida*, and *Edessa florida*), the Neotropical Brown Stink Bug (*Euschistus heros*), stink bugs from the genus *Euschistus* (*Euschistus acuminatus, Euschistus biformis, Euschistus conspersus, Euschistus crenator, Euschistus egglestoni, Euschistus ictericus, Euschistus inflatus, Euschistus latimarginatus, Euschistus obscures, Euschistus politus, Euschistus quadrator, Euschistus sevus, Euschistus strenuous, Euschistus tristigmus*, and *Euschistus variolarius*), Brown Marmorated Stink Bug (*Halyomorpha halys*), Red-Shouldered Stink Bug (*Thyanta accerra*), stink bugs of the genus *Thyanta* (*Thyanta calceata, Thyanta custator, Thyanta pallidovirens, Thyanta perditor, Thyanta maculate*, and *Thyanta pseudocasta*), the Green Belly Stink Bug (*Dichelops melacanthus*) and other stink bugs of the genus *Dichelops* (*Dichelops avilapiresi, Dichelops bicolor, Dichelops dimidatus, Dichelops furcatus, Dichelops furcifrons, Dichelops lobatus, Dichelops miriamae, Dichelops nigrum, Dichelops peruanus, Dichelops phoenix*, and *Dichelops saltensis*), the Red Banded Stink Bug (*Piezodorus guildinni*) as well as *Piezodorus lituratus*; and insects of the family of Plataspidae such as Kudzu Bug (*Megacopta cribraria*), Western tarnished plant bug (*Lygus hesperus*), and Tarnished plant bug (*Lygus lineolaris*).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further herein, an operon containing two open reading frames (ORFs) encoding the PirA protein, TIC4771 (SEQ ID NO:1) and the PirB protein, TIC4772 (SEQ ID NO:3) was discovered in DNA obtained from *Xenorhabdus nematophila* strain ISB000002 which encodes the protein toxins presented as SEQ ID NO:2 and SEQ ID NO:4, respectively. The two ORFs were used to make a PirAB fusion protein encoding DNA sequence, TIC6880 (SEQ ID NO:5) wherein the two coding sequences were operably linked and in frame to produce the TIC6880 PirAB fusion protein presented as SEQ ID NO:6. Bioassay using microbial host cell-derived TIC4771 demonstrated activity against the Lepidopteran species Corn earworm (*Helicoverpa zea*, CEW), Diamondback Moth (*Plutella xylostella*, DEM), European corn borer (*Ostrinia nubilalis*, ECB), Velvet Bean Caterpillar (*Anticarsia gemmatalis*, VBC), and Southern Army Worm (*Spodoptera eridania*, SAW); the Coleopteran species Colorado potato beetle (*Leptinotarsa decemlineata*, CPB); and the Hemipteran species Tarnished plant bug (*Lygus lineolaris*, TPB). Bioassay using microbial host cell-derived TIC4772 demonstrated activity against the Lepidopteran species CEW, DBM, and VBC and the Hemipteran species TPB. Bioassay using microbial host cell-derived PirAB fusion protein, TIC6880 comprised of TIC4771 and TIC4772, demonstrated activity against the Lepidopteran species Fall armyworm (*Spodoptera frugiperda*, FAW), CEW, Southwestern Corn Borer (*Diatraea grandiosella*, SWCB), DBM, ECB, and VBC, the Coleopteran species CPB and Western Corn Rootworm (*Diabrotica virgifera*, WCR); the Hemipteran species Tarnished plant bug (*Lygus lineolaris*, TPB), Western tarnished plant bug (*Lygus hesperus*, WTP), Southern Green Stink Bug (*Nezara viridula*, SGB), and Neotropical Brown Stink Bug (*Euschis-

*tus heros*, NBSB), and the Dipteran species Yellow fever mosquito (*Aedes aegypti*, YFM).

An operon containing two ORFs encoding the PirA protein, TIC7575 (SEQ ID NO:7) and the PirB protein, TIC7576 (SEQ ID NO:9) was discovered in DNA obtained from *Xenorhabdus ehlersii* strain 85823 which encodes the protein toxins presented as SEQ ID NO:8 and SEQ ID NO:10, respectively. The two ORFs were used to make a PirAB fusion protein encoding DNA sequence, TIC9316 (SEQ ID NO:11) wherein the two coding sequences were operably linked and in frame to produce the TIC9316 PirAB fusion protein presented as SEQ ID NO:12. Bioassay using microbial host cell-derived TIC7575 and TIC7576 did not demonstrate activity against the insects tested in assay. However, bioassay using the PirAB fusion protein TIC9316—comprised of TIC7575 and TIC7576—demonstrated activity against the Lepidopteran species SWCB, Black cutworm (*Agrotis ipsilon*, BCW), SAW, Tobacco budworm (*Heliothis virescens*, TBW), ECB, and VBC, the Coleopteran species CPB, and the Hemipteran species TPB, WTP, SGB, and NBSB.

An operon containing two ORFs encoding the PirA protein, TIC7660 (SEQ ID NO:13) and the PirB protein, TIC7661 (SEQ ID NO:15) was discovered in DNA obtained from *Xenorhabdus cabanillasii* strain 85908 which encodes the protein toxins presented as SEQ ID NO:14 and SEQ ID NO:16, respectively. The two ORFs were used to make a PirAB fusion protein encoding DNA sequence, TIC9317 (SEQ ID NO:17) wherein the two coding sequences were operably linked and in frame to produce the TIC9317 PirAB fusion protein presented as SEQ ID NO:18. Bioassay using microbial host cell-derived TIC7660 and TIC7661 did not demonstrate activity against the insects used in assay. However, bioassay using the PirAB fusion protein TIC9317—comprised of TIC7660 and TIC7661—demonstrated activity against the Lepidopteran species SWCB, ECB, and VBC, the Coleopteran species CPB and WCR, and the Hemipteran species TPB, WTP, and SGB.

An operon containing two ORFs encoding the PirA protein, TIC7662 (SEQ ID NO:19) and the PirB protein, TIC7663 (SEQ ID NO:21) was discovered in DNA obtained from *Xenorhabdus ehlersii* strain 85887 which encodes the protein toxins presented as SEQ ID NO:20 and SEQ ID NO:22, respectively. The two ORFs were used to make a PirAB fusion protein encoding DNA sequence, TIC9318 (SEQ ID NO:23) wherein the two coding sequences were operably linked and in frame to produce the TIC9318 PirAB fusion protein presented as SEQ ID NO:24. Bioassay using microbial host cell-derived TIC7662 and TIC7663 did not demonstrate activity against the insects used in assay. However, bioassay using the PirAB fusion protein TIC9318—comprised of TIC7662 and TIC7663—demonstrated activity against the Lepidopteran species SWCB, BCW, TBW, ECB, and VBC, the Coleopteran species CPB and WCR, and the Hemipteran species TPB, WTP, SGB, and NBSB.

An operon containing two ORFs encoding the PirA protein, TIC7664 (SEQ ID NO:25) and the PirB protein, TIC7665 (SEQ ID NO:27) was discovered in DNA obtained from *Xenorhabdus poinarii* strain 86198 which encodes the protein toxins presented as SEQ ID NO:26 and SEQ ID NO:28, respectively. The two ORFs were used to make a PirAB fusion protein encoding DNA sequence, TIC9319 (SEQ ID NO:29) wherein the two coding sequences were operably linked and in frame to produce the TIC9319 PirAB fusion protein presented as SEQ ID NO:30. Bioassay using microbial host cell-derived TIC7664 demonstrated activity against the Coleopteran species CPB. Bioassay using microbial host cell-derived TIC7665 demonstrated activity against the Lepidopteran species TBW. Bioassay using the PirAB fusion protein, TIC9319—comprised of TIC7664 and TIC76653—demonstrated activity against the Lepidopteran species SWCB, BCW, ECB, and VBC, the Coleopteran species CPB, and the Hemipteran species TPB, WTP, and SGB.

An operon containing two ORFs encoding the PirA protein TIC7666 (SEQ ID NO:31) and the PirB protein TIC7667 (SEQ ID NO:33) was discovered in DNA obtained from *Photorhabdus luminescens* strain 86197 which encodes the protein toxins presented as SEQ ID NO:32 and SEQ ID NO:34, respectively. The two ORFs were used to make a PirAB fusion protein encoding DNA sequence, TIC9322 (SEQ ID NO:35) wherein the two coding sequences were operably linked and in frame to produce the TIC9322 PirAB fusion protein presented as SEQ ID NO:36. Bioassay using microbial host cell-derived TIC7666 did not demonstrate activity against the insects used in assay. Bioassay using microbial host cell-derived TIC7667 demonstrated activity against the Lepidopteran species SWCB. Bioassay using the PirAB fusion protein TIC9322—comprised of TIC7666 and TIC7667—demonstrated activity against the Lepidopteran species SWCB and VBC, the Coleopteran species CPB, and the Hemipteran species TPB.

An operon containing two ORFs encoding the PirA protein, TIC7668 (SEQ ID NO:37) and the PirB protein, TIC7669 (SEQ ID NO:39) was discovered in DNA obtained from *Photorhabdus luminescens* strain 86194 which encodes the protein toxins presented as SEQ ID NO:38 and SEQ ID NO:40, respectively. The two ORFs were used to make a PirAB fusion protein encoding DNA sequence, TIC9320 (SEQ ID NO:41) wherein the two coding sequences were operably linked and in frame to produce the TIC9320 PirAB fusion protein presented as SEQ ID NO:42. Bioassay using microbial host cell-derived TIC7668 and TIC7669 did not demonstrate activity against the insects used in assay. However, bioassay using the PirAB fusion protein TIC9320—comprised of TIC7668 and TIC7669—demonstrated activity against the Lepidopteran species SWCB, ECB, and VBC, the Coleopteran species CPB and WCR, and the Hemipteran species TPB, SGB, and NBSB.

An operon containing two ORFs encoding the PirA protein, TIC7939 (SEQ ID NO:43) and the PirB protein, TIC7940 (SEQ ID NO:45) was discovered in DNA obtained from an unknown bacterial species comprised within a microbiome which encodes the protein toxins presented as SEQ ID NO:44 and SEQ ID NO:46, respectively. The two ORFs were used to make a PirAB fusion protein encoding DNA sequence, TIC9321 (SEQ ID NO:47), wherein the two coding sequences were operably linked and in frame to produce the TIC9321 PirAB fusion protein presented as SEQ ID NO:48.

An operon containing two ORFs encoding the PirA protein, TIC10357 (SEQ ID NO:57) and the PirB protein, TIC10366 (SEQ ID NO:59) was discovered in DNA obtained from *Shewanella violacea* which encodes the protein toxins presented as SEQ ID NO:58 and SEQ ID NO:60, respectively. The two open reading frames were used to make a PirAB fusion protein encoding DNA sequence, TIC10375 (SEQ ID NO:61), wherein the two coding sequences were operably linked and in frame to produce the TIC10375 PirAB fusion protein presented as SEQ ID NO:62.

An operon containing two ORFs encoding the PirA protein, TIC10358 (SEQ ID NO:63) and the PirB protein, TIC10367 (SEQ ID NO:65) was discovered in DNA obtained from *Photorhabdus luminescens* strain laumondii TTO1 which encodes the protein toxins presented as SEQ ID NO:64 and SEQ ID NO:66, respectively. The two ORFs were used to make a PirAB fusion protein encoding DNA sequence TIC10376 (SEQ ID NO:67) wherein the two coding sequences were operably linked and in frame to produce the TIC10376 PirAB fusion protein presented as SEQ ID NO:68. Bioassay using microbial host cell-derived TIC10358 and TIC10367 did not demonstrate activity against the insects used in assay. However, bioassay using the PirAB fusion protein TIC10376—comprised of TIC10358 and TIC10367—demonstrated activity against the Lepidopteran species SWCB and the Coleopteran species Northern Corn Rootworm (*Diabrotica barberi*, NCR) and WCR.

An operon containing two ORFs encoding the PirA protein, TIC10360 (SEQ ID NO:69) and the PirB protein, TIC10369 (SEQ ID NO:71) was discovered in DNA obtained from *Photorhabdus asymbiotica* which encodes the protein toxins presented as SEQ ID NO:70 and SEQ ID NO:72, respectively. The two ORFs were used to make a PirAB fusion protein encoding DNA sequence TIC10377 (SEQ ID NO:73) wherein the two coding sequences were operably linked and in frame to produce the TIC10377 PirAB fusion protein presented as SEQ ID NO:74.

An operon containing two ORFs encoding the PirA protein TIC10361 (SEQ ID NO:75) and the PirB protein TIC10370 (SEQ ID NO:77) was discovered in DNA obtained from *Xenorhabdus* sp. strain NBAII XenSa04 which encodes the protein toxins presented as SEQ ID NO:76 and SEQ ID NO:78, respectively. The two ORFs were used to make a PirAB fusion protein encoding DNA sequence TIC10378 (SEQ ID NO:79) wherein the two coding sequences were operably linked and in frame to produce the TIC10378 PirAB fusion protein presented as SEQ ID NO:80.

An operon containing two ORFs encoding the PirA protein TIC10362 (SEQ ID NO:81) and the PirB protein TIC10371 (SEQ ID NO:83) was discovered in DNA obtained from *Yersinia aldovae* strain 670-83 which encodes the protein toxins presented as SEQ ID NO:82 and SEQ ID NO:84, respectively. The two ORFs were used to make a PirAB fusion protein encoding DNA sequence TIC10379 (SEQ ID NO:85) wherein the two coding sequences were operably linked and in frame to produce the TIC10379 PirAB fusion protein presented as SEQ ID NO:86.

An operon containing two ORFs encoding the PirA protein TIC10363 (SEQ ID NO:87) and the PirB protein TIC10372 (SEQ ID NO:89) was discovered in DNA obtained from *Xenorhabdus doucetiae* strain FRM16 which encodes the protein toxins presented as SEQ ID NO:88 and SEQ ID NO:90, respectively. The two ORFs were used to make a PirAB fusion protein encoding DNA sequence TIC10380 (SEQ ID NO:91) wherein the two coding sequences were operably linked and in frame to produce the TIC10380 PirAB fusion protein presented as SEQ ID NO:92. Bioassay using microbial host cell-derived TIC10363 and TIC10372 did not demonstrate activity against the insects used in assay. However, bioassay using the PirAB fusion protein TIC10380—comprised of TIC10363 and TIC10372—demonstrated activity against the Lepidopteran species FAW, the Coleopteran species NCR and WCR and the Hemipteran species NBSB.

An operon containing two ORFs encoding the PirA protein TIC10364 (SEQ ID NO:93) and the PirB protein TIC10373 (SEQ ID NO:95) was discovered in DNA obtained from *Xenorhabdus griffiniae* strain BMMCB which encodes the protein toxins presented as SEQ ID NO:94 and SEQ ID NO:96, respectively. The two ORFs were used to make a PirAB fusion protein encoding DNA sequence TIC10381 (SEQ ID NO:97) wherein the two coding sequences were operably linked and in frame to produce the TIC10381 PirAB fusion protein presented as SEQ ID NO:98. Bioassay using microbial host cell-derived TIC10364 and TIC10373 did not demonstrate activity against the insects used in assay. However, bioassay using the PirAB fusion protein TIC10378—comprised of TIC10364 and TIC10373—demonstrated activity against the Coleopteran species NCR and WCR and the Hemipteran species NBSB.

An operon containing two ORFs encoding the PirA protein TIC10359 (SEQ ID NO:99) and the PirB protein TIC10368 (SEQ ID NO:101) was discovered in DNA obtained from *Xenorhabdus nematophila* which encodes the protein toxins presented as SEQ ID NO:100 and SEQ ID NO:102, respectively. An operon sequence comprising both TIC10359 and TIC10368 is presented as SEQ ID NO:103.

An operon containing two ORFs encoding the PirA protein PirA_ABE68878 (SEQ ID NO:104) and the PirB protein, PirB_ABE68879 (SEQ ID NO:106) was discovered in DNA obtained from *Photorhabdus luminescens* strain Hm which encodes the protein toxins presented as SEQ ID NO:105 and SEQ ID NO:107, respectively. The two ORFs were used to make a PirAB fusion protein encoding DNA sequence TIC10434 (SEQ ID NO:108) wherein the two coding sequences were operably linked and in frame to produce the TIC10378 PirAB fusion protein presented as SEQ ID NO:109. Bioassay using microbial host cell-derived PirAB fusion protein TIC10434—comprised of PirA_ABE68878 and PirB_ABE68879—demonstrated activity against the Coleopteran species NCR and WCR.

An operon containing the PirB protein ORF encoding TIC11505 (SEQ ID NO:134) was discovered from *Xenorhabdus nematophila* strain MDI-0035777 which encodes the protein toxin presented as SEQ ID NO:135. The PirAB fusion protein TIC11056 encoding sequence (SEQ ID NO:136) comprised the TIC10364 coding sequence operably linked in frame with the TIC11505 coding sequence to produce the TIC11506 PirAB fusion protein presented as SEQ ID NO:137.

An operon containing the PirB protein ORF encoding TIC11510 (SEQ ID NO:138) was discovered from *Xenorhabdus nematophila* strain MDI-0035777 which encodes the protein toxin presented as SEQ ID NO:139. The PirAB fusion protein TIC11512 encoding sequence (SEQ ID NO:140) comprised the TIC10364 coding sequence operably linked in frame with the TIC11505 coding sequence to produce the TIC11056 PirAB fusion protein presented as SEQ ID NO:141.

An operon containing the PirB protein ORF encoding TIC11511 (SEQ ID NO:142) was discovered from *Xenorhabdus nematophila* strain MDI-0035777 which encodes the protein toxin presented as SEQ ID NO:143. The PirAB fusion protein TIC11513 encoding sequence (SEQ ID NO:144) comprised the TIC10364 coding sequence operably linked in frame with the TIC11513 coding sequence to produce the TIC11056 PirAB fusion protein presented as SEQ ID NO:145.

The PirAB fusion proteins, TIC11210, TIC11211, and TIC11301 comprised the PirA protein TIC7575 and the PirB proteins, TIC7665, TIC7667, and TIC7661, respectively. The PirAB fusion protein, TIC11212 comprises the PirA protein TIC7662 and the PirB protein TIC7665. The PirAB fusion protein, TIC11302 comprises the PirA protein, TIC7660 and the PirB protein, TIC7576. The PirAB fusion proteins TIC11210 and TIC11211 demonstrated activity against the Lepidopteran species SWCB and the Hemipteran species NBSB. The PirAB fusion proteins TIC11301 and TIC11302 demonstrated activity against the Lepidopteran species SWCB, ECB, and VBC, the Coleopteran species WCR, and the Hemipteran species NBSB and WTP.

The PirAB fusion proteins, TIC11103 and TIC11104 comprised a PirB protein congruent with a PirA Protein. The PirAB fusion protein, TIC11103 is comprised of the PirB protein, TIC7661 and the PirA protein, TIC7660. The PirAB fusion protein, TIC11104 is comprised of the PirB protein TIC7663 and the PirA protein TIC7662.

The PirAB fusion protein TIC11440 is comprised of a duplication of the PirA protein TIC4771 and the PirB protein TIC4772. The PirAB fusion protein TIC11441 is comprised of a duplication of the PirA protein TIC7575 and the PirB protein TIC7576. The PirAB fusion protein TIC11442 is comprised of the PirA proteins, TIC7575 and TIC4771, and the PirB protein TIC4772. The PirAB fusion protein TIC11443 is comprised of the PirA proteins TIC7660 and TIC7575 and the PirB protein, TIC7576. The PirAB fusion protein TIC11444 is comprised of the PirA proteins TIC7575 and TIC7660 and the PirB protein TIC7661. The PirAB fusion protein TIC11445 is comprised of the PirA proteins TIC7660 and TIC7662 and the PirB protein TIC7663. The PirAB fusion protein TIC11446 is comprised of the PirA proteins TIC7662 and TIC7660 and the PirB protein TIC7661. Bacterial host cell derived TIC11442 demonstrated activity against the Hemipteran pest species NBSB. Bacterial host cell derived TIC11444 demonstrated activity against the Lepidopteran species SWCB and the Hemipteran species NBSB.

As described in the Examples, synthetic DNA sequences encoding the PirAB fusion proteins TIC6880PL (SEQ ID NO:49), TIC9316 (SEQ ID NO:51), TIC9317 (SEQ ID NO:53), TIC9318 (SEQ ID NO:55), TIC9320 (SEQ ID NO:57), TIC9322 (SEQ ID NO:59), TIC10376PL (SEQ ID NO:146), TIC10378PL (SEQ ID NO:148), TIC10380PL (SEQ ID NO:150), TIC10381PL (SEQ ID NO:152), TIC11103 (SEQ ID NO:154), TIC11104 (SEQ ID NO:156), and TIC11302 (SEQ ID NO:158) were designed for expression in a plant cell. Corn plants transformed with binary transformation plasmid constructs expressing TIC9316, TIC9317, and TIC9318 demonstrated activity against the insect pest species European corn borer and Southwestern corn borer.

For expression in plant cells, The PirAB Fusion Proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the choloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442, 1987) or the *Petunia hybrida* EPSPS CTP (CTP4) (See, della-Cioppa et al., *Proc. Natl. Acad. Sci. USA* 83:6873-6877, 1986) has been shown to target heterologous EPSPS protein sequences to chloroplasts in transgenic plants (See, U.S. Pat. Nos. 5,627,061; 5,633,435; and 5,312,910; and EP 0218571; EP 189707; EP 508909; and EP 924299). For targeting one of The PirAB Fusion Proteins to the chloroplast, a sequence encoding a chloroplast transit peptide is placed 5' in operable linkage and in frame to a synthetic coding sequence encoding one of The PirAB Fusion Proteins that has been designed for optimal expression in plant cells.

It is contemplated that additional toxin protein sequences related to The PirA Proteins, The PirB Proteins, and The PirAB Fusion Proteins can be created by using the naturally occurring amino acid sequence of The PirA Proteins, The PirB Proteins, and The PirAB Fusion Proteins to combine differences at the amino acid sequence level into novel amino acid sequence variants and making appropriate changes to the recombinant nucleic acid sequence encoding the variants.

This disclosure further contemplates that improved variants of The PirA Proteins, The PirB Proteins, and The PirAB Fusion Proteins can be engineered in planta by using various gene editing methods known in the art. Such technologies used for genome editing include, but are not limited to, ZFN (zinc-finger nuclease), meganucleases, TALEN (Transcription activator-like effector nucleases), and CRISPR (Clustered Regularly Interspaced Short Palindromic Repeats)/Cas (CRISPR-associated) systems. These genome editing methods can be used to alter the toxin protein coding sequence transformed within a plant cell to a different toxin coding sequence. Specifically, through these methods, one or more codons within the toxin coding sequence is altered to engineer a new protein amino acid sequence. Alternatively, a fragment within the coding sequence is replaced or deleted, or additional DNA fragments are inserted into the coding sequence, to engineer a new toxin coding sequence. The new coding sequence can encode a toxin protein with new properties such as increased activity or spectrum against insect pests, as well as provide activity against an insect pest species wherein resistance has developed against the original insect toxin protein. The plant cell comprising the gene edited toxin coding sequence can be used by methods known in the art to generate whole plants expressing the new toxin protein.

Proteins that resemble The PirA Proteins, The PirB Proteins, and The PirAB Fusion Proteins can be identified by comparison to each other using various computer-based algorithms known in the art. For example, amino acid sequence identities of proteins related to The PirA Proteins, The PirB Proteins, and The PirAB Fusion Proteins can be analyzed using a Clustal W alignment using these default parameters: Weight matrix: blosum, Gap opening penalty:

10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of subject protein). Other alignment algorithms are also available in the art and provide results similar to those obtained using a Clustal W alignment.

It is intended that a protein exhibiting insect inhibitory activity against a Lepidopteran, or Coleopteran, or Hemipteran insect species is related to The PirA Proteins if alignment of such query protein with TIC7939 exhibits at least 65% to about 100% amino acid identity along the length of the query protein that is about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC7664 or TIC7666 exhibits at least 97% to about 100% amino acid identity along the length of the query protein that is about 97%, 98%, 99%, 100% amino acid sequence identity (or any fraction of a percentage in this range) between query and subject protein; or if alignment of such query protein with TIC4771 exhibits at least 98% to about 100% amino acid identity along the length of the query protein that is about 98%, 99%, 100% amino acid sequence identity (or any fraction of a percentage in this range) between query and subject protein; or if alignment of such query protein with TIC7575, TIC7660, TIC7662, TIC7668, TIC10357, TIC10358, TIC10360, TIC10361, TIC10362, TIC10364, TIC10359, or PirA_ABE68878 exhibits 100% identity between query and subject protein.

It is also intended that a protein exhibiting insect inhibitory activity against a Lepidopteran, or Coleopteran, or Hemipteran insect species is related to The PirB Proteins if alignment of such query protein with TIC7940 exhibits at least 65% to about 100% amino acid identity along the length of the query protein that is about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC4772 exhibits at least 97% to about 100% amino acid identity along the length of the query protein that is about 97%, 98%, 99%, 100% amino acid sequence identity (or any fraction of a percentage in this range) between query and subject protein; or if alignment of such query protein with TIC4772 exhibits at least 97% to about 100% amino acid identity along the length of the query protein that is about 97%, 98%, 99%, 100% amino acid sequence identity (or any fraction of a percentage in this range) between query and subject protein; or if alignment of such query protein with TIC7665, TIC7667, or TIC10368 exhibits at least 98% to about 100% amino acid identity along the length of the query protein that is about 98%, 99%, 100% amino acid sequence identity (or any fraction of a percentage in this range) between query and subject protein; or if alignment of such query protein with TIC7576, TIC7661, TIC7663, TIC7669, TIC10366, TIC10367, TIC10369, TIC10370, TIC10371, TIC10372, TIC10373, PirB_ABE68879, TIC11510, or TIC11511 exhibits 100% amino acid sequence identity between query and subject protein.

It is also intended that a protein exhibiting insect inhibitory activity against a Lepidopteran, or Coleopteran, or Hemipteran insect species is related to The PirAB Fusion Proteins if alignment of such query protein with TIC9321, TIC11411, TIC11443, TIC11444, TIC11445, TIC11446, TIC11513 exhibits at least 65% to about 100% amino acid identity along the length of the query protein that is about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC10434, TIC11440, or TIC11442 exhibits at least 70% to about 100% amino acid identity along the length of the query protein that is about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC9316, TIC9317, TIC9318, TIC9322, TIC9320, TIC10375, TIC10376, TIC10377, TIC10378, TIC10379, TIC10381, TIC11211, TIC11301, TIC11302, TIC10376PL, TIC10378PL, TIC10381PL, TIC11103, or TIC11104 exhibits at least 80% to about 100% amino acid identity along the length of the query protein that is about 80%, 81%, 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC9319, TIC10380, TIC11210, TIC11212, or TIC10380PL exhibits at least 82% to about 100% amino acid identity along the length of the query protein that is about 82%, 83%, 84%, 85%, 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC6880 or TIC6880PL exhibits at least 86% to about 100% amino acid identity along the length of the query protein that is about 86%, 87%, 88%, 89%, 90%, 91%, 92%, 93%, 94%, 95%, 96%, 97%, 98%, 99%, 100% amino acid sequence identity (or any fraction of a percentage in this range) between query and subject protein; or if alignment of such query protein with TIC11506 or TIC11512 exhibits at least 94% to about 100% amino acid identity along the length of the query protein that is about 94%, 95%, 96%, 97%, 98%, 99%, 100% amino acid sequence identity (or any fraction of a percentage in this range) between query and subject protein.

Exemplary PirA proteins TIC4771, TIC7575, TIC7660, TIC7662, TIC7664, TIC7666, TIC7668, TIC7939, TIC10357, TIC10358, TIC10360, TIC10361, TIC10362, TIC10363, TIC10364, TIC10359, and PirA_ABE68878 were aligned with each other using a Clustal W algorithm. A pair-wise matrix of percent amino acid sequence identities for each of the full-length proteins was created, as reported in Tables 4 and 5.

TABLE 4

| Pair-wise matrix display of PirA proteins. | | | | | | | | |
|---|---|---|---|---|---|---|---|---|
| Sequence | TIC7666 | TIC7668 | PirA_ABE68878 | TIC10360 | TIC7660 | TIC10361 | TIC7662 | TIC10364 |
| TIC7666 | — | 94.7 | 92.5 | 85.7 | 51.1 | 48.1 | 48.1 | 49.6 |
| TIC7668 | 94.7 | — | 94 | 88.7 | 51.1 | 49.6 | 48.9 | 50.4 |
| PirA_ABE68878 | 89.1 | 90.6 | — | 81.2 | 47.8 | 46.4 | 47.1 | 48.6 |
| TIC10360 | 85.7 | 88.7 | 84.2 | — | 50.4 | 50.4 | 52.6 | 52.6 |
| TIC7660 | 48.2 | 48.2 | 46.8 | 47.5 | — | 93.6 | 75.2 | 71.6 |
| TIC10361 | 44.8 | 46.2 | 44.8 | 46.9 | 92.3 | — | 75.5 | 73.4 |
| TIC7662 | 45.4 | 46.1 | 46.1 | 49.6 | 75.2 | 76.6 | — | 85.1 |
| TIC10364 | 46.5 | 47.2 | 47.2 | 49.3 | 71.1 | 73.9 | 84.5 | — |

TABLE 5

| Pair-wise matrix display of PirA proteins. | | | | | | | | |
|---|---|---|---|---|---|---|---|---|
| Sequence | TIC7666 | TIC7668 | PirA ABE68878 | TIC10360 | TIC7660 | TIC10361 | TIC7662 | TIC10364 |
| TIC7575 | 43.3 | 45.4 | 44 | 47.5 | 72.3 | 73.8 | 87.2 | 83.7 |
| TIC4771 | 45.2 | 45.9 | 45.9 | 48.1 | 72.6 | 75.6 | 75.6 | 76.3 |
| TIC7664 | 45.2 | 45.9 | 45.9 | 48.9 | 70.4 | 71.9 | 74.1 | 74.1 |
| TIC10363 | 45.3 | 46 | 45.3 | 48.2 | 71.5 | 74.5 | 80.3 | 78.8 |
| TIC10359 | 47.4 | 48.9 | 47.4 | 51.1 | 71.9 | 71.9 | 74.1 | 72.6 |
| TIC7939 | 35.3 | 36.7 | 36 | 36.7 | 41.7 | 42.4 | 41.7 | 41.7 |
| TIC10358 | 40.3 | 41 | 41 | 40.3 | 36.8 | 38.2 | 39.6 | 37.5 |
| TIC10362 | 42.6 | 44.9 | 44.1 | 44.9 | 36.8 | 37.5 | 43.4 | 40.4 |
| TIC10357 | 23.7 | 23.7 | 22.8 | 24.6 | 21.9 | 22.8 | 26.3 | 25.4 |

Exemplary PirB proteins TIC4772, TIC7576, TIC7661, TIC7663, TIC7665, TIC7667, TIC7669, and TIC7940 were aligned with each other using a Clustal W algorithm. A pair-wise matrix of percent amino acid sequence identities for each of the full-length proteins was created, as reported in Tables 6 and 7.

TABLE 6

| Pair-wise matrix display of PirB proteins. | | | | | | | | | |
|---|---|---|---|---|---|---|---|---|---|
| Sequence | TIC7667 | TIC7669 | PirB_ABE68879 | TIC10369 | TIC7576 | TIC10373 | TIC7663 | TIC7661 | TIC10370 |
| TIC7667 | — | 95.5 | 93.6 | 93.3 | 49.6 | 48.7 | 49.6 | 48.9 | 49.4 |
| TIC7669 | 95.5 | — | 95.7 | 94.5 | 50.4 | 49.6 | 50.4 | 49.4 | 49.9 |
| PirB_ABE68879 | 93.6 | 95.7 | — | 94 | 50.1 | 49.2 | 50.8 | 49.2 | 49.9 |
| TIC10369 | 93.3 | 94.5 | 94 | — | 49.4 | 48.9 | 50.4 | 49.2 | 49.4 |
| TIC7576 | 48.9 | 49.6 | 49.4 | 48.7 | — | 94.8 | 90.6 | 87.5 | 89.9 |
| TIC10373 | 48 | 48.9 | 48.5 | 48.2 | 94.8 | — | 92.7 | 86.4 | 87.8 |
| TIC7663 | 48.9 | 49.6 | 50.1 | 49.6 | 90.6 | 92.7 | — | 84.2 | 86.1 |
| TIC7661 | 48.2 | 48.7 | 48.5 | 48.5 | 87.5 | 86.4 | 84.2 | — | 95.3 |
| TIC10370 | 48.7 | 49.2 | 49.2 | 48.7 | 89.9 | 87.8 | 86.1 | 95.3 | — |
| TIC10372 | 48.4 | 49.1 | 48.6 | 47.9 | 84.4 | 82.1 | 80.9 | 79.5 | 80.9 |
| TIC11510 | 47.1 | 47.1 | 47.6 | 47.6 | 79.5 | 79 | 79.7 | 77.2 | 78.3 |
| TIC11511 | 47.3 | 47.3 | 47.8 | 47.8 | 80 | 79.5 | 80.2 | 77.6 | 78.8 |
| TIC10368 | 47.6 | 47.6 | 48 | 48 | 80.2 | 79.7 | 80.4 | 77.9 | 79 |
| TIC11505 | 47 | 47 | 47.5 | 47.5 | 79.3 | 78.8 | 79.5 | 77 | 78.1 |
| TIC4772 | 47.2 | 47.9 | 47.9 | 47.2 | 79.7 | 78.5 | 79.7 | 76.2 | 78 |
| TIC7665 | 49 | 49.3 | 49.5 | 49.5 | 81.2 | 80.2 | 80.9 | 78.7 | 79.7 |
| TIC10367 | 41.7 | 42.4 | 42 | 42.7 | 43.2 | 42.7 | 43.6 | 42.7 | 43.2 |
| TIC10371 | 45.2 | 44.7 | 44.5 | 45 | 48.8 | 48.6 | 48.1 | 48.3 | 48.3 |
| TIC7940 | 37 | 38.2 | 37.7 | 37 | 41.5 | 42.5 | 43 | 41.8 | 42.2 |
| TIC10366 | 24.8 | 25.1 | 24.8 | 25.8 | 25.1 | 24.8 | 24.4 | 24.6 | 25.1 |

TABLE 7

Pair-wise matrix display of PirB proteins.

| Sequence | TIC10372 | TIC11510 | TIC11511 | TIC10368 | TIC11505 | TIC4772 | TIC7665 | TIC10367 | TIC10371 | TIC7940 | TIC10366 |
|---|---|---|---|---|---|---|---|---|---|---|---|
| TIC7667 | 49.6 | 48.2 | 48.4 | 48.7 | 48.7 | 48.2 | 48.4 | 41.5 | 44.9 | 37 | 25.3 |
| TIC7669 | 50.4 | 48.2 | 48.4 | 48.7 | 48.7 | 48.9 | 48.7 | 42.2 | 44.4 | 38.2 | 25.5 |
| PirB_ABE68879 | 49.9 | 48.7 | 48.9 | 49.2 | 49.2 | 48.9 | 48.9 | 41.8 | 44.2 | 37.7 | 25.3 |
| TIC10369 | 49.2 | 48.77 | 48.9 | 49.2 | 49.2 | 48.2 | 48.9 | 42.5 | 44.6 | 37 | 26.3 |
| TIC7576 | 85.4 | 80.2 | 80.7 | 80.9 | 80.9 | 80.2 | 79.1 | 42.4 | 47.8 | 40.9 | 25.2 |
| TIC10373 | 83.1 | 79.8 | 80.2 | 80.5 | 80.5 | 79.1 | 78.1 | 41.9 | 47.5 | 41.9 | 24.9 |
| TIC7663 | 81.9 | 80.5 | 80.9 | 81.2 | 81.2 | 80.2 | 78.8 | 42.8 | 47.1 | 42.4 | 24.5 |
| TIC7661 | 80.5 | 77.9 | 78.4 | 78.6 | 78.6 | 76.7 | 76.7 | 41.9 | 47.3 | 41.2 | 24.7 |
| TIC10370 | 81.9 | 79.1 | 79.5 | 79.8 | 79.8 | 78.6 | 77.6 | 42.4 | 47.3 | 41.6 | 25.2 |
| TIC10372 | — | 79.1 | 79.5 | 79.8 | 79.8 | 78.8 | 76.5 | 40.5 | 47.2 | 39.8 | 24.2 |
| TIC11510 | 79.3 | — | 99.5 | 99.3 | 99.3 | 86.5 | 81.6 | 42.2 | 46.4 | 41 | 24.5 |
| TIC11511 | 79.7 | 99.5 | — | 99.8 | 99.8 | 86.9 | 81.6 | 42.2 | 46.9 | 41 | 24.2 |
| TIC10368 | 80 | 99.3 | 99.8 | — | 100 | 87.2 | 81.8 | 42 | 46.6 | 41 | 24 |
| TIC11505 | 79 | 98.2 | 98.6 | 98.8 | — | 86.2 | 80.9 | 41.5 | 46.1 | 40.6 | 24 |
| TIC4772 | 79.2 | 86.7 | 87.1 | 87.4 | 87.4 | — | 80.8 | 42.5 | 47 | 41.8 | 24.5 |
| TIC7665 | 79.5 | 84.5 | 84.5 | 84.8 | 84.8 | 83.6 | — | 43 | 47.3 | 41.5 | 25.8 |
| TIC10367 | 41.7 | 43.4 | 43.4 | 43.2 | 43.2 | 43.6 | 42.7 | — | 57.6 | 35 | 22.1 |
| TIC10371 | 48.8 | 47.8 | 48.3 | 48.1 | 48.1 | 48.3 | 47.1 | 57.7 | — | 38.2 | 25.5 |
| TIC7940 | 40.8 | 42 | 42 | 42 | 42 | 42.7 | 41.1 | 34.8 | 37.9 | — | 24.6 |
| TIC10366 | 24.4 | 24.6 | 24.4 | 24.1 | 24.4 | 24.6 | 25.1 | 21.5 | 24.8 | 24.1 | — |

Exemplary PirAB fusion proteins TIC6880, TIC9316, TIC9317, TIC9318, TIC9319, TIC9322, TIC9320, TIC9321, TIC6880PL, TIC10375, TIC10376, TIC10377, TIC10378, TIC10379, TIC10380, TIC10381, TIC10434, TIC11210, TIC11211, TIC11212, TIC11301, TIC11302, TIC11440, TIC11441, TIC11442, TIC11443, TIC11444, TIC11445, TIC11446, TIC11506, TIC11512, TIC11513, TIC10376PL, TIC10378PL, TIC10380PL, TIC10381PL, TIC11103, and TIC11104 were aligned with each other using a Clustal W algorithm. A pair-wise matrix of percent amino acid sequence identities for each of the full-length proteins was created, as reported in Tables 8, 9, 10, and 11.

TABLE 8

Pair-wise matrix display of PirAB fusion proteins.

| Sequence | TIC9322 | TIC9320 | TIC10434 | TIC10377 | TIC11211 | TIC6880 | TIC11440 | TIC6880PL | TIC11442 | TIC11506 |
|---|---|---|---|---|---|---|---|---|---|---|
| TIC9322 | — | 95.3 | 93.3 | 91.5 | 87.3 | 47.8 | 47.8 | 47.8 | 47.8 | 48.7 |
| TIC9320 | 95.3 | — | 95.3 | 93.1 | 84.4 | 48.6 | 48.6 | 48.6 | 48.6 | 48.9 |
| TIC10434 | 92.5 | 94.4 | — | 90.8 | 82 | 48.1 | 48.1 | 48.1 | 48.1 | 48.8 |
| TIC10377 | 91.5 | 93.1 | 91.7 | — | 82.6 | 48 | 48 | 48 | 48 | 49.6 |
| TIC11211 | 86.1 | 83.2 | 81.6 | 81.4 | — | 52.7 | 52.7 | 52.9 | 52.7 | 53.4 |
| TIC6880 | 46.9 | 47.6 | 47.6 | 47.1 | 52.4 | — | 99.6 | 99.8 | 99.6 | 85.3 |
| TIC11440 | 37.8 | 38.4 | 38.4 | 38 | 42.3 | 80.4 | — | 80.2 | 95.6 | 68.8 |
| TIC6880PL | 46.8 | 47.5 | 47.5 | 47 | 52.5 | 99.6 | 99.3 | — | 99.3 | 85.11 |
| TIC11442 | 37.5 | 38.1 | 38.1 | 37.6 | 41.9 | 79.7 | 94.7 | 79.5 | — | 68.2 |
| TIC11506 | 46.7 | 46.9 | 47.2 | 47.6 | 51.9 | 83.3 | 83.3 | 83.3 | 83.3 | — |
| TIC11513 | 46.9 | 47.1 | 47.5 | 47.8 | 52.2 | 83.9 | 83.9 | 83.9 | 83.9 | 99.8 |
| TIC11512 | 46.8 | 46.9 | 47.3 | 47.6 | 52 | 83.5 | 83.5 | 83.5 | 83.5 | 99.5 |
| TIC11210 | 47.2 | 47.7 | 47.6 | 48.3 | 55.5 | 81.1 | 81.1 | 81.1 | 81.1 | 84.7 |
| TIC11212 | 47.2 | 47.6 | 47.7 | 48.5 | 54.2 | 80.9 | 80.9 | 80.9 | 80.9 | 84.7 |
| TIC9319 | 47.7 | 48.1 | 48.3 | 48.8 | 54.3 | 83.2 | 83.2 | 83.1 | 83.2 | 82.5 |
| TIC10380 | 47.8 | 48.5 | 48 | 48.1 | 53.8 | 79.2 | 79.2 | 79 | 79.2 | 79.9 |
| TIC10380PL | 47.7 | 48.4 | 47.9 | 48.1 | 53.9 | 78.9 | 78.9 | 79.2 | 78.9 | 79.8 |
| TIC10381 | 47.4 | 48.3 | 48 | 48.1 | 52.7 | 78 | 78 | 78 | 78 | 84.8 |
| TIC10381PL | 47.4 | 48.2 | 47.9 | 48.1 | 52.6 | 77.8 | 77.8 | 77.8 | 77.8 | 84.5 |
| TIC9318 | 47.5 | 48.2 | 48.6 | 48.9 | 54.4 | 78.4 | 78.4 | 78.4 | 78.4 | 81.8 |
| TIC11445 | 38 | 38.6 | 38.9 | 39.2 | 43.6 | 62.8 | 76.5 | 62.8 | 77.2 | 65.5 |
| TIC9316 | 47.5 | 48.4 | 47.9 | 48.1 | 56 | 79 | 79 | 79 | 79 | 81.3 |
| TIC11441 | 38 | 38.8 | 38.3 | 38.5 | 44.8 | 63.2 | 77.8 | 63.2 | 82.9 | 65.1 |
| TIC11302 | 48.1 | 48.8 | 48.1 | 48.1 | 52.3 | 77.7 | 77.7 | 77.7 | 77.7 | 78.3 |
| TIC11443 | 38.5 | 39 | 38.5 | 38.5 | 41.9 | 62.2 | 62.2 | 62.2 | 62.2 | 62.7 |
| TIC9317 | 47.5 | 48.1 | 47.3 | 47.9 | 51.6 | 75.4 | 75.4 | 75.4 | 75.4 | 76.9 |
| TIC11446 | 38 | 38.5 | 37.9 | 38.3 | 41.3 | 60.4 | 74.8 | 60.4 | 77.5 | 61.5 |
| TIC11444 | 38 | 38.5 | 37.9 | 38.3 | 41.3 | 60.4 | 75 | 60.4 | 80.1 | 61.5 |
| TIC11301 | 46.8 | 47.5 | 47 | 47.7 | 54.9 | 76.5 | 76.5 | 76.5 | 76.5 | 80 |
| TIC10378 | 47.7 | 48.6 | 48.1 | 48.4 | 51.8 | 76.9 | 76.9 | 76.9 | 76.9 | 78 |
| TIC10378PL | 47.6 | 48.5 | 48 | 48.3 | 51.7 | 76.8 | 76.8 | 76.8 | 76.8 | 77.7 |
| TIC11103 | 36.2 | 36.6 | 36.4 | 36.4 | 36.2 | 58.1 | 58.1 | 58.1 | 58.1 | 59 |
| TIC11104 | 36.7 | 37.3 | 37.6 | 37.3 | 36.7 | 60.1 | 60.1 | 60.1 | 60.1 | 60.6 |
| TIC10376 | 41.2 | 41.9 | 41.5 | 41.9 | 40.8 | 41.9 | 41.9 | 41.9 | 41.9 | 41.5 |
| TIC10376PL | 41.1 | 41.8 | 41.5 | 41.8 | 40.7 | 41.8 | 41.8 | 41.8 | 41.8 | 41.5 |

TABLE 8-continued

Pair-wise matrix display of PirAB fusion proteins.

| Sequence | TIC9322 | TIC9320 | TIC10434 | TIC10377 | TIC11211 | TIC6880 | TIC11440 | TIC6880PL | TIC11442 | TIC11506 |
|---|---|---|---|---|---|---|---|---|---|---|
| TIC10379 | 43.7 | 43.7 | 43.7 | 43.5 | 43.1 | 46.2 | 46.2 | 46.2 | 46.2 | 46.6 |
| TIC9321 | 36.4 | 37.5 | 37.3 | 36.2 | 37.6 | 42.1 | 42.1 | 42.1 | 42.1 | 41.2 |
| TIC10375 | 24.4 | 24.6 | 24.2 | 25.3 | 24.2 | 23.7 | 23.7 | 23.7 | 23.7 | 23.3 |

TABLE 9

Pair-wise matrix display of PirAB fusion proteins.

| Sequence | TIC11513 | TIC11512 | TIC11210 | TIC11212 | TIC9319 | TIC10380 | TIC10380PL | TIC10381 | TIC10381PL | TIC9318 |
|---|---|---|---|---|---|---|---|---|---|---|
| TIC9322 | 48.6 | 48.4 | 47.5 | 47.5 | 47.5 | 49.1 | 49.1 | 48.7 | 48.7 | 48.7 |
| TIC9320 | 48.7 | 48.6 | 48 | 47.8 | 47.8 | 49.8 | 49.8 | 49.6 | 49.6 | 49.5 |
| TIC10434 | 48.7 | 48.5 | 47.417 | 47.6 | 47.6 | 48.8 | 48.8 | 48.8 | 48.8 | 49.4 |
| TIC10377 | 49.5 | 49.3 | 48.6 | 48.7 | 48.6 | 49.5 | 49.5 | 49.5 | 49.5 | 50.2 |
| TIC11211 | 53.2 | 53 | 55 | 53.8 | 53.2 | 54.5 | 54.6 | 53.4 | 53.4 | 55 |
| TIC6880 | 85.1 | 84.7 | 79.9 | 79.8 | 81.2 | 79.8 | 79.6 | 78.5 | 78.5 | 78.9 |
| TIC11440 | 68.6 | 68.3 | 64.5 | 64.3 | 65.5 | 64.3 | 64.2 | 63.3 | 63.3 | 63.6 |
| TIC6880PL | 84.9 | 84.6 | 79.8 | 79.6 | 80.9 | 79.4 | 79.8 | 78.4 | 78.4 | 78.7 |
| TIC11442 | 68 | 67.8 | 63.9 | 63.8 | 64.9 | 63.8 | 63.6 | 62.8 | 62.8 | 63.1 |
| TIC11506 | 99 | 98.6 | 81.6 | 81.6 | 78.6 | 78.6 | 78.6 | 83.5 | 83.3 | 80.4 |
| TIC11513 | — | 99.6 | 82.1 | 82.1 | 79.2 | 79.2 | 79.2 | 84.1 | 83.9 | 80.9 |
| TIC11512 | 99.6 | — | 82.1 | 82.1 | 79.2 | 78.8 | 78.8 | 83.7 | 83.5 | 80.6 |
| TIC11210 | 84.5 | 84.5 | — | 96.8 | 93.2 | 79.1 | 79.1 | 80.9 | 80.7 | 82.2 |
| TIC11212 | 84.5 | 84.5 | 96.8 | — | 92.8 | 79.3 | 79.3 | 80.9 | 80.7 | 85.2 |
| TIC9319 | 82.3 | 82.3 | 94.2 | 93.8 | — | 79.4 | 79.2 | 78.7 | 78.7 | 79.2 |
| TIC10380 | 79.77 | 79.4 | 77.4 | 77.6 | 76.9 | — | 99.8 | 81.7 | 81.7 | 81.1 |
| TIC10380PL | 79.6 | 79.2 | 77.3 | 77.5 | 76.6 | 99.6 | — | 81.5 | 81.5 | 81 |
| TIC10381 | 84.7 | 84.3 | 79.2 | 79.2 | 76.2 | 81.7 | 81.7 | — | 99.8 | 90.7 |
| TIC10381PL | 84.3 | 84 | 78.9 | 78.9 | 76.1 | 81.5 | 81.5 | 99.6 | — | 90.3 |
| TIC9318 | 81.6 | 81.3 | 80.6 | 83.6 | 76.9 | 81.3 | 81.3 | 90.8 | 90.6 | — |
| TIC11445 | 65.3 | 65.1 | 64.5 | 66.9 | 61.5 | 65.1 | 65.1 | 72.7 | 72.6 | 80.1 |
| TIC9316 | 81.1 | 80.7 | 83.4 | 80.4 | 77.2 | 83.7 | 83.7 | 92 | 91.9 | 89.8 |
| TIC11441 | 64.9 | 64.6 | 66.8 | 64.4 | 61.8 | 67 | 67 | 73.7 | 73.6 | 71.9 |
| TIC11302 | 78.1 | 77.7 | 77.2 | 77.7 | 76.1 | 81.6 | 81.6 | 89 | 88.9 | 86.7 |
| TIC11443 | 62.5 | 62.2 | 61.8 | 62.2 | 61 | 65.3 | 65.3 | 71.3 | 71.1 | 69.4 |
| TIC9317 | 76.7 | 76.3 | 75.8 | 76.1 | 74.4 | 77.9 | 77.9 | 82.7 | 82.5 | 82 |
| TIC11446 | 61.4 | 61.1 | 60.7 | 61 | 59.5 | 62.4 | 62.4 | 66.2 | 66.1 | 65.6 |
| TIC11444 | 61.4 | 61.1 | 60.7 | 61 | 59.5 | 62.4 | 62.4 | 66.2 | 66.1 | 65.6 |
| TIC11301 | 79.9 | 79.5 | 82.3 | 79.2 | 75.6 | 79.9 | 79.9 | 85.9 | 85.7 | 84.8 |
| TIC10378 | 77.8 | 77.5 | 76.6 | 76.9 | 75.4 | 79.4 | 79.4 | 84.3 | 84.2 | 83.5 |
| TIC10378PL | 77.5 | 77.2 | 76.3 | 76.6 | 75.2 | 79.3 | 79.3 | 84 | 84.4 | 83.1 |
| TIC11103 | 58.8 | 58.5 | 57.4 | 57.4 | 57.4 | 60.4 | 60.4 | 64.8 | 64.8 | 63.3 |
| TIC11104 | 60.4 | 60.1 | 59 | 59 | 59 | 61.5 | 61.5 | 69.6 | 69.6 | 75.1 |
| TIC10376 | 41.7 | 41.7 | 41.4 | 41.7 | 40.8 | 40.6 | 40.6 | 41.5 | 41.5 | 42.8 |
| TIC10376PL | 41.6 | 41.6 | 41.3 | 41.6 | 40.7 | 40.6 | 40.6 | 41.5 | 41.5 | 42.7 |
| TIC10379 | 46.7 | 46.4 | 45.5 | 46.6 | 45.3 | 47.1 | 47.1 | 46.9 | 46.7 | 47.3 |
| TIC9321 | 41.2 | 41.2 | 40.3 | 40.9 | 40.9 | 41 | 41 | 41.9 | 41.9 | 42.5 |
| TIC10375 | 23.5 | 23.7 | 24.6 | 24.6 | 25 | 24.2 | 24.2 | 24.2 | 24.2 | 24 |

TABLE 10

Pair-wise matrix display of PirAB fusion proteins.

| Sequence | TIC11445 | TIC9316 | TIC11441 | TIC11302 | TIC11443 | TIC9317 | TIC11446 | TIC11444 | TIC11301 |
|---|---|---|---|---|---|---|---|---|---|
| TIC9322 | 48.7 | 48.7 | 48.7 | 49.3 | 49.3 | 48.7 | 48.7 | 48.7 | 48 |
| TIC9320 | 49.5 | 49.6 | 49.6 | 50 | 50 | 49.3 | 49.3 | 49.3 | 48.7 |
| TIC10434 | 49.4 | 48.7 | 48.7 | 48.8 | 48.8 | 48.1 | 48.1 | 48.1 | 47.8 |
| TIC10377 | 50.2 | 49.3 | 49.3 | 49.3 | 49.3 | 49.1 | 49.1 | 49.1 | 48.9 |
| TIC11211 | 55 | 56.6 | 56.6 | 52.9 | 52.9 | 52.1 | 52.1 | 52.1 | 55.5 |
| TIC6880 | 78.9 | 79.4 | 79.4 | 78.2 | 78.2 | 75.8 | 75.8 | 75.8 | 76.9 |
| TIC11440 | 77.5 | 64 | 78.8 | 63 | 63 | 61.2 | 75.815 | 75.9 | 62 |
| TIC6880PL | 78.7 | 79.3 | 79.3 | 78 | 78 | 75.7 | 75.7 | 75.7 | 76.8 |
| TIC11442 | 77.6 | 63.5 | 83.2 | 62.5 | 62.5 | 60.7 | 77.8 | 80.4 | 61.5 |
| TIC11506 | 80.4 | 79.9 | 79.9 | 76.9 | 76.9 | 75.5 | 75.5 | 75.5 | 78.6 |
| TIC11513 | 80.9 | 80.4 | 80.4 | 77.4 | 77.4 | 76 | 76 | 76 | 79.2 |
| TIC11512 | 80.6 | 80 | 80 | 77.1 | 77.1 | 75.7 | 75.7 | 75.7 | 78.8 |

TABLE 10-continued

Pair-wise matrix display of PirAB fusion proteins.

| Sequence | TIC11445 | TIC9316 | TIC11441 | TIC11302 | TIC11443 | TIC9317 | TIC11446 | TIC11444 | TIC11301 |
|---|---|---|---|---|---|---|---|---|---|
| TIC11210 | 82.2 | 85 | 85 | 78.7 | 78.7 | 77.3 | 77.3 | 77.3 | 84 |
| TIC11212 | 85.2 | 82 | 82 | 79.3 | 79.3 | 77.7 | 77.7 | 77.7 | 80.7 |
| TIC9319 | 79.2 | 79.6 | 79.6 | 78.5 | 78.5 | 76.7 | 76.7 | 76.7 | 78 |
| TIC10380 | 81.1 | 83.6 | 83.6 | 81.5 | 81.5 | 77.8 | 77.8 | 77.8 | 79.7 |
| TIC10380PL | 81 | 83.5 | 83.5 | 81.3 | 81.3 | 77.6 | 77.6 | 77.6 | 79.6 |
| TIC10381 | 90.7 | 91.9 | 91.9 | 88.9 | 88.9 | 82.5 | 82.5 | 82.5 | 85.7 |
| TIC10381PL | 90.3 | 91.5 | 91.5 | 88.6 | 88.6 | 82.2 | 82.2 | 82.2 | 85.4 |
| TIC9318 | 100 | 89.8 | 89.8 | 86.7 | 86.7 | 82 | 82 | 82 | 84.8 |
| TIC11445 | — | 71.9 | 86.6 | 69.4 | 69.4 | 65.6 | 80.6 | 80.3 | 67.9 |
| TIC9316 | 89.8 | — | 100 | 93.5 | 93.5 | 83.9 | 83.9 | 83.9 | 90.1 |
| TIC11441 | 86.6 | 80.1 | — | 74.8 | 74.8 | 67.2 | 84.6 | 87.1 | 72.1 |
| TIC11302 | 86.7 | 93.5 | 93.5 | — | 100 | 90.1 | 90.1 | 90.1 | 83.9 |
| TIC11443 | 69.4 | 74.8 | 74.8 | 80.1 | — | 72.1 | 72.1 | 72.1 | 67.2 |
| TIC9317 | 82 | 83.9 | 83.9 | 90.1 | 90.1 | — | 100 | 100 | 93.5 |
| TIC11446 | 80.6 | 67.2 | 84.6 | 72.1 | 72.1 | 80.1 | — | 97.5 | 74.8 |
| TIC11444 | 80.3 | 67.2 | 87.1 | 72.1 | 72.1 | 80.1 | 97.5 | — | 74.8 |
| TIC11301 | 84.8 | 90.1 | 90.1 | 83.9 | 83.9 | 93.5 | 93.5 | 93.5 | — |
| TIC10378 | 83.5 | 85.7 | 85.7 | 90.3 | 90.3 | 94.4 | 94.4 | 94.4 | 90 |
| TIC10378PL | 83.1 | 85.4 | 85.4 | 90 | 90 | 94 | 94 | 94 | 89.6 |
| TIC11103 | 63.3 | 65.7 | 65.7 | 65.7 | 65.7 | 75.1 | 75.1 | 75.1 | 75.1 |
| TIC11104 | 75.1 | 68 | 68 | 68 | 68 | 63.3 | 63.3 | 63.3 | 63.3 |
| TIC10376 | 42.8 | 42.1 | 42.1 | 41.7 | 41.7 | 41.4 | 41.4 | 41.4 | 41.7 |
| TIC10376PL | 42.7 | 42 | 42 | 41.6 | 41.6 | 41.3 | 41.3 | 41.3 | 41.6 |
| TIC10379 | 47.3 | 46.916 | 46.9 | 46 | 46 | 45.7 | 45.7 | 45.7 | 46.4 |
| TIC9321 | 42.5 | 40.9 | 40.9 | 41.2 | 41.2 | 41.4 | 41.4 | 41.4 | 41 |
| TIC10375 | 24 | 24.6 | 24.6 | 24 | 24 | 23.7 | 23.7 | 23.7 | 24.2 |

TABLE 11

Pair-wise matrix display of PirAB fusion proteins.

| Sequence | TIC10378 | TIC10378PL | TIC11103 | TIC11104 | TIC10376 | TIC10376PL | TIC10379 | TIC9321 | TIC10375 |
|---|---|---|---|---|---|---|---|---|---|
| TIC9322 | 49.1 | 49.1 | 37.1 | 37.7 | 41.8 | 41.8 | 43.7 | 36.8 | 23.9 |
| TIC9320 | 50 | 50 | 37.5 | 38.2 | 42.6 | 42.6 | 43.7 | 37.9 | 24.1 |
| TIC10434 | 49 | 49 | 37 | 38.2 | 41.8 | 41.8 | 43.3 | 37.3 | 23.5 |
| TIC10377 | 49.8 | 49.8 | 37.3 | 38.2 | 42.6 | 42.6 | 43.5 | 36.6 | 24.8 |
| TIC11211 | 52.5 | 52.5 | 36.6 | 37.1 | 40.9 | 40.9 | 42.5 | 37.5 | 23.4 |
| TIC6880 | 77.6 | 77.6 | 58.4 | 60.4 | 41.7 | 41.7 | 45.3 | 41.7 | 22.7 |
| TIC11440 | 62.6 | 62.6 | 47.1 | 48.7 | 33.7 | 33.7 | 36.5 | 33.7 | 18.3 |
| TIC6880PL | 77.5 | 77.5 | 58.3 | 60.3 | 41.7 | 41.7 | 45.2 | 41.7 | 22.7 |
| TIC11 42 | 62.1 | 62.1 | 46.7 | 48.3 | 33.4 | 33.4 | 36.2 | 33.4 | 18.2 |
| TIC11506 | 76.9 | 76.7 | 58 | 59.5 | 40.5 | 40.5 | 44.6 | 39.9 | 21.9 |
| TIC11513 | 77.4 | 77.2 | 58.3 | 59.9 | 41 | 41 | 45.2 | 40.3 | 22.2 |
| TIC11512 | 77.1 | 76.9 | 58 | 59.5 | 41 | 41 | 44.8 | 40.3 | 22.4 |
| TIC11210 | 78.4 | 78.2 | 58.6 | 60.2 | 41.8 | 41.8 | 45.2 | 40.5 | 24 |
| TIC11212 | 78.7 | 78.6 | 58.6 | 60.2 | 42.2 | 42.2 | 46.3 | 41.1 | 24 |
| TIC9319 | 78 | 78 | 59.2 | 60.8 | 41.7 | 41.7 | 45.5 | 41.5 | 24.6 |
| TIC10380 | 79.5 | 79.5 | 60.3 | 61.4 | 40.2 | 40.2 | 45.9 | 40.4 | 23.1 |
| TIC10380PL | 79.4 | 79.4 | 60.2 | 61.3 | 40.1 | 40.1 | 45.8 | 40.3 | 23.1 |
| TIC10381 | 84.5 | 84.3 | 64.7 | 69.5 | 41.1 | 41.1 | 45.7 | 41.3 | 23.1 |
| TIC10381PL | 84.2 | 84.5 | 64.6 | 69.4 | 41 | 41 | 45.4 | 41.2 | 23.1 |
| TIC9318 | 83.7 | 83.6 | 63.3 | 75.1 | 42.4 | 42.4 | 46.1 | 41.9 | 23 |
| TIC11445 | 67 | 66.9 | 50.6 | 60.1 | 33.9 | 33.9 | 36.9 | 33.5 | 18.4 |
| TIC9316 | 86 | 85.9 | 65.7 | 68 | 41.77 | 41.7 | 45.8 | 40.3 | 23.5 |
| TIC11441 | 68.9 | 68.7 | 52.6 | 54.5 | 33.4 | 33.4 | 36.6 | 32.2 | 18.8 |
| TIC11302 | 90.6 | 90.5 | 65.7 | 68 | 41.3 | 41.3 | 44.9 | 40.6 | 23 |
| TIC11443 | 72.6 | 72.4 | 52.6 | 54.5 | 33.1 | 33.1 | 35.9 | 32.5 | 18.4 |
| TIC9317 | 94.7 | 94.5 | 75.1 | 63.3 | 41 | 41 | 44.5 | 40.8 | 22.6 |
| TIC11446 | 75.8 | 75.7 | 60.1 | 50.6 | 32.8 | 32.8 | 35.6 | 32.7 | 18.1 |
| TIC11444 | 75.8 | 75.7 | 60.1 | 50.6 | 32.8 | 32.8 | 35.6 | 32.7 | 18.1 |
| TIC11301 | 90.3 | 90.1 | 75.1 | 63.3 | 41.3 | 41.3 | 45.2 | 40.5 | 23.1 |
| TIC10378 | — | 99.8 | 71.3 | 64.4 | 41.5 | 41.5 | 44.5 | 41.4 | 23.1 |
| TIC10378PL | 99.6 | — | 71.2 | 64.3 | 41.5 | 41.5 | 44.3 | 41.3 | 23 |
| TIC11103 | 71.6 | 71.6 | — | 82 | 31.6 | 31.6 | 35.7 | 30.9 | 18.4 |
| TIC11104 | 64.7 | 64.7 | 82 | — | 32.3 | 32.3 | 35.5 | 31.8 | 18.2 |
| TIC10376 | 42.1 | 42.1 | 31.9 | 32.6 | — | 99.8 | 54.9 | 34.8 | 21.6 |
| TIC10376PL | 42 | 42 | 31.9 | 32.6 | 99.6 | — | 54.8 | 34.7 | 21.5 |
| TIC10379 | 45.8 | 45.7 | 36.6 | 36.4 | 55.8 | 55.8 | — | 37.1 | 24.5 |
| TIC9321 | 42.1 | 42.1 | 31.4 | 32.3 | 34.9 | 34.9 | 36.7 | — | 22 |
| TIC10375 | 24.2 | 24.2 | 19.2 | 19 | 22.4 | 22.4 | 25 | 22.7 | — |

In addition to percent identity, The PirA Proteins, The PirB Proteins, and the PrAB Fusion Proteins can also be related by primary structure (conserved amino acid motifs), by length (about 133 to about 141 amino acids for PirA; about 414 to about 428 amino acids for PirB; about 549 to about 566 amino acids for the PirAB fusion proteins) and by other characteristics. Characteristics of The PirA Proteins, The PirB Proteins, and The PirAB Fusion Proteins are reported in Table 12.

TABLE 12

Selected characteristics of PirA proteins, PirB proteins, and PirAB proteins.

| Protein | Molecular Weight (in Daltons) | Amino Acid Length | Isoelectric Point | Charge at PH 7.0 | No. of Strongly Basic (-) Amino Acids | No. of Strongly Acidic Amino Acids | No. of Hydrophobic Amino Acids | No. of Polar Amino Acids |
|---|---|---|---|---|---|---|---|---|
| TIC4771 | 14963.57 | 135 | 5.6164 | -1.5 | 14 | 14 | 65 | 70 |
| TIC4772 | 48146.05 | 428 | 4.5643 | −16.0 | 41 | 53 | 216 | 212 |
| TIC6880 | 63092.59 | 563 | 4.6836 | −17.5 | 55 | 67 | 281 | 282 |
| TIC6880PL | 63163.67 | 564 | 4.6836 | −17.5 | 55 | 67 | 282 | 282 |
| TIC7575 | 15655.22 | 141 | 5.0636 | −2.0 | 12 | 13 | 68 | 73 |
| TIC7576 | 47775.12 | 425 | 4.7039 | −12.5 | 44 | 53 | 221 | 204 |
| TIC9316 | 63412.32 | 566 | 4.7572 | −14.5 | 56 | 66 | 289 | 277 |
| TIC7660 | 15352.83 | 141 | 4.5839 | −4.0 | 11 | 14 | 72 | 69 |
| TIC7661 | 47774.39 | 425 | 4.7572 | −5.5 | 50 | 51 | 222 | 203 |
| TIC9317 | 63109.20 | 566 | 5.1542 | −9.5 | 61 | 65 | 294 | 272 |
| TIC7662 | 15761.42 | 141 | 4.6130 | −3.5 | 11 | 14 | 68 | 73 |
| TIC7663 | 47895.35 | 425 | 5.0745 | −7.5 | 48 | 52 | 221 | 204 |
| TIC9318 | 63638.76 | 566 | 4.9378 | −11.0 | 59 | 66 | 289 | 277 |
| TIC7664 | 14950.65 | 135 | 5.0636 | −2.0 | 12 | 13 | 68 | 67 |
| TIC7665 | 46819.71 | 414 | 4.6887 | −12.5 | 43 | 52 | 214 | 200 |
| TIC9319 | 61752.34 | 549 | 4.7452 | −14.5 | 55 | 65 | 282 | 267 |
| TIC7666 | 14751.43 | 133 | 4.6137 | −4.0 | 12 | 15 | 68 | 65 |
| TIC7667 | 46246.08 | 419 | 5.4603 | −5.5 | 50 | 51 | 220 | 199 |
| TIC9322 | 60979.49 | 552 | 5.1485 | −9.5 | 62 | 66 | 288 | 264 |
| TIC7668 | 14785.54 | 133 | 5.1215 | −2.5 | 14 | 15 | 68 | 65 |
| TIC7669 | 46249.04 | 419 | 5.3001 | −6.5 | 50 | 52 | 222 | 197 |
| TIC9320 | 61016.56 | 552 | 5.2518 | −9.0 | 64 | 67 | 290 | 262 |
| TIC7939 | 15470.32 | 139 | 6.2480 | −0.5 | 15 | 14 | 70 | 69 |
| TIC7940 | 47493.26 | 419 | 4.8783 | −11.0 | 53 | 60 | 218 | 201 |
| TIC9321 | 62945.57 | 558 | 5.0432 | −11.5 | 68 | 74 | 288 | 270 |
| TIC10357 | 12838.48 | 114 | 4.7910 | −3.0 | 11 | 13 | 68 | 46 |
| TIC10366 | 47691.61 | 427 | 4.3657 | −22.0 | 43 | 62 | 221 | 206 |
| TIC10375 | 60512.07 | 541 | 4.4263 | −25.0 | 54 | 75 | 289 | 252 |
| TIC10358 | 16198.29 | 144 | 7.7512 | 1.5 | 20 | 17 | 68 | 76 |
| TIC10367 | 47147.69 | 417 | 7.7679 | 5.5 | 60 | 49 | 222 | 195 |
| TIC10376 | 63327.96 | 561 | 7.8092 | 7.0 | 80 | 66 | 290 | 271 |
| TIC10376PL | 63399.04 | 562 | 7.8092 | 7.0 | 80 | 66 | 291 | 271 |
| TIC10360 | 14976.76 | 133 | 4.8490 | −2.5 | 14 | 16 | 64 | 69 |
| TIC10369 | 46322.33 | 419 | 5.6804 | −4.0 | 50 | 50 | 224 | 195 |
| TIC10377 | 61281.07 | 552 | 5.3889 | −6.5 | 64 | 66 | 288 | 264 |
| TIC10361 | 15629.20 | 143 | 4.7632 | −3.0 | 11 | 13 | 71 | 72 |
| TIC10370 | 47710.32 | 425 | 5.0742 | −8.0 | 48 | 52 | 225 | 200 |
| TIC10378 | 63321.51 | 568 | 4.9947 | −11.0 | 59 | 65 | 296 | 272 |
| TIC10378PL | 63392.59 | 569 | 4.9947 | −11.0 | 59 | 65 | 297 | 272 |
| TIC10362 | 15173.94 | 136 | 5.1440 | −1.5 | 13 | 14 | 62 | 74 |
| TIC10371 | 46947.97 | 416 | 5.8572 | −3.5 | 47 | 46 | 218 | 198 |
| TIC10379 | 62103.90 | 552 | 5.6801 | −5.0 | 60 | 60 | 280 | 272 |
| TIC10363 | 15195.80 | 137 | 4.7774 | −3.0 | 11 | 13 | 67 | 70 |
| TIC10372 | 48400.97 | 430 | 4.7717 | −11.0 | 45 | 53 | 229 | 201 |
| TIC10380 | 63578.76 | 567 | 4.7697 | −14.0 | 56 | 66 | 296 | 271 |
| TIC10380PL | 63649.84 | 568 | 4.7697 | −14.0 | 56 | 66 | 297 | 271 |
| TIC10364 | 15833.53 | 142 | 4.4792 | −5.0 | 11 | 15 | 72 | 70 |
| TIC10373 | 47791.02 | 425 | 4.7003 | −12.5 | 44 | 53 | 220 | 205 |
| TIC10381 | 63606.54 | 567 | 4.6406 | −17.5 | 55 | 68 | 292 | 275 |
| TIC10381PL | 63677.62 | 568 | 4.6406 | −17.5 | 55 | 68 | 293 | 275 |
| TIC10359 | 14949.54 | 135 | 4.7873 | −3.5 | 12 | 14 | 68 | 67 |
| TIC10368 | 48194.25 | 429 | 4.7481 | −11.5 | 43 | 51 | 219 | 210 |
| PirA_ABE68878 | 15303.18 | 138 | 6.2470 | −5.0 | 15 | 14 | 71 | 67 |
| PirB_ABE68879 | 46424.34 | 419 | 5.2938 | −6.5 | 50 | 52 | 224 | 195 |
| TIC10434 | 61709.50 | 557 | 5.4906 | −7.0 | 65 | 66 | 295 | 262 |
| TIC11103 | 63109.20 | 566 | 5.1542 | −9.5 | 61 | 65 | 294 | 272 |
| TIC11104 | 63638.76 | 566 | 4.9378 | −11.0 | 59 | 66 | 289 | 277 |
| TIC11210 | 62456.91 | 555 | 4.7452 | −14.5 | 55 | 65 | 282 | 273 |
| TIC11211 | 61883.28 | 560 | 5.3591 | −7.5 | 62 | 64 | 288 | 272 |
| TIC11212 | 62563.12 | 555 | 4.6679 | −16.0 | 54 | 66 | 282 | 273 |
| TIC11301 | 63411.60 | 566 | 5.3685 | −7.5 | 62 | 64 | 290 | 276 |
| TIC11302 | 63109.93 | 566 | 4.6735 | −16.5 | 55 | 67 | 293 | 273 |
| TIC11440 | 78037.15 | 698 | 4.7751 | −19.0 | 69 | 81 | 346 | 352 |
| TIC11441 | 79049.52 | 707 | 4.7960 | −16.5 | 68 | 79 | 357 | 350 |
| TIC11442 | 78728.81 | 704 | 4.7287 | −19.5 | 67 | 80 | 349 | 355 |

TABLE 12-continued

Selected characteristics of PirA proteins, PirB proteins, and PirAB proteins.

| Protein | Molecular Weight (in Daltons) | Amino Acid Length | Isoelectric Point | Charge at PH 7.0 | No. of Strongly Basic (-) Amino Acids | No. of Strongly Acidic Amino Acids | No. of Hydrophobic Amino Acids | No. of Polar Amino Acids |
|---|---|---|---|---|---|---|---|---|
| TIC11443 | 78747.13 | 707 | 4.7204 | −18.5 | 67 | 80 | 361 | 346 |
| TIC11444 | 78746.41 | 707 | 5.1362 | −11.5 | 73 | 78 | 362 | 345 |
| TIC11445 | 78973.57 | 707 | 4.8575 | −15.0 | 70 | 80 | 361 | 346 |
| TIC11446 | 78852.61 | 707 | 5.0123 | −13.0 | 72 | 79 | 362 | 345 |
| TIC10364 | 15833.53 | 142 | 4.4792 | −5.0 | 11 | 15 | 72 | 70 |
| TIC11505 | 48750.86 | 434 | 4.6998 | −12.5 | 43 | 52 | 221 | 213 |
| TIC11506 | 64566.38 | 576 | 4.6400 | −17.5 | 54 | 67 | 293 | 283 |
| TIC11510 | 48184.21 | 429 | 4.7481 | −11.5 | 43 | 51 | 218 | 211 |
| TIC11512 | 63999.72 | 571 | 4.6730 | −16.5 | 54 | 66 | 290 | 281 |
| TIC11511 | 48208.27 | 429 | 4.7481 | −11.5 | 43 | 51 | 219 | 210 |
| TIC11513 | 64023.79 | 571 | 4.6730 | −16.5 | 54 | 66 | 291 | 280 |

As described further in the Examples of this application, recombinant nucleic acid molecule sequences encoding The PirAB Fusion Proteins were designed for use in plants. Exemplary plant-optimized recombinant nucleic acid molecule sequences that were designed for use in plants are presented as SEQ ID NOs:49, 51, 52, 53, 54, 55, 56, 146, 148, 150, 152, 154, 156, and 158.

Expression cassettes and vectors containing these recombinant nucleic acid molecule sequences can be constructed and introduced into corn, soybean, cotton or other plant cells in accordance with transformation methods and techniques known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), 2001/0042257 A1 (sugar beet), U.S. Pat. No. 5,750,871 (canola), U.S. Pat. No. 7,026,528 (wheat), and U.S. Pat. No. 6,365,807 (rice), and in Arencibia et al. (1998) Transgenic Res. 7:213-222 (sugarcane) all of which are incorporated herein by reference in their entirety. Transformed cells can be regenerated into transformed plants that express the PirAB fusion proteins TIC6880PL, TIC9316, TIC9317, TIC9318, TIC9319, TIC9320, or TIC9322. To test pesticidal activity, bioassays are performed in the presence of Lepidoptera pest larvae using plant leaf disks obtained from transformed plants as described in the Examples. To test pesticidal activity against Coleopteran pests, transformed plants of $R_o$ and $F_1$ generation are used in root worm assay as described in the example below. To test pesticidal activity against Hemipteran pests, pods, corn ears or leaves of transformed plants are used in assay, either from tissue removed from the plant or remaining on the plant as described in the Examples.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. As understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

Recombinant nucleic acid molecule compositions that encode The PirA Proteins, The PirB Proteins, or the PirAB Fusion Proteins, or related insecticidal proteins are contemplated. For example, The PirA Proteins, The PirB Proteins, or The PirAB Fusion Proteins, or related insecticidal proteins can be expressed with recombinant DNA constructs in which a polynucleotide molecule with an ORF encoding the protein is operably linked to genetic expression elements such as a promoter and any other regulatory element necessary for expression in the system for which the construct is intended. Non-limiting examples include a plant-functional promoter operably linked to the PirAB fusion proteins, TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 or related family member insecticidal protein encoding sequences for expression of the protein in plants or a Bt-functional promoter operably linked to a PirA proteins such as PirA_ABE68878, or the PirB proteins TIC4772, TIC7576, TIC7661, TIC7663, TIC7665, TIC7667, TIC7669, TIC7940, TIC10366, TIC10367, TIC10369, TIC10370, TIC10371, TIC10372, TIC10373, TIC10368, PirB_ABE68879, TIC11505, TIC11510, and TIC11511; or the PirAB fusion proteins, TIC6880, TIC9316, TIC9317, TIC9318, TIC9319, TIC9322, TIC9320, TIC9321, TIC6880PL, TIC10375, TIC10376, TIC10377, TIC10378, TIC10379, TIC10380, TIC10381, TIC10434, TIC11210, TIC11211, TIC11212, TIC11301, TIC11302, TIC11440, TIC11441, TIC11442, TIC11443, TIC11444, TIC11445, TIC11446, TIC11506, TIC11512, TIC11513, TIC10376PL, TIC10378PL, TIC10380PL, TIC10381PL, TIC11103, and TIC11104; or related insecticidal protein encoding sequences for expression of the protein in a Bt bacterium or other *Bacillus* species. Other elements can be operably linked to the PirA protein PirA_ABE68878, the PirB proteins TIC4772, TIC7576, TIC7661, TIC7663, TIC7665, TIC7667, TIC7669, TIC7940, TIC10366, TIC10367, TIC10369, TIC10370, TIC10371, TIC10372, TIC10373, TIC10368, PirB_ABE68879, TIC11505, TIC11510, and TIC11511, or the PirAB fusion proteins, TIC6880, TIC9316, TIC9317, TIC9318, TIC9319, TIC9322, TIC9320, TIC9321, TIC6880PL, TIC10375, TIC10376, TIC10377, TIC10378, TIC10379, TIC10380, TIC10381, TIC10434, TIC11210, TIC11211, TIC11212, TIC11301, TIC11302, TIC11440, TIC11441, TIC11442, TIC11443, TIC11444, TIC11445, TIC11446, TIC11506, TIC11512, TIC11513, TIC10376PL, TIC10378PL, TIC10380PL, TIC10381PL, TIC11103, and TIC11104, or related insecticidal protein encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites.

Exemplary recombinant polynucleotide molecules provided herewith include, but are not limited to, a heterologous promoter operably linked to a polynucleotide such as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:52, SEQ ID NO:53, SEQ ID NO:54, SEQ ID NO:55, SEQ ID NO:56, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, and SEQ ID NO:158 that encodes a polypeptide or protein having the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:105, SEQ ID NO:107, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, and SEQ ID NO:157. A heterologous promoter can also be operably linked to synthetic DNA coding sequences encoding a plastid targeted TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 or untargeted TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 or related insecticidal proteins. The codons of a recombinant nucleic acid molecule encoding for proteins disclosed herein can be substituted by synonymous codons (known in the art as a silent substitution).

As used herein, the term "recombinant" refers to a non-natural DNA, protein, or organism that would not normally be found in nature and was created by human intervention. A "recombinant DNA molecule" is a DNA molecule comprising a combination of DNA molecules that would not naturally occur together and is the result of human intervention. For example, a DNA molecule that is comprised of a combination of at least two DNA molecules heterologous to each other, such as a DNA molecule that comprises a transgene and the plant genomic DNA adjacent to the transgene, is a recombinant DNA molecule.

As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule does not naturally occur operably linked to the regulatory element.

A recombinant DNA construct comprising an encoding sequence for The PirA Proteins, The PirB Proteins, or The PirAB Fusion Proteins, or related insecticidal protein can further comprise a region of DNA that encodes for one or more insect inhibitory agents which can be configured to concomitantly express or co-express with a DNA sequence encoding The PirA Protein, The PirB Protein, or The PirAB Fusion Protein, or a related insecticidal protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA construct can be assembled so that all proteins or dsRNA molecules are expressed from one promoter or each protein or dsRNA molecules is under separate promoter control or some combination thereof. The PirA Proteins, The PirB Proteins, or the PirAB Fusion Proteins, and related proteins of this invention can be expressed from a multi-gene expression system in which one or more of The PirA Proteins, The PirB Proteins, or The PirAB Fusion Proteins, or related proteins is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes each expressing a different protein or other agent such as one or more dsRNA molecules.

Recombinant nucleic acid molecules or recombinant DNA constructs comprising The PirA Proteins, The PirB Proteins, or the PirAB Fusion Proteins, or related family member protein encoding sequence can be delivered to host cells by vectors, e.g., a plasmid, baculovirus, synthetic chromosome, virion, cosmid, phagemid, phage, or viral vector. Such vectors can be used to achieve stable or transient expression of The PirA Proteins, The PirB Proteins, or the PirAB Fusion Proteins, or related protein encoding sequences in a host cell, or subsequent expression of the encoded polypeptide. An exogenous recombinant polynucleotide or recombinant DNA construct that comprises a protein encoding sequence and that is introduced into a host cell is referred herein as a "transgene."

Transgenic bacteria, transgenic plant cells, transgenic plants, and transgenic plant parts that contain a recombinant polynucleotide that expresses any one or more of The PirA Proteins, The PirB Proteins, or the PirAB Fusion Proteins, or related protein encoding sequences. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, *Brassica*, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In other embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise insect, Coleoptera- or Lepidoptera- or Hemiptera-inhibitory amounts of a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302; or related protein are provided. Such plants can be made by introducing a recombinant polynucleotide that encodes any TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related protein provided in this application into a plant cell, and selecting a plant derived from said plant cell that expresses an insect, Coleoptera-, Lepidoptera-, or Hempitera-inhibitory amount of the proteins. Plants can be derived from the plant cells by regeneration, seed, pollen, or meristem transformation techniques. Methods for transforming plants are known in the art.

Processed plant products, wherein the processed product comprises a detectable amount of a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302; or related protein.

Plants expressing a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related protein can be crossed by breeding with transgenic events expressing other toxin proteins and/or expressing other transgenic traits such as herbicide tolerance genes, genes conferring yield or stress tolerance traits, and the like, or such traits can be combined in a single vector so that the traits are all linked.

As described further in the Examples, sequences encoding TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 were designed for use in plants. Expression cassettes and vectors containing these synthetic or artificial nucleotide sequences can be constructed and introduced into corn, cotton, and soybean plant cells in accordance with transformation methods and techniques which are known in the art. Transformed cells are regenerated into transformed plants that are observed to be expressing TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302. To test pesticidal activity, bioassays are performed in the presence of Lepidopteran, Coleopteran and Hemipteran pests.

As further described in the Examples, sequences encoding a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related protein and sequences having a substantial percentage identity to these proteins can be identified using methods known to those of ordinary skill in the art such as polymerase chain reaction (PCR), thermal amplification and hybridization. For example, a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein or related proteins can be used to produce antibodies that bind specifically to related proteins, and can be used to screen for and to find other protein members that are closely related.

Furthermore, nucleotide sequences encoding a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related protein can be used as probes and primers for screening to identify other members of the class using thermal-cycle or isothermal amplification and hybridization methods. For example, oligonucleotides derived from sequences as set forth as SEQ ID NO:49, SEQ ID NO:51, SEQ ID NO:52, SEQ ID NO:53, SEQ ID NO:54, SEQ ID NO:55, SEQ ID NO:56, SEQ ID NO:146, SEQ ID NO:148, SEQ ID NO:150, SEQ ID NO:152, SEQ ID NO:154, SEQ ID NO:156, and SEQ ID NO:158 can be used to determine the presence or absence of a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related protein transgene in a deoxyribonucleic acid sample derived from a commodity product. Given the sensitivity of certain nucleic acid detection methods that employ oligonucleotides, it is anticipated that oligonucleotides derived from the sequences as set forth as SEQ ID NO:49, SEQ ID NO:51, SEQ ID NO:52, SEQ ID NO:53, SEQ ID NO:54, SEQ ID NO:55, SEQ ID NO:56, SEQ ID NO:146, SEQ ID NO:148, SEQ ID NO:150, SEQ ID NO:152, SEQ ID NO:154, SEQ ID NO:156, and SEQ ID NO:158 can be used to detect a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 transgene in commodity products derived from pooled sources where only a fraction of the commodity product is derived from a transgenic plant containing any of SEQ ID NO:49, SEQ ID NO:51, SEQ ID NO:52, SEQ ID NO:53, SEQ ID NO:54, SEQ ID NO:55, SEQ ID NO:56, SEQ ID NO:146, SEQ ID NO:148, SEQ ID NO:150, SEQ ID NO:152, SEQ ID NO:154, SEQ ID NO:156, or SEQ ID NO:158. It is further recognized that such oligonucleotides can be used to introduce nucleotide sequence variation in SEQ ID NO:49, SEQ ID NO:51, SEQ ID NO:52, SEQ ID NO:53, SEQ ID NO:54, SEQ ID NO:55, SEQ ID NO:56, SEQ ID NO:146, SEQ ID NO:148, SEQ ID NO:150, SEQ ID NO:152, SEQ ID NO:154, SEQ ID NO:156, or SEQ ID NO:158. Such "mutagenesis" oligonucleotides are useful for identification of TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related amino acid sequence variants exhibiting a range of insect inhibitory activity or varied expression in transgenic plant host cells.

Nucleotide sequence homologs, e.g., insecticidal proteins encoded by nucleotide sequences that hybridize to each or any of the sequences disclosed in this application under hybridization conditions, are also an embodiment of the present invention. The invention also provides a method for detecting a first nucleotide sequence that hybridizes to a second nucleotide sequence, wherein the first nucleotide sequence (or its reverse complement sequence) encodes a pesticidal protein or pesticidal fragment thereof and hybridizes under stringent hybridization conditions to the second nucleotide sequence. In such case, the second nucleotide sequence can be the nucleotide sequence selected from the group consisting of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:52, SEQ ID NO:53, SEQ ID NO:54, SEQ ID NO:55, SEQ ID NO:56, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:104, SEQ ID NO:106, SEQ ID NO:108, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, and SEQ ID NO:158 under stringent hybridization conditions. Nucleotide coding sequences hybridize to one another under appropriate hybridization conditions and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Washes at even higher temperatures constitute even more stringent conditions, e.g., hybridization conditions of 68° C., followed by washing at 68° C., in 2×SSC containing 0.1% SDS.

One skilled in the art will recognize that, due to the redundancy of the genetic code, many other sequences are capable of encoding proteins related to The PirA Proteins, The PirB Proteins, or the PirAB Fusion Proteins, and those sequences, to the extent that they function to express pesticidal proteins either in *Bacillus* strains or in plant cells, are embodiments of the present invention, recognizing of course that many such redundant coding sequences will not hybridize under these conditions to the native *Xenorhabdus* or *Photorhabdus* sequences encoding The PirA Proteins, The PirB Proteins, or The PirAB Fusion Proteins. This application contemplates the use of these and other identification methods known to those of ordinary skill in the art, to identify The PirA Proteins, The PirB Proteins, or The PirAB Fusion Proteins, or related protein-encoding sequences and sequences having a substantial percentage identity thereto.

Methods of controlling insects, in particular Lepidoptera, Coleoptera, or Hempiteran infestations of crop plants, with the TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related proteins, are also disclosed in this application. Such methods can comprise growing a plant comprising an insect-, Coleoptera-, or Lepidoptera- or Hemiptera-inhibitory amount of a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302, or related toxin protein. In certain embodiments, such methods can further comprise any one or more of: (i) applying any composition comprising or encoding a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related toxin protein to a plant or a seed that gives rise to a plant; and (ii) transforming a plant or a plant cell that gives rise to a plant with a polynucleotide encoding a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related toxin protein. In general, it is contemplated that a TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 protein, or related toxin protein can be provided in a composition, provided in a microorganism, or provided in a transgenic plant to confer insect inhibitory activity against Lepidopteran, Coleopteran or Hemipteran insects.

In certain embodiments, a recombinant nucleic acid molecule of a The PirA Proteins, The PirB Proteins, or The PirAB Fusion Proteins, or related toxin protein is the insecticidally active ingredient of an insect inhibitory composition prepared by culturing recombinant *Bacillus* or any other recombinant bacterial cell transformed to express one of The PirA Proteins, The PirB Proteins, or The PirAB Fusion Proteins, or related toxin protein under conditions suitable for expression. Such a composition can be prepared by desiccation, lyophilization, homogenization, extraction, filtration, centrifugation, sedimentation, or concentration of a culture of such recombinant cells expressing/producing said recombinant polypeptide. Such a process can result in a *Bacillus* or other entomopathogenic bacterial cell extract, cell suspension, cell homogenate, cell lysate, cell supernatant, cell filtrate, or cell pellet. By obtaining the recombinant polypeptides so produced, a composition that includes the recombinant polypeptides can include bacterial cells, bacterial spores, and parasporal inclusion bodies and can be formulated for various uses, including as agricultural insect inhibitory spray products or as insect inhibitory formulations in diet bioassays.

In one embodiment, to reduce the likelihood of resistance development, an insect inhibitory composition comprising one of The PirA Proteins, The PirB Proteins, or The PirAB Fusion Proteins, or a related protein can further comprise at least one additional polypeptide known to those of ordinary skill in the art that exhibits insect inhibitory activity against the same Lepidopteran, Coleopteran, or Hemipteran insect species, but which is different from The PirA Proteins, The PirB Proteins, or The PirAB Fusion Proteins, or a related toxin protein. Possible additional polypeptides for such a composition include an insect inhibitory protein and an insect inhibitory dsRNA molecule. One example for the use of such ribonucleotide sequences to control insect pests is described in Baum, et al. (U.S. Patent Publication 2006/0021087 A1).

Such additional polypeptide for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Publication Ser. No. 10/525,318), Cry1C (U.S. Pat. No. 6,033,874), Cry1D, Cry1 Da and variants thereof, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry1-type chimeras such as, but not limited to, TIC836, TIC860, TIC867, TIC869, and TIC1100 (International Application Publication WO2016/061391 (A2)), TIC2160 (International Application Publication WO2016/061392(A2)), Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), AXMI-335 (International Application Publication WO2013/134523(A2)), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), DIG-657 (International Application Publication WO2015/195594(A2)), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1), Cry71Aa1 and Cry72Aa1 (US Patent Publication US2016-0230187 A1), Axmi422 (US Patent Publication US2016-0201082 A1), Axmi440 (US Patent Publication US2016-0185830 A1), Axmi281 (US Patent Publication 2016-0177332 A1), BT-0044, BT-0051, BT-0068, BT-0128 and variants thereof (WO 2016-094159 A1), BT-009, BT-0012, BT-0013, BT-0023, BT0067 and variants thereof (WO 2016-094165 A1), Cry1JP578V, Cry1JPS1, Cry1 JPS1P578V (WO 2016-061208 A1); and the like.

Such additional polypeptide for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), AXMI-207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), $\overline{\omega}$-Hiexatoxin-Hv1a (U.S. Patent Application Publication 2014-0366227 A1), PHI-4 variants (U.S. Patent Application Publication 2016-0281105 A1), PIP-72 variants (WO 2016-144688 A1), PIP-45 variants, PIP-64 variants, PIP-74 variants, PIP-75 variants, and PIP-77 variants (WO 2016-144686 A1), DIG-305 (WO 2016109214 A1), PIP-47 variants (U.S. Patent Publication 2016-086204 A1), DIG-17, DIG-90, DIG-79 (WO 2016-057123 A1), DIG-303 (WO 2016-070079 A1); and the like.

Such additional polypeptides for the control of Hemipteran pests may be selected from the group consisting of Hemipteran-active proteins such as, but not limited to, TIC1415 (US Patent Publication 2013-0097735 A1), TIC807 (U.S. Pat. No. 8,609,936), TIC852 and TIC853 (U.S. Patent Publication 2010-0064394 A1), TIC834 and variants thereof (U.S. Patent Publication 2013-0269060 A1), AXMI-036 (U.S. Patent Publication 2010-0137216 A1), and AXMI-171 (U.S. Patent Publication 2013-0055469 A1), Cry64Ba and Cry64Ca (Liu et al., (2018) Cry64Ba and Cry64Ca, Two ETX/MTX2-Type *Bacillus thuringiensis* Insecticidal Protein Active against Hemipteran Pests. Applied and Environmental Microbiology, 84(3): 1-11).

In other embodiments, such composition/formulation can further comprise at least one additional polypeptide that exhibits insect inhibitory activity to an insect that is not inhibited by an otherwise insect inhibitory protein of the present invention to expand the spectrum of insect inhibition obtained, e.g., an additional polypeptide that exhibits insect inhibitory activity to *Thysanopterans.*

The possibility for insects to develop resistance to certain insecticides has been documented in the art. One insect resistance management strategy is to employ transgenic crops that express two distinct insect inhibitory agents that operate through different modes of action. Therefore, any insects with resistance to either one of the insect inhibitory agents can be controlled by the other insect inhibitory agent. Another insect resistance management strategy employs the use of plants that are not protected to the targeted Coleopteran or Lepidopteran pest species to provide a refuge for such unprotected plants. One particular example is described in U.S. Pat. No. 6,551,962, which is incorporated by reference in its entirety.

Other embodiments such as topically applied pesticidal chemistries that are designed for controlling pests that are also controlled by the proteins disclosed herein to be used with proteins in seed treatments, spray on, drip on, or wipe on formulations can be applied directly to the soil (a soil drench), applied to growing plants expressing the proteins disclosed herein, or formulated to be applied to seed containing one or more transgenes encoding one or more of the proteins disclosed. Such formulations for use in seed treatments can be applied with various stickers and tackifiers known in the art. Such formulations can contain pesticides that are synergistic in mode of action with the proteins disclosed, so that the formulation pesticides act through a different mode of action to control the same or similar pests that can be controlled by the proteins disclosed, or that such pesticides act to control pests within a broader host range or plant pest species that are not effectively controlled by one of The PirA Proteins, The PirB Proteins, or The PirAB Fusion Proteins, or related pesticidal proteins.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

EXAMPLES

In view of the foregoing, those of skill in the art should appreciate that changes can be made in the specific aspects which are disclosed and still obtain a like or similar result without departing from the spirit and scope of the invention. Thus, specific structural and functional details disclosed herein are not to be interpreted as limiting. It should be understood that the entire disclosure of each reference cited herein is incorporated within the disclosure of this application.

Example 1

Discovery of the PirA Proteins and the PirB Proteins and the Construction of the PirAB Fusion Proteins This Example describes the discovery of the pesticidal PirA proteins TIC4771, TIC7575, TIC7660, TIC7662, TIC7664, TIC7666, TIC7668, TIC7939, TIC10357, TIC10358, TIC10360, TIC10361, TIC10362, TIC10363, TIC10364, TIC10359, and PirA_ABE68878 (collectively, "The PirA Proteins"), PirB proteins TIC4772, TIC7576, TIC7661, TIC7663, TIC7665, TIC7667, TIC7669, TIC7940, TIC10366, TIC10367, TIC10369, TIC10370, TIC10371, TIC10372, TIC10373, TIC10368, PirB-_ABE68879, TIC11505, TIC11510, and TIC11511 (collectively "The PirB Proteins"), and the creation of the PirAB fusion proteins, TIC6880, TIC9316, TIC9317, TIC9318, TIC9319, TIC9322, TIC9320, TIC9321, TIC6880PL, TIC10375, TIC10376, TIC10377, TIC10378, TIC10379, TIC10380, TIC10381, TIC10434, TIC11210, TIC11211, TIC11212, TIC11301, TIC11302, TIC11440, TIC11441, TIC11442, TIC11443, TIC11444, TIC11445, TIC11446, TIC11506, TIC11512, TIC11513, TIC10376PL, TIC10378PL, TIC10380PL, TIC10381PL, TIC11103, and TIC11104 (collectively, "The PirAB Fusion Proteins").

Sequences encoding *Photorabdus* and *Xenorabdus* PirAB pesticidal proteins were identified from proprietary collections as well as public sequence information, synthesized, cloned, sequence confirmed, and tested in insect bioassay. Bacterial operons were identified from *Photorabdus* and *Xenorabdus* species, each operon comprising a PirA and a PirB coding sequence. The pesticidal PirA proteins TIC4771, TIC7575, TIC7660, TIC7662, TIC7664, TIC7666, TIC7668, TIC7939, TIC10357, TIC10358, TIC10360, TIC10361, TIC10362, TIC10363, TIC10364, TIC10359, and PirA_ABE68878; and PirB proteins TIC4772, TIC7576, TIC7661, TIC7663, TIC7665, TIC7667, TIC7669, TIC7940, TIC10366, TIC10367, TIC10369, TIC10370, TIC10371, TIC10372, TIC10373, TIC10368, PirB_ABE68879, TIC11505, TIC11510, and TIC11511, were isolated from the *Photorabdus* and *Xenorabdus* species listed in Table 13. With respect to the proteins TIC7939 and TIC7940, the operon was identified from a microbiome sample and the bacterial species from which it was derived is still unknown.

TABLE 13

Novel PirA and PirB pesticidal toxin proteins and corresponding *Photorabdus* and *Xenorabdus* species.

| | PirA Protein | | | PirB Protein | | |
|---|---|---|---|---|---|---|
| Bacterial Species | Toxin | Nucleotide SEQ ID NO: | Protein SEQ ID NO: | Toxin | Nucleotide SEQ ID NO: | Protein SEQ ID NO: |
| *Xenorhabdus nematophila* ISB000002 | TIC4771 | 1 | 2 | TIC4772 | 3 | 4 |
| *Xenorhabdus ehlersii* 85823 | TIC7575 | 7 | 8 | TIC7576 | 9 | 10 |
| *Xenorhabdus cabanillasii* 85908 | TIC7660 | 13 | 14 | TIC7661 | 15 | 16 |
| *Xenorhabdus ehlersii* 85887 | TIC7662 | 19 | 20 | TIC7663 | 21 | 22 |
| *Xenorhabdus poinarii* 86198 | TIC7664 | 25 | 26 | TIC7665 | 27 | 28 |
| *Photorhabdus luminescens* 86197 | TIC7666 | 31 | 32 | TIC7667 | 33 | 34 |
| *Photorhabdus luminescens* 86194 | TIC7668 | 37 | 38 | TIC7669 | 39 | 40 |
| Microbiome | TIC7939 | 43 | 44 | TIC7940 | 45 | 46 |
| *Shewanella violacea* DSS12 | TIC10357 | 57 | 58 | TIC10366 | 59 | 60 |
| *Photorhabdus luminescens laumondii* TTO1 | TIC10358 | 63 | 64 | TIC10367 | 65 | 66 |
| *Photorhabdus asymbiotica* | TIC10360 | 69 | 70 | TIC10369 | 71 | 72 |
| *Xenorhabdus* sp. NBAII XenSa04 | TIC10361 | 75 | 76 | TIC10370 | 77 | 78 |
| *Yersinia aldovae* 670-83 | TIC10362 | 81 | 82 | TIC10371 | 83 | 84 |
| *Xenorhabdus doucetiae* FRM16 | TIC10363 | 87 | 88 | TIC10372 | 89 | 90 |
| *Xenorhabdus griffiniae* BMMCB | TIC10364 | 93 | 94 | TIC10373 | 95 | 96 |

TABLE 13-continued

Novel PirA and PirB pesticidal toxin proteins and corresponding *Photorabdus* and *Xenorabdus* species.

| | PirA Protein | | | PirB Protein | | |
|---|---|---|---|---|---|---|
| Bacterial Species | Toxin | Nucleotide SEQ ID NO: | Protein SEQ ID NO: | Toxin | Nucleotide SEQ ID NO: | Protein SEQ ID NO: |
| *Xenorhabdus nematophila* | TIC10359 | 99 | 100 | TIC10368 | 101 | 102 |
| *Photorhabdus luminescens* Hm | PirA_ABE68878 | 104 | 105 | PirB_ABE68879 | 106 | 107 |
| *Xenorhabdus nematophila* MDI-0035777 | | | | TIC11505 | 134 | 135 |
| *Xenorhabdus bovienii* MDI-0035808 | | | | TIC11510 | 138 | 139 |
| *Xenorhabdus nematophila* AN6/1 | | | | TIC11511 | 142 | 143 |

Sequences encoding *Photorabdus* and *Xenorabdus* PirA and PirB pesticidal proteins were identified from proprietary collections as well as public sequence information, synthesized, cloned, sequence confirmed, and tested in insect bioassay. Bacterial operons were identified and polymerase chain reaction (PCR) primers were designed based upon contigs derived from sequencing of each *Photorabdus* and *Xenorabdus* species listed in Table 13. Amplicons of the full-length coding sequence for each protein toxin were produced using total DNA isolated from each species listed in Table 13. Each of the amplicons were cloned using methods known in the art into *Bacillus thuringiensis* (Bt) expression vectors in operable linkage with a Bt expressible promoter.

Fusion proteins comprising the PirA and PirB proteins were made using methods known in the art. The coding sequences encoding the PirAB fusion proteins comprised PirA and PirB protein coding sequences operably linked, so when expressed in a cell a protein was produced comprising the PirA and PirB proteins contiguous with each other. PirAB fusion proteins comprised of a PirA protein contiguous with a PirB protein are presented in Table 1. The PirAB fusion proteins presented in Table 1 are comprised of a PirA and PirB protein derived from the same bacterial operon, or a PirA and PirB protein derived from different bacterial operons. PirAB fusion proteins comprised of a PirB protein contiguous with a PirA protein are presented in Table 2. The PirAB fusion proteins in Table 2 are comprised of a PirA and PirB protein derived from the same bacterial operon. PirAB fusion proteins comprised of a PirA protein contiguous with another PirA protein which is in turn contiguous with a PirB protein are presented in Table 3. The PirA protein components of the PirAB fusion proteins presented in Table 3 can be duplicated PirA proteins or different PirA proteins.

Example 2

PirA Proteins, PirB Proteins, and PirAB Fusion Proteins Demonstrate Lepidopteran, Coleopteran, and Hemipteran Activity in Insect Bioassay This Example illustrates inhibitory activity exhibited by The PirA Proteins, The PirB Proteins, and The PirAB Fusion Proteins against various species of Lepidoptera, Coleoptera, and Hemiptera.

The PirA Proteins, The PirB proteins, and The PirAB Fusion Proteins were expressed in Bt and *E. coli* and assayed for toxicity against various species of Lepidoptera, Coleoptera, Hemiptera, and Dipteran. Preparations of each toxin were assayed against the Lepidopteran pest species Fall Armyworm (*Spodoptera frugiperda*, FAW), Corn Earworm (*Helicoverpa zea*, (CEW), also known as Soybean Podworm and Cotton Bollworm), Southwestern Corn Borer (*Diatraea grandiosella*, SWCB), Diamondback Moth (*Plutella xylostella*, DBM), European Corn Borer (*Ostrinia nubilalis*, ECB), Velvetbean Caterpillar (*Anticarsia gemmatalis*, VBC), Black Cutworm (*Agrotis ipsilon*, BCW), Southern Armyworm (*Spodoptera eridania*, SAW), Soybean Looper (*Pseudoplusia* includes, SBL), and Tobacco Budworm (*Heliothis virescens*, TBW); the Coleopteran pest species Colorado potato beetle (*Leptinotarsa decemlineata*, CPB), Northern Corn Rootworm (*Diabrotica barberi*, NCR), Southern Corn Rootworm (*Diabrotica undecimpunctata howardii*, SCR), and Western Corn Rootworm (*Diabrotica virgifera*, WCR); the Hemipteran species Southern Green Stink Bug (*Nezara viridula*, SG), Neotropical Brown Stink Bug (*Euschistus heros*, NBSB), Tarnished plant bug (*Lygus lineolaris*, TPB), and Western tarnished plant bug (*Lygus Hesperus*, WTP); and the Dipteran species Yellow Fever Mosquito (*Aedes aegypti*, YFM).

Transformed Bt and *E. coli* expressing The PirA Proteins, The PirB Proteins, and The PirAB Fusion Proteins were grown and spores or solubilized proteins were added to the insect diet for assay. Mortality and stunting were evaluated by comparing the growth and development of insects on a diet containing one or more of The PirA Proteins, The PirB Proteins, and The PirAB Fusion Proteins, to insects on a diet with an untreated control culture. Activity was observed for Lepidopteran, Coleopteran, Hemipteran, and Dipteran insect pests. The bioassay activity observed for each protein is presented in Tables 14 (Lepidopteran) and 15 (Coleopteran, Hemipteran, and Dipteran), wherein "+" indicates activity, an empty cell indicates no activity observed, and "NT" indicates the toxin was not assayed against that specific insect pest.

TABLE 14

Bioassay activity of PirA Proteins, PirB Proteins, and PirAB Fusion proteins, against Lepidopteran insect pests.

| Type | Toxin | FAW | CEW | SWCB | DBM | ECB | VBC | BCW | SAW | SBL | TBW |
|---|---|---|---|---|---|---|---|---|---|---|---|
| PirA | TIC4771 | | + | | + | + | + | | + | | |
| PirB | TIC4772 | | + | | + | | + | | | | |
| Fusion | TIC6880 | + | + | + | + | + | + | | | | |
| PirA | TIC7575 | NT | NT | | NT | | | | | | |
| PirB | TIC7576 | NT | NT | | NT | | | | | | |
| Fusion | TIC9316 | NT | | + | NT | + | + | + | + | | + |
| PirA | TIC7660 | NT | NT | | NT | | | | | | |
| PirB | TIC7661 | NT | NT | | NT | | | | | | |
| Fusion | TIC9317 | NT | NT | + | NT | + | + | | | | |
| PirA | TIC7662 | NT | NT | | NT | | | | | | |
| PirB | TIC7663 | NT | NT | | NT | | | | | | |
| Fusion | TIC9318 | NT | NT | + | NT | + | + | + | | | + |
| PirA | TIC7664 | NT | NT | | NT | | | | | | |
| PirB | TIC7665 | NT | NT | | NT | | | | | | + |
| Fusion | TIC9319 | NT | NT | + | NT | + | + | + | | | |
| PirA | TIC7666 | NT | NT | | NT | | | | | | |
| PirB | TIC7667 | NT | NT | + | NT | | | | | | |
| Fusion | TIC9322 | + | + | + | NT | | + | | | | |
| PirA | TIC7668 | NT | NT | | NT | | | | | | |
| PirB | TIC7669 | NT | NT | | NT | | | | | | |
| Fusion | TIC9320 | NT | NT | + | NT | + | + | | | | |
| Fusion | TIC9321 | NT | NT | | NT | | | | | | |
| PirA | TIC10357 | NT | NT | | NT | NT | NT | | | | NT |
| PirB | TIC10366 | NT | NT | | NT | NT | NT | | | | NT |
| Fusion | TIC10375 | NT | NT | | NT | NT | NT | | | | NT |
| PirA | TIC10358 | NT | NT | | NT | NT | NT | | | | NT |
| PirB | TIC10367 | NT | NT | | NT | NT | NT | | | | NT |
| Fusion | TIC10376 | NT | NT | + | NT | NT | NT | | | | NT |
| PirA | TIC10360 | NT | NT | | NT | NT | NT | | | | NT |
| PirB | TIC10369 | NT | NT | | NT | NT | NT | | | | NT |
| Fusion | TIC10377 | NT | NT | | NT | NT | NT | | | | NT |
| PirA | TIC10361 | NT | NT | | NT | NT | NT | | | | NT |
| PirB | TIC10370 | NT | NT | | NT | NT | NT | | | | NT |
| Fusion | TIC10378 | NT | NT | + | NT | NT | NT | | | | NT |
| PirA | TIC10362 | NT | NT | | NT | NT | NT | | | | NT |
| PirB | TIC10371 | NT | NT | | NT | NT | NT | | | | NT |
| Fusion | TIC10379 | NT | | + | NT | NT | NT | | | | NT |
| PirA | TIC10363 | NT | NT | | NT | NT | NT | | | | NT |
| PirB | TIC10372 | NT | NT | + | NT | NT | NT | | | | NT |
| Fusion | TIC10380 | + | NT | | NT | NT | NT | | | | NT |
| PirA | TIC10364 | NT | NT | | NT | NT | NT | | | | NT |
| PirB | TIC10373 | NT | NT | | NT | NT | NT | | | | NT |
| Fusion | TIC10381 | | NT | | NT | NT | NT | | | | NT |
| PirB | TIC10368 | NT | NT | | NT | NT | NT | | | | NT |
| Fusion | TIC10434 | | NT | | NT | NT | NT | | | | NT |
| Fusion | TIC11103 | NT | NT | + | NT | NT | NT | NT | NT | NT | NT |
| Fusion | TIC11104 | NT | NT | | NT | NT | NT | NT | NT | NT | NT |
| Fusion | TIC11210 | NT | NT | + | NT | NT | NT | + | | | NT |
| Fusion | TIC11211 | NT | NT | + | NT | NT | NT | NT | NT | NT | NT |
| Fusion | TIC11212 | NT | NT | + | NT | NT | NT | | | | NT |
| Fusion | TIC11301 | | NT | + | NT | + | + | | NT | NT | NT |
| Fusion | TIC11302 | | NT | + | NT | + | + | | NT | NT | NT |

TABLE 15

Bioassay activity of PirA Proteins, PirB Proteins, and PirAB Fusion Proteins against Coleopteran, Hemipteran, and Dipteran insect pests.

| | | Coleopteran | | | | Hemipteran | | | | Dipteran |
|---|---|---|---|---|---|---|---|---|---|---|
| Type | Toxin | CPB | NCR | SCR | WCR | SGB | NBSB | TPB | WTP | YFM |
| PirA | TIC4771 | + | NT | NT | NT | NT | | + | | NT |
| PirB | TIC4772 | | NT | NT | | NT | | + | | NT |
| Fusion | TIC6880 | + | NT | | + | + | + | + | + | + |
| PirA | TIC7575 | | NT | NT | | NT | NT | | | NT |
| PirB | TIC7576 | | NT | NT | NT | NT | NT | | | |
| Fusion | TIC9316 | + | NT | NT | | + | + | + | + | NT |
| PirA | TIC7660 | | NT | NT | NT | NT | NT | | | NT |
| PirB | TIC7661 | | NT | NT | NT | NT | NT | | | NT |
| Fusion | TIC9317 | + | | | + | + | | + | + | NT |
| PirA | TIC7662 | | NT | NT | | NT | NT | | | NT |

TABLE 15-continued

Bioassay activity of PirA Proteins, PirB Proteins, and PirAB Fusion Proteins against Coleopteran, Hemipteran, and Dipteran insect pests.

| | | Coleopteran | | | | Hemipteran | | | | Dipteran |
|---|---|---|---|---|---|---|---|---|---|---|
| Type | Toxin | CPB | NCR | SCR | WCR | SGB | NBSB | TPB | WTP | YFM |
| PirB | TIC7663 | | NT | NT | NT | NT | NT | | | NT |
| Fusion | TIC9318 | + | | | + | + | + | + | + | NT |
| PirA | TIC7664 | + | NT | NT | NT | NT | NT | | | NT |
| PirB | TIC7665 | | NT | NT | NT | NT | NT | | | NT |
| Fusion | TIC9319 | + | NT | NT | | + | | + | + | NT |
| PirA | TIC7666 | | NT | NT | | NT | NT | | | NT |
| PirB | TIC7667 | | NT | NT | NT | NT | NT | | | NT |
| Fusion | TIC9322 | + | NT | NT | | | | + | | NT |
| PirA | TIC7668 | | NT | NT | NT | NT | NT | | | NT |
| PirB | TIC7669 | | NT | NT | NT | NT | NT | | | NT |
| Fusion | TIC9320 | + | NT | NT | | + | + | + | | NT |
| Fusion | TIC9321 | + | NT | NT | | NT | NT | | | NT |
| PirA | TIC10357 | NT | NT | NT | NT | NT | NT | NT | | NT |
| PirB | TIC10366 | NT | NT | NT | NT | NT | NT | NT | | NT |
| Fusion | TIC10375 | NT | NT | NT | NT | NT | NT | NT | | NT |
| PirA | TIC10358 | NT | NT | NT | NT | NT | NT | NT | | NT |
| PirB | TIC10367 | NT | NT | NT | NT | NT | NT | NT | | NT |
| Fusion | TIC10376 | NT | + | NT | + | NT | | NT | | NT |
| PirA | TIC10360 | NT | NT | NT | NT | NT | NT | NT | | NT |
| PirB | TIC10369 | NT | NT | NT | NT | NT | NT | NT | | NT |
| Fusion | TIC10377 | NT | NT | NT | NT | NT | NT | NT | | NT |
| PirA | TIC10361 | NT | NT | NT | NT | NT | NT | NT | | NT |
| PirB | TIC10370 | NT | NT | NT | NT | NT | NT | NT | | NT |
| Fusion | TIC10378 | NT | + | NT | + | NT | + | NT | | NT |
| PirA | TIC10362 | NT | NT | NT | NT | NT | NT | NT | | NT |
| PirB | TIC10371 | NT | NT | NT | NT | NT | NT | NT | | NT |
| Fusion | TIC10379 | NT | + | NT | + | NT | NT | NT | | NT |
| PirA | TIC10363 | NT | NT | NT | NT | NT | NT | NT | | NT |
| PirB | TIC10372 | NT | NT | NT | NT | NT | NT | NT | | NT |
| Fusion | TIC10380 | NT | + | NT | + | NT | + | NT | NT | NT |
| PirA | TIC10364 | NT | NT | NT | NT | NT | NT | NT | | NT |
| PirB | TIC10373 | NT | NT | NT | NT | NT | NT | NT | | NT |
| Fusion | TIC10381 | NT | + | NT | + | NT | + | NT | | NT |
| PirB | TIC10368 | NT | NT | NT | NT | NT | NT | NT | | NT |
| Fusion | TIC10434 | NT | + | NT | + | NT | | NT | NT | NT |
| Fusion | TIC11103 | NT | NT | NT | NT | NT | | NT | | NT |
| Fusion | TIC11104 | NT | NT | NT | NT | NT | + | NT | NT | NT |
| Fusion | TIC11210 | NT | NT | NT | NT | NT | + | NT | | NT |
| Fusion | TIC11211 | NT | NT | NT | NT | NT | + | NT | | NT |
| Fusion | TIC11212 | NT | NT | NT | NT | NT | | NT | NT | NT |
| Fusion | TIC11301 | NT | + | NT | + | NT | + | NT | + | NT |
| Fusion | TIC11302 | NT | NT | NT | + | NT | + | NT | + | NT |

As can be seen in Tables 14 and 15, the PirA and PirB toxin proteins alone in most instances did not demonstrate insecticidal activity. However, the fusion proteins comprising the PirA and PirB protein from each operon showed a wide spectrum of activity against Lepidopteran, Coleopteran, Hemipteran, and Dipteran insect pest species. Some of the PirA and PirB proteins did demonstrate oral activity when tested in their individual capacity. For example the PirA protein TIC4771 demonstrated activity against the Lepidopteran species CEW, DBM, ECB, VBC, SAW, the Coleopteran species CPB, and the Hemipteran species TPB. The PirB Protein TIC4772 demonstrated activity against the Lepidopteran species CEW, DBM, VBC, SAW, and the Hemipteran species TPB. When the TIC4771 and TIC4772 proteins were combined into the PirAB fusion protein TIC6880 most of the activity against the Lepidopteran activity was retained (CEW, DBM, ECB, and VBC). Activity against SAW was lost, but activity against two more insect species FAW and SWCB was seen. TIC6880 also demonstrated additional activity relative to the individual TIC4771 and TIC4772 with respect to Coleopteran and Hemipteran insect pest species. With respect to Coleoptera, TIC6880 retained activity against CPB, and added activity against WCR. With respect to Hemiptera, TIC6880 retained activity against TPB and added observed activity against SGB, NBSB, and WTP. TIC6880 also demonstrated activity against the Dipteran species YFM, which was not seen by TIC4771 or TIC4772.

While the PirA and PirB proteins TIC7575 and TIC7576, respectively, did not demonstrate insect inhibitory activity against the insects assayed, the corresponding PirAB fusion protein, TIC9316 demonstrated activity against the Lepidopteran species SWCB, ECB, VBC, BCW, SAW, and TBW. TIC9316 also demonstrated activity against the Coleopteran species CPB and the Hemipteran species SGB, NBSB, TPB, and WTP.

The PirA and PirB proteins TIC7660 and TIC7661, respectively did not demonstrate activity. However, the corresponding PirAB fusion protein TIC9317 demonstrated activity against the Lepidopteran species SWCB, ECB, and VBC, the Coleopteran species CPB and WCR, and the Hemipteran species SGB, TPB, and WTP.

The PirA and PirB proteins TIC7662 and TIC7663, respectively, did not demonstrate activity. However, the corresponding PirAB fusion protein TIC9318 demonstrated activity against the Lepidopteran species SWCB, ECB, VBC, BCW, and TBW, the Coleopteran species CPB and WCR, and the Hemipteran species SGB, NBSB, TPB, and WTP.

The PirA protein TIC7664 demonstrated activity against the Coleopteran species CPB. The PirB protein TIC7665 demonstrated activity against the Lepidopteran species TBW. The corresponding PirAB fusion protein TIC9319 demonstrated activity against the Lepidopteran species SWCB, ECB, VBC, and BCW, the Coleopteran species CPB and WCR, and the Hemipteran species SGB, TPB, and WTP.

The PirA protein TIC7666 did not demonstrate insect inhibitory activity. The PirB protein TIC7667 demonstrated activity against the Lepidopteran species SWCB. The corresponding PirAB fusion protein TIC9322 demonstrated activity against the Lepidopteran species FAW, CEW, SWCB and VBC, the Coleopteran species CPB, and the Hemipteran species TPB.

The PirA and PirB proteins TIC7668 and TIC7669, respectively, did not demonstrate activity. The corresponding PirAB fusion protein TIC9320 demonstrated activity against the Lepidopteran species SWCB, ECB, and VBC, the Coleopteran species CPB, and the Hemipteran species SGB, NBSB, and TPB.

The PirAB fusion protein TIC9321 demonstrated activity against the Coleopteran pest CPB.

The PirA protein TIC10357, PirB protein TIC10366, and the corresponding PirAB fusion protein TIC10375 did not demonstrate activity against the limited number of Lepidopteran assayed.

The PirA protein TIC10358 and PirB protein TIC10367, respectively, did not show activity against the insect species assayed. However, the corresponding PirAB fusion protein TIC10376 demonstrated activity against the Lepidopteran insect pest species, SWCB and the Coleopteran insect pest species, NCR and WCR.

The PirA protein TIC10360 and the PirB protein TIC10369, respectively, did not demonstrate activity against the limited number of Lepidopteran insect pest species assayed.

The PirA protein TIC10361 and PirB protein TIC10370, respectively, did not demonstrate activity against the limited number of Lepidopteran insect pest species assayed. However, the corresponding fusion protein TIC10378 demonstrated activity against the Lepidopteran insect pest species, SWCB, the Coleopteran pest species, NCR and WCR, and the Hemipteran pest species, NBSB.

The PirA protein TIC10362 and the PirB protein TIC10371 did not demonstrate activity against the limited number of Lepidopteran insect pest species assayed.

The PirA protein TIC10363 did not demonstrate activity against the limited number of insect pest species assayed. The PirB protein TIC10372 demonstrated activity against the Lepidopteran insect species SWCB. The corresponding fusion protein TIC10380 retained activity against the Lepidopteran insect pest species, SWCB and added activity against the Coleopteran pest species NCR and WCR and the Hemipteran pest species NBSB.

The PirA protein TIC10364 and PirB protein TIC10373 did not demonstrate activity against the limited number of insect pest species assayed. The corresponding fusion protein TIC10381 demonstrated activity against the Coleopteran pest species, NCR and WCR, and the Hemipteran pest species NBSB.

The PirAB fusion protein TIC10434 demonstrated activity against the Coleopteran pest species NCR and WCR.

The PirAB fusion protein TIC11103 demonstrated activity against the Lepidopteran pest species SWCB.

The PirAB fusion protein TIC1104 demonstrated activity against the Hemipteran species NBSB.

The PirAB fusion protein TIC11210 demonstrated activity against the Lepidopteran pest species SWCB and BCW and the Hemipteran pest species NBSB.

The PirAB fusion protein TIC11211 demonstrated activity against the Lepidopteran pest species SWCB and the Hemipteran species NBSB.

The PirAB fusion protein TIC11212 demonstrated activity against the Lepidopteran insect pest species SWCB.

The PirAB fusion protein TIC11301 demonstrated activity against the Lepidopteran pest species SWCB, ECB, and VBC, the Coleopteran pest species NCR and WCR, and the Hemipteran pest species NBSB and WTP.

The PirAB fusion protein TIC11302 demonstrated activity against the Lepidopteran pest species SWCB, ECB, and VBC, the Coleopteran pest species WCR, and the Hemipteran pest species NBS and WTP.

Example 3

Mixtures of the PirA, PirB, and PirAB Fusion Proteins Demonstrate Lepidopteran, Coleopteran, and Hemipteran Activity in Insect Bioassay This Example illustrates inhibitory activity exhibited by mixing the PirA proteins TIC7575 and TIC7660 with the PirB proteins TIC7576 and TIC7661, as well as by mixing the PirAB fusion proteins TIC9316 and TIC9317; TIC9316 with TIC11301; and TIC9317 and TIC11302 in various concentrations.

Mixtures of the PirA and PirB proteins and mixtures of the PirAB fusion proteins at various concentrations were presented in insect diet and assayed for activity against the Lepidopteran pest species BCW, SWC, and VBC, the Coleopteran pest species WCR and NCR, and the Hemipteran pest species NBSB. The mixtures comprised different concentrations of the toxin proteins. Table 16 below shows the insect species in which activity was observed for each mixture.

TABLE 16

Bioassay activity of mixtures of the PirA and PirB toxin proteins and mixtures of the PirAB fusion proteins.

| Mixture | Activity |
|---|---|
| TIC7575 0.0625 mg/mL; TIC7576 0.1875 mg/mL | BCW; VBC; NBSB |
| TIC7575 0.0625 mg/mL; TIC7576 0.1875 mg/mL; double for .5 mg/mL final | NCR; WCR; NBSB |
| TIC7575 0.0625 mg/mL; TIC7661 0.1875 mg/mL; double for .5 mg/mL final | NCR; WCR |
| TIC7660 0.0625 mg/mL; TIC7576 0.1875 mg/mL; double for .5 mg/mL final | NCR; WCR |
| TIC7660 0.0625 mg/mL; TIC7661 0.1875 mg/mL; double for .5 mg/mL final | NCR; WCR |
| TIC7575 0.0625 mg/mL; TIC7576 0.125 mg/mL; TIC7660 0.0625 mg/mL | WCR; VBC |
| TIC7575 0.0625 mg/ml; TIC7660 0.0625 mg/mL; TIC7661 0.125 mg/mL | WCR |
| TIC9316 0.04 mg/mL; TIC9317 0.01 mg/mL | VBC |
| TIC9316 0.025 mg/mL; TIC9317 0.025 mg/mL | VBC |
| TIC9316 0.25 mg/ml; TIC9317 0.25 mg/mL | NBS |
| TIC9316 0.4 mg/mL; TIC9317 0.1 mg/mL | NBS |
| TIC9316 0.04 mg/mL; TIC11301 0.01 mg/mL | VBC; SWC |
| TIC9316 0.025 mg/mL; TIC11301 0.025 mg/mL | VBC |
| TIC9316 0.01 mg/mL; TIC11301 0.04 mg/mL | VBC |

TABLE 16-continued

Bioassay activity of mixtures of the PirA and PirB toxin proteins and mixtures of the PirAB fusion proteins.

| Mixture | Activity |
| --- | --- |
| TIC9316 0.1 mg/mL; TIC11301 0.4 mg/mL | NBS |
| TIC9316 0.4 mg/mL; TIC11301 0.1 mg/mL | VBC; NBSB |
| TIC9317 0.01 mg/mL; TIC11302 0.04 mg/mL | VBC |
| TIC9317 0.25 mg/mL; TIC11302 0.25 mg/mL | NBS |

As can be seen in Table 16, mixtures of the PirA proteins TIC7575 and TIC7660 with the PirB proteins TIC7576 and TIC7661 provided activity similar to corresponding the corresponding fusion proteins, TIC9316 and TIC9317. Mixtures of the PirAB fusion proteins TIC9316 and TIC9317; TIC9316 with TIC11301; and TIC9317 and TIC11302 demonstrated activity similar to one or both of the fusion proteins.

Example 4

Design of Synthetic Coding Sequences Encoding the PirAB Fusion Proteins TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 for Expression in Plant Cells Synthetic or artificial coding sequences were constructed for use in expression of the PirAB fusion proteins TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 in plants. These synthetic coding sequences were cloned into a binary plant transformation vectors and used to transform plant cells. The synthetic nucleic acid sequences were synthesized according to methods generally described in U.S. Pat. No. 5,500,365, avoiding certain inimical problem sequences such as ATTTA and A/T rich plant polyadenylation sequences while preserving the amino acid sequence of the PirAB Fusion protein. The synthetic coding sequence for the PirAB fusion proteins TIC6880PL, TIC9316, TIC9317, TIC9318, TIC9319, TIC9320, TIC9322, TIC10376PL, TIC10378PL, TIC10380PL, TIC10381PL, and TIC11302 are presented in Table 17. The coding sequences encoding TIC6880PL, TIC10376PL, TIC10378PL, TIC10380PL, and TIC10381PL contained an additional alanine codon immediately following the initiating methionine residue of the corresponding PirA coding sequences portion within the PirAB fusion protein coding sequence.

TABLE 17

Synthetic coding sequences used for expression in plant cells encoding PirAB fusion proteins TIC6880PL, TIC9316, TIC9317, TIC9318, TIC9319, TIC9320, TIC9322, TIC10376PL, TIC10378PL, TIC10380PL, TIC10381PL, and TIC11302.

| PirAB Fusion Protein | Nucleotide SEQ ID NO: | Protein SEQ ID NO: | PirA Protein | PirB Protein |
| --- | --- | --- | --- | --- |
| TIC6880PL* | 49 | 50 | TIC4771* | TIC4772 |
| TIC9316 | 51 | 12 | TIC7575 | TIC7576 |
| TIC9317 | 52 | 18 | TIC7660 | TIC7661 |
| TIC9318 | 53 | 24 | TIC7662 | TIC7663 |
| TIC9319 | 54 | 30 | TIC7664 | TIC7665 |
| TIC9320 | 55 | 42 | TIC7668 | TIC7669 |
| TIC9322 | 56 | 36 | TIC7666 | TIC7667 |
| TIC10376PL* | 146 | 147 | TIC10358* | TIC10367 |
| TIC10378PL* | 148 | 149 | TIC10361* | TIC10370 |
| TIC10380PL* | 150 | 151 | TIC10363* | TIC10372 |
| TIC10381PL* | 152 | 153 | TIC10364* | TIC10373 |
| TIC11302 | 158 | 119 | TIC7660 | TIC7576 |

*comprises an additional alanine residue immediately following the initiating methionine residue.

The synthetic coding sequences and corresponding protein sequences for TIC11103 and TIC11104 are presented in Table 18 below.

TABLE 18

Synthetic coding sequences used for expression in plant cells encoding PirAB fusion proteins TIC11103 and TIC11104.

| PirAB Fusion Protein | Nucleotide SEQ ID NO: | Protein SEQ ID NO: | PirB Protein | PirA Protein |
| --- | --- | --- | --- | --- |
| TIC11103 | 154 | 155 | TIC7661 | TIC7660 |
| TIC11104 | 156 | 157 | TIC7663 | TIC7662 |

Example 5

Expression Cassettes for Expression of PirAB Fusion Proteins in Plant Cells

A variety of plant expression cassettes were designed with the sequences as set forth in Table 17. Such expression cassettes are useful for transient expression in plant protoplasts or transformation of plant cells. Typical expression cassettes are designed with respect to the eventual placement of the protein within the plant cell. For a plastid targeted protein, the synthetic TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 pesticidal protein coding sequences are operably linked in frame with a chloroplast targeting signal peptide coding sequence. The resulting plant transformation vectors comprise a first transgene cassette for expression of the pesticidal protein which comprises a constitutive promoter, operably linked 5' to a leader, operably linked 5' to an intron (or optionally no intron), operably linked 5' to a synthetic coding sequence encoding a plastid targeted or untargeted TIC6880PL, TIC9316, TIC9317, TIC9318, TIC9319, TIC9320, TIC9322, TIC10376PL, TIC10378PL, TIC10380PL, TIC10381PL, TIC11103, TIC11104, and TIC11302 protein, which is in turn operably linked 5' to a 3' UTR and, a second transgene cassette for the selection of transformed plant cells using glyphosate or antibiotic selection. All of the elements described above are arranged contiguously often with additional sequence provided for the construction of the expression cassette such as restriction endonuclease sites or ligation independent cloning sites.

Example 6

Transgenic Corn Plants Expressing TIC9316, TIC9317, TIC9318, TIC10376, TIC10378, TIC10380, and TIC10381 Demonstrate Activity Against Lepidopteran Pest Species This Example illustrates the inhibitory activity of the PirAB fusion proteins TIC9316, TIC9317, TIC9318, TIC10378, TIC10380, and TIC10381 when expressed in transgenic corn plants and assayed against Lepidopteran insect pest species.

Binary plant transformation vectors comprising transgene cassettes designed to express TIC9316, TIC9317, TIC9318, TIC10376, TIC10378, TIC10380, or TIC10381 were cloned using methods known in the art. The plant transformation vector comprised a first transgene cassette for expression of the TIC9316, TIC9317, TIC9318, TIC10376, TIC10378, TIC10380, or TIC10381 pesticidal protein which comprised a plant expressible promoter, operably linked 5' to a leader, operably linked 5' to an intron, operably linked 5' to a synthetic coding sequence encoding TIC9316, TIC9317, TIC9318, TIC10376, TIC10378, TIC10380, or TIC10381, operably linked 5' to a 3' UTR and, a second transgene cassette for the selection of transformed plant cells using glyphosate. The resulting vectors were used to stably transform corn plants using an *Agrobacterium*-mediated transformation method. The transformed cells were induced to form plants by methods known in the art. Bioassays using plant leaf disks were performed analogous to those described in U.S. Pat. No. 8,344,207. A non-transformed corn plant was used to obtain tissue to be used as a negative control. Multiple transformation events from each binary vector were assessed against the Lepidopteran pest species FAW, CEW, SWCB, ECB, and BCW.

Several transformed events expressing TIC9316 demonstrated good to moderate inhibitory activity against SWCB and ECB. Likewise, transformed events expressing TIC9317 also demonstrated good to moderate inhibitory activity against SWCB and ECB. Transformed events expressing TIC9318 demonstrated good to excellent inhibitory activity against SWCB and ECB. Transformed events expressing TIC10376, TIC10378, TIC10380, and TIC10381 demonstrated good to moderate activity against SWCB.

Example 7

Assay of Activity of PirAB Fusion Proteins Against Coleopteran Corn Rootworm Pests when Expressed in Stably Transformed Corn Plants This Example illustrates the inhibitory activity of TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 against different Coleopteran species that feed on corn roots.

Binary plant transformation vectors comprising transgene cassettes designed to express both plastid targeted and untargeted TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 are cloned using methods known in the art and comprise the sequences as shown in Tables 17 and 18. The resulting vectors are used to stably transform corn plants using methods known in the art. Single T-DNA insertion events are selected and grown. Pesticidal activity is assayed against the Coleopteran pests NCR, SCR, and WCR feeding on the roots of the stably transformed corn plants.

$R_0$ stably transformed plants are used to assay for Coleopteran resistance as well as generating $F_1$ progeny. Multiple single copy events are selected from each binary vector transformation. A portion of the events arising from each binary vector transformation are used in the $R_0$ Coleopteran assay, while another portion of events are used to generate $F_1$ progeny for further testing.

The $R_0$ assay plants are transplanted to eight inch pots. The plants are inoculated with eggs from WCR, NCR, or SCR. The eggs are incubated for approximately ten (10) days prior to inoculation to allow hatching to occur four (4) days after inoculation to ensure a sufficient number of larvae survive and are able to attack the corn roots. The transformed plants are inoculated at approximately V2 to V3 stage. The plants are grown after infestation for approximately twenty-eight (28) days. The plants are removed from the pots with the roots being carefully washed to remove all soil. The damage to the roots is assessed using a damage rating scale of 1-5, as presented in Table 19. Comparison is also made to the negative controls to assure the assay has been performed properly. Multiple $R_0$ events for each binary vector transformation are used in the Coleopteran assay. Low root damage scores indicate resistance conferred by the tested PirAB fusion protein to the tested Coleopteran pest.

TABLE 19

$R_0$ root damage rating scores.

| Root Damage Score | Description |
|---|---|
| 1 | No visible feeding |
| 2 | Some feeding; no pruning |
| 3 | Pruning of at least one root |
| 4 | Entire node pruned |
| 5 | More than one node pruned |

A portion of the $R_0$ stably transformed events arising from each binary vector transformation are used to produce $F_1$ progeny. The $R_0$ stably transformed plants are allowed to self-fertilize, producing $F_1$ progeny. The $F_1$ seed is planted. Heterozygous plants are identified through molecular methods known in the art and used for assay against Coleopteran pests, as well as ELISA expression measurements of toxin protein. A portion of the heterozygous $F_1$ progeny from each event are used for insect assay, while another portion is used to measure toxin protein expression.

Eggs from WCR, NCR, or SCR are incubated for approximately ten (10) days to allow hatching within four (4) days after inoculation. For WCR, each pot is inoculated with about two thousand eggs. For NCR, less eggs may be used due to the lower availability of eggs from this species. The plants are inoculated at approximately V2 to V3 stage. The plants are grown after infestation for approximately twenty-eight (28) days. The plants are removed from the pots with the roots being carefully washed to remove all soil. The damage to the roots are assessed using a damage rating scale of 0-3, as presented in Table 20. Comparison is made to the negative control to assure the assay has been performed properly. Low root damage scores indicate resistance conferred by TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302 to the Coleopteran pest.

TABLE 20

$F_1$ root damage rating scores.

| Root Damage Score | Description |
|---|---|
| 0 | No visible feeding |
| 0.01-0.09 | Feeding scars and tracks |
| 0.1-0.9 | Root pruning, but less than a full node |
| 1.0-1.9 | At least a full node (or equivalent) destroyed to within 1.5 inches of plant |
| 2.0-2.9 | Two or more nodes gone |
| 3 | Three or more nodes gone |

Example 8

Assay of Activity of the PirAB Fusion Proteins Against Lepidopteran Pests when Expressed in Stably Transformed Corn, Soybean or Cotton Plants This Example illustrates the assay of activity against various Lepidopteran pest species fed tissue from stably transformed corn, soybean or cotton plants expressing one of The PirAB Fusion Proteins.

Binary plant transformation vectors comprising transgene cassettes designed to express both plastid targeted and untargeted versions of The PirAB Fusion Proteins are cloned using methods known in the art and comprise the coding sequences as presented in Tables 17 and 18.

Corn, soybean, or cotton is transformed with the binary transformation vectors described above using an *Agrobacterium*-mediated transformation method. The transformed cells are induced to form plants by methods known in the art. Bioassays using plant leaf disks are performed analogous to those described in U.S. Pat. No. 8,344,207. A non-transformed corn, soybean, or cotton plant is used to obtain tissue to be used as a negative control. Multiple transformation events from each binary vector are assessed against Lepidopteran pests such as, but not limited to, BCW, CEW, DBM, ECB, FAW, SAW, SBL, SWCB, TBW, and VBC. Those insects demonstrating stunting and/or mortality in the insect bioassay are determined to be susceptible to the effects of The PirAB Fusion Proteins tested.

Example 9

Assay of Activity of The PirAB Fusion Proteins Against Flea Beetle Pests When Expressed in Stably Transformed Canola Plants This Example illustrates the assay of activity of against various species of Flea Beetle when allowed to feed on whole transgenic canola plants or tissues derived from transgenic canola plants expressing one of The PirAB Fusion Proteins.

Binary plant transformation vectors comprising transgene cassettes designed to express both plastid targeted and untargeted versions of The PirAB Fusion Proteins are cloned using methods known in the art and comprise the coding sequences as presented in Tables 17 and 18.

The resulting binary transformation vectors are used to stably transform canola plant cells using methods known in the art. The transformed cells are induced to form plants. Bioassays using plant leaf disks are performed analogous to those described in U.S. Pat. No. 8,344,207 using field collected Flea Beetles. A non-transformed canola plant is used to obtain tissue to be used as a negative control. Multiple transformation events from each binary vector are assessed against Coleopteran Flea Beetle pests such as, but not limited to, Crucifer Flea Beetle (*Phyllotreta cruciferae*), Striped Flea Beetle (*Phyllotreta striolata*), and Western Black Flea Beetle (*Phyllotreta pusilla*). Flea Beetle mortality is determined each day as the Beetles continue to feed. Leaf discs are changed every two (2) to three (3) days over a twelve (12) day period to assure fresh material is available to the Flea Beetles for feeding, and to reduce any impact of protein degradation in the sample.

Alternatively, transformed canola plants can be planted in a field where Flea Beetle infestations are present. The plants can be housed in a tent to prevent those Flea Beetles that emerge from the soil from escaping the experimental plots. Damage ratings of the canola leaves can be taken to determine which plants experienced lesser damage and demonstrated resistance to the Flea Beetles.

Example 10

Assay of the Activity of the PirAB Fusion Proteins Against Hemipteran Pests in Stably Transformed Soybean Plants This Example describes the assay of activity against Hemipteran insect pests in soybean plants stably transformed to express one of The PirAB Fusion Proteins.

Binary plant transformation vectors comprising transgene cassettes designed to express both plastid targeted and untargeted versions of one of The PirAB Fusion Proteins are cloned using methods known in the art and comprise the coding sequences as presented in Tables 17 and 18. Soybean plants are transformed using the binary plant transformation vectors. The transformed soybean plant cells are induced to form whole plants. Assay for activity against the Hemipteran pests is performed using a variety of techniques which will depend upon the species of Hemipteran pests and the preferred target tissue of that pest. For example, the Hemipteran pest species of Stink Bugs typically feed on the developing seeds and pods of the soybean plant. To assay for activity against Stink Bugs, R5 stage pods are harvested from the transgenic soybean plants expressing one of The PirAB Fusion Proteins and placed in a covered Petri dish or large multi-well plate containing a layer of either agar or wet paper to provide humidity to the feeding environment. Second instar Stink Bug nymphs are placed in the Petri dish or large multi-well plate. A cover providing for the exchange of oxygen while preventing desiccation is placed over the feeding environment. The Stink Bug nymphs are allowed to feed for several days. Measurements of stunting and mortality are taken and compared to Stink Bugs nymphs feeding on pods from untransformed soybean plants.

Alternatively, assay of activity can also be performed on whole stably transformed plants. Transformed plants expressing one of The PirAB Fusion Proteins are grown in a growth chamber or in the greenhouse. At R5 stage, the plants are enclosed in a cage made from breathable plastic "pollination" sheets (Vilutis and Company Inc, Frankfort, IL). The sheet sleeves are secured to the main stem just above the soil surface using a Velcro® tie. Each plant is infested with a specific number of second instar Stink Bug nymphs. The nymphs are released into each individual cage through a small slit on the cage side and then the cage is securely closed ensuring the insects won't escape. The nymphs are allowed to feed on the soybean pods for several days to a week or more. Observations are taken each day to determine measurements of stunting and mortality. At the end of the feeding period, the live and dead nymphs are collected. The plants are cut below the cages and moved to a laboratory where the insects are collected for each plant. Before opening the cage, the plants are vigorously shaken to ensure all of the insects fall off from their feeding sites to the base of the cage. Then the cage base is opened and all plant material is removed and placed on a black sheet. The insects can be collected using an aspirator or some other means. The number of insects and their developmental stage is recorded for each plant. Also, the number and developmental stage of dead nymphs is also recorded. These measurements are compared to the measurements obtained from negative control, un-transformed plants.

Delays in development of the Stink Bug nymphs (stunting) or mortality are interpreted as an indication of toxicity if, when compared to the un-transformed controls, there is a significant difference.

Example 11

Assay of the Activity of the PirAB Fusion Proteins Against Hemipteran Pests in Stably Transformed Corn Plants This Example describes the assay of activity against Hemipteran insect pests in corn plants stably transformed to express one of The PirAB Fusion Proteins.

Binary plant transformation vectors comprising transgene cassettes designed to express both plastid targeted and untargeted versions of one of The PirAB Fusion Proteins are cloned using methods known in the art and comprise the coding sequences as presented in Tables 17 and 18. Corn plants are transformed using the binary plant transformation vectors. The transformed corn plant cells are induced to form whole plants. Assay for activity against the Hemipteran pests is performed using a variety of techniques which will depend upon the species of Hemipteran pests and the preferred target tissue of that pest. For example, the Hemipteran pest species of Stink Bugs typically feed on the young corn plants in late spring or early summer, resulting in holes in the leaf, and if severe, deformed plants. In late summer, Stink Bugs typically feed on the ear itself, directly destroying the kernels.

One method to assay for Stink Bug activity is to expose the Stink Bug nymphs to leaf discs derived from stably transformed corn plants expressing one of The PirAB Fusion Proteins in large multi-well plates. Second stage instar Stink Bug nymphs are placed in large multi-well plates with leaf discs derived from the stably transformed corn plants and allowed to feed for several days. Measurements of stunting and mortality are taken and compared to Stink Bug nymphs who have fed on un-transformed corn leaf discs.

Alternatively, whole transformed plants can be used to assay for Stink Bug activity. Stably transformed corn plants expressing one of The PirAB Fusion Proteins are enclosed in cages in a similar manner as described for soybean plants in Example 4. Second instar nymphs are introduced to V3 stage corn plants and allowed to feed for several days to a week. After the prescribed feeding period, the live and dead nymphs are collected. Measurements of stunting and mortality are compared to un-transformed control plants.

To assay Stink Bug activity using stably transformed corn ears, a similar approach can be taken as that of assaying in V3 stage plants. The developing corn ears of stably transformed corn plants expressing one of The PirAB Fusion Proteins are encapsulated using sheets of material that permit the free exchange of air while preventing escape of the Stink Bug nymphs. The encapsulated ears are infested with second instar stage Stink Bug nymphs and allowed to feed on the developing kernels of the ear for several days to a week. Measurements of stunting and mortality are compared to un-transformed control plant ears.

Example 12

Assay of the Activity of the PirAB Fusion Proteins Against Hemipteran Pests in Stably Transformed Cotton Plants This Example describes the assay of activity against Hemipteran insect pests in cotton plants stably transformed to express one of The PirAB Fusion Proteins.

Binary plant transformation vectors comprising transgene cassettes designed to express both plastid targeted and untargeted versions of one of The PirAB Fusion Proteins are cloned using methods known in the art and comprise the coding sequences as presented in Tables 17 and 18. Cotton plants are transformed using the binary plant transformation vectors. The transformed cotton plant cells are induced to form whole plants. Assay for activity against the Hemipteran pests is performed using a variety of techniques which will depend upon the species of Hemipteran pests and the preferred target tissue of that pest. For example, the Hemipteran pest species of Stink Bugs are typically seed feeders, and thus, injury to cotton bolls is the primary concern. They primarily damage cotton by piercing the bolls and feeding on the seeds. Their feeding activity can result in dark spots about 1/16 of an inch in diameter on the outside of larger bolls where feeding occurred. Seed feeding may result in reduced lint production and stained lint near the feeding site. Because of their size, adults and fourth and fifth instar nymphs have the greatest potential for damaging bolls, and it is therefore important to kill the insect in its earlier nymphal stages. The Hemipteran pest species of *Lygus* primarily feed on the squares and young bolls. The nymphs are more voracious feeders and tend to cause the most severe damage. When feeding on squares, *Lygus* target the developing anthers which often results in the square shriveling and falling from the plant. For those squares that develop into bolls, the bolls may have anthers that are incapable of forming pollen, unfertilized seeds, and empty locules. When feeding on bolls, *Lygus* target the developing seeds, causing small black sunken spots on the outside of the boll.

One method to assay activity of The PirAB Fusion Proteins in stably transformed cotton plants is to use squares in an insect bioassay. The squares are harvested from transformed cotton plants expressing TIC6880PL, TIC9316, TIC9317, TIC9318, TIC9319, TIC9320, TIC9322, TIC10376PL, TIC10378PL, TIC10380PL, TIC10381PL, TIC11103, TIC11104, or TIC11302. The squares can be put into a petri dish or each square into a well of a large well plate. Young neonate *Lygus* or Stink Bug nymphs are placed into the petri dish or large well plate and allowed to feed for a prescribed time. Measurements of stunting and mortality are taken over the time course of feeding and compared to controls in which squares derived from untransformed cotton plants are used in assay.

Alternatively, assay of activity can be performed on whole transformed cotton plants. For example, to assay against *Lygus* species, $R_1$ seeds derived from plants expressing one of The PirAB Fusion Proteins are sown in 10 inch pots. An untransformed cotton plant, preferably from the same variety as the transformed plants, is used as a negative control. Plants are maintained in an environment chamber with a photoperiod of sixteen (16) hours of light at thirty-two (32) degrees Celsius and eight (8) hours of dark at twenty three (23) degrees Celsius, and a light intensity between eight hundred (800) and nine hundred (900) micro-Einsteins. At forty (40) to forty-five (45) days after planting, the individual plants are enclosed in a cage made from breathable plastic "pollination" sheets (Vilutis and Company Inc, Frankfort, IL). The sheet sleeves are secured to the main stem just above the soil surface using a Velcro® tie. Two pairs of sexually mature male and female *Lygus lineolaris* or *Lygus hesperus* adults (six days old) from a laboratory culture are collected into a fourteen-milliliter round-bottom plastic tube (Bacton Dickson Labware, Franklin Lakes, NJ) and used for each plant. The adults are released into each individual cage through a small slit on the cage side and then the cage is securely closed ensuring the insects would not escape. The insects are allowed to mate and the plants are kept in the cage for twenty-one (21) days.

After twenty-one (21) days, the plants are then cut below the cages and moved to a laboratory where the insects are collected for each plant and counted. Before opening the cage, the plants are vigorously shaken to ensure all of the insects fall off from their feeding sites to the base of the cage. Then the cage base is opened and all plant material removed and placed on a black sheet. The insects are collected using an aspirator. The plant is then thoroughly inspected to recover any remaining insects. The number of insects collected and their developmental stage are recorded for each plant. The insect counts are divided into several groups based upon maturity of the *Lygus*: nymphs up to $3^{rd}$ instar, $4^{th}$ instar, $5^{th}$ instar and adults.

To assay against Stink Bug species, R1 seeds derived from plants expressing one of The PirAB Fusion Proteins are sown into pots and grown and caged as described above. Untransformed cotton plants are also used as a negative control. Second instar Stink Bug nymphs are used to infest the plants and allowed to feed on the squares and bolls for several days or weeks. The caged plants are collected as described above and the collected stink bugs are examined and scored for mortality, as well as, maturity of the nymphs recorded. These scores are then compared to the negative control plants.

Example 13

TIC9318 and TIC11302 Demonstrates Activity Against Western Corn Rootworm Pests When Expressed in Stably Transformed Corn Plants This Example illustrates the inhibitory activity of TIC9318 and TIC11302 against Western Corn Rootworm (*Diabrotica virgifera*, WCR) in stably transformed corn plants.

Corn plants were transformed with binary plant transformation constructs comprising an expression cassette for the expression of either TIC9318 or TIC11302. The binary plant transformation vectors comprised transgene cassettes designed to express TIC9318 and TIC11302, and were cloned using methods known in the art. The plant transformation vectors comprised a first transgene cassette for expression of the TIC9318 or TIC11302 pesticidal protein which comprised a plant expressible promoter, operably linked 5' to a leader, operably linked 5' to an intron, operably linked 5' to a synthetic coding sequence encoding TIC9318 or TIC11302, operably linked 5' to a 3' UTR and, a second transgene cassette for the selection of transformed plant cells using glyphosate. The resulting vectors were used to stably transform corn plants using an *Agrobacterium*-mediated transformation method. The transformed cells were induced to form plants by methods known in the art.

$R_0$ stably transformed plants were used to assay TIC11302 for WCR resistance as well as generating $F_1$ progeny. Multiple single copy events were selected from each binary vector transformation. A portion of the events arising from each binary vector transformation were used in the $R_0$ WCR assay.

The $R_0$ assay plants were transplanted to eight inch pots. The plants were inoculated with approximately two thousand eggs each from WCR. The eggs were incubated for approximately ten (10) days prior to inoculation to allow hatching to occur four (4) days after inoculation to ensure a sufficient number of larvae survive and were able to attack the corn roots. Each pot was inoculated with approximately two thousand WCR eggs. The transformed plants were inoculated at approximately V2 to V3 stage. The plants were grown after infestation for approximately twenty-eight (28) days. The plants were removed from the pots with the roots being carefully washed to remove all soil. The damage to the roots was assessed using a damage rating scale of 1-5, as presented in Table 19 of Example 17. Comparison was also made to the negative controls to assure the assay has been performed properly. Multiple $R_0$ events for each TIC11302 binary vector transformation were used in the WCR assay.

A portion of the $R_0$ stably transformed events arising from each binary vector transformation of TIC9318 and TIC11302 were used to produce $F_1$ progeny. The $R_0$ stably transformed plants were allowed to self-fertilize, producing $F_1$ progeny. The $F_1$ seed was planted in eight inch pots. Heterozygous plants were identified through molecular methods known in the art and were used for assay against WCR. Inoculation with the WCR eggs was as described for the $R_0$ stably transformed events as described above. The damage to the roots were assessed using a damage rating scale of 0-3, as presented in Table 20 of Example 7. Comparison was made to the negative control to assure the assay has been performed properly. The average Root Damage Rating (RDR) for each construct is presented in Table 21 below, wherein "NT" indicates not tested.

TABLE 21

Average Root Damage Rating (RDR) for corn plants stably transformed with TIC9318 or TIC11302.

| Construct | PirAB Fusion Protein | Nucleotide SEQ ID NO: | Protein SEQ ID NO: | $R_0$ RDR | $R_0$ Neg. Control RDR | $F_1$ RDR | $F_1$ Neg. Control RDR |
|---|---|---|---|---|---|---|---|
| Construct_1 | TIC9318 | 53 | 24 | NT | NT | 1.4 | 2.8 |
| Construct_2 | TIC9318 | 53 | 24 | NT | NT | 1.5 | 1.8 |
| Construct_3 | TIC9318 | 53 | 24 | NT | NT | 1.2 | 1.8 |
| Construct_4 | TIC11302 | 158 | 119 | 2.9 | 4.1 | 1.5 | 1.8 |
| Construct_5 | TIC11302 | 158 | 119 | 2.8 | 4.1 | 1.4 | 1.8 |
| Construct_6 | TIC11302 | 158 | 119 | 2.9 | 4.1 | 1.4 | 1.8 |

As can be seen in Table 21 above, both TIC9318 and TIC11302 demonstrated resistance to Western Corn Rootworm (*Diabrotica virgifera virgifera*) when compared to the negative controls.

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

SEQUENCE LISTING

```
Sequence total quantity: 160
SEQ ID NO: 1            moltype = DNA  length = 408
FEATURE                 Location/Qualifiers
misc_feature            1..408
                        note = A nucleic acid sequence obtained from Xenorhabdus
                         nematophilastrain ISB000002 encoding a TIC4771 PirA
                         pesticidal proteinsequence.
source                  1..408
                        mol_type = other DNA
                        organism = Xenorhabdus nematophila
SEQUENCE: 1
atgattacaa taaatataag tggtggtagt ataaaaatta gtaacaacat aggatcagaa  60
actgatatca aaaatacacc tttttcagaa cctctttcaa ttagtaatta taaggatatg  120
acaatagagc cacattcgtc tatccaagca acaagaactg atacaccaat tattcctgaa  180
acacgaccaa attattatgt agctaattcc ggccctgccg catcagtgag agctgttttt  240
tattggtctc attcttttac atcagaatgg ttcgaacatt catctatcat tgtaaaagca  300
ggagaagatg gaatattgaa ctcacctagc aattctgtat attacagtaa ggttgtcatt  360
tacaacgata cggataaacg ggcctttgtc acaggttatg acaaataa              408

SEQ ID NO: 2            moltype = AA  length = 135
FEATURE                 Location/Qualifiers
REGION                  1..135
                        note = The amino acid sequence of the TIC4771 PirA protein.
source                  1..135
                        mol_type = protein
                        organism = Xenorhabdus nematophila
SEQUENCE: 2
MITINISGGS IKISNNIGSE TDIKNTPFSE PLSISNYKDM TIEPHSSIQA TRTDTPIIPE  60
TRPNYYVANS GPAASVRAVF YWSHSFTSEW FEHSSIIVKA GEDGILNSPS NSVYYSKVVI  120
YNDTDKRAFV TGYDK                                                  135

SEQ ID NO: 3            moltype = DNA  length = 1287
FEATURE                 Location/Qualifiers
misc_feature            1..1287
                        note = A nucleic acid sequence obtained from Xenorhabdus
                         nematophilastrain ISB000002 encoding a TIC4772 PirB
                         pesticidal proteinsequence.
source                  1..1287
```

```
                        mol_type = other DNA
                        organism = Xenorhabdus nematophila
SEQUENCE: 3
atgaataacg aacttatgaa cacaaatgaa tcacaacctt cagagacatt atctttaatt  60
aatgaatcta tattaacagc accttatgcc gtttctaccc ctaattatga atgggatatg  120
tcatcaataa taaaagatgc cattattgga ggtataggat ttattcccgg gccgggttca  180
gcaatatcgt ttttgctagg gctattttgg ccgcaacaaa cagacaatac ctgggagcaa  240
attctccaaa aagtagaaca gatgatagag gaagcgaatt taaaaactat tcaaggaata  300
ctgaacggag atatacaaga aataaaagga aagatggaac atgtggaata tatgctagaa  360
acctcaccag gcactcaaga aagccatgac gcatatatgt tcttagcgag atatctggta  420
agtatagatg aaaaattcaa atcttttgat aataaaacaa attatcaaat tcttccaatg  480
tacaccaata cgcttatgtt acaggcacct tactggaaaa tgggtataga gaagaaaaat  540
gatattttgc taacagatat agaagttaat gaattaaaac agcttatcga aaatctatat  600
gccaaggcca atagctatat tcatgaagtg tatacccgtg aatacgataa tgcggtaaat  660
acctcaacag caacaacgat taccaataat ttattgtctg taagagggta ttgtttatta  720
catggattag agtgccttga agtccttgat catatacaaa ataataatct tgatcagagc  780
ttctatccga aaactatcag ttattctact gtatttgatc gctcaacaaa caaaacaaga  840
ctccaggctc ttaccgaaga cgagcaaatg gaagaaccac tcaaaccctc ttttattaat  900
ggggaatata ataaaataaa atcactgatt ggatatgtac agagaattgg aaacgcccct  960
agagttggag gtataaaaat tacatttact aatggatcat ctcatactct gggtacagtg  1020
acctcagaat caaactcaat tgaactaaat gatagtgtta taaccagtgt ggaagtatgg  1080
ggaaatggtg ctgttgatga ggcattcttt acattaagtg acggtcgtca atttaggctt  1140
ggtcaacgct atgccagtaa ctacagaaaa tatgctgttg atggccacta tatttcagga  1200
ttgtacttag ccagtgatga gccttcactt gctggtcaag ccgcaggtat tgcagtttca  1260
tatcatatat tggttgataa gaaataa                                    1287

SEQ ID NO: 4            moltype = AA  length = 428
FEATURE                 Location/Qualifiers
REGION                  1..428
                        note = The amino acid sequence of the TIC4772 PirB protein.
source                  1..428
                        mol_type = protein
                        organism = Xenorhabdus nematophila
SEQUENCE: 4
MNNELMNTNE SQPSETLSLI NESILTAPYA VSTPNYEWDM SSIIKDAIIG GIGFIPGPGS  60
AISFLLGLFW PQQTDNTWEQ ILQKVEQMIE EANLKTIQGI LNGDIQEIKG KMEHVEYMLE  120
TSPGTQESHD AYMFLARYLV SIDEKFKSFD NKTNYQILPM YTNTLMLQAP YWKMGIEKKN  180
DILLTDIEVN ELKQLIENLY AKANSYIHEV YTREYDNAVN TSTATTITNN LLSVRGYCLL  240
HGLECLEVLD HIQNNNLDQS FYPKTISYST VFDRSTNKTR LQALTEDEQM EEPLKPSFIN  300
GEYNKIKSLI GYVQRIGNAP RVGGIKITFT NGSSHTLGTV TSESNSIELN DSVITSVEVW  360
GNGAVDEAFF TLSDGRQFRL GQRYASNYRK YAVDGHYISG LYLASDEPSL AGQAAGIAVS  420
YHILVDKK                                                          428

SEQ ID NO: 5            moltype = DNA  length = 1692
FEATURE                 Location/Qualifiers
misc_feature            1..1692
                        note = A nucleic acid sequence encoding a PirAB fusion
                         protein, TIC6880comprised of the TIC4771 and TIC4772
                         coding sequences in operablelinkage and in frame.
source                  1..1692
                        mol_type = other DNA
                        organism = synthetic construct
SEQUENCE: 5
atgattacaa taaatataag tggtggtagt ataaaaaatta gtaacaacat aggatcagaa  60
actgatatca gaaatacacc tttttcagaa cctctttcaa ttagtaatta taaggatatg  120
acaatagagc cacattcgtc tatccaagca acaagaactg atacaccaat tattcctgaa  180
acacgaccaa attattatgt agctaattcc ggccctgccg catcagtgag agctgttttt  240
tattggtctc attcttttac atcagaatgg ttcgaacatt catctatcat tgtaaaagca  300
ggagaagatg gaatattgaa ctcacctagc aattctgtat attacagtaa ggttgtcatt  360
tacaacgata cggataaacg ggcctttgtc acaggttatg acaaaatgaa taacgaactt  420
atgaacacaa atgaatcaca accttcagag acattatctt taattaatga atctatatta  480
acagcacctt atgccgtttc taccccctaat tatgaatggg atatgtcatc aataataaaa  540
gatgccatta ttggaggtat aggatttatt cccgggccgg gttcagcaat atcgtttttg  600
ctagggctat tttggccgca acaaacagac aatacctggg agcaaattct ccaaaaagta  660
gaacagatga tagaggaagc gaatttaaaa actattcaag gaatactgaa cggagatata  720
caagaaataa aaggaaagat ggaacatgtg gaatatatgc tagaaacctc accaggcact  780
caagaaagcc atgacgcata tatgttctta gcgagatatc tggtaagtat agatgaaaaa  840
ttcaaatctt ttgataataa aacaaattat caaattcttc caatgtacac caatacgctt  900
atgttacagg caccttactg gaaaatgggt atagagaaga aaaatgatat tttgctaaca  960
gatatagaag ttaatgaatt aaaacagctt atcgaaaatc tatatgccaa ggccaatagc  1020
tatattcatg aagtgtatac ccgtgaatac gataatgcgg taaatacctc aacagcaaca  1080
acgattacca ataatttatt gtctgtaaga gggtattgtt tattacatgg attagagtgc  1140
cttgaagtcc ttgatcatat acaaaataat aatcttgatc agagcttcta tccgaaaact  1200
atcagttatt ctactgtatt tgatcgctca acaaacaaaa caagactcca ggctcttacc  1260
gaagacgagc aaatggaaga accactcaaa ccctctttta ttaatgggga atataataaa  1320
ataaaatcac tgattggata tgtacagaga attggaaacg cccctagagt tggaggtata  1380
aaaattacat ttactaatgg atcatctcat actctgggta cagtgacctc agaatcaaac  1440
tcaattgaac taaatgatag tgttataacc agtgtggaag tatggggaaa tggtgctgtt  1500
gatgaggcat tctttacatt aagtgacggt cgtcaattta ggcttggtca acgctatgcc  1560
```

```
agtaactaca gaaaatatgc tgttgatggc cactatattt caggattgta cttagccagt  1620
gatgagcctt cacttgctgg tcaagccgca ggtattgcag tttcatatca tatattggtt  1680
gataagaaat aa                                                      1692

SEQ ID NO: 6           moltype = AA  length = 563
FEATURE                Location/Qualifiers
REGION                 1..563
                       note = The amino acid sequence of the TIC6880 PirAB fusion
                        protein
source                 1..563
                       mol_type = protein
                       organism = synthetic construct
SEQUENCE: 6
MITINISGGS IKISNNIGSE TDIRNTPFSE PLSISNYKDM TIEPHSSIQA TRTDTPIIPE  60
TRPNYYVANS GPAASVRAVF YWSHSFTSEW FEHSSIIVKA GEDGILNSPS NSVYYSKVVI  120
YNDTDKRAFV TGYDKMNNEL MNTNESQPSE TLSLINESIL TAPYAVSTPN YEWDMSSIIK  180
DAIIGGIGFI PGPGSAISFL LGLFWPQQTD NTWEQILQKV EQMIEEANLK TIQGILNGDI  240
QEIKGKMEHV EYMLETSPGT QESHDAYMFL ARYLVSIDEK FKSFDNKTNY QILPMYTNTL  300
MLQAPYWKMG IEKKNDILLT DIEVNELKQL IESLYAKANS YIHEVYTREY DNAVNTSTAT  360
TITNNLLSVR GYCLLHGLEC LEVLDHIQNN NLDQSFYPKT ISYSTVFDRS TNKTRLQALT  420
EDEQMEEPLK PSFINGEYNK IKSLIGYVQR IGNAPRVGGI KITFTNGSSH TLGTVTSESN  480
SIELNDSVIT SVEVWGNGAV DEAFFTLSDG RQFRLGQRYA SNYRKYAVDG HYISGLYLAS  540
DEPSLAGQAA GIAVSYHILV DKK                                          563

SEQ ID NO: 7           moltype = DNA  length = 426
FEATURE                Location/Qualifiers
misc_feature           1..426
                       note = A nucleic acid sequence obtained from Xenorhabdus
                        ehlersii strain85823 encoding a TIC7575 PirA pesticidal
                        protein sequence.
source                 1..426
                       mol_type = other DNA
                       organism = Xenorhabdus ehlersii
SEQUENCE: 7
atgaatacaa tcaatataaa tataagtggc agtaccgtta cagtcataag caataacgat  60
tccaatccag aaccattaac ttataataca aacacaccag catcagaccc tcttacagcc  120
agtccttata gggatatgac aatagagcca cactcttcta ttgaagcaac aagaaccgat  180
acaccgatta ttcccgaaac tcgtcccaat tactatgtag ccaattctgg ccccgcatca  240
tcagttaggg ctgtttttta ttggtctcat tctttcacat cagaatggtt cgaatattcc  300
tctatcatag tgaaagccgg gaaagacgga atattacaat caccgaataa cgctttatat  360
tacagtaaag ttgtcattta taacgatacc gataaacgtg cctttgttac cggatataat  420
aagtaa                                                             426

SEQ ID NO: 8           moltype = AA  length = 141
FEATURE                Location/Qualifiers
REGION                 1..141
                       note = The amino acid sequence of the TIC7575 PirA protein.
source                 1..141
                       mol_type = protein
                       organism = Xenorhabdus ehlersii
SEQUENCE: 8
MNTININISG STVTVISNND SNPEPLTYNT NTPASDPLTA SPYRDMTIEP HSSIEATRTD  60
TPIIPETRPN YYVANSGPAS SVRAVFYWSH SFTSEWFEYS SIIVKAGKDG ILQSPNNALY  120
YSKVVIYNDT DKRAFVTGYN K                                            141

SEQ ID NO: 9           moltype = DNA  length = 1278
FEATURE                Location/Qualifiers
misc_feature           1..1278
                       note = A nucleic acid sequence obtained from Xenorhabdus
                        ehlersii strain85823 encoding a TIC7576 PirB pesticidal
                        protein sequence.
source                 1..1278
                       mol_type = other DNA
                       organism = Xenorhabdus ehlersii
SEQUENCE: 9
atgaatatct caccgattaa tgtatctgaa aatgaaacat tacctgaact cactgatgtt  60
atgcttattg tgccttatac aacatctacc cctgattatg aatgggatat gtcatcaatt  120
ataaaggatg cgattattgg cggcgtaggg tttattccag gagcaggctc tgcaatgtcc  180
ttcctattgg gactattttg gcctcaacag aaagataata catgggaaca gatcctccaa  240
aaagtagaac agatgataga gaatgccgtt ctgcaaacta ttaaaggaat acttaatgga  300
gatatacaag aaatcaaggg gaaaatggaa catgtgcaat acatgctgga aacctcgcct  360
ggcagtcagg aaagtcatga cgcatatatg ttcctggcta gatacctggt gagtatagat  420
gaaaaattca agtcttttga taataaaaca aactaccaga tcctgccgat gtacactaac  480
acggttatgt tacaaatccc ttattggaaa atgggaatag agaagaaaaa tgatattggg  540
ctgacagata ttgaagtcaa tgagttaaaa cagcttatcg ataaattggt cgacaaggcc  600
aagagttaca tccatacgat gtatacgaat gaatataatg atgccataaa tacatcaaca  660
gcatcgagtg tcactaataa tttactctct gtaagaggat attgtttatt acacggttta  720
gagtgtattg agttaattga acatctacaa aacaatagcc tcgaaagtgg tttttatcct  780
aaaactatca gttattcaac tgtatttgat cgtcagacta acaaaatgag aattcaggct  840
```

```
cttacagaag acgatcaaat gcaggaaccc tttaagccat ctttaatcaa cggcaaatac  900
aataaaatac aatccttgct tggatatgta caaagaattg gaaatgcacc tagagtgggg  960
ggtattaaaa tcacctttgc caacggttca tcctatacac ttggcacagt aacatcagaa  1020
acgagttcaa ttgaactcaa tgatagtgtt atcgaaagat tggaagtatg gggcaatggc  1080
gctgttgatg aggcattatt tacgttaagt gatgggcgtc aactcagagt cggtgagcgc  1140
tacgcgacaa aatatagaaa atatgctgtt gatggacact atattgcagg actgtactta  1200
gctagcgatg aaccttcact tgctggtcaa gccgcaggta ttgccgtttc ataccatatg  1260
ttggatgata aaaaataa                                                1278

SEQ ID NO: 10          moltype = AA  length = 425
FEATURE                Location/Qualifiers
REGION                 1..425
                       note = The amino acid sequence of the TIC7576 PirB protein.
source                 1..425
                       mol_type = protein
                       organism = Xenorhabdus ehlersii
SEQUENCE: 10
MNISPINVSE NETLPELTDV MLIVPYTTST PDYEWDMSSI IKDAIIGGVG FIPGAGSAMS  60
FLLGLFWPQQ KDNTWEQILQ KVEQMIENAV LQTIKGILNG DIQEIKGKME HVQYMLETSP  120
GSQESHDAYM FLARYLVSID EKFKSFDNKT NYQILPMYTN TVMLQIPYWK MGIEKKNDIG  180
LTDIEVNELK QLIDKLVDKA KSYIHTMYTN EYNDAINTST ASSVTNNLLS VRGYCLLHGL  240
ECIELIEHLQ NNSLESGFYP KTISYSTVFD RQTNKMRIQA LTEDDQMQEP FKPSLINGKY  300
NKIQSLLGYV QRIGNAPRVG GIKITFANGS SYTLGTVTSE TSSIELNDSV IERLEVWGNG  360
AVDEALFTLS DGRQLRVGER YATKYRKYAV DGHYIAGLYL ASDEPSLAGQ AAGIAVSYHM  420
LDDKK                                                              425

SEQ ID NO: 11          moltype = DNA  length = 1701
FEATURE                Location/Qualifiers
misc_feature           1..1701
                       note = A nucleic acid sequence encoding a PirAB fusion
                        protein, TIC9316comprised of the TIC7575 and TIC7576
                        coding sequences in operablelinkage and in frame.
source                 1..1701
                       mol_type = other DNA
                       organism = synthetic construct
SEQUENCE: 11
atgaatacaa tcaatataaa tataagtggc agtaccgtta cagtcataag caataacgat  60
tccaatccag aaccattaac ttataataca aacacaccag catcagaccc tcttacagcc  120
agtccttata gggatatgac aatagagcca cactcttcta ttgaagcaac aagaaccgat  180
acaccgatta ttcccgaaac tcgtcccaat tactatgtag ccaattctgg ccccgcatca  240
tcagttaggg ctgtttttta ttggtctcat tctttcacat cagaatggtt cgaatattcc  300
tctatcatag tgaaagccgg gaaagacgga atattacaat caccgaataa cgctttatat  360
tacagtaaag ttgtcattta taacgatacc gataaacgtg cctttgttac cggatataat  420
aagatgaata tctcaccgat taatgtatct gaaaatgaaa cattacctga actcactgat  480
gttatgctta ttgtgcctta tacaacatct acccctgatt atgaatggga tatgtcatca  540
attataaagg atgcgattat tggcggcgta gggtttattc caggagcagg ctctgcaatg  600
tccttcctat tgggactatt ttggcctcaa cagaaagata atacatggga acagatcctc  660
caaaaagtag aacagatgat agagaatgcc gttctgcaaa ctattaaagg aatacttaat  720
ggagatatac aagaaatcaa ggggaaaatg gaacatgtgc aatacatgct ggaaacctcg  780
cctggcagtc aggaaagtca tgacgcatat atgttcctgg ctagatacct ggtgagtata  840
gatgaaaaat tcaagtcttt tgataataaa acaaactacc agatcctgcc gatgtacact  900
aacacggtta tgttacaaat ccccttattgg aaaatgggaa tagagaagaa aaatgatatt  960
gggctgacag atattgaagt caatgagtta aaacagctta tcgataaatt ggtcgacaag  1020
gccaagagtt acatccatac gatgtatacg aatgaatata atgatgccat aaatacatca  1080
acagcatcga gtgtcactaa taatttactc tctgtaagag gatattgttt attacacggt  1140
ttagagtgta ttgagttaat tgaacatcta caaaacaata gcctcgaaag tggtttttat  1200
cctaaaacta tcagttattc aactgtattt gatcgtcaga ctaacaaaat gagaattcag  1260
gctcttacag aagacgatca aatgcaggaa ccctttaagc catctttaat caacggcaaa  1320
tacaataaaa tacaatcctt gcttggatat gtacaaagaa ttggaaatgc acctagagtg  1380
gggggtatta aaatcacctt tgccaacggt tcatcctata cacttggcac agtaacatca  1440
gaaacgagtt caattgaact caatgatagt gttatcgaaa gattggaagt atggggcaat  1500
ggcgctgttg atgaggcatt atttacgtta agtgatgggc gtcaactcag agtcggtgag  1560
cgctacgcga caaaatatag aaaatatgct gttgatggac actatattgc aggactgtac  1620
ttagctagcg atgaaccttc acttgctggt caagccgcag gtattgccgt ttcataccat  1680
atgttggatg ataaaaaata a                                            1701

SEQ ID NO: 12          moltype = AA  length = 566
FEATURE                Location/Qualifiers
REGION                 1..566
                       note = The amino acid sequence of the TIC9316 PirAB fusion
                        protein.
source                 1..566
                       mol_type = protein
                       organism = synthetic construct
SEQUENCE: 12
MNTININISG STVTVISNND SNPEPLTYNT NTPASDPLTA SPYRDMTIEP HSSIEATRTD  60
TPIIPETRPN YYVANSGPAS SVRAVFYWSH SFTSEWFEYS SIIVKAGKDG ILQSPNNALY  120
YSKVVIYNDT DKRAFVTGYN KMNISPINVS ENETLPELTD VMLIVPYTTS TPDYEWDMSS  180
IIKDAIIGGV GFIPGAGSAM SFLLGLFWPQ QKDNTWEQIL QKVEQMIENA VLQTIKGILN  240
```

```
GDIQEIKGKM EHVQYMLETS PGSQESHDAY MFLARYLVSI DEKFKSFDNK TNYQILPMYT  300
NTVMLQIPYW KMGIEKKNDI GLTDIEVNEL KQLIDKLVDK AKSYIHTMYT NEYNDAINTS  360
TASSVTNNLL SVRGYCLLHG LECIELIEHL QNNSLESGFY PKTISYSTVF DRQTNKMRIQ  420
ALTEDDQMQE PFKPSLINGK YNKIQSLLGY VQRIGNAPRV GGIKITFANG SSYTLGTVTS  480
ETSSIELNDS VIERLEVWGN GAVDEALFTL SDGRQLRVGE RYATKYRKYA VDGHYIAGLY  540
LASDEPSLAG QAAGIAVSYH MLDDKK                                       566

SEQ ID NO: 13          moltype = DNA  length = 426
FEATURE                Location/Qualifiers
misc_feature           1..426
                       note = A nucleic acid sequence obtained from Xenorhabdus
                        cabanillasiistrain 85908 encoding a TIC7660 PirA
                        pesticidal protein sequence.
source                 1..426
                       mol_type = other DNA
                       organism = Xenorhabdus cabanillasii
SEQUENCE: 13
atgatcacaa taaatataaa tgtaaacggc aatgatgtta caggtacaaa taataatgaa  60
cctactccag tatcgacaac ttacggtcca aatacaccag catcagaacc ccctgtagtc  120
agtaattata gtgatataac aatagaaccg cattcttctg tgcaggcaac aagaattgat  180
acgcctgtta ttcctgaagc acgccccgat tactatgtag ccaactccgg ccctgcacca  240
tcagttaggg ctgtttttta ttggtctcat tctttcacat cagaatggtt cgaatcttcc  300
tctatcacag tgaaagcagg agaggacgga atattaaaag cacctggtaa ctctttatat  360
tacagcaaag tcgtcattta taatgatacg gataaacgag cctttgttac tggatataat  420
aaataa                                                             426

SEQ ID NO: 14          moltype = AA  length = 141
FEATURE                Location/Qualifiers
REGION                 1..141
                       note = The amino acid sequence of the TIC7660 PirA protein.
source                 1..141
                       mol_type = protein
                       organism = Xenorhabdus cabanillasii
SEQUENCE: 14
MITININVNG NDVTGTNNNE PTPVSTTYGP NTPASEPPVV SNYSDITIEP HSSVQATRID  60
TPVIPEARPD YYVANSGPAP SVRAVFYWSH SFTSEWFESS SITVKAGEDG ILKAPGNSLY  120
YSKVVIYNDT DKRAFVTGYN K                                            141

SEQ ID NO: 15          moltype = DNA  length = 1278
FEATURE                Location/Qualifiers
misc_feature           1..1278
                       note = A nucleic acid sequence obtained from Xenorhabdus
                        cabanillasiistrain 85908 encoding a TIC7661 PirB
                        pesticidal protein sequence.
source                 1..1278
                       mol_type = other DNA
                       organism = Xenorhabdus cabanillasii
SEQUENCE: 15
atgaatacta cacctattac tgtatctaca aatgaaacat cgcctttaat gactgacgta  60
atgcccatgg atctttatgc aatatccaca cctgattatg aatgggacat gtcgtcaatc  120
ataaaggatg ctgttattgg tggcatagga tttattccag gtccgggccc ggcaatatcc  180
ttcctgttag ggctattttg gcctcagcag aaagacaata cttgggagca aattctccag  240
aaagtagagc agatgataga gaatgctgtt ctacaaacta ttaaaggaat acttaatgga  300
gaagttcaag agatcaaagg gaaaatggaa catgtagaat ccatgctgaa aaactcgcct  360
ggcagtcagg aaagtcatga tgcatatatg ttcctggcga gatatctggt tagtatagat  420
gaaaaattca aatcttttga caatagaaca aattaccagc ttctcccaat gtatactaac  480
actattatgt tacagatccc ttattggaaa atgggaatag agaagaaaaa agatattggg  540
ctgacagata ttgaagttaa tgaattaaaa gaacttatcg ataaattggt tgataaggcc  600
aaaaactata ttcatacgat gtatactaat gaacataata atgctgtaaa cacatcaaca  660
gcagagagtg tcactaataa tttattatct gtaagaggat attgtttatt acacggttta  720
gaatgtattg agttaatcga gcatatacag aataatagcc ttgagagtgg tttctatcct  780
aaaattatca gttattcgac tgcgtttgat cgtcctacta acaaaatgag aattcaggct  840
cttacagaag atgatgcaat gcaggagcct ttcaaaccat ctttaatcaa tgggaaatat  900
aataaaatcc aatccttgac tggatatgta caaagaattg ggaatgcacc tagagttggt  960
ggtatcagaa tcacatttac caacggctca tcttatacac ttggtacagt gacctcagaa  1020
acgcattcaa ttaagctaaa cgatagtgtt atcgaaagct tggaagtatg ggggaatggt  1080
gctgttgatg aggcgttatt taagttaagt gatgggcgtt tattgcgtat tggtgagcgc  1140
tacgcgaaaa aatacagaaa atatgctgtt gataatcact atattgcggg gatttactta  1200
gccagcgatg agccttcact tgctggtcaa gccgcaggta ttgccgtttc atatcatatg  1260
atggctgaca aaaaataa                                                1278

SEQ ID NO: 16          moltype = AA  length = 425
FEATURE                Location/Qualifiers
REGION                 1..425
                       note = The amino acid sequence of the TIC7661 PirB protein.
source                 1..425
                       mol_type = protein
                       organism = Xenorhabdus cabanillasii
SEQUENCE: 16
```

```
MNTTPITVST NETSPLMTDV MPMDLYAIST PDYEWDMSSI IKDAVIGGIG FIPGPGPAIS  60
FLLGLFWPQQ KDNTWEQILQ KVEQMIENAV LQTIKGILNG EVQEIKGKME HVESMLKNSP  120
GSQESHDAYM FLARYLVSID EKFKSFDNRT NYQLLPMYTN TIMLQIPYWK MGIEKKKDIG  180
LTDIEVNELK ELIDKLVDKA KNYIHTMYTN EHNNAVNTST AESVTNNLLS VRGYCLLHGL  240
ECIELIEHIQ NNSLESGFYP KIISYSTAFD RPTNKMRIQA LTEDDAMQEP FKPSLINGKY  300
NKIQSLTGYV QRIGNAPRVG GIRITFTNGS SYTLGTVTSE THSIKLNDSV IESLEVWGNG  360
AVDEALFKLS DGRLLRIGER YAKKYRKYAV DNHYIAGIYL ASDEPSLAGQ AAGIAVSYHM  420
MADKK                                                              425

SEQ ID NO: 17          moltype = DNA  length = 1701
FEATURE                Location/Qualifiers
misc_feature           1..1701
                       note = A nucleic acid sequence encoding a PirAB fusion
                        protein, TIC9317comprised of the TIC7660 and TIC7661
                        coding sequences in operablelinkage and in frame.
source                 1..1701
                       mol_type = other DNA
                       organism = synthetic construct
SEQUENCE: 17
atgatcacaa taaatataaa tgtaaacggc aatgatgtta caggtacaaa taataatgaa  60
cctactccag tatcgacaac ttacggtcca aatacaccag catcagaacc ccctgtagtc  120
agtaattata gtgatataac aatagaaccg cattcttctg tgcaggcaac aagaattgat  180
acgcctgtta ttcctgaagc acgccccgat tactatgtag ccaactccgg ccctgcacca  240
tcagttaggg ctgtttttta ttggtctcat tctttcacat cagaatggtt cgaatcttcc  300
tctatcacag tgaaagcagg agaggacgga atattaaaag cacctggtaa ctctttatat  360
tacagcaaag tcgtcattta taatgatacg gataaacgag cctttgttac tggatataat  420
aaaatgaata ctacacctat tactgtatct acaaatgaaa catcgccttt aatgactgac  480
gtaatgccca tggatcttta tgcaatatcc acacctgatt atgaatggga catgtcgtca  540
atcataaagg atgctgttat tggtggcata ggatttattc caggtccggg cccggcaata  600
tccttcctgt tagggctatt ttggcctcag cagaaagaca atacttggga gcaaattctc  660
cagaaagtag agcagatgat agagaatgct gttctacaaa ctattaaagg aatacttaat  720
ggagaagttc aagagatcaa agggaaaatg gaacatgtag aatccatgct gaaaaactcg  780
cctggcagtc aggaaagtca tgatgcatat atgttcctgg cgagatatct ggttagtata  840
gatgaaaaat tcaaatcttt tgacaataga acaaattacc agcttctccc aatgtatact  900
aacactatta tgttacagat cccttattgg aaaatgggaa tagagaagaa aaaagatatt  960
gggctgacag atattgaagt taatgaatta aaagaactta tcgataaatt ggttgataag  1020
gccaaaaact atattcatac gatgtatact aatgaacata ataatgctgt aaacacatca  1080
acagcagaga gtgtcactaa taatttatta tctgtaagag gatattgttt attacacggt  1140
ttagaatgta ttgagttaat cgagcatata cagaataata gccttgagag tggtttctat  1200
cctaaaatta tcagttattc gactgcgttt gatcgtccta ctaacaaaat gagaattcag  1260
gctcttacag aagatgatgc aatgcaggag cctttcaaac catctttaat caatgggaaa  1320
tataataaaa tccaatcctt gactggatat gtacaaagaa ttgggaatgc acctagagtt  1380
ggtggtatca gaatcacatt taccaacggc tcatcttata cacttggtac agtgacctca  1440
gaaacgcatt caattaagct aaacgatagt gttatcgaaa gcttggaagt atgggggaat  1500
ggtgctgttg atgaggcgtt atttaagtta agtgatgggc gtttattgcg tattggtgag  1560
cgctacgcga aaaaatacag aaaatatgct gttgataatc actatattgc ggggatttac  1620
ttagccagcg atgagccttc acttgctggt caagccgcag gtattgccgt ttcatatcat  1680
atgatggctg acaaaaaata a                                             1701

SEQ ID NO: 18          moltype = AA  length = 566
FEATURE                Location/Qualifiers
REGION                 1..566
                       note = The amino acid sequence of the TIC9317 PirAB fusion
                        protein.
source                 1..566
                       mol_type = protein
                       organism = synthetic construct
SEQUENCE: 18
MITININVNG NDVTGTNNNE PTPVSTTYGP NTPASEPPVV SNYSDITIEP HSSVQATRID  60
TPVIPEARPD YYVANSGPAP SVRAVFYWSH SFTSEWFESS SITVKAGEDG ILKAPGNSLY  120
YSKVVIYNDT DKRAFVTGYN KMNTTPITVS TNETSPLMTD VMPMDLYAIS TPDYEWDMSS  180
IIKDAVIGGI GFIPGPGPAI SFLLGLFWPQ QKDNTWEQIL QKVEQMIENA VLQTIKGILN  240
GEVQEIKGKM EHVESMLKNS PGSQESHDAY MFLARYLVSI DEKFKSFDNR TNYQLLPMYT  300
NTIMLQIPYW KMGIEKKKDI GLTDIEVNEL KELIDKLVDK AKNYIHTMYT NEHNNAVNTS  360
TAESVTNNLL SVRGYCLLHG LECIELIEHI QNNSLESGFY PKIISYSTAF DRPTNKMRIQ  420
ALTEDDAMQE PFKPSLINGK YNKIQSLTGY VQRIGNAPRV GGIRITFTNG SSYTLGTVTS  480
ETHSIKLNDS VIESLEVWGN GAVDEALFKL SDGRLLRIGE RYAKKYRKYA VDNHYIAGIY  540
LASDEPSLAG QAAGIAVSYH MMADKK                                        566

SEQ ID NO: 19          moltype = DNA  length = 420
FEATURE                Location/Qualifiers
misc_feature           1..420
                       note = A nucleic acid sequence obtained from Xenorhabdus
                        ehlersii strain85887 encoding a TIC7662 PirA pesticidal
                        protein sequence.
source                 1..420
                       mol_type = other DNA
                       organism = Xenorhabdus ehlersii
SEQUENCE: 19
```

```
atgagtacaa tcaatatcaa tataagtagc agtaccgtta ccgtcatcac gaataacgga  60
gaaacgccag tcccactcac ttacaataca aatacacctg aatcagaacc tcttaccgtc  120
aatccttata gggatatgac aatagagcca cgctcttcta ttgaagcaac aaggattgat  180
acaccgatta ttcccgaaac acgccctaat tattatgtag ccaattcagg cccggcttca  240
tcagttaggg ccgtttttta ttggtcccat tctttcacat cacaatggtt cgaatattcc  300
tctatcatcg tcaaagccgg ggaagatggc atattagaat caccaagcaa ttctttatat  360
tacagcaaag tcgtcattta taatgatacc gataaacgcg cctttgtgac gggatataat  420

SEQ ID NO: 20          moltype = AA  length = 141
FEATURE                Location/Qualifiers
REGION                 1..141
                       note = The amino acid sequence of the TIC7662 PirA protein.
source                 1..141
                       mol_type = protein
                       organism = Xenorhabdus ehlersii
SEQUENCE: 20
MSTININISS STVTVITNNG ETPVPLTYNT NTPESEPLTV NPYRDMTIEP RSSIEATRID  60
TPIIPETRPN YYVANSGPAS SVRAVFYWSH SFTSQWFEYS SIIVKAGEDG ILESPSNSLY  120
YSKVVIYNDT DKRAFVTGYN K                                            141

SEQ ID NO: 21          moltype = DNA  length = 1278
FEATURE                Location/Qualifiers
misc_feature           1..1278
                       note = A nucleic acid sequence obtained from Xenorhabdus
                        ehlersii strain85887 encoding a TIC7663 PirB pesticidal
                        protein sequence.
source                 1..1278
                       mol_type = other DNA
                       organism = Xenorhabdus ehlersii
SEQUENCE: 21
atgaatacca ctctgattaa tgtatctgaa aaagaaacat tgcctgtaca aactgatatc  60
atgcttatcg cgccttattc agtatcgacc cccgattatg aatgggatat gtcctcactc  120
atcaaggatg ccattattgg tggcgtaggg tttattcccg tcgtaggttc cgcaatgtcc  180
ttcctgctag gattattttg gccccaacag aaagataata cttgggagca aattctccaa  240
aaagtcgagc agatgatcga gaatgcccag ctaaatacga ttaaaggaat acttaatggc  300
gatatacaag agatcaaagg aaaaatggag catgtacaat acatgttgga aacctcgccg  360
ggcagtcaag aaagtcatga tgcctatatg ttcctggcca gatatctggt gagtatcgat  420
gagaaattta agtcttttga taataaaaca aactatcaaa ttttgccgat gtatacgaac  480
acggttatgt tgcagatccc ttattggaaa atggggatcg agaagaaaaa tgatattggg  540
ctgaccgata ttgaagtcaa tgagttaaaa cagcttatcg acacattggt tgacagagcc  600
aggaactata ttcatacgat gtatgaaaga gaatatgata atgccatcaa cacctcaacc  660
gcggcgagcg tcactaataa tttattgtcc gtcagaggat attgcctgtt acacggttta  720
gagtgtattg aaaccattga acatctgcaa aataatagcc ttaatagtgg tttctatcct  780
aaaaccatta gttattcaac ggtatttgat cgtcccacga acaaaacgag aattcaggct  840
ctgaccgaag atgaccaaat gcaagagcct ttcaagccag ctttaattgg cggtaagtac  900
aataaaataa aatcattgct tggctatgta cgaagaattg ggaatgcccc cagagtgggg  960
ggaattaagg tcacctttac caacggatca tcttatacac ttggcacagt cacatcagaa  1020
acggactcaa ttgagctaaa tgagagtgtt atcgaaagat tagaagtatg gggcaatggt  1080
gctgttgatg aggcattatt tacgttaagc gatgggcgcc aactcaggat cggcgagcgc  1140
tacgcgaaaa aatacagaaa atatgctgtt gatggacact atatttcagg gctgtactta  1200
gccagcgatg aaccttccct tgctggtcag gccgcaggta ttgccgtttc ataccatatg  1260
cttgctgata aaaaataa                                                1278

SEQ ID NO: 22          moltype = AA  length = 425
FEATURE                Location/Qualifiers
REGION                 1..425
                       note = The amino acid sequence of the TIC7663 PirB protein.
source                 1..425
                       mol_type = protein
                       organism = Xenorhabdus ehlersii
SEQUENCE: 22
MNTTLINVSE KETLPVQTDI MLIAPYSVST PDYEWDMSSL IKDAIIGGVG FIPVVGSAMS  60
FLLGLFWPQQ KDNTWEQILQ KVEQMIENAQ LNTIKGILNG DIQEIKGKME HVQYMLETSP  120
GSQESHDAYM FLARYLVSID EKFKSFDNKT NYQILPMYTN TVMLQIPYWK MGIEKKNDIG  180
LTDIEVNELK QLIDTLVDRA RNYIHTMYER EYDNAINTST AASVTNNLLS VRGYCLLHGL  240
ECIETIEHLQ NNSLNSGFYP KTISYSTVFD RPTNKTRIQA LTEDDQMQEP FKPALIGGKY  300
NKIKSLLGYV RRIGNAPRVG GIKVTFTNGS SYTLGTVTSE TDSIELNESV IERLEVWGNG  360
AVDEALFTLS DGRQLRIGER YAKKYRKYAV DGHYISGLYL ASDEPSLAGQ AAGIAVSYHM  420
LADKK                                                              425

SEQ ID NO: 23          moltype = DNA  length = 1701
FEATURE                Location/Qualifiers
misc_feature           1..1701
                       note = A nucleic acid sequence encoding a PirAB fusion
                        protein, TIC9318comprised of the TIC7662 and TIC7663
                        coding sequences in operablelinkage and in frame.
source                 1..1701
                       mol_type = other DNA
                       organism = synthetic construct
```

```
SEQUENCE: 23
atgagtacaa tcaatatcaa tataagtagc agtaccgtta ccgtcatcac gaataacgga  60
gaaacgccag tcccactcac ttacaataca aatacacctg aatcagaacc tcttaccgtc  120
aatccttata gggatatgac aatagagcca cgctcttcta ttgaagcaac aaggattgat  180
acaccgatta ttcccgaaac acgccctaat tattatgtag ccaattcagg cccggcttca  240
tcagttaggg ccgtttttta ttggtcccat tctttcacat cacaatggtt cgaatattcc  300
tctatcatcg tcaaagccgg ggaagatggc atattagaat caccaagcaa ttctttatat  360
tacagcaaag tcgtcattta taatgatacc gataaacgcg cctttgtgac gggatataat  420
aagatgaata ccactctgat taatgtatct gaaaaagaaa cattgcctgt acaaactgat  480
atcatgctta tcgcgcctta ttcagtatcg acccccgatt atgaatggga tatgtcctca  540
ctcatcaagg atgccattat tggtggcgta gggtttattc ccgtcgtagg ttccgcaatg  600
tccttcctgc taggattatt ttggccccaa cagaaagata atacttggga gcaaattctc  660
caaaaagtcg agcagatgat cgagaatgcc cagctaaata cgattaaagg aatacttaat  720
ggcgatatac aagagatcaa aggaaaaatg gagcatgtac aatacatgtt ggaaacctcg  780
ccgggcagtc aagaaagtca tgatgcctat atgttcctgg ccagatatct ggtgagtatc  840
gatgagaaat ttaagtcttt tgataataaa acaaactatc aaattttgcc gatgtatacg  900
aacacggtta tgttgcagat cccttattgg aaaatgggga tcgagaagaa aaatgatatt  960
gggctgaccg atattgaagt caatgagtta aaacagctta tcgacacatt ggttgacaga  1020
gccaggaact atattcatac gatgtatgaa agagaatatg ataatgccat caacacctca  1080
accgcggcga gcgtcactaa taatttattg tccgtcagag gatattgcct gttacacggt  1140
ttagagtgta ttgaaaccat tgaacatctg caaaataata gccttaatag tggtttctat  1200
cctaaaacca ttagttattc aacggtattt gatcgtccca cgaacaaaac gagaattcag  1260
gctctgaccg aagatgacca aatgcaagag cctttcaagc cagctttaat tggcggtaag  1320
tacaataaaa taaaatcatt gcttggctat gtacgaagaa ttgggaatgc ccccagagtg  1380
gggggaatta aggtcacctt taccaacgga tcatcttata cacttggcac agtcacatca  1440
gaaacggact caattgagct aaatgagagt gttatcgaaa gattagaagt atggggcaat  1500
ggtgctgttg atgaggcatt atttacgtta agcgatgggc gccaactcag gatcggcgag  1560
cgctacgcga aaaaatacag aaaatatgct gttgatggac actatatttc agggctgtac  1620
ttagccagcg atgaaccttc ccttgctggt caggccgcag gtattgccgt ttcataccat  1680
atgcttgctg ataaaaaata a                                          1701

SEQ ID NO: 24           moltype = AA  length = 566
FEATURE                 Location/Qualifiers
REGION                  1..566
                        note = The amino acid sequence of the TIC9318 PirAB fusion
                         protein.
source                  1..566
                        mol_type = protein
                        organism = synthetic construct
SEQUENCE: 24
MSTININISS STVTVITNNG ETPVPLTYNT NTPESEPLTV NPYRDMTIEP RSSIEATRID  60
TPIIPETRPN YYVANSGPAS SVRAVFYWSH SFTSQWFEYS SIIVKAGEDG ILESPSNSLY  120
YSKVVIYNDT DKRAFVTGYN KMNTTLINVS EKETLPVQTD IMLIAPYSVS TPDYEWDMSS  180
LIKDAIIGGV GFIPVVGSAM SFLLGLFWPQ QKDNTWEQIL QKVEQMIENA QLNTIKGILN  240
GDIQEIKGKM EHVQYMLETS PGSQESHDAY MFLARYLVSI DEKFKSFDNK TNYQILPMYT  300
NTVMLQIPYW KMGIEKKNDI GLTDIEVNEL KQLIDTLVDR ARNYIHTMYE REYDNAINTS  360
TAASVTNNLL SVRGYCLLHG LECIETIEHL QNNSLNSGFY PKTISYSTVF DRPTNKTRIQ  420
ALTEDDQMQE PFKPALIGGK YNKIKSLLGY VRRIGNAPRV GGIKVTFTNG SSYTLGTVTS  480
ETDSIELNES VIERLEVWGN GAVDEALFTL SDGRQLRIGE RYAKKYRKYA VDGHYISGLY  540
LASDEPSLAG QAAGIAVSYH MLADKK                                     566

SEQ ID NO: 25           moltype = DNA  length = 408
FEATURE                 Location/Qualifiers
misc_feature            1..408
                        note = A nucleic acid sequence obtained from Xenorhabdus
                         poinarii strain86198 encoding a TIC7664 PirA pesticidal
                         protein sequence.
source                  1..408
                        mol_type = other DNA
                        organism = Xenorhabdus poinarii
SEQUENCE: 25
atgatcacaa tcaatatcag tggtggtaat gtaacaatta ataacaatat cagttcagta  60
acggatatcc aaaaacccct tgatgcagaa cccctctcag tcacgaatta taaggatctg  120
acaatagagc cgcactcatc tattcaagca accagaacgg acacccccat tattcctgaa  180
acacgcccta attattatgt tgctaactca ggccctgctt catccgttaa agcggtgttt  240
tattggtcgc attcgtttac atcggaatgg ttcgagtatt catctatcat agtaaaagca  300
ggagaggatg gaatattaaa atcaccgagt aatgccgtat attacagtaa agtagtaatt  360
tataatgata cagataagcg ggcttttgtg actggatata acatgtaa             408

SEQ ID NO: 26           moltype = AA  length = 135
FEATURE                 Location/Qualifiers
REGION                  1..135
                        note = The amino acid sequence of the TIC7664 PirA protein.
source                  1..135
                        mol_type = protein
                        organism = Xenorhabdus poinarii
SEQUENCE: 26
MITINISGGN VTINNNISSV TDIQKPLDAE PLSVTNYKDL TIEPHSSIQA TRTDTPIIPE  60
TRPNYYVANS GPASSVKAVF YWSHSFTSEW FEYSSIIVKA GEDGILKSPS NAVYYSKVVI  120
```

```
YNDTDKRAFV TGYNM                                                  135

SEQ ID NO: 27          moltype = DNA  length = 1245
FEATURE                Location/Qualifiers
misc_feature           1..1245
                       note = A nucleic acid sequence obtained from Xenorhabdus
                        poinarii strain86198 encoding a TIC7665 PirB pesticidal
                        protein sequence.
source                 1..1245
                       mol_type = other DNA
                       organism = Xenorhabdus poinarii
SEQUENCE: 27
atgaataata gtccaatgaa tgatcagtta tcaatagcac cttattcaat ttcgacaccc  60
aattatgaat gggatatgtc atcaatcata aaagatgcca ttatcggtgg cataggattt  120
attcccggac caggctctgc aatctctttt ttattagggc tgttctggcc tcaacagaca  180
gacaatacct gggatcaaat cctccaaaaa atcgaacaga tgatagaaga agcgaattta  240
aaaaccatta aaggtatatt aaatggagat atacaagaaa ttaaaggaaa aatggaccat  300
gtgcaatata tgctagagaa ttctcctggc agccaggaaa gccatgatgc ttatatgttt  360
ttagcaaggt ttttggtcag tattgatgaa aaattcaaat ctttcgatga tagaacaaat  420
tatcaaattc ttcccatgta tacgaacacc attatgttac aagcgcctta ttggaaaatg  480
ggcctcgaaa agaaagagga tatcggttta agcgatattg aagttagcga attaaaagaa  540
cttatcgata aattatatac taaatcatat gattatatcc ataacacgta taatcgtgaa  600
tatgataatg caatcaatac gtcaaccgca gagagtatca ccaataattt attgtctgtc  660
agaggatatt gtttattaca tggttgtgaa tgtcttgaag ttattgcgca tatacaaaac  720
aatagccttg ataaaggctt ctaccctaaa acgatcagct attcgagtgt tttcgatcgt  780
cctacaaaca aaatgaggat tcaggcgctt acagaagatg accaaatgca agaaccgttc  840
aaaccttctt tcgtcaatgg tcaatataat aaaataaaat cattggaggg ttatgtcaca  900
aggatcggca atgccccccg agtcggtgga attaaaatca catttgaaaa caacgcatct  960
tatactcttg gtactgtgac ttcagaaaca acctttattg aactcaatga gagtgttata  1020
accagcatag aagtgtgggg aaatggggcc gttgatgagg cattctttac attgagtgac  1080
ggtcgccaaa tgcggcttgg tcaacgctat gccagtcgct acagaaaata tgctgtcgat  1140
ggtcattata tctcaggatt gtacttagcc agtgatgaac catcccttgc tggtcaagcc  1200
gccggtattg ccgtttcata tcatatgatt gttgataaac aataa                 1245

SEQ ID NO: 28          moltype = AA  length = 414
FEATURE                Location/Qualifiers
REGION                 1..414
                       note = The amino acid sequence of the TIC7665 PirB protein.
source                 1..414
                       mol_type = protein
                       organism = Xenorhabdus poinarii
SEQUENCE: 28
MNNSPMNDQL SIAPYSISTP NYEWDMSSII KDAIIGGIGF IPGPGSAISF LLGLFWPQQT  60
DNTWDQILQK IEQMIEEANL KTIKGILNGD IQEIKGKMDH VQYMLENSPG SQESHDAYMF  120
LARFLVSIDE KFKSFDDRTN YQILPMYTNT IMLQAPYWKM GLEKKEDIGL SDIEVSELKE  180
LIDKLYTKSY DYIHNTYNRE YDNAINTSTA ESITNNLLSV RGYCLLHGCE CLEVIAHIQN  240
NSLDKGFYPK TISYSSVFDR PTNKMRIQAL TEDDQMQEPF KPSFVNGQYN KIKSLEGYVT  300
RIGNAPRVGG IKITFENNAS YTLGTVTSET TFIELNESVI TSIEVWGNGA VDEAFFTLSD  360
GRQMRLGQRY ASRYRKYAVD GHYISGLYLA SDEPSLAGQA AGIAVSYHMI VDKQ        414

SEQ ID NO: 29          moltype = DNA  length = 1650
FEATURE                Location/Qualifiers
misc_feature           1..1650
                       note = A nucleic acid sequence encoding a PirAB fusion
                        protein, TIC9319comprised of the TIC7664 and TIC7665
                        coding sequences in operablelinkage and in frame.
source                 1..1650
                       mol_type = other DNA
                       organism = synthetic construct
SEQUENCE: 29
atgatcacaa tcaatatcag tggtggtaat gtaacaatta ataacaatat cagttcagta  60
acggatatcc aaaaacccct tgatgcagaa cccctctcag tcacgaatta taaggatctg  120
acaatagagc cgcactcatc tattcaagca accagaacgg acaccccccat tattcctgaa  180
acacgcccta attattatgt tgctaactca ggccctgctt catccgttaa agcggtgttt  240
tattggtcgc attcgtttac atcggaatgg ttcgagtatt catctatcat agtaaaagca  300
ggagaggatg gaatattaaa atcaccgagt aatgccgtat attacagtaa agtagtaatt  360
tataatgata cagataagcg ggcttttgtg actggatata acatgatgaa taatagtcca  420
atgaatgatc agttatcaat agcaccttat tcaatttcga cacccaatta tgaatgggat  480
atgtcatcaa tcataaaaga tgccattatc ggtggcatag gatttattcc cggaccaggc  540
tctgcaatct cttttttatt agggctgttc tggcctcaac agacagacaa tacctgggat  600
caaatcctcc aaaaaatcga acagatgata gaagaagcga atttaaaaac cattaaaggt  660
atattaaatg gagatataca agaaattaaa ggaaaaatgg accatgtgca atatatgcta  720
gagaattctc ctggcagcca ggaaagccat gatgcttata tgtttttagc aaggtttttg  780
gtcagtattg atgaaaaatt caaatctttc gatgatagaa caaattatca aattcttccc  840
atgtatacga acaccattat gttacaagcg ccttattgga aaatgggcct cgaaaagaaa  900
gaggatatcg gtttaagcga tattgaagtt agcgaattaa aagaacttat cgataaatta  960
tatactaaat catatgatta tatccataac acgtataatc gtgaatatga taatgcaatc  1020
aatacgtcaa ccgcagagag tatcaccaat aatttattgt ctgtcagagg atattgttta  1080
ttacatggtt gtgaatgtct tgaagttatt gcgcatatac aaaacaatag ccttgataaa  1140
```

```
ggcttctacc ctaaaacgat cagctattcg agtgttttcg atcgtcctac aaacaaaatg  1200
aggattcagg cgcttacaga agatgaccaa atgcaagaac cgttcaaacc ttctttcgtc  1260
aatggtcaat ataataaaat aaaatcattg gagggttatg tcacaaggat cggcaatgcc  1320
ccccgagtcg gtggaattaa aatcacattt gaaaacaacg catcttatac tcttggtact  1380
gtgacttcag aaacaacctt tattgaactc aatgagagtg ttataaccag catagaagtg  1440
tggggaaatg gggccgttga tgaggcattc tttacattga gtgacggtcg ccaaatgcgg  1500
cttggtcaac gctatgccag tcgctacaga aaatatgctg tcgatggtca ttatatctca  1560
ggattgtact tagccagtga tgaaccatcc cttgctggtc aagccgccgg tattgccgtt  1620
tcatatcata tgattgttga taaacaataa                                    1650

SEQ ID NO: 30          moltype = AA  length = 549
FEATURE                Location/Qualifiers
REGION                 1..549
                       note = The amino acid sequence of the TIC9319 PirAB fusion
                        protein.
source                 1..549
                       mol_type = protein
                       organism = synthetic construct
SEQUENCE: 30
MITINISGGN VTINNNISSV TDIQKPLDAE PLSVTNYKDL TIEPHSSIQA TRTDTPIIPE  60
TRPNYYVANS GPASSVKAVF YWSHSFTSEW FEYSSIIVKA GEDGILKSPS NAVYYSKVVI  120
YNDTDKRAFV TGYNMMNNSP MNDQLSIAPY SISTPNYEWD MSSIIKDAII GGIGFIPGPG  180
SAISFLLGLF WPQQTDNTWD QILQKIEQMI EEANLKTIKG ILNGDIQEIK GKMDHVQYML  240
ENSPGSQESH DAYMFLARFL VSIDEKFKSF DDRTNYQILP MYTNTIMLQA PYWKMGLEKK  300
EDIGLSDIEV SELKELIDKL YTKSYDYIHN TYNREYDNAI NTSTAESITN NLLSVRGYCL  360
LHGCECLEVI AHIQNNSLDK GFYPKTISYS SVFDRPTNKM RIQALTEDDQ MQEPFKPSFV  420
NGQYNKIKSL EGYVTRIGNA PRVGGIKITF ENNASYTLGT VTSETTFIEL NESVITSIEV  480
WGNGAVDEAF FTLSDGRQMR LGQRYASRYR KYAVDGHYIS GLYLASDEPS LAGQAAGIAV  540
SYHMIVDKQ                                                           549

SEQ ID NO: 31          moltype = DNA  length = 402
FEATURE                Location/Qualifiers
misc_feature           1..402
                       note = A nucleic acid sequence obtained from Photorhabdus
                        luminescensstrain 86197 encoding a TIC7666 PirA pesticidal
                        protein sequence.
source                 1..402
                       mol_type = other DNA
                       organism = Photorhabdus luminescens
SEQUENCE: 31
atgtctagaa taaccattgt tgttgattca gatgatcaga aagcagaatt ttattctaat  60
tctcctgttc cagtatataa agatttaaat gcagttggtc ctttgagtga tgtgactata  120
tcacctcatg ccagtgtgga agtgtttaga atagatacac cagtaattcc agaatccaga  180
agctctctga gagttgtaaa tacagggcta tcaaatagtg ttacggctaa attttactgg  240
tctcatagtt ttacctctga atggtttgag tctggttcta tagatgtagg attaggagaa  300
gagaaggtgt taaacgtgcc tagcaactct ttttattata gtaaatttgt tatctataat  360
aacacggaca aagttgctta tgtgacggca aatttggttt aa                      402

SEQ ID NO: 32          moltype = AA  length = 133
FEATURE                Location/Qualifiers
REGION                 1..133
                       note = The amino acid sequence of the TIC7666 PirA protein.
source                 1..133
                       mol_type = protein
                       organism = Photorhabdus luminescens
SEQUENCE: 32
MSRITIVVDS DDQKAEFYSN SPVPVYKDLN AVGPLSDVTI SPHASVEVFR IDTPVIPESR  60
SSLRVVNTGL SNSVTAKFYW SHSFTSEWFE SGSIDVGLGE EKVLNVPSNS FYYSKFVIYN  120
NTDKVAYVTA NLV                                                      133

SEQ ID NO: 33          moltype = DNA  length = 1260
FEATURE                Location/Qualifiers
misc_feature           1..1260
                       note = A nucleic acid sequence obtained from Photorhabdus
                        luminescensstrain 86197 encoding a TIC7667 pesticidal PirB
                        protein sequence.
source                 1..1260
                       mol_type = other DNA
                       organism = Photorhabdus luminescens
SEQUENCE: 33
atgcatacag aaaatgtttt agacataaga accattgtgg ctaatgaata tgctgtaaaa  60
acgagtgcat tagagtggga tgttactgat attgtaaaaa atgcaatcat agggggaata  120
tcctttatcc cttcggttgg tcccgctata tcttttttag tcggtttatt ctggcctcaa  180
tcgaaagaaa atatatggga agggattgtc aaacaaattg aaaggatgat agaggagtct  240
gcgttaaaga cgattaaagg tatccttgct ggtgatattg catatataca agaacgaatg  300
gcaaccgttg ctgatcttct tgataagcat ccaggatcag aagaagcgag gagtgctttt  360
aataacctgg cagaaaatat agatggctat cacaaaaagt ttagtaattt ttcggatgat  420
gttaattatc agatattacc catgttttct actacggtta tgatgcagat aacatattgg  480
gttgctggtt tagagagaaa agatgaaatt gggcttagta atattgatgt tgaaaaagtc  540
```

```
cgaggattaa ttaaaaagac ggtagaacag gctaatagtt atattaacaa tatatatgat  600
agagagctta atgatgctct taataactcg acggctgaca ctgttgcaaa taatgttatg  660
tctgttcatg gtcactgtcg tttacatggg attgaatata tcagtatttg ggataaatta  720
agtgaagctg agtcggtaaa taataaaatc tatgttgatg ttttaagtta ttctactttc  780
tttgaccgtc aaacagcaaa agccagaatt caggcattga ctccagagaa agatatgact  840
ccacctctca aaccggctct taatggagga aaaagaagaa agatagattc gttaacggga  900
catattgtgc gtattggagg ggctgcgagg gtaggagggc tgacagttgt atttgatgat  960
ggtaatcgcc atcaattagg tacaatatct ggtgagacgt catctatttc tctgaatggt  1020
agtcgaatta ccagtttgga agtatgggga aatggtgctg ttgatcaagc ggtctttact  1080
ttaaatgatg gtcgttcatt gtcattgggc tcgcctggaa catctcgata taggaagttt  1140
tatgttggtg aaagccacta tattgcaggg atatatttgt ccagtgatta caacccatta  1200
gctggtcagg cagcaaatat tgctgtatct tatcagttga taaatgatga tgaaaaataa  1260

SEQ ID NO: 34           moltype = AA  length = 419
FEATURE                 Location/Qualifiers
REGION                  1..419
                        note = The amino acid sequence of the TIC7667 PirB protein.
source                  1..419
                        mol_type = protein
                        organism = Photorhabdus luminescens
SEQUENCE: 34
MHTENVLDIR TIVANEYAVK TSALEWDVTD IVKNAIIGGI SFIPSVGPAI SFLVGLFWPQ  60
SKENIWEGIV KQIERMIEES ALKTIKGILA GDIAYIQERM ATVADLLDKH PGSEEARSAF  120
NNLAENIDGY HKKFSNFSDD VNYQILPMFS TTVMMQITYW VAGLERKDEI GLSNIDVEKV  180
RGLIKKTVEQ ANSYINNIYD RELNDALNNS TADTVANNVM SVHGHCRLHG IEYISIWDKL  240
SEAESVNNKI YVDVLSYSTF FDRQTAKARI QALTPEKDMT PPLKPALNGG KRRKIDSLTG  300
HIVRIGGAAR VGGLTVVFDD GNRHQLGTIS GETSSISLNG SRITSLEVWG NGAVDQAVFT  360
LNDGRSLSLG SPGTSRYRKF YVGESHYIAG IYLSSDYNPL AGQAANIAVS YQLINDDEK   419

SEQ ID NO: 35           moltype = DNA  length = 1659
FEATURE                 Location/Qualifiers
misc_feature            1..1659
                        note = A nucleic acid sequence encoding a PirAB fusion
                         protein, TIC9322comprised of the TIC7666 and TIC7667
                         coding sequences in operablelinkage and in frame.
source                  1..1659
                        mol_type = other DNA
                        organism = synthetic construct
SEQUENCE: 35
atgtctagaa taaccattgt tgttgattca gatgatcaga aagcagaatt ttattctaat  60
tctcctgttc cagtatataa agatttaaat gcagttggtc ctttgagtga tgtgactata  120
tcacctcatg ccagtgtgga agtgtttaga atagatacac cagtaattcc agaatccaga  180
agctctctga gagttgtaaa tacagggcta tcaaatagtg ttacggctaa attttactgg  240
tctcatagtt ttacctctga atggtttgag tctggttcta tagatgtagg attaggagaa  300
gagaaggtgt taaacgtgcc tagcaactct ttttattata gtaaatttgt tatctataat  360
aacacggaca aagttgctta tgtgacggca aatttggtta tgcatacaga aaatgtttta  420
gacataagaa ccattgtggc taatgaatat gctgtaaaaa cgagtgcatt agagtgggat  480
gttactgata ttgtaaaaaa tgcaatcata gggggaatat cctttatccc ttcggttggt  540
cccgctatat ctttttagt cggtttattc tggcctcaat cgaaagaaaa tatatgggaa  600
gggattgtca aacaaattga aaggatgata gaggagtctg cgttaaagac gattaaaggt  660
atccttgctg gtgatattgc atatatacaa gaacgaatgg caaccgttgc tgatcttctt  720
gataagcatc caggatcaga agaagcgagg agtgctttta ataacctggc agaaaatata  780
gatggctatc acaaaaagtt tagtaatttt tcggatgatg ttaattatca gatattaccc  840
atgttttcta ctacggttat gatgcagata acatattggg ttgctggttt agagagaaaa  900
gatgaaattg ggcttagtaa tattgatgtt gaaaaagtcc gaggattaat taaaaagacg  960
gtagaacagg ctaatagtta tattaacaat atatatgata gagagcttaa tgatgctctt  1020
aataactcga cggctgacac tgttgcaaat aatgttatgt ctgttcatgg tcactgtcgt  1080
ttacatggga ttgaatatat cagtatttgg gataaattaa gtgaagctga gtcggtaaat  1140
aataaaatct atgttgatgt tttaagttat tctactttct ttgaccgtca aacagcaaaa  1200
gccagaattc aggcattgac tccagagaaa gatatgactc cacctctcaa accggctctt  1260
aatggaggaa aaagaagaaa gatagattcg ttaacgggac atattgtgcg tattggaggg  1320
gctgcgaggg taggagggct gacagttgta tttgatgatg gtaatcgcca tcaattaggt  1380
acaatatctg gtgagacgtc atctatttct ctgaatggta gtcgaattac cagtttggaa  1440
gtatggggaa atggtgctgt tgatcaagcg gtctttactt taaatgatgg tcgttcattg  1500
tcattgggct cgcctggaac atctcgatat aggaagtttt atgttggtga aagccactat  1560
attgcaggga tatatttgtc cagtgattac aacccattag ctggtcaggc agcaaatatt  1620
gctgtatctt atcagttgat aaatgatgat gaaaaataa                        1659

SEQ ID NO: 36           moltype = AA  length = 552
FEATURE                 Location/Qualifiers
REGION                  1..552
                        note = The amino acid sequence of the TIC9322 PirAB fusion
                         protein.
source                  1..552
                        mol_type = protein
                        organism = synthetic construct
SEQUENCE: 36
MSRITIVVDS DDQKAEFYSN SPVPVYKDLN AVGPLSDVTI SPHASVEVFR IDTPVIPESR  60
SSLRVVNTGL SNSVTAKFYW SHSFTSEWFE SGSIDVGLGE EKVLNVPSNS FYYSKFVIYN  120
```

```
NTDKVAYVTA NLVMHTENVL DIRTIVANEY AVKTSALEWD VTDIVKNAII GGISFIPSVG  180
PAISFLVGLF WPQSKENIWE GIVKQIERMI EESALKTIKG ILAGDIAYIQ ERMATVADLL  240
DKHPGSEEAR SAFNNLAENI DGYHKKFSNF SDDVNYQILP MFSTTVMMQI TYWVAGLERK  300
DEIGLSNIDV EKVRGLIKKT VEQANSYINN IYDRELNDAL NNSTADTVAN NVMSVHGHCR  360
LHGIEYISIW DKLSEAESVN NKIYVDVLSY STFFDRQTAK ARIQALTPEK DMTPPLKPAL  420
NGGKRRKIDS LTGHIVRIGG AARVGGLTVV FDDGNRHQLG TISGETSSIS LNGSRITSLE  480
VWGNGAVDQA VFTLNDGRSL SLGSPGTSRY RKFYVGESHY IAGIYLSSDY NPLAGQAANI  540
AVSYQLINDD EK                                                     552

SEQ ID NO: 37          moltype = DNA  length = 402
FEATURE                Location/Qualifiers
misc_feature           1..402
                       note = A nucleic acid sequence obtained from Photorhabdus
                        luminescensstrain 86194 encoding a TIC7668 PirA pesticidal
                        protein sequence.
source                 1..402
                       mol_type = other DNA
                       organism = Photorhabdus luminescens
SEQUENCE: 37
atgtctagaa taactattgt tgttgattca gatgaacaga aagcagaagt ttactctaat  60
tcccctgttc cagtacataa agacttaaat gcagttggtc ctttgagtga tgtgactata  120
tcacctcatg ctagtgtgga agtatttaga atagatacac caataattcc agaatccaga  180
agatctctga gagttgtaaa taccgggcta gcaaatagtg tcacggctaa attttactgg  240
tctcatagtt ttacctctga atggtttgag tctggttcta tagatgtagg attaggagaa  300
gagaaggtgt taaacgtgcc taataactct ttttattata gtaaatttgt tatctataat  360
aatacggata aagttgctta tgtgacggca aatttggttt aa                    402

SEQ ID NO: 38          moltype = AA  length = 133
FEATURE                Location/Qualifiers
REGION                 1..133
                       note = The amino acid sequence of the TIC7668 PirA protein.
source                 1..133
                       mol_type = protein
                       organism = Photorhabdus luminescens
SEQUENCE: 38
MSRITIVVDS DEQKAEVYSN SPVPVHKDLN AVGPLSDVTI SPHASVEVFR IDTPIIPESR  60
RSLRVVNTGL ANSVTAKFYW SHSFTSEWFE SGSIDVGLGE EKVLNVPNNS FYYSKFVIYN  120
NTDKVAYVTA NLV                                                    133

SEQ ID NO: 39          moltype = DNA  length = 1260
FEATURE                Location/Qualifiers
misc_feature           1..1260
                       note = A nucleic acid sequence obtained from Photorhabdus
                        luminescensstrain 86194 encoding a TIC7669 PirB pesticidal
                        protein sequence.
source                 1..1260
                       mol_type = other DNA
                       organism = Photorhabdus luminescens
SEQUENCE: 39
atgcatacag aaaatgtttt agacataaga accattgtgg ctaatgaata tgccgtaaaa  60
acgagtgcag tagagtggga tgttactgat attgtaaaaa atgcaatcat cgggggaata  120
tcttttatac cttcagttgg ccctgctata tcttttttag tcggtttatt ctggcctcaa  180
tcaaaagaaa atatatggga agggattgtc aaacaaattg aaaggatgat agaggagtct  240
gcattaaaga cgattaaagg tatccttgct ggtgatattg catatataca agaacgaatg  300
gcaaccgttg ctgatcttct tgataagcat ccgggatctg aagaagcgag gagtgctttt  360
aataacctgg cagaaaatat agatggttat cacaaaaaat ttaataattt ttccgatgat  420
gttaactatc agatattacc catgttttct actacggtta tgatgcagat aacatattgg  480
gtcgctggtt tagagagaag aaatgaaatc gggcttagtg atattgatat tgaaaaagtc  540
cgagggttaa tcaaaaagac ggtagaacag gcgaatagtt atattaataa tatatatgat  600
agagagctta atgatgctct taataactcg acggctgaca ctgttgcaaa taatgtgatg  660
tctgttcatg gtcactgtcg tttacatggg attgaatata tcagtatttg ggataaatta  720
agtgaagcag agtcagtaaa taatagaatc tatgttgatg ttttaagtta ttctactttc  780
tttgaccgtc aaacagcaaa agccagaatt caggcattga ctccagagaa agatatggct  840
ccacctctca aaccggctct taatgacggg aaaagaagaa agatcgattc gttaacggga  900
catattgtgc gtattggagg ggctccgaga gtcggagggc tgacagttgt atttgatgat  960
ggtagtagcc atcgattagg tacaatatct ggtgagacgg catctatttc tctgaatggc  1020
agtcgaatta ccagtttgga agtatggggc aatggtgctg ttgatcaagc ggtctttact  1080
ttgagtgatg gtcgttcatt atcatttggc gcacctggaa catctcgata taggaaattt  1140
tatgttggcg aaagtcacta tattgcaggg gtatatttgt ccagtgacta cagcccatta  1200
gcaggtcagg cagcaaatat cgctgtatct tatcagttga taaatgatga tgaaaaataa  1260

SEQ ID NO: 40          moltype = AA  length = 419
FEATURE                Location/Qualifiers
REGION                 1..419
                       note = The amino acid sequence of the TIC7669 PirB protein.
source                 1..419
                       mol_type = protein
                       organism = Photorhabdus luminescens
SEQUENCE: 40
```

```
MHTENVLDIR TIVANEYAVK TSAVEWDVTD IVKNAIIGGI SFIPSVGPAI SFLVGLFWPQ  60
SKENIWEGIV KQIERMIEES ALKTIKGILA GDIAYIQERM ATVADLLDKH PGSEEARSAF  120
NNLAENIDGY HKKFNNFSDD VNYQILPMFS TTVMMQITYW VAGLERRNEI GLSDIDIEKV  180
RGLIKKTVEQ ANSYINNIYD RELNDALNNS TADTVANNVM SVHGHCRLHG IEYISIWDKL  240
SEAESVNNRI YVDVLSYSTF FDRQTAKARI QALTPEKDMA PPLKPALNDG KRRKIDSLTG  300
HIVRIGGAPR VGGLTVVFDD GSSHRLGTIS GETASISLNG SRITSLEVWG NGAVDQAVFT  360
LSDGRSLSFG APGTSRYRKF YVGESHYIAG VYLSSDYSPL AGQAANIAVS YQLINDDEK   419

SEQ ID NO: 41          moltype = DNA  length = 1659
FEATURE                Location/Qualifiers
misc_feature           1..1659
                       note = A nucleic acid sequence encoding a PirAB fusion
                        protein, TIC9320comprised of the TIC7668 and TIC7669
                        coding sequences in operablelinkage and in frame.
source                 1..1659
                       mol_type = other DNA
                       organism = synthetic construct
SEQUENCE: 41
atgtctagaa taactattgt tgttgattca gatgaacaga aagcagaagt ttactctaat  60
tcccctgttc cagtacataa agacttaaat gcagttggtc ctttgagtga tgtgactata  120
tcacctcatg ctagtgtgga agtatttaga atagatacac caataattcc agaatccaga  180
agatctctga gagttgtaaa taccgggcta gcaaatagtg tcacggctaa attttactgg  240
tctcatagtt ttacctctga atggtttgag tctggttcta tagatgtagg attaggagaa  300
gagaaggtgt taaacgtgcc taataactct ttttattata gtaaatttgt tatctataat  360
aatacggata aagttgctta tgtgacggca aatttggtta tgcatacaga aaatgtttta  420
gacataagaa ccattgtggc taatgaatat gccgtaaaaa cgagtgcagt agagtgggat  480
gttactgata ttgtaaaaaa tgcaatcatc gggggaatat cttttatacc ttcagttggc  540
cctgctatat ctttttagt cggtttattc tggcctcaat caaaagaaaa tatatgggaa  600
gggattgtca aacaaattga aaggatgata gaggagtctg cattaaagac gattaaaggt  660
atccttgctg gtgatattgc atatatacaa gaacgaatgg caaccgttgc tgatcttctt  720
gataagcatc cgggatctga agaagcgagg agtgctttta ataacctggc agaaaatata  780
gatggttatc acaaaaaatt taataatttt tccgatgatg ttaactatca gatattaccc  840
atgttttcta ctacggttat gatgcagata acatattggg tcgctggttt agagagaaga  900
aatgaaatcg ggcttagtga tattgatatt gaaaaagtcc gagggttaat caaaaagacg  960
gtagaacagg cgaatagtta tattaataat atatatgata gagagcttaa tgatgctctt  1020
aataactcga cggctgacac tgttgcaaat aatgtgatgt ctgttcatgg tcactgtcgt  1080
ttacatggga ttgaatatat cagtatttgg gataaattaa gtgaagcaga gtcagtaaat  1140
aatagaatct atgttgatgt tttaagttat tctactttct ttgaccgtca aacagcaaaa  1200
gccagaattc aggcattgac tccagagaaa gatatggctc cacctctcaa accggctctt  1260
aatgacggga aaagaagaaa gatcgattcg ttaacgggac atattgtgcg tattggaggg  1320
gctccgagag tcggagggct gacagttgta tttgatgatg gtagtagcca tcgattaggt  1380
acaatatctg gtgagacggc atctatttct ctgaatggca gtcgaattac cagtttggaa  1440
gtatggggca atggtgctgt tgatcaagcg gtctttactt tgagtgatgg tcgttcatta  1500
tcatttggcg cacctggaac atctcgatat aggaaatttt atgttggcga aagtcactat  1560
attgcagggg tatatttgtc cagtgactac agcccattag caggtcaggc agcaaatatc  1620
gctgtatctt atcagttgat aaatgatgat gaaaaataa                        1659

SEQ ID NO: 42          moltype = AA  length = 552
FEATURE                Location/Qualifiers
REGION                 1..552
                       note = The amino acid sequence of the TIC9320 PirAB fusion
                        protein
source                 1..552
                       mol_type = protein
                       organism = synthetic construct
SEQUENCE: 42
MSRITIVVDS DEQKAEVYSN SPVPVHKDLN AVGPLSDVTI SPHASVEVFR IDTPIIPESR  60
RSLRVVNTGL ANSVTAKFYW SHSFTSEWFE SGSIDVGLGE EKVLNVPNNS FYYSKFVIYN  120
NTDKVAYVTA NLVMHTENVL DIRTIVANEY AVKTSAVEWD VTDIVKNAII GGISFIPSVG  180
PAISFLVGLF WPQSKENIWE GIVKQIERMI EESALKTIKG ILAGDIAYIQ ERMATVADLL  240
DKHPGSEEAR SAFNNLAENI DGYHKKFNNF SDDVNYQILP MFSTTVMMQI TYWVAGLERR  300
NEIGLSDIDI EKVRGLIKKT VEQANSYINN IYDRELNDAL NNSTADTVAN NVMSVHGHCR  360
LHGIEYISIW DKLSEAESVN NRIYVDVLSY STFFDRQTAK ARIQALTPEK DMAPPLKPAL  420
NDGKRRKIDS LTGHIVRIGG APRVGGLTVV FDDGSSHRLG TISGETASIS LNGSRITSLE  480
VWGNGAVDQA VFTLSDGRSL SFGAPGTSRY RKFYVGESHY IAGVYLSSDY SPLAGQAANI  540
AVSYQLINDD EK                                                     552

SEQ ID NO: 43          moltype = DNA  length = 420
FEATURE                Location/Qualifiers
misc_feature           1..420
                       note = A nucleic acid sequence obtained from an unknown
                        bacterial straincomprised within a microbiome encoding a
                        TIC7939 pesticidal PirAprotein sequence.
source                 1..420
                       mol_type = other DNA
                       organism = unidentified
SEQUENCE: 43
atgacgtgtg agattctgca tatgacaagc aaaggcgatg aaatgcagtc gattgcagcg  60
acggatgctc aaacgttaca ggaggcgcct aaagatgaag tgaattttaa gcagacaaaa  120
```

```
ggggatatga tggtccctgg ggggcagtct gcacagggag cgcgctacga tactccgatt  180
attcctgaac ttcatccgtc ttactatgta tcaaattcag gacctgcagc tacggtgaaa  240
gctgtcttct actggtccca ctcatttacc tcgaagtggt ttgaatataa ttcagttacg  300
gttctcaggg ggactactga gcggcttagt gcgccaagca actcacttta ttacagcaag  360
gtcgttgtct ttaataatga gaaagagcct gcttatgtta ctgtaacgac cattcggtaa  420

SEQ ID NO: 44           moltype = AA  length = 139
FEATURE                 Location/Qualifiers
REGION                  1..139
                        note = The amino acid sequence of the TIC7939 PirA protein.
source                  1..139
                        mol_type = protein
                        organism = unidentified
SEQUENCE: 44
MTCEILHMTS KGDEMQSIAA TDAQTLQEAP KDEVNFKQTK GDMMVPGGQS AQGARYDTPI  60
IPELHPSYYV SNSGPAATVK AVFYWSHSFT SKWFEYNSVT VLRGTTERLS APSNSLYYSK  120
VVVFNNEKEP AYVTVTTIR                                               139

SEQ ID NO: 45           moltype = DNA  length = 1260
FEATURE                 Location/Qualifiers
misc_feature            1..1260
                        note = A nucleic acid sequence obtained from an unknown
                         bacterial straincomprised within a microbiome encoding a
                         TIC7940 PirB pesticidalprotein sequence.
source                  1..1260
                        mol_type = other DNA
                        organism = unidentified
SEQUENCE: 45
atgaccacga accccattgt tcatagagag tttgattatg cggaccttta cggcgacgat  60
agtcgatcca gcccacaaaa caatgattgg gactatttag ttgtagcaaa gattcttgtt  120
gttcaggggc ttaagcatat tcctgtcgtg ggcggggctc tttcgagtct aactaacgct  180
ctctggccga aaaaaaaaga taatgtctgg acgcaagctc ttggagagat tgagcagtat  240
attgatagtc agaatctgaa ggtgattcag ggcatactca atggtgagat acttgagatc  300
caagggaaga tggagcacgt tacagcgctt cttgagaagc atcctaatac caaggaatct  360
tacaatgcgt ataaggattt agctcagtat cttgatagta agcagagaaa gtttggagca  420
tttgatgctg agcagaacta tcatttgatt cctatgtatg catctatgat tttgctgcag  480
gcgacgtatt ggcgaaccgg aattgacagg cgaaatgaaa tcggcctgac tgatatcgat  540
gttgagtctc taaagaggct tattgctgat cttgttttcg aatcgaggga atatatcggt  600
cgcgtctacg atgaggcggt cgaaagggtg tatgctgaag ctaatcccag agatgtgaca  660
aattatatgt actctgttag gggttatagc ttgctgcacg gtgttgagac tgttgaaata  720
atcgatcgcg ttagaagatt gggcgttgat agcggcttca atgttggtgt ggtaagttat  780
tctacggtgg ttgggacagt tacaaaccgc gtaagaactc aagctctcac tccagatgat  840
gaaatgaaag agccattaag gccggagttc gttgacgatg aagttaatca gatcgcgtct  900
ataactgggt atattggtcc tcttattgat agtaagccca cgattggcgg cttgttcgtg  960
gtctttgaaa acggcaactg ctacaaaatg ggggcggagt caggcacgtc ttattctata  1020
gaccttcgtg gaagtactat ctcaaccgtt gaagtttggt atcagggatt actagaaggg  1080
gttcggttta cattgagtga tgatagagat ctgctgattg gccagcggca atccgagagg  1140
tccaaatata gacgatttga agtggaaggg cattacgttt caggagtgta tttggatcgt  1200
gatgaaacga cctatcgcgg gcgagctgcc aatatttcag tgtcttacca tatcgcgtag  1260

SEQ ID NO: 46           moltype = AA  length = 419
FEATURE                 Location/Qualifiers
REGION                  1..419
                        note = The amino acid sequence of the TIC7940 PirB protein.
source                  1..419
                        mol_type = protein
                        organism = unidentified
SEQUENCE: 46
MTTNPIVHRE FDYADLYGDD SRSSPQNNDW DYLVVAKILV VQGLKHIPVV GGALSSLTNA  60
LWPKKKDNVW TQALGEIEQY IDSQNLKVIQ GILNGEILEI QGKMEHVTAL LEKHPNTKES  120
YNAYKDLAQY LDSKQRKFGA FDAEQNYHLI PMYASMILLQ ATYWRTGIDR RNEIGLTDID  180
VESLKRLIAD LVFESREYIG RVYDEAVERV YAEANPRDVT NYMYSVRGYS LLHGVETVEI  240
IDRVRRLGVD SGFNVGVVSY STVVGTVTNR VRTQALTPDD EMKEPLRPEF VDDEVNQIAS  300
ITGYIGPLID SKPTIGGLFV VFENGNCYKM GAESGTSYSI DLRGSTISTV EVWYQGLLEG  360
VRFTLSDDRD LLIGQRQSER SKYRRFEVEG HYVSGVYLDR DETTYRGRAA NISVSYHIA   419

SEQ ID NO: 47           moltype = DNA  length = 1677
FEATURE                 Location/Qualifiers
misc_feature            1..1677
                        note = A nucleic acid sequence encoding a PirAB fusion
                         protein, TIC9321comprised of the TIC7939 and TIC7940
                         coding sequences in operablelinkage and in frame.
source                  1..1677
                        mol_type = other DNA
                        organism = synthetic construct
SEQUENCE: 47
atgacgtgtg agattctgca tatgacaagc aaaggcgatg aaatgcagtc gattgcagcg  60
acggatgctc aaacgttaca ggaggcgcct aaagatgaag tgaattttaa gcagacaaaa  120
ggggatatga tggtccctgg ggggcagtct gcacagggag cgcgctacga tactccgatt  180
```

```
attcctgaac ttcatccgtc ttactatgta tcaaattcag gacctgcagc tacggtgaaa  240
gctgtcttct actggtccca ctcatttacc tcgaagtggt ttgaatataa ttcagttacg  300
gttctcaggg ggactactga gcggcttagt gcgccaagca actcacttta ttacagcaag  360
gtcgttgtct ttaataatga gaaagagcct gcttatgtta ctgtaacgac cattcggatg  420
accacgaacc ccattgttca tagagagttt gattatgcgg acctttacgg cgacgatagt  480
cgatccagcc cacaaaacaa tgattgggac tatttagttg tagcaaagat tcttgttgtt  540
caggggctta agcatattcc tgtcgtgggc ggggctcttt cgagtctaac taacgctctc  600
tggccgaaaa aaaaagataa tgtctggacg caagctcttg gagagattga gcagtatatt  660
gatagtcaga atctgaaggt gattcagggc atactcaatg gtgagatact tgagatccaa  720
gggaagatgg agcacgttac agcgcttctt gagaagcatc ctaataccaa ggaatcttac  780
aatgcgtata aggatttagc tcagtatctt gatagtaagc agagaaagtt tggagcattt  840
gatgctgagc agaactatca tttgattcct atgtatgcat ctatgatttt gctgcaggcg  900
acgtattggc gaaccggaat tgacaggcga aatgaaatcg gcctgactga tatcgatgtt  960
gagtctctaa agaggcttat tgctgatctt gttttcgaat cgagggaata tatcggtcgc  1020
gtctacgatg aggcggtcga aagggtgtat gctgaagcta atcccagaga tgtgacaaat  1080
tatatgtact ctgttagggg ttatagcttg ctgcacggtg ttgagactgt tgaaataatc  1140
gatcgcgtta gaagattggg cgttgatagc ggcttcaatg ttggtgtggt aagttattct  1200
acggtggttg ggacagttac aaaccgcgta agaactcaag ctctcactcc agatgatgaa  1260
atgaaagagc cattaaggcc ggagttcgtt gacgatgaag ttaatcagat cgcgtctata  1320
actgggtata ttggtcctct tattgatagt aagcccacga ttggcggctt gttcgtggtc  1380
tttgaaaacg gcaactgcta caaaatgggg gcggagtcag gcacgtctta ttctatagac  1440
cttcgtggaa gtactatctc aaccgttgaa gtttggtatc agggattact agaaggggtt  1500
cggtttacat tgagtgatga tagagatctg ctgattggcc agcggcaatc cgagaggtcc  1560
aaatatagac gatttgaagt ggaagggcat tacgtttcag gagtgtattt ggatcgtgat  1620
gaaacgacct atcgcgggcg agctgccaat atttcagtgt cttaccatat cgcgtag     1677
```

```
SEQ ID NO: 48           moltype = AA  length = 558
FEATURE                 Location/Qualifiers
REGION                  1..558
                        note = The amino acid sequence of the TIC9321 PirAB fusion
                         protein.
source                  1..558
                        mol_type = protein
                        organism = synthetic construct
SEQUENCE: 48
MTCEILHMTS KGDEMQSIAA TDAQTLQEAP KDEVNFKQTK GDMMVPGGQS AQGARYDTPI  60
IPELHPSYYV SNSGPAATVK AVFYWSHSFT SKWFEYNSVT VLRGTTERLS APSNSLYYSK  120
VVVFNNEKEP AYVTVTTIRM TTNPIVHREF DYADLYGDDS RSSPQNNDWD YLVVAKILVV  180
QGLKHIPVVG GALSSLTNAL WPKKKDNVWT QALGEIEQYI DSQNLKVIQG ILNGEILEIQ  240
GKMEHVTALL EKHPNTKESY NAYKDLAQYL DSKQRKFGAF DAEQNYHLIP MYASMILLQA  300
TYWRTGIDRR NEIGLTDIDV ESLKRLIADL VFESREYIGR VYDEAVERVY AEANPRDVTN  360
YMYSVRGYSL LHGVETVEII DRVRRLGVDS GFNVGVVSYS TVVGTVTNRV RTQALTPDDE  420
MKEPLRPEFV DDEVNQIASI TGYIGPLIDS KPTIGGLFVV FENGNCYKMG AESGTSYSID  480
LRGSTISTVE VWYQGLLEGV RFTLSDDRDL LIGQRQSERS KYRRFEVEGH YVSGVYLDRD  540
ETTYRGRAAN ISVSYHIA                                              558
```

```
SEQ ID NO: 49           moltype = DNA  length = 1695
FEATURE                 Location/Qualifiers
misc_feature            1..1695
                        note = A synthetic coding sequence used for expression in
                         plant cellsencoding a TIC6880PL PirAB fusion protein with
                         an additionalalanine codon inserted after the initiating
                         methionine codon.
source                  1..1695
                        mol_type = other DNA
                        organism = synthetic construct
SEQUENCE: 49
atggctatca cgataaacat ctcgggcggg agcatcaaga tttccaacaa cattggctcc  60
gagacggaca tccgcaacac gcccttctcc gagccgctct ccatctccaa ctacaaagac  120
atgacgatag agcctcattc ctccatccag gccacgcgga ccgacacacc catcatccct  180
gagacccggc cgaactacta cgtggccaac tctggcccgg cggcctccgt gcgcgccgtc  240
ttctactggt cgcacagttt cacatcggag tggtttgagc actcctccat cattgtcaaa  300
gctggcgagg acggcatcct taactcgccc tccaacagcg tgtactacag caaggtggtc  360
atctacaatg acacggacaa gcgcgccttc gtcacgggct acgacaagat gaacaacgaa  420
ctcatgaaca ccaacgagtc gcagccttcc gagactctga gcctgattaa cgagtccatc  480
ctcaccgcgc cctacgcggt ctccacgccg aactacgagt gggacatgtc gtcgattatt  540
aaggacgcca taatcggcgg tattggcttc atccctggcc ctgggagcgc catctccttc  600
ctccttggtt tgttctggcc gcagcaaacc gacaacacct gggagcagat actccagaag  660
gtcgagcaaa tgattgagga agccaacctc aagaccatcc agggcatcct gaacggcgac  720
atccaggaga tcaagggcaa gatggagcac gtagagtaca tgctggagac ctcgccaggc  780
actcaggaga gtcacgacgc ctacatgttc ctggcgcgct acttagtttc catcgacgag  840
aagttcaaga gcttcgacaa caagacgaac taccagatcc tgcccatgta caccaacacc  900
ctgatgctcc aggctcccta ctggaagatg ggcatcgaga agaagaacga catcctactt  960
actgacattg aggtgaacga actcaagcag ctcatcgaga gcctgtacgc gaaggccaac  1020
agctacatcc acgaagtgta cacccgagag tacgacaacg cggtgaacac cagtaccgcg  1080
accaccatca ccaacaacct cctgagcgtg cgaggctact gcctcttgca cgggctcgaa  1140
tgcctggagg tgctcgacca catccagaac aacaacctgg accagtcgtt ctacccgaag  1200
accatctcct actccaccgt ctttgaccgg tccaccaaca agactcggct gcaagcgctg  1260
accgaggacg agcagatgga ggaacctctg aaaccatcct tcatcaacgg cgagtacaac  1320
```

```
aagatcaaga gcctgatcgg gtacgtgcag cggattggca acgcgccgcg agtgggcggc  1380
atcaagataa ccttcacgaa cgggtccagc cacaccttgg gcaccgtcac gagcgagtcc  1440
aactccatcg agctgaacga ctccgtcatc acctccgtcg aggtgtgggg caatggtgcg  1500
gtggacgagg cgttcttcac tctctcggac ggtcgccagt tccgcctggg ccagcgttac  1560
gcctccaact accgcaagta cgcggtggac gggcactaca tctccggcct gtacctggcc  1620
tcggacgagc catccctggc cgggcaagcg gctggcattg ccgtcagcta ccacatcctg  1680
gtggacaaga agtga                                                   1695

SEQ ID NO: 50           moltype = AA  length = 564
FEATURE                 Location/Qualifiers
REGION                  1..564
                        note = The amino acid sequence of the TIC6880PL PirAB
                         fusion protein.
source                  1..564
                        mol_type = protein
                        organism = synthetic construct
SEQUENCE: 50
MAITINISGG SIKISNNIGS ETDIRNTPFS EPLSISNYKD MTIEPHSSIQ ATRTDTPIIP  60
ETRPNYYVAN SGPAASVRAV FYWSHSFTSE WFEHSSIIVK AGEDGILNSP SNSVYYSKVV  120
IYNDTDKRAF VTGYDKMNNE LMNTNESQPS ETLSLINESI LTAPYAVSTP NYEWDMSSII  180
KDAIIGGIGF IPGPGSAISF LLGLFWPQQT DNTWEQILQK VEQMIEEANL KTIQGILNGD  240
IQEIKGKMEH VEYMLETSPG TQESHDAYMF LARYLVSIDE KFKSFDNKTN YQILPMYTNT  300
LMLQAPYWKM GIEKKNDILL TDIEVNELKQ LIESLYAKAN SYIHEVYTRE YDNAVNTSTA  360
TTITNNLLSV RGYCLLHGLE CLEVLDHIQN NNLDQSFYPK TISYSTVFDR STNKTRLQAL  420
TEDEQMEEPL KPSFINGEYN KIKSLIGYVQ RIGNAPRVGG IKITFTNGSS HTLGTVTSES  480
NSIELNDSVI TSVEVWGNGA VDEAFFTLSD GRQFRLGQRY ASNYRKYAVD GHYISGLYLA  540
SDEPSLAGQA AGIAVSYHIL VDKK                                         564

SEQ ID NO: 51           moltype = DNA  length = 1701
FEATURE                 Location/Qualifiers
misc_feature            1..1701
                        note = A synthetic coding sequence used for expression in
                         plant cellsencoding a TIC9316 PirAB fusion protein.
source                  1..1701
                        mol_type = other DNA
                        organism = synthetic construct
SEQUENCE: 51
atgaacacca tcaacatcaa catctccggc tcgaccgtga cggtgatctc gaacaacgac  60
tccaacccgg agccgctcac ctacaacacg aacacaccag cgagcgatcc tctgacggcc  120
agcccgtacc gggacatgac catcgagccg cacagctcca ttgaggcgac gcgcacagac  180
acgcccatca tcccggagac ccggccgaac tactacgtcg ccaactccgg cccggcctcc  240
tcagtccgcg ctgtgttcta ctggtcgcac agcttcacgt cagaatggtt cgagtacagc  300
tctatcatag tcaaggcggg caaggacggc atcctccagt cgcccaacaa cgccctgtac  360
tacagcaagg tcgtgatcta caacgacacc gacaagcgcg ccttcgtcac cggctacaac  420
aagatgaaca tcagcccgat caacgtctcg gagaacgaga cgctcccgga gctgaccgac  480
gtgatgctga tcgtcccata cacgaccagc acgccggatt acgagtggga catgtcgtcg  540
atcattaagg atgcgatcat cggaggcgtt ggcttcatcc ctggcgcggg ctcggccatg  600
agcttcctgc tcggcctgtt ctggccgcag cagaaggata acacttggga gcagatactt  660
cagaaggtgg aacagatgat cgagaacgcg gtcctccaaa cgatcaaggg catcctcaac  720
ggcgacatcc aggagattaa gggaaagatg gagcacgttc agtacatgct cgaaaccagc  780
cctgggagcc aggagagcca cgacgcctac atgttcttgg cacgttacct cgtctcgatt  840
gacgagaagt tcaagtcctt cgacaacaag acaaactacc agatcttgcc aatgtacacc  900
aatacggtta tgttacagat tccgtactgg aagatgggca tcgagaagaa gaatgacatc  960
ggcttgaccg acatcgaggt caatgagctt aagcaactta tcgacaagct ggtggacaag  1020
gccaagtcct acatccacac aatgtacacc aacgagtaca acgacgcgat caacaccagc  1080
accgcctcaa gcgtcacaaa caacctcctg tccgtgcgcg gttactgcct tctgcacggc  1140
ctggagtgca tcgaacttat tgagcatctc cagaacaaca gcctggagtc cggcttctac  1200
ccgaagacga tcagctactc cacggtcttc gaccggcaga ccaacaagat gcggatacaa  1260
gcgctcactg aggacgacca gatgcaagaa cccttcaagc cctcgctcat caacgggaag  1320
tacaacaaga tccagagcct cctcggctac gtccagcgca tcggcaacgc gccgcgcgtc  1380
ggcgggatca agatcacgtt cgccaacggg tctagttaca cgctgggcac cgtgaccagc  1440
gagacctcca gtattgagct taacgactcg gtgatcgagc ggctggaggt gtggggcaac  1500
ggcgcggtgg acgaggcgct gttcaccctc tcggacgggc ggcagctccg ggtcggcgag  1560
cggtacgcga ccaagtaccg taagtacgcc gtggacggcc actacatcgc cggtctgtac  1620
ctcgccagtg acgagcccag cctagcgggc caggcggctg gcatcgccgt gtcgtaccac  1680
atgctcgacg acaagaagtg a                                            1701

SEQ ID NO: 52           moltype = DNA  length = 1701
FEATURE                 Location/Qualifiers
misc_feature            1..1701
                        note = A synthetic coding sequence used for expression in
                         plant cellsencoding a TIC9317 PirAB fusion protein.
source                  1..1701
                        mol_type = other DNA
                        organism = synthetic construct
SEQUENCE: 52
atgattacga tcaacatcaa cgtgaacggc aacgacgtga cgggcaccaa caacaatgag  60
cccactccag tcagcacgac gtacggcccg aacactccgg cctcggagcc accggtcgtc  120
tcgaactact ccgacatcac cattgagccg cacagctcgg tccaggccac gcggatcgac  180
```

```
acgccggtga tcccggaggc ccggccggac tactacgtgg cgaactcggg ccctgcgccg  240
tccgtgcggg ccgtgttcta ctggtcgcac tcgttcacct ccgagtggtt cgagtcgtcc  300
agcatcaccg tgaaggcggg cgaggacgga atcctcaagg ctccagggaa cagcctgtac  360
tacagcaagg tcgtcatcta caacgacaca gacaagcggg ccttcgttac cgggtacaac  420
aagatgaaca ccactccgat tactgtaagc actaacgaaa catcgcctct catgacggac  480
gtgatgccga tggacctgta cgccatctcg acgccagact acgagtggga catgagttcc  540
atcatcaagg acgccgtaat tggcggcatc gggttcatcc ctgggcccgg cccggccatc  600
tccttcctgc tgggcctgtt ctggccgcag cagaaggaca acacatggga gcagatactc  660
cagaaggtcg agcaaatgat tgagaatgcc gtgttgcaga cgatcaaggg aatcctaaac  720
ggcgaagtac aggagatcaa gggcaagatg gagcacgtcg agtctatgct caagaactcg  780
ccaggctctc aggagtcaca cgacgcctac atgttcctgg ctcgttacct cgtttcaatt  840
gacgagaagt tcaagagctt cgacaaccgc accaactacc aactgttgcc gatgtacacc  900
aatacgatta tgctccagat accttattgg aagatgggca tcgagaagaa gaaggacatt  960
ggcctgaccg acattgaagt caacgagctt aaggagctga tcgacaagct ggtggacaag  1020
gccaagaact acatccacac aatgtacacg aacgagcaca acaacgccgt gaacaccagc  1080
actgccgagt ccgtcacgaa caatctcctc agcgtgcgcg gctactgcct gttacacggg  1140
ctggagtgca ttgagctaat cgagcacatc cagaacaact ccctggagag cgggttctac  1200
ccgaagatca tcagctacag caccgctttc gaccgcccga caaacaagat gcgtatccaa  1260
gcgctcacgg aggacgacgc gatgcaagag ccgtttaaac cgtcgctcat taacggcaag  1320
tacaacaaga tccagagcct cacgggctac gtgcagcgga tcggcaacgc gccgcgcgtc  1380
ggcggcatcc gcatcacgtt caccaacggg tcgtcctaca cgctcgggac ggtgacctcc  1440
gagacgcaca gcatcaagct gaacgactcc gtgatcgagt cgttagaggt ctggggaaac  1500
ggtgccgtgg acgaggccct gttcaagctg tccgacgggc ggctcctccg catcggcgag  1560
cggtacgcca agaagtaccg caagtacgcg gtggacaacc actacatcgc gggcatctac  1620
ctagcgagcg acgagccgtc cctggcgggt caagccgccg ggatcgccgt gagctatcac  1680
atgatggcgg acaagaaatg a                                            1701
```

```
SEQ ID NO: 53          moltype = DNA  length = 1701
FEATURE                Location/Qualifiers
misc_feature           1..1701
                       note = A synthetic coding sequence used for expression in
                        plant cellsencoding a TIC9318 PirAB fusion protein.
source                 1..1701
                       mol_type = other DNA
                       organism = synthetic construct
SEQUENCE: 53
atgtccacca tcaacatcaa catctcctcc agcacggtca ctgtgattac aaacaatggc  60
gagacgcccg tcccgctcac ctacaacacc aacacgccgg agtcggagcc gctgacggtc  120
aacccgtacc gcgacatgac catcgagccg cgctcctcca ttgaggcgac ccgcatcgac  180
acgccgatca tcccggagac gagaccgaac tactatgtgg cgaactccgg cccggccagc  240
agcgtccggg cggtattcta ctggtcgcac agcttcacct cgcaatggtt cgagtattcg  300
tcgatcatcg tgaaggcggg tgaggacggc atactggagt cgccgtcgaa cagcctctac  360
tacagcaagg tggtgatcta caacgacacg gacaagaggg cattcgtcac gggctacaac  420
aagatgaaca ccaccctcat caacgtaagt gagaaggaga cgctgccggt gcagaccgac  480
atcatgctga tcgcgccgta ctccgtgtcc acgccggact acgagtggga catgtcatcg  540
ctcatcaagg acgcgatcat cggcggcgtc ggattcatcc ctgtcgtcgg ctcggccatg  600
tccttcctcc tcggcctgtt ctggccgcag cagaaggaca acacttggga acaaatactg  660
cagaaggtcg agcagatgat cgagaacgcg cagctcaaca cgattaaggg cattctgaac  720
ggcgacatcc aggagattaa gggcaagatg gagcacgtgc agtacatgct tgagacaagt  780
ccagggagtc aggagtcaca cgacgcctac atgttcttag cccgctacct agtgagcatc  840
gacgagaagt tcaagtcgtt cgacaacaag acaaactacc aaatcttgcc aatgtacacg  900
aataccgtca tgctacagat cccatactgg aagatgggaa ttgagaagaa gaacgacatt  960
ggcttgacgg acatcgaagt caacgagctt aaacagctta tcgacactct ggtggaccgc  1020
gcgcgcaact acatccacac catgtacgag cgagagtacg acaacgccat caacacctca  1080
accgctgcct cggtgaccaa caacctgctc tccgtgcgcg ggtactgcct cctgcacggg  1140
ctggagtgca tcgagactat cgagcacctt cagaacaaca gcctcaacag tgggttctac  1200
ccgaagacca tcagctacag cactgtcttc gaccggccca cgaacaagac ccgcatccag  1260
gctctgacgg aagacgacca aatgcaagag ccgttcaagc ccgcgctgat cggcggcaag  1320
tacaacaaga tcaagtccct gttgggctac gtgcgaagga tcggcaacgc tccacgggtc  1380
ggcggcatca aggtgacgtt caccaatggg tcgagctaca cgctcgggac ggtcacgtcg  1440
gaaaccgact ccatcgaact gaacgagtcg gtcatcgagc ggctggaggt gtggggcaac  1500
ggagccgtgg acgaggccct ctttaccctg agcgatggcc gccagctccg catcggcgag  1560
cggtacgcca agaaataccg gaagtacgcg gtggatgggc actacatcag cggcctctac  1620
ctcgcgtcgg acgagccctc cctcgccggt caagcagccg ggatcgcggt gtcctaccac  1680
atgctcgcag acaagaagtg a                                            1701
```

```
SEQ ID NO: 54          moltype = DNA  length = 1650
FEATURE                Location/Qualifiers
misc_feature           1..1650
                       note = A synthetic coding sequence used for expression in
                        plant cellsencoding a TIC9319 PirAB fusion protein.
source                 1..1650
                       mol_type = other DNA
                       organism = synthetic construct
SEQUENCE: 54
atgattacca tcaacatctc cggcgggaac gtgaccatca acaacaacat ctccagcgta  60
accgacatcc agaagccgct ggacgccgag ccgctgtccg tgacgaacta caaggacttg  120
acgatagagc cgcactcctc gatccaggcg acccgcacgg acacgccgat catcccggag  180
acccgcccga actactacgt ggccaactcg ggtccggctt ccagcgtgaa ggccgtgttc  240
```

-continued

```
tactggagcc actccttcac gtcggagtgg ttcgagtaca gctccatcat tgtgaaggcc  300
ggtgaggacg gcatcctcaa gagcccgtcc aacgccgtgt actactcgaa ggtcgtcatc  360
tacaacgaca cggacaagcg ggccttcgtg acgggctaca acatgatgaa caatagcccg  420
atgaacgacc agctctccat cgcgccgtac tccatctcca cgcccaacta cgagtgggac  480
atgagcagta tcatcaagga cgccatcatc ggcggcatcg gcttcatacc gggccctggc  540
agcgccatct ccttcctgct gggcctgttc tggccgcagc aaacggataa cacttgggac  600
caaatacttc agaagatcga gcaaatgatt gaggaagcta accttaagac catcaaggga  660
atactgaacg gcgacatcca ggagatcaag ggcaagatgg accacgtgca gtacatgctg  720
gagaactctc ccggaagcca ggaatcccac gacgcctaca tgttcctggc ccgtttcctc  780
gtgtccatcg acgagaagtt caagagcttc gacgaccgga ccaactacca aatcttgcca  840
atgtacacca acactatcat gttgcaagct ccttactgga agatgggcct ggagaagaag  900
gaagacattg gcctgtcgga cattgaggtt tcggaattga aggagctaat tgacaagctc  960
tacaccaaga gctacgacta catccacaac acctacaacc gcgagtacga caacgcgatc  1020
aacacatcca ccgccgagtc aatcaccaac aatctgctca gcgtgcgcgg ctactgcctc  1080
ctccacggct gtgaatgtct cgaagtcatc gcccacatcc agaacaacag cctcgacaag  1140
ggcttctacc cgaagaccat cagctactca agcgtgttcg accgccctac gaacaagatg  1200
cgaatccagg cgctgaccga agacgaccag atgcaagaac ccttcaagcc ctcgttcgta  1260
aacggccagt acaacaagat caagagcctg gagggctacg tgacccggat cggcaacgcg  1320
ccgcgcgtcg gcgggatcaa gatcacgttc gagaacaacg ccagctacac gctgggcacc  1380
gtcacctcgg agaccacgtt catcgagctg aacgagtcgg tcatcaccag cattgaggtc  1440
tggggcaacg gcgcggtgga cgaggcgttc ttcacgctga gcgacgggag gcagatgagg  1500
ctcgggcagc ggtacgcgag ccgctaccgc aagtacgcgg tggacgggca ctacatctcg  1560
ggcctgtacc tcgccagcga cgagcctagc ctcgcgggcc aggcagccgg gatcgccgtg  1620
agctaccaca tgatcgtgga caagcagtga                                  1650
```

```
SEQ ID NO: 55           moltype = DNA  length = 1659
FEATURE                 Location/Qualifiers
misc_feature            1..1659
                        note = A synthetic coding sequence used for expression in
                         plant cellsencoding a TIC9320 PirAB fusion protein.
source                  1..1659
                        mol_type = other DNA
                        organism = synthetic construct
SEQUENCE: 55
atgagccgaa tcacaattgt cgtggattcg gacgaacaga aggccgaggt gtacagcaat  60
tctccggtcc cggtccacaa ggacttaaat gccgtgggcc cgctttccga cgtcaccatc  120
tcgccgcacg cctcagtcga ggtcttccgc atcgacacgc cgatcatccc ggagtcccgg  180
cgctcgctga gggtggtgaa cacgggcctg gccaacagcg tgacggccaa gttctactgg  240
agccactcct tcacgagcga gtggttcgag tcgggctcaa tcgacgtggg cctgggcgag  300
gagaaggtgc taaatgtccc gaacaactca ttctactact cgaagttcgt gatctacaac  360
aacaccgaca aggtggcgta cgttaccgcc aacctcgtaa tgcacacgga gaacgtgctc  420
gacattcgta ccattgtggc aaacgagtac gccgtcaaga cgtcggcggt cgagtgggac  480
gtcaccgaca ttgttaagaa cgcgatcatc ggcggcatct cattcatccc tagcgtgggc  540
ccggccatca gcttcctggt gggcctattc tggccacaga gcaaggagaa catctgggag  600
ggcatcgtca agcagataga gcgcatgatc gaggagtccg ccctcaagac gattaagggc  660
atcctggcgg gcgacatcgc ctacatacag gagcggatgg ccacggtggc cgacctcctg  720
gataaacacc ctgggagtga ggaggcccga tctgccttta acaacctcgc cgagaacatt  780
gacggctacc acaagaaatt caacaacttc tcagatgatg tcaattacca gatcctgcca  840
atgttcagca ctaccgtgat gatgcagatc acatactggg tcgctgggct tgagcgccgc  900
aacgaaatcg gattgtccga catcgacatc gagaaggttc gcgggcttat taagaagacc  960
gtggaacaag ctaactccta catcaataac atctacgacc gggagcttaa cgatgccctg  1020
aacaattcca ccgctgatac cgttgccaac aacgttatgt ctgtgcacgg gcactgccgc  1080
ctccacggca ttgagtacat ctccatctgg gacaagctga gtgaggccga gtcggtcaac  1140
aaccgcatct atgtggacgt actgtcctac tcaaccttct tcgaccgcca gacggcgaag  1200
gcccgcatac aagctctgac accggagaag gacatggctc cgccgctgaa acccgcgctg  1260
aacgacggga agcgccggaa gatcgacagc ctaacgggcc acatcgtccg aatcggcggc  1320
gcaccacgag tcggcggcct gacggtggtg ttcgacgacg gcagttcgca tcgtctcggc  1380
acgataagtg gcgaaaccgc ttcaatcagc ctcaacgggt cgcggatcac gtcgctggag  1440
gtgtggggaa atggtgccgt ggaccaggcg gtcttcacgc tctcggacgg gcggtccctc  1500
agcttcggag cgcctggcac ctcgcgctac cgtaagttct acgtcggcga gtcgcattac  1560
atcgcgggcg tttatctgtc gtccgactac tcacctctgg cgggtcaagc tgcgaacatc  1620
gcggtgtcct accaactcat caacgacgac gagaagtga                        1659
```

```
SEQ ID NO: 56           moltype = DNA  length = 1659
FEATURE                 Location/Qualifiers
misc_feature            1..1659
                        note = A synthetic coding sequence used for expression in
                         plant cellsencoding a TIC9322 PirAB fusion protein.
source                  1..1659
                        mol_type = other DNA
                        organism = synthetic construct
SEQUENCE: 56
atgtcccgca tcacaatcgt agtggactcg gacgaccaga aggccgagtt ctacagcaac  60
tcgccggtgc ctgtgtacaa ggacttgaac gccgtgggtc cgctcagcga cgtcacaatc  120
tctcctcacg catctgtgga ggtcttccgg atcgacacgc cggtgatccc ggagtctcgg  180
tcgtctctgc gcgtcgtcaa caccggcctc tccaattcgg tgacggctaa gttctactgg  240
agccactcgt tcacatcgga gtggttcgag tccggctcca tcgacgtggg cctcggcgag  300
gagaaggtgc ttaatgtgcc gtccaactcc ttctactatt ccaagttcgt gatctacaac  360
aacaccgaca aggtggccta cgtcaccgcg aacctcgtga tgcacaccga gaacgtccta  420
```

```
gacatcagga ccatcgtggc gaacgagtac gcggtgaaga cctccgccct ggaatgggac  480
gtgaccgaca ttgtcaagaa tgcgatcatc ggcgggatct cgttcatccc gagcgtggga  540
ccggctatct cctttctcgt gggattgttc tggccgcaat cgaaggagaa catctgggag  600
ggaatcgtga agcagatcga gcggatgatc gaggaatctg ctctcaagac gatcaagggc  660
atcctcgcgg gagacatcgc ctacatccag gagcggatgg ccacggtggc cgacctcctg  720
gacaagcacc ctggatcgga ggaggcccga agcgcgttca acaacctcgc cgagaacatc  780
gacggctacc acaagaaatt ctcaaacttt agtgatgatg tcaactacca gatacttccg  840
atgttcagca ccaccgtgat gatgcagatt acatactggg tggcgggcct agagcgaaag  900
gacgagatcg gcctctcgaa catcgacgtg gagaaggtgc gtgggcttat taagaagacc  960
gtagaacaag caaactctta catcaacaac atctacgaca gagagttaaa cgacgcattg  1020
aacaactcta ccgcagatac tgtggcaaac aacgtcatga gcgtgcacgg gcactgccgc  1080
ctgcacggga ttgagtacat cagtatttgg gataagctga gtgaggccga aagcgtgaac  1140
aacaaaatct acgttgacgt gctgagctac tctacattct ttgaccgcca gacggcgaag  1200
gccaggatac aggcgttgac gccggagaag gacatgacgc cgccgctcaa gccagccctg  1260
aacggcggca agcggcgcaa gatcgactcc ctcaccggcc acatcgtccg tatcggcggt  1320
gccgcgcggg tcggcggcct gaccgtggtg ttcgacgacg ggaacaggca ccagcttgga  1380
acgatcagcg gcgagactag ctcaatctcc cttaatggct cccgcatcac ctcgctggag  1440
gtgtggggaa acggcgcggt ggatcaggcc gtgttcacgc tgaacgacgg tcgttcgctc  1500
agcctgggct cgcccggcac ctctcgctac cgcaagttct acgtgggcga gtcgcactac  1560
atcgcgggca tctacctcag cagtgactac aacccgctcg ctgggcaagc tgcgaacatc  1620
gccgtctcct accagctcat caacgacgac gagaagtag                        1659
```

```
SEQ ID NO: 57           moltype = DNA  length = 345
FEATURE                 Location/Qualifiers
misc_feature            1..345
                        note = A nucleic acid sequence obtained from Shewanella
                         violacea strainDSS12 encoding a TIC10357 pesticidal PirA
                         protein sequence.
source                  1..345
                        mol_type = other DNA
                        organism = Shewanella violacea
SEQUENCE: 57
atgagtgatt tagaagtaaa aataggtgtt aatcctgctg atgttcgtta tacagctaat  60
tttaaagttg caccaaacga cggatatgtg atgtatgaaa aaaatacgcc aatcattcca  120
gaaattggtg tgaatattac ggttataaat acaggtcgtg aagaaatgga agttcactat  180
gaatgggctc caccatttgg tggatggcaa tgtgcatcta caacaataat cccacctgat  240
ggtaagcctg tttatattgc tcatccgtca aatgcttttt attatcagcg aatcattgct  300
tataacaaaa aagaatcaac agcgttcggg aattgcgaat actaa                345
```

```
SEQ ID NO: 58           moltype = AA  length = 114
FEATURE                 Location/Qualifiers
REGION                  1..114
                        note = The amino acid sequence of the TIC10357 PirA protein.
source                  1..114
                        mol_type = protein
                        organism = Shewanella violacea
SEQUENCE: 58
MSDLEVKIGV NPADVRYTAN FKVAPNDGYV MYEKNTPIIP EIGVNITVIN TGREEMEVHY  60
EWAPPFGGWQ CASTTIIPPD GKPVYIAHPS NAFYYQRIIA YNKKESTAFG NCEY        114
```

```
SEQ ID NO: 59           moltype = DNA  length = 1284
FEATURE                 Location/Qualifiers
misc_feature            1..1284
                        note = A nucleic acid sequence obtained from Shewanella
                         violacea strainDSS12 encoding a TIC10366 pesticidal PirB
                         protein sequence.
source                  1..1284
                        mol_type = other DNA
                        organism = Shewanella violacea
SEQUENCE: 59
atgaataatg aatatatcgt aacaatggaa aagaaaaaca acatagaatt aaaaagtagt  60
ggtcgttata cattagatga tttttaccat gatcatgctt atgcatttaa agtcgctttg  120
actattggac ttaaaaaaat accttatgtt ggaagtattt tatctacact tgttaaaata  180
ttatggccta ctggagcatc aggtgaatct ttacaaaact tatgggaaat ggaaagaaat  240
gaaattcaat caatgattga tgaagctaca cttcatacta taaacgatat attaaacgga  300
attgtaaatt cactcggtga taaaatagcc gatattaata gaactataga aaattacggg  360
tttgcagctg caaaagatga ttatataaac ttaatttcaa attatataat tggattggaa  420
gaacagttta aatttgaaag tgaaggctct gaatttatag cttatgcaac aatgccactg  480
ttatctatta ctgttggttt gcaattatca tatttggcat ttggtttaga taataaagct  540
aactttggac ttgatagtgc tgatatagat aaatgtagta gaaacataga tgaaatttat  600
aaagatgtta aaaaatatat agaaaaatat gctaagtggt ctgattctga ctcttacagt  660
aatgctaata gtgaaaacat atataatgaa gttatgggat ctcgtgcttt ttgtgcttta  720
aatggatttg aacacattga aatctggtct gaaatacaat cacgtaaatc acttgatttt  780
tcaattataa gtacatctgt atcttattct gttgaggtcg gtgttttaac gcctaacatg  840
acaaggatgg caacagctgt tgaagttggc ccgcctttgt tacctgttat ggttgatgga  900
catagaaaca agatagttaa aattgagggt tgggatagtg tagaaattaa tagttatcgt  960
cgtgtcggtt gccttaaaat cacttatgaa aatggtgatg tttacgatat gggtgttaaa  1020
acatctaatc ctgttagcat ttcacttgat ggtgaatttg tagataccgt aaaagtcgtt  1080
caaggtgata catatgcaat taattacatc aaattcacat taactgatgg acgcacaatg  1140
```

```
tcagttggtg aacaaagcgg tgatacacaa ctattaggtt ttgataatca tactattgct  1200
gcaatttttg ttgatgaagg ttcttcagat aaaatttcat gtgttagcgt ttcatgcatt  1260
cctaagcagt acgaagaaga atag                                         1284

SEQ ID NO: 60          moltype = AA  length = 427
FEATURE                Location/Qualifiers
REGION                 1..427
                       note = The amino acid sequence of the TIC10366 PirB protein.
source                 1..427
                       mol_type = protein
                       organism = Shewanella violacea
SEQUENCE: 60
MNNEYIVTME KKNNIELKSS GRYTLDDFYH DHAYAFKVAL TIGLKKIPYV GSILSTLVKI  60
LWPTGASGES LQNLWEMERN EIQSMIDEAT LHTINDILNG IVNSLGDKIA DINRTIENYG  120
FAAAKDDYIN LISNYIIGLE EQFKFESEGS EFIAYATMPL LSITVGLQLS YLAFGLDNKA  180
NFGLDSADID KCSRNIDEIY KDVKKYIEKY AKWSDSDSYS NANSENIYNE VMGSRAFCAL  240
NGFEHIEIWS EIQSRKSLDF SIISTSVSYS VEVGVLTPNM TRMATAVEVG PPLLPVMVDG  300
HRNKIVKIEG WDSVEINSYR RVGCLKITYE NGDVYDMGVK TSNPVSISLD GEFVDTVKVV  360
QGDTYAINYI KFTLTDGRTM SVGEQSGDTQ LLGFDNHTIA AIFVDEGSSD KISCVSVSCI  420
PKQYEEE                                                            427

SEQ ID NO: 61          moltype = DNA  length = 1626
FEATURE                Location/Qualifiers
misc_feature           1..1626
                       note = A nucleic acid sequence encoding a PirAB fusion
                        protein, TIC10375comprised of the TIC10357 and TIC10366
                        coding sequences inoperable linkage and in frame.
source                 1..1626
                       mol_type = other DNA
                       organism = synthetic construct
SEQUENCE: 61
atgagtgatt tagaagtaaa aataggtgtt aatcctgctg atgttcgtta tacagctaat  60
tttaaagttg caccaaacga cggatatgtg atgtatgaaa aaaatacgcc aatcattcca  120
gaaattggtg tgaatattac ggttataaat acaggtcgtg aagaaatgga agttcactat  180
gaatgggctc caccatttgg tggatggcaa tgtgcatcta caacaataat cccacctgat  240
ggtaagcctg tttatattgc tcatccgtca aatgcttttt attatcagcg aatcattgct  300
tataacaaaa aagaatcaac agcgttcggg aattgcgaat acatgaataa tgaatatatc  360
gtaacaatgg aaaagaaaaa caacatagaa ttaaaaagta gtggtcgtta tacattagat  420
gatttttacc atgatcatgc ttatgcattt aaagtcgctt tgactattgg acttaaaaaa  480
ataccttatg ttggaagtat tttatctaca cttgttaaaa tattatggcc tactggagca  540
tcaggtgaat ctttacaaaa cttatgggaa atggaaagaa atgaaattca atcaatgatt  600
gatgaagcta cacttcatac tataaacgat atattaaacg gaattgtaaa ttcactcggt  660
gataaaatag ccgatattaa tagaactata gaaaattacg ggtttgcagc tgcaaaagat  720
gattatataa acttaatttc aaattatata attggattgg aagaacagtt taaatttgaa  780
agtgaaggct ctgaatttat agcttatgca acaatgccac tgttatctat tactgttggt  840
ttgcaattat catatttggc atttggttta gataataaag ctaactttgg acttgatagt  900
gctgatatag ataaatgtag tagaaacata gatgaaattt ataaagatgt taaaaaatat  960
atagaaaaat atgctaagtg gtctgattct gactcttaca gtaatgctaa tagtgaaaac  1020
atatataatg aagttatggg atctcgtgct ttttgtgctt taaatggatt tgaacacatt  1080
gaaatctggt ctgaaataca atcacgtaaa tcacttgatt tttcaattat aagtacatct  1140
gtatcttatt ctgttgaggt cggtgtttta acgcctaaca tgacaaggat ggcaacagct  1200
gttgaagttg gcccgccttt gttacctgtt atggttgatg gacatagaaa caagatagtt  1260
aaaattgagg gttgggatag tgtagaaatt aatagttatc gtcgtgtcgg ttgccttaaa  1320
atcacttatg aaaatggtga tgtttacgat atgggtgtta aaacatctaa tcctgttagc  1380
atttcacttg atggtgaatt tgtagatacc gtaaaagtcg ttcaaggtga tacatatgca  1440
attaattaca tcaaattcac attaactgat ggacgcacaa tgtcagttgg tgaacaaagc  1500
ggtgatacac aactattagg ttttgataat catactattg ctgcaatttt tgttgatgaa  1560
ggttcttcag ataaaatttc atgtgttagc gtttcatgca ttcctaagca gtacgaagaa  1620
gaatag                                                             1626

SEQ ID NO: 62          moltype = AA  length = 541
FEATURE                Location/Qualifiers
REGION                 1..541
                       note = The amino acid sequence of the TIC10375 PirAB fusion
                        protein.
source                 1..541
                       mol_type = protein
                       organism = synthetic construct
SEQUENCE: 62
MSDLEVKIGV NPADVRYTAN FKVAPNDGYV MYEKNTPIIP EIGVNITVIN TGREEMEVHY  60
EWAPPFGGWQ CASTTIIPPD GKPVYIAHPS NAFYYQRIIA YNKKESTAFG NCEYMNNEYI  120
VTMEKKNNIE LKSSGRYTLD DFYHDHAYAF KVALTIGLKK IPYVGSILST LVKILWPTGA  180
SGESLQNLWE MERNEIQSMI DEATLHTIND ILNGIVNSLG DKIADINRTI ENYGFAAAKD  240
DYINLISNYI IGLEEQFKFE SEGSEFIAYA TMPLLSITVG LQLSYLAFGL DNKANFGLDS  300
ADIDKCSRNI DEIYKDVKKY IEKYAKWSDS DSYSNANSEN IYNEVMGSRA FCALNGFEHI  360
EIWSEIQSRK SLDFSIISTS VSYSVEVGVL TPNMTRMATA VEVGPPLLPV MVDGHRNKIV  420
KIEGWDSVEI NSYRRVGCLK ITYENGDVYD MGVKTSNPVS ISLDGEFVDT VKVVQGDTYA  480
INYIKFTLTD GRTMSVGEQS GDTQLLGFDN HTIAAIFVDE GSSDKISCVS VSCIPKQYEE  540
E                                                                  541
```

```
SEQ ID NO: 63          moltype = DNA  length = 435
FEATURE                Location/Qualifiers
misc_feature           1..435
                       note = A nucleic acid sequence obtained from Photorhabdus
                        luminescensstrain laumondii TTO1 encoding a TIC10358
                        pesticidal PirA proteinsequence.
source                 1..435
                       mol_type = other DNA
                       organism = Photorhabdus luminescens
SEQUENCE: 63
atgccagtca atcagattgg cttacataat gaaaaggtga aaaatatgag aaaaataaca  60
gttgataatg atgtggtagg acatgatact gaaatcaact cggttgtttc atcaactgcg  120
gagaaaattc gccaacagtt tggagtaaag gtcgacccta attcaagtca ggaaaagttc  180
tacattgcaa caccgattat tcctgaatcc cgaaagaata tcgttgtaac caatgaaggt  240
ctcgccgatg ttatcacggc gaaatattac tggtcacatt cttttacgtc agaatatttt  300
gaggataact cagttgatgt caaggttgga gagagcaaag tgttggttgc cccttcaaac  360
ccgttgtatt acagcaaagt agtcattttc aacaacacta aatccgtggc atttgtaaca  420
gtaagagaaa aataa                                                   435

SEQ ID NO: 64          moltype = AA  length = 144
FEATURE                Location/Qualifiers
REGION                 1..144
                       note = The amino acid sequence of the TIC10358 PirA protein.
source                 1..144
                       mol_type = protein
                       organism = Photorhabdus luminescens
SEQUENCE: 64
MPVNQIGLHN EKVKNMRKIT VDNDVVGHDT EINSVVSSTA EKIRQQFGVK VDPNSSQEKF  60
YIATPIIPES RKNIVVTNEG LADVITAKYY WSHSFTSEYF EDNSVDVKVG ESKVLVAPSN  120
PLYYSKVVIF NNTKSVAFVT VREK                                         144

SEQ ID NO: 65          moltype = DNA  length = 1254
FEATURE                Location/Qualifiers
misc_feature           1..1254
                       note = A nucleic acid sequence obtained from Photorhabdus
                        luminescensstrain laumondii TTO1 encoding a TIC10367
                        pesticidal PirB proteinsequence.
source                 1..1254
                       mol_type = other DNA
                       organism = Photorhabdus luminescens
SEQUENCE: 65
atgagcgata ttgttaagta taacgatgta agtgcaccga tcccttatgc tgtttattca  60
aatgccgtat atgcatttga gtgggattca tctgctattc taaagcaagc cgtcgtcaag  120
ggattgtcgt atgtaccaca tgtagggaaa tatctttctt acattgttgg ttttttttgg  180
aaagataaag agaaagacat ttggcaggag gttgtaggaa aagttcaaca actggttgaa  240
gatagtatat taaaagcagt taaaggtata ctctcaggta acatcaatga attaaaagaa  300
aaaatgaatg aggtaatccg ttctctggag aagaatttag gtacccaaga agcaagggat  360
gactacatgc atcttgccag gagtatggtt ggaaaagaag ctagcttgat ttttcatgaa  420
aataagacaa attttcacat attgccgatg tattccacac ttgccctgat gcagattatg  480
tattggactg ttggcattga gcgtcgcaag gaaatcggat tgagtgatat tgaagtcgag  540
aatctaaggt catatatcaa aaagttagtt agtgatgcag agcatcacgt gaatagagtt  600
tataagttag aacttgatag tgtagtgtca gactctgatg ttaatcgcgt ggctgataat  660
atcatgtatg tccatggata ttgtcaaata catggtctgg aatatatgga catcattaaa  720
aatatccaat ccagaggtaa taatattact gggttttatc cgagaactat cagctactct  780
acattctttg gttcgccaac aagtgatgcg cgtattttgg cattaaggcc agagaaggat  840
atgccagaac cgttcaaacc caaattttta aatgaacggt ttaataaaat tgcatcggtc  900
aaagggtaca tagtacgaat tggtggcgct aaacgtgttg gggggctgga gataacattt  960
gagaatggca gcaagtatca acagggccaa gcaacgaatg agcatgaaat cgtcaatctc  1020
aaaggtaatt tgattaagac gttggaagta tgggggaatg gggccattga tgaagcaaaa  1080
tttacattaa cgaatggaga tgtgttgaca ataggtcaac gtaattcctc taattaccgt  1140
aagttctctc ttgatggtca ttatatttgc ggggtgttca tcgcaaatga tcgttctgga  1200
ctggctggtc aagcagctaa tattgccgtt tcttatcacc aattagttga gtaa        1254

SEQ ID NO: 66          moltype = AA  length = 417
FEATURE                Location/Qualifiers
REGION                 1..417
                       note = The amino acid sequence of the TIC10367 PirB protein.
source                 1..417
                       mol_type = protein
                       organism = Photorhabdus luminescens
SEQUENCE: 66
MSDIVKYNDV SAPIPYAVYS NAVYAFEWDS SAILKQAVVK GLSYVPHVGK YLSYIVGFFW  60
KDKEKDIWQE VVGKVQQLVE DSILKAVKGI LSGNINELKE KMNEVIRSLE KNLGTQEARD  120
DYMHLARSMV GKEASLIFHE NKTNFHILPM YSTLALMQIM YWTVGIERRK EIGLSDIEVE  180
NLRSYIKKLV SDAEHHVNRV YKLELDSVVS DSDVNRVADN IMYVHGYCQI HGLEYMDIIK  240
NIQSRGNNIT GFYPRTISYS TFFGSPTSDA RILALRPEKD MPEPFKPKFL NERFNKIASV  300
KGYIVRIGGA KRVGGLEITF ENGSKYQQGQ ATNEHEIVNL KGNLIKTLEV WGNGAIDEAK  360
FTLTNGDVLT IGQRNSSNYR KFSLDGHYIC GVFIANDRSG LAGQAANIAV SYHQLVE     417
```

```
SEQ ID NO: 67          moltype = DNA  length = 1686
FEATURE                Location/Qualifiers
misc_feature           1..1686
                       note = A nucleic acid sequence encoding a PirAB fusion
                        protein, TIC10376comprised of the TIC10358 and TIC10367
                        coding sequences inoperable linkage and in frame.
source                 1..1686
                       mol_type = other DNA
                       organism = synthetic construct
SEQUENCE: 67
atgccagtca atcagattgg cttacataat gaaaaggtga aaaatatgag aaaaataaca  60
gttgataatg atgtggtagg acatgatact gaaatcaact cggttgtttc atcaactgcg  120
gagaaaattc gccaacagtt tggagtaaag gtcgacccta attcaagtca ggaaaagttc  180
tacattgcaa caccgattat tcctgaatcc cgaaagaata tcgttgtaac caatgaaggt  240
ctcgccgatg ttatcacggc gaaatattac tggtcacatt cttttacgtc agaatatttt  300
gaggataact cagttgatgt caaggttgga gagagcaaag tgttggttgc cccttcaaac  360
ccgttgtatt acagcaaagt agtcattttc aacaacacta aatccgtggc atttgtaaca  420
gtaagagaaa aaatgagcga tattgttaag tataacgatg taagtgcacc gatcccttat  480
gctgtttatt caaatgccgt atatgcattt gagtgggatt catctgctat tctaaagcaa  540
gccgtcgtca agggattgtc gtatgtacca catgtaggga aatatctttc ttacattgtt  600
ggtttttttt ggaaagataa agagaaagac atttggcagg aggttgtagg aaaagttcaa  660
caactggttg aagatagtat attaaaagca gttaaaggta tactctcagg taacatcaat  720
gaattaaaag aaaaaatgaa tgaggtaatc cgttctctgg agaagaattt aggtacccaa  780
gaagcaaggg atgactacat gcatcttgcc aggagtatgg ttggaaaaga agctagcttg  840
atttttcatg aaaataagac aaattttcac atattgccga tgtattccac acttgccctg  900
atgcagatta tgtattggac tgttggcatt gagcgtcgca aggaaatcgg attgagtgat  960
attgaagtcg agaatctaag gtcatatatc aaaaagttag ttagtgatgc agagcatcac  1020
gtgaatagag tttataagtt agaacttgat agtgtagtgt cagactctga tgttaatcgc  1080
gtggctgata atatcatgta tgtccatgga tattgtcaaa tacatggtct ggaatatatg  1140
gacatcatta aaaatatcca atccagaggt aataatatta ctgggtttta tccgagaact  1200
atcagctact ctacattctt tggttcgcca acaagtgatg cgcgtatttt ggcattaagg  1260
ccagagaagg atatgccaga accgttcaaa cccaaatttt taaatgaacg gtttaataaa  1320
attgcatcgg tcaaagggta catagtacga attggtggcg ctaaacgtgt tgggggggctg  1380
gagataacat ttgagaatgg cagcaagtat caacagggcc aagcaacgaa tgagcatgaa  1440
atcgtcaatc tcaaaggtaa tttgattaag acgttggaag tatgggggaa tggggccatt  1500
gatgaagcaa aatttacatt aacgaatgga gatgtgttga caataggtca acgtaattcc  1560
tctaattacc gtaagttctc tcttgatggt cattatattt gcggggtgtt catcgcaaat  1620
gatcgttctg gactggctgg tcaagcagct aatattgccg tttcttatca ccaattagtt  1680
gagtaa                                                            1686

SEQ ID NO: 68          moltype = AA  length = 561
FEATURE                Location/Qualifiers
REGION                 1..561
                       note = The amino acid sequence of the TIC10376 PirAB fusion
                        protein.
source                 1..561
                       mol_type = protein
                       organism = synthetic construct
SEQUENCE: 68
MPVNQIGLHN EKVKNMRKIT VDNDVVGHDT EINSVVSSTA EKIRQQFGVK VDPNSSQEKF  60
YIATPIIPES RKNIVVTNEG LADVITAKYY WSHSFTSEYF EDNSVDVKVG ESKVLVAPSN  120
PLYYSKVVIF NNTKSVAFVT VREKMSDIVK YNDVSAPIPY AVYSNAVYAF EWDSSAILKQ  180
AVVKGLSYVP HVGKYLSYIV GFFWKDKEKD IWQEVVGKVQ QLVEDSILKA VKGILSGNIN  240
ELKEKMNEVI RSLEKNLGTQ EARDDYMHLA RSMVGKEASL IFHENKTNFH ILPMYSTLAL  300
MQIMYWTVGI ERRKEIGLSD IEVENLRSYI KKLVSDAEHH VNRVYKLELD SVVSDSDVNR  360
VADNIMYVHG YCQIHGLEYM DIIKNIQSRG NNITGFYPRT ISYSTFFGSP TSDARILALR  420
PEKDMPEPFK PKFLNERFNK IASVKGYIVR IGGAKRVGGL EITFENGSKY QQGQATNEHE  480
IVNLKGNLIK TLEVWGNGAI DEAKFTLTNG DVLTIGQRNS SNYRKFSLDG HYICGVFIAN  540
DRSGLAGQAA NIAVSYHQLV E                                           561

SEQ ID NO: 69          moltype = DNA  length = 402
FEATURE                Location/Qualifiers
misc_feature           1..402
                       note = A nucleic acid sequence obtained from Photorhabdus
                        asymbioticaencoding a TIC10360 pesticidal PirA protein
                        sequence.
source                 1..402
                       mol_type = other DNA
                       organism = Photorhabdus asymbiotica
SEQUENCE: 69
atgtctagaa taactatttt tattgattca gatgaacaaa aatcagaatt taattctgat  60
tctcctgttc cggtacgtaa agacttaaat acagttgttc ctttgagtga tctgactata  120
tcccctcgtt ctagtgtgga agtatttaga atagatacac caataattcc agaatccaga  180
agatctctga gagttgtaaa tacagggctg gcaagtagtg ttacggctaa attttactgg  240
tctcatagtt ttacctctga atggtttgag tctggttcta tcgatgtagg attaggagaa  300
gataaggtat taaacgtgcc taacaactct ttttattata gtaaatttgt tatctataat  360
aacacggata aagttgctta tattacggca aatttggttt aa                    402
```

```
SEQ ID NO: 70           moltype = AA  length = 133
FEATURE                 Location/Qualifiers
REGION                  1..133
                        note = The amino acid sequence of the TIC10360 PirA protein.
source                  1..133
                        mol_type = protein
                        organism = Photorhabdus asymbiotica
SEQUENCE: 70
MSRITIFIDS DEQKSEFNSD SPVPVRKDLN TVVPLSDLTI SPRSSVEVFR IDTPIIPESR  60
RSLRVVNTGL ASSVTAKFYW SHSFTSEWFE SGSIDVGLGE DKVLNVPNNS FYYSKFVIYN  120
NTDKVAYITA NLV                                                     133

SEQ ID NO: 71           moltype = DNA  length = 1260
FEATURE                 Location/Qualifiers
misc_feature            1..1260
                        note = A nucleic acid sequence obtained from Photorhabdus
                         asymbioticaencoding a TIC10369 pesticidal PirB protein
                         sequence.
source                  1..1260
                        mol_type = other DNA
                        organism = Photorhabdus asymbiotica
SEQUENCE: 71
atgcagacag agaatgtttt agacataaga accattgtgg ctaatgaata tgctataaaa  60
acgagtgcat tagagtggga tgttactgat attgtaaaaa atgcaatcat aggaggcata  120
tcttttatac ctacggttgg tcctgctata tcttttttag tcggtttatt ttggcctcaa  180
tcaaaagaaa atatatggga agggattgtc aaacaaattg agaggatgat agaggaatct  240
gcattaaaga cgattaaagg tatccttgct ggtgatattg cctatataca agagcgaatg  300
gcaactgttg ctgatcttct tgagaaacat ccaggatcgg cagaagcgcg gagtgctttt  360
aataacctgg cagaaaatat agatggttat cacaaaaaat ttaataattt ctcggatgat  420
gtaaattatc agatattacc catgttttct actacagtta tgatgcagat aacatattgg  480
gttgctggtt tagagagaaa agatgaaata gggcttagtg atattgatat tgaaaaagtc  540
cgagggttaa ttaaaaagac agtagaacag gctaataatt atattaataa tatatatggt  600
agagaactta atgatgctct taataattcg acggctgaca ctgttgcaaa taatgttatg  660
tctgttcatg gtcattgtcg tttacatgga attgaatata tcagtatttg ggatagatta  720
agtgaaactg agtctgtaaa taatagaatc tatgttgatg ttttaagtta ttctactttc  780
tttgaccgtc aaacagcaaa ggccagaatt caggcattga cgccagagaa agatatggct  840
ccacctctca aaccggctct taatggagga aagagaagaa agataaattc gttaatggga  900
catattgtac gtattggagg ggcgccaagg gtaggagggc tgacagttat atttgatgat  960
ggtagtcgcc atcaattagg gacaatatct ggtgagacgg catctatttc tctggatggt  1020
aatcgaatta ctagtttgga agtatggggc aatggtgctg ttgataaagc tgtctttact  1080
ttgagtgatg gtcgttcgtt gtcatttggc gcacctggaa catccagata taggaagttt  1140
tatgttggtg aaagtcacta catttcaggg atctatttgt ccagtgatta cagcccgtta  1200
gcaggtcagg cagcaaatat agctgtatct tatcagctga taaatgatga tgaaaaataa  1260

SEQ ID NO: 72           moltype = AA  length = 419
FEATURE                 Location/Qualifiers
REGION                  1..419
                        note = The amino acid sequence of the TIC10369 PirB protein.
source                  1..419
                        mol_type = protein
                        organism = Photorhabdus asymbiotica
SEQUENCE: 72
MQTENVLDIR TIVANEYAIK TSALEWDVTD IVKNAIIGGI SFIPTVGPAI SFLVGLFWPQ  60
SKENIWEGIV KQIERMIEES ALKTIKGILA GDIAYIQERM ATVADLLEKH PGSAEARSAF  120
NNLAENIDGY HKKFNNFSDD VNYQILPMFS TTVMMQITYW VAGLERKDEI GLSDIDIEKV  180
RGLIKKTVEQ ANNYINNIYG RELNDALNNS TADTVANNVM SVHGHCRLHG IEYISIWDRL  240
SETESVNNRI YVDVLSYSTF FDRQTAKARI QALTPEKDMA PPLKPALNGG KRRKINSLMG  300
HIVRIGGAPR VGGLTVIFDD GSRHQLGTIS GETASISLDG NRITSLEVWG NGAVDKAVFT  360
LSDGRSLSFG APGTSRYRKF YVGESHYISG IYLSSDYSPL AGQAANIAVS YQLINDDEK   419

SEQ ID NO: 73           moltype = DNA  length = 1659
FEATURE                 Location/Qualifiers
misc_feature            1..1659
                        note = A nucleic acid sequence encoding a PirAB fusion
                         protein, TIC10377comprised of the TIC10360 and TIC10369
                         coding sequences inoperable linkage and in frame.
source                  1..1659
                        mol_type = other DNA
                        organism = synthetic construct
SEQUENCE: 73
atgtctagaa taactatttt tattgattca gatgaacaaa aatcagaatt taattctgat  60
tctcctgttc cggtacgtaa agacttaaat acagttgttc ctttgagtga tctgactata  120
tcccctcgtt ctagtgtgga agtatttaga atagatacac caataattcc agaatccaga  180
agatctctga gagttgtaaa tacagggctg gcaagtagtg ttacggctaa attttactgg  240
tctcatagtt ttacctctga atggtttgag tctggttcta tcgatgtagg attaggagaa  300
gataaggtat taaacgtgcc taacaactct ttttattata gtaaatttgt tatctataat  360
aacacggata aagttgctta tattacggca aatttggtta tgcagacaga gaatgtttta  420
gacataagaa ccattgtggc taatgaatat gctataaaaa cgagtgcatt agagtgggat  480
gttactgata ttgtaaaaaa tgcaatcata ggaggcatat cttttatacc tacggttggt  540
```

```
cctgctatat ctttttttagt cggtttattt tggcctcaat caaaagaaaa tatatgggaa  600
gggattgtca aacaaattga gaggatgata gaggaatctg cattaaagac gattaaaggt  660
atccttgctg gtgatattgc ctatatacaa gagcgaatgg caactgttgc tgatcttctt  720
gagaaacatc caggatcggc agaagcgcgg agtgctttta ataacctggc agaaaatata  780
gatggttatc acaaaaaatt taataatttc tcggatgatg taaattatca gatattaccc  840
atgttttcta ctacagttat gatgcagata acatattggg ttgctggttt agagagaaaa  900
gatgaaatag ggcttagtga tattgatatt gaaaaagtcc gagggttaat taaaaagaca  960
gtagaacagg ctaataatta tattaataat atatatggta gagaacttaa tgatgctctt  1020
aataattcga cggctgacac tgttgcaaat aatgttatgt ctgttcatgg tcattgtcgt  1080
ttacatggaa ttgaatatat cagtatttgg gatagattaa gtgaaactga gtctgtaaat  1140
aatagaatct atgttgatgt tttaagttat tctactttct ttgaccgtca aacagcaaag  1200
gccagaattc aggcattgac gccagagaaa gatatggctc cacctctcaa accggctctt  1260
aatggaggaa agagaagaaa gataaattcg ttaatgggac atattgtacg tattggaggg  1320
gcgccaaggg taggagggct gacagttata tttgatgatg gtagtcgcca tcaattaggg  1380
acaatatctg gtgagacggc atctatttct ctggatggta atcgaattac tagtttggaa  1440
gtatggggca atggtgctgt tgataaagct gtctttactt tgagtgatgg tcgttcgttg  1500
tcatttggcg cacctggaac atccagtatat aggaagtttt atgttggtga aagtcactac  1560
atttcaggga tctatttgtc cagtgattac agcccgttag caggtcaggc agcaaatata  1620
gctgtatctt atcagctgat aaatgatgat gaaaaataa                        1659

SEQ ID NO: 74          moltype = AA  length = 552
FEATURE                Location/Qualifiers
REGION                 1..552
                       note = The amino acid sequence of the TIC10377 PirAB fusion
                        protein.
source                 1..552
                       mol_type = protein
                       organism = synthetic construct
SEQUENCE: 74
MSRITIFIDS DEQKSEFNSD SPVPVRKDLN TVVPLSDLTI SPRSSVEVFR IDTPIIPESR  60
RSLRVVNTGL ASSVTAKFYW SHSFTSEWFE SGSIDVGLGE DKVLNVPNNS FYYSKFVIYN  120
NTDKVAYITA NLVMQTENVL DIRTIVANEY AIKTSALEWD VTDIVKNAII GGISFIPTVG  180
PAISFLVGLF WPQSKENIWE GIVKQIERMI EESALKTIKG ILAGDIAYIQ ERMATVADLL  240
EKHPGSAEAR SAFNNLAENI DGYHKKFNNF SDDVNYQILP MFSTTVMMQI TYWVAGLERK  300
DEIGLSDIDI EKVRGLIKKT VEQANNYINN IYGRELNDAL NNSTADTVAN NVMSVHGHCR  360
LHGIEYISIW DRLSETESVN NRIYVDVLSY STFFDRQTAK ARIQALTPEK DMAPPLKPAL  420
NGGKRRKINS LMGHIVRIGG APRVGGLTVI FDDGSRHQLG TISGETASIS LDGNRITSLE  480
VWGNGAVDKA VFTLSDGRSL SFGAPGTSRY RKFYVGESHY ISGIYLSSDY SPLAGQAANI  540
AVSYQLINDD EK                                                     552

SEQ ID NO: 75          moltype = DNA  length = 432
FEATURE                Location/Qualifiers
misc_feature           1..432
                       note = A nucleic acid sequence obtained from Xenorhabdus
                        sp. strainNBAII XenSa04 encoding a TIC10361 pesticidal
                        PirA proteinsequence.
source                 1..432
                       mol_type = other DNA
                       organism = Xenorhabdus sp.
SEQUENCE: 75
atgatcacaa taaatataaa tacaaacggt gttaatggta ttaccattac aaatagtaat  60
aatgaaccta ctccagtatc gacaacttac ggtccaaata caccagcatc agaacccctt  120
acagtcagta attatagtga tatcacaata gaaccacatt cttctgtgca ggcaacaaga  180
attgacacgc ctattattcc tgaaacacgt ccagattact atgtagccaa ctccggccct  240
gcaccaacag ttagggctgt tttttattgg tctcattctt tcacatcaga atggttcgaa  300
tcttcctcta tcacagtgaa agcaggagag gatggaatat taaaagcacc tggtaattct  360
ttatattaca gcaaagtcgt catttataat gacaccgata aacgggcttt tgttactgga  420
tataataaat aa                                                     432

SEQ ID NO: 76          moltype = AA  length = 143
FEATURE                Location/Qualifiers
REGION                 1..143
                       note = The amino acid sequence of the TIC10361 PirA protein.
source                 1..143
                       mol_type = protein
                       organism = Xenorhabdus sp.
SEQUENCE: 76
MITININTNG VNGITITNSN NEPTPVSTTY GPNTPASEPL TVSNYSDITI EPHSSVQATR  60
IDTPIIPETR PDYYVANSGP APTVRAVFYW SHSFTSEWFE SSSITVKAGE DGILKAPGNS  120
LYYSKVVIYN DTDKRAFVTG YNK                                         143

SEQ ID NO: 77          moltype = DNA  length = 1278
FEATURE                Location/Qualifiers
misc_feature           1..1278
                       note = A nucleic acid sequence obtained from Xenorhabdus
                        sp. strainNBAII XenSa04 encoding a TIC10370 pesticidal
                        PirB proteinsequence.
source                 1..1278
                       mol_type = other DNA
```

```
                        organism = Xenorhabdus sp.
SEQUENCE: 77
atgaatacca cacctattac tgtatctgaa aatgaaacat cgcctttact gactgacgta  60
atgcctatgg atctttatgc agtatccacc cctgattatg aatgggatat gtcgtcaatc  120
ataaaggatg ctattattgg tggcatagga tttattccag gtccgggtcc ggcattatcc  180
ttcctgttag gactattttg gcctcagcag aaagacaata cttgggagca aattctccaa  240
aaagtagagc agatgataga gaatgctgtt ctacaaacca ttaaaggaat acttaatgga  300
gaaatacaag agatcaaagg gaaaatggaa catgtagaat ctatgctgaa aaactcgccg  360
ggtagtcagg aaagtcatga tgcatatatg ttcctggcaa gatatctggt gagtatagat  420
gaaaaattca aatcttttga taatagaaca aattaccaga ttctcccaat gtatactaat  480
actattatgt tacagatccc ttattggaaa atgggaatag agaagaaaaa agatattggg  540
ctgacagata ttgaagtcaa tgaattaaaa gaacttatcg acaaattagt aggtaaggcc  600
aagaactata ttcatacgat gtatactaat gaatataacg atgctataaa cacatcaaca  660
gcagggagtg tcactaataa tttattatct gtaaggggat attgtttatt acacggtttg  720
gagtgtattg agttaattga gcatatacag aataatagcc ttgaaagtgg tttctatcct  780
aaaactatca gttattcgac agtgtttgat cgtccgacta ataaaatgag aattcaggct  840
cttacagaag acgatgcaat gcaggagcct ttcaagccat ctttaattaa tgggaaatac  900
aataaaatac aatccataat tggatatgta caaagaattg ggaatgcacc tagagttggt  960
ggtattaaaa ttacatttac caatggctca tcttatacac ttggtacggt gacctcagaa  1020
acaaattcaa ttgaactaaa tgatagtgtt atcgagagct tggaagtatg ggaaatggt  1080
gctgttgatg aggcattatt taagttgagt gatgggcgtt tattgcgtat tggtgagcgt  1140
tacgcgaaaa aatacagaaa atatgctgtt gatcatcact atattgcggg aatttacttg  1200
gccagcgatg agccttcact tgctggtcaa gccgcaggta ttgccgtttc atatcatatg  1260
atggccgaca aaaaataa                                               1278

SEQ ID NO: 78           moltype = AA  length = 425
FEATURE                 Location/Qualifiers
REGION                  1..425
                        note = The amino acid sequence of the TIC10370 PirB protein.
source                  1..425
                        mol_type = protein
                        organism = Xenorhabdus sp.
SEQUENCE: 78
MNTTPITVSE NETSPLLTDV MPMDLYAVST PDYEWDMSSI IKDAIIGGIG FIPGPGPALS  60
FLLGLFWPQQ KDNTWEQILQ KVEQMIENAV LQTIKGILNG EIQEIKGKME HVESMLKNSP  120
GSQESHDAYM FLARYLVSID EKFKSFDNRT NYQILPMYTN TIMLQIPYWK MGIEKKKDIG  180
LTDIEVNELK ELIDKLVGKA KNYIHTMYTN EYNDAINTST AGSVTNNLLS VRGYCLLHGL  240
ECIELIEHIQ NNSLESGFYP KTISYSTVFD RPTNKMRIQA LTEDDAMQEP FKPSLINGKY  300
NKIQSIIGYV QRIGNAPRVG GIKITFTNGS SYTLGTVTSE TNSIELNDSV IESLEVWGNG  360
AVDEALFKLS DGRLLRIGER YAKKYRKYAV DHHYIAGIYL ASDEPSLAGQ AAGIAVSYHM  420
MADKK                                                             425

SEQ ID NO: 79           moltype = DNA  length = 1707
FEATURE                 Location/Qualifiers
misc_feature            1..1707
                        note = A nucleic acid sequence encoding a PirAB fusion
                         protein, TIC10378comprised of the TIC10361 and TIC10370
                         coding sequences inoperable linkage and in frame.
source                  1..1707
                        mol_type = other DNA
                        organism = synthetic construct
SEQUENCE: 79
atgatcacaa taaatataaa tacaaacggt gttaatggta ttaccattac aaatagtaat  60
aatgaaccta ctccagtatc gacaacttac ggtccaaata caccagcatc agaacccctt  120
acagtcagta attatagtga tatcacaata gaaccacatt cttctgtgca ggcaacaaga  180
attgacacgc ctattattcc tgaaacacgt ccagattact atgtagccaa ctccggccct  240
gcaccaacag ttagggctgt tttttattgg tctcattctt tcacatcaga atggttcgaa  300
tcttcctcta tcacagtgaa agcaggagag gatggaatat taaaagcacc tggtaattct  360
ttatattaca gcaaagtcgt catttataat gacaccgata aacgggcttt tgttactgga  420
tataataaaa tgaataccac acctattact gtatctgaaa atgaaacatc gcctttactg  480
actgacgtaa tgcctatgga tctttatgca gtatccaccc ctgattatga atgggatatg  540
tcgtcaatca taaaggatgc tattattggt ggcataggat ttattccagg tccgggtccg  600
gcattatcct tcctgttagg actattttgg cctcagcaga aagacaatac ttgggagcaa  660
attctccaaa aagtagagca gatgatagag aatgctgttc tacaaaccat taaaggaata  720
cttaatggag aaatacaaga gatcaaaggg aaaatggaac atgtagaatc tatgctgaaa  780
aactcgccgg gtagtcagga aagtcatgat gcatatatgt tcctggcaag atatctggtg  840
agtatagatg aaaaattcaa atcttttgat aatagaacaa attaccagat tctcccaatg  900
tatactaata ctattatgtt acagatccct tattggaaaa tgggaataga gaagaaaaaa  960
gatattgggc tgacagatat tgaagtcaat gaattaaaag aacttatcga caaattagta  1020
ggtaaggcca agaactatat tcatacgatg tatactaatg aatataacga tgctataaac  1080
acatcaacag cagggagtgt cactaataat ttattatctg taaggggata ttgtttatta  1140
cacggtttgg agtgtattga gttaattgag catatacaga ataatagcct tgaaagtggt  1200
ttctatccta aaactatcag ttattcgaca gtgtttgatc gtccgactaa taaaatgaga  1260
attcaggctc ttacagaaga cgatgcaatg caggagcctt tcaagccatc tttaattaat  1320
gggaaataca ataaaataca atccataatt ggatatgtac aaagaattgg gaatgcacct  1380
agagttggtg gtattaaaat tacatttacc aatggctcat cttatacact tggtacggtg  1440
acctcagaaa caaattcaat tgaactaaat gatagtgtta tcgagagctt ggaagtatgg  1500
ggaaatggtg ctgttgatga ggcattattt aagttgagtg atgggcgttt attgcgtatt  1560
ggtgagcgtt acgcgaaaaa atacagaaaa tatgctgttg atcatcacta tattgcggga  1620
```

```
atttacttgg ccagcgatga gccttcactt gctggtcaag ccgcaggtat tgccgtttca  1680
tatcatatga tggccgacaa aaaataa                                      1707

SEQ ID NO: 80          moltype = AA  length = 568
FEATURE                Location/Qualifiers
REGION                 1..568
                       note = The amino acid sequence of the TIC10378 PirAB fusion
                        protein.
source                 1..568
                       mol_type = protein
                       organism = synthetic construct
SEQUENCE: 80
MITININTNG VNGITITNSN NEPTPVSTTY GPNTPASEPL TVSNYSDITI EPHSSVQATR  60
IDTPIIPETR PDYYVANSGP APTVRAVFYW SHSFTSEWFE SSSITVKAGE DGILKAPGNS  120
LYYSKVVIYN DTDKRAFVTG YNKMNTTPIT VSENETSPLL TDVMPMDLYA VSTPDYEWDM  180
SSIIKDAIIG GIGFIPGPGP ALSFLLGLFW PQQKDNTWEQ ILQKVEQMIE NAVLQTIKGI  240
LNGEIQEIKG KMEHVESMLK NSPGSQESHD AYMFLARYLV SIDEKFKSFD NRTNYQILPM  300
YTNTIMLQIP YWKMGIEKKK DIGLTDIEVN ELKELIDKLV GKAKNYIHTM YTNEYNDAIN  360
TSTAGSVTNN LLSVRGYCLL HGLECIELIE HIQNNSLESG FYPKTISYST VFDRPTNKMR  420
IQALTEDDAM QEPFKPSLIN GKYNKIQSII GYVQRIGNAP RVGGIKITFT NGSSYTLGTV  480
TSETNSIELN DSVIESLEVW GNGAVDEALF KLSDGRLLRI GERYAKKYRK YAVDHHYIAG  540
IYLASDEPSL AGQAAGIAVS YHMMADKK                                     568

SEQ ID NO: 81          moltype = DNA  length = 411
FEATURE                Location/Qualifiers
misc_feature           1..411
                       note = A nucleic acid sequence obtained from Yersinia
                        aldovae strain670-83 encoding a TIC10362 pesticidal PirA
                        protein sequence.
source                 1..411
                       mol_type = other DNA
                       organism = Yersinia aldovae
SEQUENCE: 81
atgagcaagg taaccatcac tattgatagc tgttcaaatg aagtcgaagt taaaaatcaa  60
actgaggttg ataccgaaag tctagcgttg accactgcac aagttagagc cagggtgcca  120
actgaggtcg cacctaattc aagcaccgaa gttctgtatc ggagtacacc gattattcct  180
gaaagtcgtc gaaatgtaat gatcactaat gatggtgctg caaatgtcat tacagcccaa  240
tactactggt cgcatagttt cacgagtcaa tggttcttat atacgtctat tgacgtcaat  300
gttggtgatt ctaagctatt agtctcaccc tccaactcat tgtattacag taaggttgtt  360
ctgattaata acacaaaccg taaagcatat gttactgccg aggaaaaata g           411

SEQ ID NO: 82          moltype = AA  length = 136
FEATURE                Location/Qualifiers
REGION                 1..136
                       note = The amino acid sequence of the TIC10362 PirA protein.
source                 1..136
                       mol_type = protein
                       organism = Yersinia aldovae
SEQUENCE: 82
MSKVTITIDS CSNEVEVKNQ TEVDTESLAL TTAQVRARVP TEVAPNSSTE VLYRSTPIIP  60
ESRRNVMITN DGAANVITAQ YYWSHSFTSQ WFLYTSIDVN VGDSKLLVSP SNSLYYSKVV  120
LINNTNRKAY VTAEEK                                                  136

SEQ ID NO: 83          moltype = DNA  length = 1251
FEATURE                Location/Qualifiers
misc_feature           1..1251
                       note = A nucleic acid sequence obtained from Yersinia
                        aldovae strain670-83 encoding a TIC10371 pesticidal PirB
                        protein sequence.
source                 1..1251
                       mol_type = other DNA
                       organism = Yersinia aldovae
SEQUENCE: 83
atgaataaca ttacagaata taacaataca gagaactttg tcccttataa tgtatacgct  60
acttcagcct ttgaatttga ctgggattct tcagccattc ttaagcaagc agtgcttaaa  120
ggtatatcat tcattcctta tgtcggtgat tatttatcct ctattattgg cttcttttgg  180
aaagaccaag agagagatat ctggcaggaa attttgggcc gggtacagca acttatcgaa  240
gagaatgtgc ttaaagctat taaaggcatt ttattgggcg atattgctga acttaaaggg  300
aaggttgcat ccgttgtcgc ggccttgcag gaccatcctg gtacaccgga agccaaaagt  360
ttatttatga gcgtatcggt acatttggat agcgtacaac gcaagtttac tacttttgat  420
cacaaaacta attaccatat cctgccgatg tattcagcaa ccgcgttgat gcaaataatg  480
tactggacca tgggcattga gcgtaaagac gatatcggat tgaacagtaa tgaagttggg  540
caacttcaac gaaatattaa tctattggtt acacatgtcg aggattatat tcaagagatt  600
tacgatacag aattagagat ccaatacaac gactcggcac ctaatactgt agccaacaat  660
gttatgtatg tacatggcta ctgtcgggtg catggtttgg agtataccga gatcattcaa  720
agtattcaga agaatagaag caatacacag ggactgtatt caaaaatact gagctactcg  780
actttctttg gttggccaac cagtcaggcg cgaattctcg cattaaaaga cgaaataaat  840
atgccggagc catttaagcc aaaattaata aatggccgta taaaccaagt taagtcagtt  900
aaaggctata tacgacgtat cggaggtgct ttacgggtag gtggattaga aatcaccttt  960
```

```
gagaatggta gtaagtactc gcaaggaact gttactggtg aatttagttc aattgacctt  1020
aatgggagtg tcattgaaac aatggaaact tggggtagtg gcgcaattga cgaagctaaa  1080
tttaccttaa gcgatggccg tacctttact gtcggtcaac gttattcaac aaattacaga  1140
aagtttgcac ttgagggaca ctatatttct ggcattttta ttgccagcga tcgaagtgaa  1200
cttgccggcc aagctgcaaa tatttgtgtt tcttatcatc agaaacagtg a           1251

SEQ ID NO: 84          moltype = AA  length = 416
FEATURE                Location/Qualifiers
REGION                 1..416
                       note = The amino acid sequence of the TIC10371 PirB protein.
source                 1..416
                       mol_type = protein
                       organism = Yersinia aldovae
SEQUENCE: 84
MNNITEYNNT ENFVPYNVYA TSAFEFDWDS SAILKQAVLK GISFIPYVGD YLSSIIGFFW  60
KDQERDIWQE ILGRVQQLIE ENVLKAIKGI LLGDIAELKG KVASVVAALQ DHPGTPEAKS  120
LFMSVSVHLD SVQRKFTTFD HKTNYHILPM YSATALMQIM YWTMGIERKD DIGLNSNEVG  180
QLQRNINLLV THVEDYIQEI YDTELEIQYN DSAPNTVANN VMYVHGYCRV HGLEYTEIIQ  240
SIQKNRSNTQ GLYSKILSYS TFFGWPTSQA RILALKDEIN MPEPFKPKLI NGRINQVKSV  300
KGYIRRIGGA LRVGGLEITF ENGSKYSQGT VTGEFSSIDL NGSVIETMET WGSGAIDEAK  360
FTLSDGRTFT VGQRYSTNYR KFALEGHYIS GIFIASDRSE LAGQAANICV SYHQKQ      416

SEQ ID NO: 85          moltype = DNA  length = 1659
FEATURE                Location/Qualifiers
misc_feature           1..1659
                       note = A nucleic acid sequence encoding a PirAB fusion
                        protein, TIC10379comprised of the TIC10362 and TIC10371
                        coding sequences inoperable linkage and in frame.
source                 1..1659
                       mol_type = other DNA
                       organism = synthetic construct
SEQUENCE: 85
atgagcaagg taaccatcac tattgatagc tgttcaaatg aagtcgaagt taaaaatcaa  60
actgaggttg ataccgaaag tctagcgttg accactgcac aagttagagc cagggtgcca  120
actgaggtcg cacctaattc aagcaccgaa gttctgtatc ggagtacacc gattattcct  180
gaaagtcgtc gaaatgtaat gatcactaat gatggtgctg caaatgtcat tacagcccaa  240
tactactggt cgcatagttt cacgagtcaa tggttcttat atacgtctat tgacgtcaat  300
gttggtgatt ctaagctatt agtctcaccc tccaactcat tgtattacag taaggttgtt  360
ctgattaata acacaaaccg taaagcatat gttactgccg aggaaaaaat gaataacatt  420
acagaatata acaatacaga gaactttgtc ccttataatg tatacgctac ttcagccttt  480
gaatttgact gggattcttc agccattctt aagcaagcag tgcttaaagg tatatcattc  540
attccttatg tcggtgatta tttatcctct attattggct tcttttggaa agaccaagag  600
agagatatct ggcaggaaat tttgggccgg gtacagcaac ttatcgaaga gaatgtgctt  660
aaagctatta aaggcatttt attgggcgat attgctgaac ttaaagggaa ggttgcatcc  720
gttgtcgcgg ccttgcagga ccatcctggt acaccggaag ccaaaagttt atttatgagc  780
gtatcggtac atttggatag cgtacaacgc aagtttacta cttttgatca caaaactaat  840
taccatatcc tgccgatgta ttcagcaacc gcgttgatgc aaataatgta ctggaccatg  900
ggcattgagc gtaaagacga tatcggattg aacagtaatg aagttgggca acttcaacga  960
aatattaatc tattggttac acatgtcgag gattatattc aagagattta cgatacagaa  1020
ttagagatcc aatacaacga ctcggcacct aatactgtag ccaacaatgt tatgtatgta  1080
catggctact gtcgggtgca tggtttggag tataccgaga tcattcaaag tattcagaag  1140
aatagaagca atacacaggg actgtattca aaaatactga gctactcgac tttctttggt  1200
tggccaacca gtcaggcgcg aattctcgca ttaaaagacg aaataaatat gccggagcca  1260
tttaagccaa aattaataaa tggccgtata aaccaagtta agtcagttaa aggctatata  1320
cgacgtatcg gaggtgcttt acgggtaggt ggattagaaa tcacctttga gaatggtagt  1380
aagtactcgc aaggaactgt tactggtgaa tttagttcaa ttgaccttaa tgggagtgtc  1440
attgaaacaa tggaaacttg gggtagtggc gcaattgacg aagctaaatt taccttaagc  1500
gatggccgta cctttactgt cggtcaacgt tattcaacaa attacagaaa gtttgcactt  1560
gagggacact atatttctgg catttttatt gccagcgatc gaagtgaact tgccggccaa  1620
gctgcaaata tttgtgtttc ttatcatcag aaacagtga                        1659

SEQ ID NO: 86          moltype = AA  length = 552
FEATURE                Location/Qualifiers
REGION                 1..552
                       note = The amino acid sequence of the TIC10379 PirAB fusion
                        protein.
source                 1..552
                       mol_type = protein
                       organism = synthetic construct
SEQUENCE: 86
MSKVTITIDS CSNEVEVKNQ TEVDTESLAL TTAQVRARVP TEVAPNSSTE VLYRSTPIIP  60
ESRRNVMITN DGAANVITAQ YYWSHSFTSQ WFLYTSIDVN VGDSKLLVSP SNSLYYSKVV  120
LINNTNRKAY VTAEEKMNNI TEYNNTENFV PYNVYATSAF EFDWDSSAIL KQAVLKGISF  180
IPYVGDYLSS IIGFFWKDQE RDIWQEILGR VQQLIEENVL KAIKGILLGD IAELKGKVAS  240
VVAALQDHPG TPEAKSLFMS VSVHLDSVQR KFTTFDHKTN YHILPMYSAT ALMQIMYWTM  300
GIERKDDIGL NSNEVGQLQR NINLLVTHVE DYIQEIYDTE LEIQYNDSAP NTVANNVMYV  360
HGYCRVHGLE YTEIIQSIQK NRSNTQGLYS KILSYSTFFG WPTSQARILA LKDEINMPEP  420
FKPKLINGRI NQVKSVKGYI RRIGGALRVG GLEITFENGS KYSQGTVTGE FSSIDLNGSV  480
IETMETWGSG AIDEAKFTLS DGRTFTVGQR YSTNYRKFAL EGHYISGIFI ASDRSELAGQ  540
```

```
AANICVSYHQ KQ                                                552

SEQ ID NO: 87          moltype = DNA  length = 414
FEATURE                Location/Qualifiers
misc_feature           1..414
                       note = A nucleic acid sequence obtained from Xenorhabdus
                        doucetiaestrain FRM16 encoding a TIC10363 pesticidal PirA
                        proteinsequence.
source                 1..414
                       mol_type = other DNA
                       organism = Xenorhabdus doucetiae
SEQUENCE: 87
atgattacaa ttaatataag tggtggttca gtaacaatta ataacactta caatatcaca  60
tcagaatctg gcattcaaaa taccccctgcc tcagaacctc tcaccgtcat tccttataga  120
gatatgacaa tagaaccaca ctcttctatt gaggcaacaa gaactgatac gcctattatt  180
cctgaaacac gccccaatta ttatatcgcc aattccggcc ctgcatcaga agttagagca  240
gtgttttatt ggtcgcattc tttcacatca caatggttcg aatcttcctc tatcatagtg  300
aaagcagggg aagacggcat attacaatca ccaagcaact cgctatatta cagcaaggtt  360
gtcatttata atgatacaga taaacgcgcc tttgtgactg gatataataa gtaa        414

SEQ ID NO: 88          moltype = AA  length = 137
FEATURE                Location/Qualifiers
REGION                 1..137
                       note = The amino acid sequence of the TIC10363 PirA protein.
source                 1..137
                       mol_type = protein
                       organism = Xenorhabdus doucetiae
SEQUENCE: 88
MITINISGGS VTINNTYNIT SESGIQNTPA SEPLTVIPYR DMTIEPHSSI EATRTDTPII  60
PETRPNYYIA NSGPASEVRA VFYWSHSFTS QWFESSSIIV KAGEDGILQS PSNSLYYSKV  120
VIYNDTDKRA FVTGYNK                                           137

SEQ ID NO: 89          moltype = DNA  length = 1293
FEATURE                Location/Qualifiers
misc_feature           1..1293
                       note = A nucleic acid sequence obtained from Xenorhabdus
                        doucetiaestrain FRM16 encoding a TIC10372 pesticidal PirB
                        proteinsequence.
source                 1..1293
                       mol_type = other DNA
                       organism = Xenorhabdus doucetiae
SEQUENCE: 89
atgaataaca catctataaa tatcaatgag aatgaaacat tacctttaga agttatccct  60
tcaatgcctg aacccatgtt aatcgttcct tatgcaactt ctactcctga ttatgaatgg  120
gatgcctccg gaataataaa agatgccatt attggtggta taggatttat tcctggccca  180
ggtccggcaa tatcttttct gttaggactc ttttggcctc aacaggcaga caatacttgg  240
gaacaaattc tgcaaaaagt cgagcagatg atagaggatg ctgttctcaa aaccattcaa  300
ggtatattga atggcgatat acaagaaatt aaaggtaaaa tggaacatgt ccaatacatg  360
ttggaaacct caccgggtag ccaagaaagc cgtgaagctt atatgtttct ggcgagatat  420
ctggtgagta tagatgaaaa attcaagtcc tttgataata aaacaaatta ccaaattctc  480
ccgatgtata ccaacactct catgttacag gttccttatt ggaaaatggg catagagaag  540
caaaaggata ttggtttatc cgatatagaa gttaatgaat taaaacagct tatcgataaa  600
ttatatacca aggctaacag ctatattcat gaaacgtata cgcgtcaata taacgatgcg  660
ataaacacgt caaccgcagc aaatatcacc aataatttat tttctgtcag aggatattgt  720
ttgttacacg gtttagagtg tcttgaaatg attgagcatc tacaaaagaa tagccttgaa  780
agtggtttct atcccaaaac catcagttat tctaccgtat tcgatcgtca gactcccaaa  840
atgagaattc aggctctgac agaagacgat caaatgcagg agccattaaa gccatcttta  900
atcaacggca aatacaatca aataaaatca ttgactggat atgtccgtag aattggcaat  960
gctcccagag tggggggat gacgatcaca tttgccaacg gtgcatctta cacactgggt  1020
acagtaacat cagaaacgac gtcaattgag ctcaatggca gtgtgatcga aagcttggaa  1080
gtctggggag atggcgcggt tgatgaggca ttatttacgt taagtgataa acgcctattc  1140
cgtatcggtg agcgctacgc cagaaaatac aaaaaatatg ctgttgatag ccactatatt  1200
gcagggcttt atttagccag tgatgagcct tcacttgcag gtcaagccgc aggtattgcc  1260
gtttcatacc atatgctgga tgacaaaaaa taa                         1293

SEQ ID NO: 90          moltype = AA  length = 430
FEATURE                Location/Qualifiers
REGION                 1..430
                       note = The amino acid sequence of the TIC10372 PirB protein.
source                 1..430
                       mol_type = protein
                       organism = Xenorhabdus doucetiae
SEQUENCE: 90
MNNTSININE NETLPLEVIP SMPEPMLIVP YATSTPDYEW DASGIIKDAI IGGIGFIPGP  60
GPAISFLLGL FWPQQADNTW EQILQKVEQM IEDAVLKTIQ GILNGDIQEI KGKMEHVQYM  120
LETSPGSQES REAYMFLARY LVSIDEKFKS FDNKTNYQIL PMYTNTLMLQ VPYWKMGIEK  180
QKDIGLSDIE VNELKQLIDK LYTKANSYIH ETYTRQYNDA INTSTAANIT NNLFSVRGYC  240
LLHGLECLEM IEHLQKNSLE SGFYPKTISY STVFDRQTPK MRIQALTEDD QMQEPLKPSL  300
INGKYNQIKS LTGYVRRIGN APRVGGMTIT FANGASYTLG TVTSETTSIE LNGSVIESLE  360
```

```
VWGDGAVDEA LFTLSDKRLF RIGERYARKY KKYAVDSHYI AGLYLASDEP SLAGQAAGIA  420
VSYHMLDDKK                                                         430

SEQ ID NO: 91          moltype = DNA  length = 1704
FEATURE                Location/Qualifiers
misc_feature           1..1704
                       note = A nucleic acid sequence encoding a PirAB fusion
                        protein, TIC10380comprised of the TIC10363 and TIC10372
                        coding sequences inoperable linkage and in frame.
source                 1..1704
                       mol_type = other DNA
                       organism = synthetic construct
SEQUENCE: 91
atgattacaa ttaatataag tggtggttca gtaacaatta ataacactta caatatcaca  60
tcagaatctg gcattcaaaa taccccctgcc tcagaacctc tcaccgtcat tccttataga  120
gatatgacaa tagaaccaca ctcttctatt gaggcaacaa gaactgatac gcctattatt  180
cctgaaacac gccccaatta ttatatcgcc aattccggcc ctgcatcaga agttagagca  240
gtgttttatt ggtcgcattc tttcacatca caatggttcg aatcttcctc tatcatagtg  300
aaagcagggg aagacggcat attacaatca ccaagcaact cgctatatta cagcaaggtt  360
gtcatttata atgatacaga taaacgcgcc tttgtgactg gatataataa gatgaataac  420
acatctataa atatcaatga gaatgaaaca ttacctttag aagttatccc ttcaatgcct  480
gaacccatgt taatcgttcc ttatgcaact tctactcctg attatgaatg ggatgcctcc  540
ggaataataa aagatgccat tattggtggt ataggattta ttcctggccc aggtccggca  600
atatcttttc tgttaggact cttttggcct caacaggcag acaatacttg ggaacaaatt  660
ctgcaaaaag tcgagcagat gatagaggat gctgttctca aaaccattca aggtatattg  720
aatggcgata tacaagaaat taaaggtaaa atggaacatg tccaatacat gttggaaacc  780
tcaccgggta gccaagaaag ccgtgaagct tatatgtttc tggcgagata tctggtgagt  840
atagatgaaa aattcaagtc ctttgataat aaaacaaatt accaaattct cccgatgtat  900
accaacactc tcatgttaca ggttccttat tggaaaatgg gcatagagaa gcaaaaggat  960
attggtttat ccgatataga agttaatgaa ttaaaacagc ttatcgataa attatatacc  1020
aaggctaaca gctatattca tgaaacgtat acgcgtcaat ataacgatgc gataaacacg  1080
tcaaccgcag caaatatcac caataattta ttttctgtca gaggatattg tttgttacac  1140
ggtttagagt gtcttgaaat gattgagcat ctacaaaaga atagccttga aagtggtttc  1200
tatcccaaaa ccatcagtta ttctaccgta ttcgatcgtc agactcccaa aatgagaatt  1260
caggctctga cagaagacga tcaaatgcag gagccattaa agccatcttt aatcaacggc  1320
aaatacaatc aaataaaatc attgactgga tatgtccgta gaattggcaa tgctcccaga  1380
gtggggggga tgacgatcac atttgccaac ggtgcatctt acacactggg tacagtaaca  1440
tcagaaacga cgtcaattga gctcaatggc agtgtgatcg aaagcttgga agtctgggga  1500
gatggcgcgg ttgatgaggc attatttacg ttaagtgata aacgcctatt ccgtatcggt  1560
gagcgctacg ccagaaaata caaaaaatat gctgttgata gccactatat tgcagggctt  1620
tatttagcca gtgatgagcc ttcacttgca ggtcaagccg caggtattgc cgtttcatac  1680
catatgctgg atgacaaaaa ataa                                         1704

SEQ ID NO: 92          moltype = AA  length = 567
FEATURE                Location/Qualifiers
REGION                 1..567
                       note = The amino acid sequence of the TIC10380 PirAB fusion
                        protein.
source                 1..567
                       mol_type = protein
                       organism = synthetic construct
SEQUENCE: 92
MITINISGGS VTINNTYNIT SESGIQNTPA SEPLTVIPYR DMTIEPHSSI EATRTDTPII  60
PETRPNYYIA NSGPASEVRA VFYWSHSFTS QWFESSSIIV KAGEDGILQS PSNSLYYSKV  120
VIYNDTDKRA FVTGYNKMNN TSININENET LPLEVIPSMP EPMLIVPYAT STPDYEWDAS  180
GIIKDAIIGG IGFIPGPGPA ISFLLGLFWP QQADNTWEQI LQKVEQMIED AVLKTIQGIL  240
NGDIQEIKGK MEHVQYMLET SPGSQESREA YMFLARYLVS IDEKFKSFDN KTNYQILPMY  300
TNTLMLQVPY WKMGIEKQKD IGLSDIEVNE LKQLIDKLYT KANSYIHETY TRQYNDAINT  360
STAANITNNL FSVRGYCLLH GLECLEMIEH LQKNSLESGF YPKTISYSTV FDRQTPKMRI  420
QALTEDDQMQ EPLKPSLING KYNQIKSLTG YVRRIGNAPR VGGMTITFAN GASYTLGTVT  480
SETTSIELNG SVIESLEVWG DGAVDEALFT LSDKRLFRIG ERYARKYKKY AVDSHYIAGL  540
YLASDEPSLA GQAAGIAVSY HMLDDKK                                      567

SEQ ID NO: 93          moltype = DNA  length = 429
FEATURE                Location/Qualifiers
misc_feature           1..429
                       note = A nucleic acid sequence obtained from Xenorhabdus
                        griffiniaestrain BMMCB encoding a TIC10364 pesticidal PirA
                        proteinsequence.
source                 1..429
                       mol_type = other DNA
                       organism = Xenorhabdus griffiniae
SEQUENCE: 93
atgagcataa tcaatataaa tataagtggt agtagtgaca ttacaatcat aaacaatacc  60
ccatctaacc cagaaccact catttacaat acagacacac ccgcatcaga acctcttacc  120
gtcaatcctt atagggatat gacaatagag ccacactctt ctattgaggc aataagaatt  180
gatacgccaa ttattcccga aacccgcccc aattattacg tagccaattc tggccccgca  240
tcatcagtta gagccgtttt ttattggtct cactctttca catcagaatg gttcgaatat  300
tctgctatca cagtgaaagc cggggaagac ggcatattac aatcaccgag caactctgtg  360
```

```
tattacagca aggtcgtcat ttataacgaa accgataaac gcgcctttgt tactggatat  420
aataagtaa                                                          429

SEQ ID NO: 94          moltype = AA  length = 142
FEATURE                Location/Qualifiers
REGION                 1..142
                       note = The amino acid sequence of the TIC10364 PirA protein.
source                 1..142
                       mol_type = protein
                       organism = Xenorhabdus griffiniae
SEQUENCE: 94
MSIININISG SSDITIINNT PSNPEPLIYN TDTPASEPLT VNPYRDMTIE PHSSIEAIRI  60
DTPIIPETRP NYYVANSGPA SSVRAVFYWS HSFTSEWFEY SAITVKAGED GILQSPSNSV  120
YYSKVVIYNE TDKRAFVTGY NK                                           142

SEQ ID NO: 95          moltype = DNA  length = 1278
FEATURE                Location/Qualifiers
misc_feature           1..1278
                       note = A nucleic acid sequence obtained from Xenorhabdus
                        griffiniaestrain BMMCB encoding a TIC10373 pesticidal PirB
                        proteinsequence.
source                 1..1278
                       mol_type = other DNA
                       organism = Xenorhabdus griffiniae
SEQUENCE: 95
atgaatacca caccgattaa tgtatctgaa aatgacacat tgcctgtact cactgacgtc  60
atgcttatcg tgccttatac cacctctacc cccgattatg aatgggatat gtcatcaata  120
ataaaggatg ccattattgg cggcgtaggg tttattccag gagtaggttc cgcaatgtct  180
ttcctgttag ggctattttg gccgcaacag aaagataata cctgggagca aatcctccaa  240
aaagtagagc aaatgataga gaatgctgct ctacaaacga ttaaaggaat acttaatgga  300
gatatacaag aaatcaaagg aaaaatggaa catgtgcaat acatgctgga aacctcgcct  360
ggcagccagg aaagccatga cgcctatatg ttcctggcta gatatctggt gagtatcgat  420
gaaagattca agtcttttga taataaaaca aactaccaga tcctgccgat gtacactaac  480
acggttatgt tacagatccc ttattggaaa atggggatag aaaagaaaaa tgatattggg  540
ctgaccgata ttgaagtcaa tgagttaaaa caacttatcg acacattggt tgacagagcc  600
agaaactata ttcatacgat gtatactaat gaatataata atgccataaa tacatcaaca  660
gcagagagtg tcactaataa tttattgtct gtaagagggt attgtttatt acacggttta  720
gagtgtattg agttaattga acatctacaa aataatagcc tggaaagtgg ttttaatcct  780
aaaactatca gttattcaac cgtatttgat cgtcctacta acaaaacgag aattcaggct  840
ctgacagaag acgatcaaat gcaggaaccc ttcaagccct ctttaatcga cggtaaatac  900
aataaaataa aatcattgct tggctatgta cgaagaatcg gcaatgcccc cagagtgggt  960
ggtattcaaa tcacatttgc caacgattca tcctatacac tcggcaccgt aacatcagaa  1020
acgagttcta ttgaactcaa tgatagtgtt atcgaaaggt tggaagtatg gggcaatggc  1080
gcggttgatg aggcgttatt tacgttaagt gatgggcgtc aactcagagt cggtgaacgc  1140
tacgcgacaa aatacagaaa atacgctgtt gatggccact atattgcagg gctgtactta  1200
gccagcgatg aaccttcact tgctggtcag gccgcaggta ttgccgtttc ataccatatg  1260
ttagctgata aaaaataa                                                1278

SEQ ID NO: 96          moltype = AA  length = 425
FEATURE                Location/Qualifiers
REGION                 1..425
                       note = The amino acid sequence of the TIC10373 PirB protein.
source                 1..425
                       mol_type = protein
                       organism = Xenorhabdus griffiniae
SEQUENCE: 96
MNTTPINVSE NDTLPVLTDV MLIVPYTTST PDYEWDMSSI IKDAIIGGVG FIPGVGSAMS  60
FLLGLFWPQQ KDNTWEQILQ KVEQMIENAA LQTIKGILNG DIQEIKGKME HVQYMLETSP  120
GSQESHDAYM FLARYLVSID ERFKSFDNKT NYQILPMYTN TVMLQIPYWK MGIEKKNDIG  180
LTDIEVNELK QLIDTLVDRA RNYIHTMYTN EYNNAINTST AESVTNNLLS VRGYCLLHGL  240
ECIELIEHLQ NNSLESGFNP KTISYSTVFD RPTNKTRIQA LTEDDQMQEP FKPSLIDGKY  300
NKIKSLLGYV RRIGNAPRVG GIQITFANDS SYTLGTVTSE TSSIELNDSV IERLEVWGNG  360
AVDEALFTLS DGRQLRVGER YATKYRKYAV DGHYIAGLYL ASDEPSLAGQ AAGIAVSYHM  420
LADKK                                                              425

SEQ ID NO: 97          moltype = DNA  length = 1704
FEATURE                Location/Qualifiers
misc_feature           1..1704
                       note = A nucleic acid sequence encoding a PirAB fusion
                        protein, TIC10381comprised of the TIC10364 and TIC10364
                        coding sequences inoperable linkage and in frame.
source                 1..1704
                       mol_type = other DNA
                       organism = synthetic construct
SEQUENCE: 97
atgagcataa tcaatataaa tataagtggt agtagtgaca ttacaatcat aaacaatacc  60
ccatctaacc cagaaccact catttacaat acagacacac ccgcatcaga acctcttacc  120
gtcaatcctt atagggatat gacaatagag ccacactctt ctattgaggc aataagaatt  180
gatacgccaa ttattcccga aacccgcccc aattattacg tagccaattc tggccccgca  240
```

```
tcatcagtta gagccgtttt ttattggtct cactctttca catcagaatg gttcgaatat  300
tctgctatca cagtgaaagc cggggaagac ggcatattac aatcaccgag caactctgtg  360
tattacagca aggtcgtcat ttataacgaa accgataaac gcgcctttgt tactggatat  420
aataagatga ataccacacc gattaatgta tctgaaaatg acacattgcc tgtactcact  480
gacgtcatgc ttatcgtgcc ttataccacc tctacccccg attatgaatg ggatatgtca  540
tcaataataa aggatgccat tattggcggc gtagggttta ttccaggagt aggttccgca  600
atgtctttcc tgttagggct attttggccg caacagaaag ataatacctg ggagcaaatc  660
ctccaaaaag tagagcaaat gatagagaat gctgctctac aaacgattaa aggaatactt  720
aatggagata tacaagaaat caaaggaaaa atggaacatg tgcaatacat gctggaaacc  780
tcgcctggca gccaggaaag ccatgacgcc tatatgttcc tggctagata tctggtgagt  840
atcgatgaaa gattcaagtc ttttgataat aaaacaaact accagatcct gccgatgtac  900
actaacacgg ttatgttaca gatcccttat tggaaaatgg ggatagaaaa gaaaaatgat  960
attgggctga ccgatattga agtcaatgag ttaaaacaac ttatcgacac attggttgac  1020
agagccagaa actatattca tacgatgtat actaatgaat ataataatgc cataaataca  1080
tcaacagcag agagtgtcac taataattta ttgtctgtaa gagggtattg tttattacac  1140
ggtttagagt gtattgagtt aattgaacat ctacaaaata atagcctgga aagtggtttt  1200
aatcctaaaa ctatcagtta ttcaaccgta tttgatcgtc ctactaacaa aacgagaatt  1260
caggctctga cagaagacga tcaaatgcag gaacccttca agccctcttt aatcgacggt  1320
aaatacaata aaataaaatc attgcttggc tatgtacgaa gaatcggcaa tgccccccaga  1380
gtgggtggta ttcaaatcac atttgccaac gattcatcct atacactcgg caccgtaaca  1440
tcagaaacga gttctattga actcaatgat agtgttatcg aaaggttgga agtatggggc  1500
aatggcgcgg ttgatgaggc gttatttacg ttaagtgatg ggcgtcaact cagagtcggt  1560
gaacgctacg cgacaaaata cagaaaatac gctgttgatg gccactatat tgcagggctg  1620
tacttagcca gcgatgaacc ttcacttgct ggtcaggccg caggtattgc cgtttcatac  1680
catatgttag ctgataaaaa ataa                                       1704

SEQ ID NO: 98          moltype = AA  length = 567
FEATURE                Location/Qualifiers
REGION                 1..567
                       note = The amino acid sequence of the TIC10381 PirAB fusion
                        protein.
source                 1..567
                       mol_type = protein
                       organism = synthetic construct
SEQUENCE: 98
MSIININISG SSDITIINNT PSNPEPLIYN TDTPASEPLT VNPYRDMTIE PHSSIEAIRI  60
DTPIIPETRP NYYVANSGPA SSVRAVFYWS HSFTSEWFEY SAITVKAGED GILQSPSNSV  120
YYSKVVIYNE TDKRAFVTGY NKMNTTPINV SENDTLPVLT DVMLIVPYTT STPDYEWDMS  180
SIIKDAIIGG VGFIPGVGSA MSFLLGLFWP QQKDNTWEQI LQKVEQMIEN AALQTIKGIL  240
NGDIQEIKGK MEHVQYMLET SPGSQESHDA YMFLARYLVS IDERFKSFDN KTNYQILPMY  300
TNTVMLQIPY WKMGIEKKND IGLTDIEVNE LKQLIDTLVD RARNYIHTMY TNEYNNAINT  360
STAESVTNNL LSVRGYCLLH GLECIELIEH LQNNSLESGF NPKTISYSTV FDRPTNKTRI  420
QALTEDDQMQ EPFKPSLIDG KYNKIKSLLG YVRRIGNAPR VGGIQITFAN DSSYTLGTVT  480
SETSSIELND SVIERLEVWG NGAVDEALFT LSDGRQLRVG ERYATKYRKY AVDGHYIAGL  540
YLASDEPSLA GQAAGIAVSY HMLADKK                                    567

SEQ ID NO: 99          moltype = DNA  length = 408
FEATURE                Location/Qualifiers
misc_feature           1..408
                       note = A nucleic acid sequence obtained from Xenorhabdus
                        nematophilaencoding a TIC10359 pesticidal PirA protein
                        sequence.
source                 1..408
                       mol_type = other DNA
                       organism = Xenorhabdus nematophila
SEQUENCE: 99
atgattacaa tcaatatcac tggtgataat gtaagagtta ataacaatat agcaacagaa  60
accgacctcc aaaatacacc tgcttcagca cccttatcaa ttattaattt tagggatatg  120
acaatagaac ctcattcatc tgttgaggcg ataagaaccg atacaccgat tattcctgaa  180
tcacgaccaa attactatgt tgctaattct ggcccggcct catcagtcag agctgttttc  240
tattggtccc actcttttac atcagaatgg tttgaatctt cctctattat tgtaaaagca  300
ggcgaagacg gagtcttaca ttcaccgggt aattctttat attacagcaa ggttgtaatt  360
tataacgata cagacaaacg tgcttttgtt accggctaca atctataa             408

SEQ ID NO: 100         moltype = AA  length = 135
FEATURE                Location/Qualifiers
REGION                 1..135
                       note = The amino acid sequence of the TIC10359 PirA protein.
source                 1..135
                       mol_type = protein
                       organism = Xenorhabdus nematophila
SEQUENCE: 100
MITINITGDN VRVNNNIATE TDLQNTPASA PLSIINFRDM TIEPHSSVEA IRTDTPIIPE  60
SRPNYYVANS GPASSVRAVF YWSHSFTSEW FESSSIIVKA GEDGVLHSPG NSLYYSKVVI  120
YNDTDKRAFV TGYNL                                                 135

SEQ ID NO: 101         moltype = DNA  length = 1290
FEATURE                Location/Qualifiers
misc_feature           1..1290
```

```
                        note = A nucleic acid sequence obtained from Xenorhabdus
                         nematophilaencoding a TIC10368 pesticidal PirB protein
                         sequence.
source                  1..1290
                        mol_type = other DNA
                        organism = Xenorhabdus nematophila
SEQUENCE: 101
atgaataatg aaccgatgaa tactaatgaa tcacaagctt cagagatagt accctcaatg  60
aatgaatcta tattagcagc accttattca atttctacac ctaattatga atgggatatg  120
tcatcaataa taaaagatgc cattattggt ggtataggct ttattcctgg tccgggctca  180
gcaatatcat ttttgttagg gttattttgg ccacaacaaa ccgacaatac ttgggagcaa  240
attctccaaa aagtagaaca aatgatcgag caagccaatc tcaaaactat tcaaggaata  300
ttgaacggcg atatacaaga aattaaaggc aaaatggaac atgtgcaatt catgctagaa  360
tcctcacctg gcactcaaga aagccatgac gcatacatgt ttctggcgag atatctggtc  420
agtatagacg aaaaattcaa gtcttttgat aacaaaacaa attatcaaat tcttcccatg  480
tataccaata cgattatgtt acaagcccct tattggaaaa tgggtataga gagaaaagat  540
gagataaaac taacagatat agaagttaat gaattaaaag agctgatagg aaaattatct  600
accagcgccg ataaatatat tcatgatgtc tatactcgtg aatatgataa tgcgatgaac  660
acttcaacag cagcaaatat caccaataat ttattatctg taagaggcta ttgtttatta  720
catggtttag aatgtctcga agtcattaac catatacaaa ataatagcct tgagcaaagt  780
ttttatccta aaactatcag ctactccacc gtattcgatc gccagacaaa taaaacaagg  840
gttcaagccc tgacagaaga cgatcaaatg caagagccat tcaagcctgc tttaattaat  900
gggaagtaca acaaaataaa atcattgatt gggtatgtac aaagaatcgg aaacgcaccc  960
agagttggag gcattaaagt cacatttgca aacgatgcat cttataccct cggtacagta  1020
acttcagaag taaactcaat tgaactgaat gacagcgtta taaccagcct ggaagtatgg  1080
ggaaatggcg ctgttgatga ggcattcttt acattaagtg acggacgtca atttaggctt  1140
ggccaacgct atgccagtaa ctatagaaaa tatgctgtcg ataaccacta tatttcagga  1200
ttgtacttag ccagtgatga accttcattg gcaggccaag cagcaggcat tgcagtttca  1260
taccatatga tagctgataa aaaatcatag                                  1290

SEQ ID NO: 102          moltype = AA  length = 429
FEATURE                 Location/Qualifiers
REGION                  1..429
                        note = The amino acid sequence of the TIC10368 PirB protein.
source                  1..429
                        mol_type = protein
                        organism = Xenorhabdus nematophila
SEQUENCE: 102
MNNEPMNTNE SQASEIVPSM NESILAAPYS ISTPNYEWDM SSIIKDAIIG GIGFIPGPGS  60
AISFLLGLFW PQQTDNTWEQ ILQKVEQMIE QANLKTIQGI LNGDIQEIKG KMEHVQFMLE  120
SSPGTQESHD AYMFLARYLV SIDEKFKSFD NKTNYQILPM YTNTIMLQAP YWKMGIERKD  180
EIKLTDIEVN ELKELIGKLS TSADKYIHDV YTREYDNAMN TSTAANITNN LLSVRGYCLL  240
HGLECLEVIN HIQNNSLEQS FYPKTISYST VFDRQTNKTR VQALTEDDQM QEPFKPALIN  300
GKYNKIKSLI GYVQRIGNAP RVGGIKVTFA NDASYTLGTV TSEVNSIELN DSVITSLEVW  360
GNGAVDEAFF TLSDGRQFRL GQRYASNYRK YAVDNHYISG LYLASDEPSL AGQAAGIAVS  420
YHMIADKKS                                                         429

SEQ ID NO: 103          moltype = DNA  length = 1766
FEATURE                 Location/Qualifiers
misc_feature            1..1766
                        note = A nucleic acid sequence encoding an operon comprised
                         of thecoding sequences TIC10359 and TIC10368.
source                  1..1766
                        mol_type = other DNA
                        organism = synthetic construct
SEQUENCE: 103
atgattacaa tcaatatcac tggtgataat gtaagagtta ataacaatat agcaacagaa  60
accgacctcc aaaatacacc tgcttcagca cccttatcaa ttattaattt tagggatatg  120
acaatagaac ctcattcatc tgttgaggcg ataagaaccg atacaccgat tattcctgaa  180
tcacgaccaa attactatgt tgctaattct ggcccggcct catcagtcag agctgttttc  240
tattggtccc actcttttac atcagaatgg tttgaatctt cctctattat tgtaaaagca  300
ggcgaagacg gagtcttaca ttcaccgggt aattctttat attacagcaa ggttgtaatt  360
tataacgata cagacaaacg tgcttttgtt accggctaca atctataatg acgcagaaat  420
acaatccata tttccaatga atttcaaata acatccttaa ggcaagaaac aaaatcatga  480
ataatgaacc gatgaatact aatgaatcac aagcttcaga gatagtaccc tcaatgaatg  540
aatctatatt agcagcacct tattcaattt ctacacctaa ttatgaatgg gatatgtcat  600
caataataaa agatgccatt attggtggta taggctttat tcctggtccg ggctcagcaa  660
tatcattttt gttagggtta ttttggccac aacaaaccga caatacttgg gagcaaattc  720
tccaaaaagt agaacaaatg atcgagcaag ccaatctcaa aactattcaa ggaatattga  780
acggcgatat acaagaaatt aaaggcaaaa tggaacatgt gcaattcatg ctagaatcct  840
cacctggcac tcaagaaagc catgacgcat acatgtttct ggcgagatat ctggtcagta  900
tagacgaaaa attcaagtct tttgataaca aaacaaatta tcaaattctt cccatgtata  960
ccaatacgat tatgttacaa gccccttatt ggaaaatggg tatagagaga aaagatgaga  1020
taaaactaac agatatagaa gttaatgaat taaaagagct gataggaaaa ttatctacca  1080
gcgccgataa atatattcat gatgtctata ctcgtgaata tgataatgcg atgaacactt  1140
caacagcagc aaatatcacc aataatttat tatctgtaag aggctattgt ttattacatg  1200
gtttagaatg tctcgaagtc attaaccata tacaaaataa tagccttgag caaagttttt  1260
atcctaaaac tatcagctac tccaccgtat tcgatcgcca gacaaataaa acaagggttc  1320
aagccctgac agaagacgat caaatgcaag agccattcaa gcctgcttta attaatggga  1380
```

```
agtacaacaa aataaaatca ttgattgggt atgtacaaag aatcggaaac gcacccagag  1440
ttggaggcat taaagtcaca tttgcaaacg atgcatctta taccctcggt acagtaactt  1500
cagaagtaaa ctcaattgaa ctgaatgaca gcgttataac cagcctggaa gtatggggaa  1560
atggcgctgt tgatgaggca ttctttacat taagtgacgg acgtcaattt aggcttggcc  1620
aacgctatgc cagtaactat agaaaatatg ctgtcgataa ccactatatt tcaggattgt  1680
acttagccag tgatgaacct tcattggcag gccaagcagc aggcattgca gtttcatacc  1740
atatgatagc tgataaaaaa tcatag                                       1766

SEQ ID NO: 104         moltype = DNA  length = 417
FEATURE                Location/Qualifiers
misc_feature           1..417
                       note = A nucleic acid sequence obtained from Photorhabdus
                        luminescensstrain Hm encoding a PirA_ABE68878 pesticidal
                        PirA proteinsequence.
source                 1..417
                       mol_type = other DNA
                       organism = Photorhabdus luminescens
SEQUENCE: 104
atgaggaaaa taaatatgtc tagaataacc attgttgttg attcagatac acaaaaagca  60
gaagtttatt ctaattctcc tgtgccggta catagagatt taaatgcagt tggtcctttg  120
agtgatgtga ctatatcacc tcatgctagt gtggaagtat ttagaataga caccccaata  180
attccagaat ccagaagctc tctgagagtt gtaaatacag ggttagcaaa tagtgttacg  240
gctaaatttt actggtctca tagttttacc tctgaatggt ttgaagctgg atctatagat  300
gtaggattag gagaagataa ggtattaaac gtgcctagca gctcttttta ttatagtaaa  360
tttgttatct ataataacac ggatagagtg gcttatgtta cggcaaattt ggtttaa     417

SEQ ID NO: 105         moltype = AA  length = 138
FEATURE                Location/Qualifiers
REGION                 1..138
                       note = The amino acid sequence of the PirA_ABE68878 PirA
                        protein.
source                 1..138
                       mol_type = protein
                       organism = Photorhabdus luminescens
SEQUENCE: 105
MRKINMSRIT IVVDSDTQKA EVYSNSPVPV HRDLNAVGPL SDVTISPHAS VEVFRIDTPI  60
IPESRSSLRV VNTGLANSVT AKFYWSHSFT SEWFEAGSID VGLGEDKVLN VPSSSFYYSK  120
FVIYNNTDRV AYVTANLV                                               138

SEQ ID NO: 106         moltype = DNA  length = 1260
FEATURE                Location/Qualifiers
misc_feature           1..1260
                       note = A nucleic acid sequence obtained from Photorhabdus
                        luminescensstrain Hm encoding a PirB_ABE68879 pesticidal
                        PirB proteinsequence.
source                 1..1260
                       mol_type = other DNA
                       organism = Photorhabdus luminescens
SEQUENCE: 106
atgcatacag aaaatgtttt agacatcaga accattgtgg ctaatgaata tgtggtaaaa  60
acgagtgcat tagagtggga tgttacggat attgtaaaaa atgcaatcat agggggtatc  120
tcttttatac cttcggttgg tcctgcgata tcttttttgg tcggtttatt ctggcctcaa  180
tcgaaagaaa atatatggga aggaattgtc aaacaaattg agaggatgat agaggagtct  240
gcgttaaaga cgattaaagg tatccttgcg ggtgatattg cctatataca agagcgcatg  300
gcaaccgttg ctgatcttct tgataagcat ccaggatctg acgaagcgag gagcgccttt  360
aataacctgg cagaaaatat agatggttat cacaaaaaat ttaataattt ttcggatgat  420
gttaactatc aaatattacc catgttttct actacggtta tgatgcagat aacctattgg  480
gttgctggtt tagagagaag agctgaaatt gggcttagtg atattgatat tgaaaaagtc  540
cgaggattaa tcaaaaagac ggtagaacaa gctaatagtt atattaatag tatctatgat  600
agagagctta atgatgctct taataactcg acggcggaca ctgttgcaaa taatgttatg  660
tctgttcatg gtcactgtcg tttacatggg attgaatata tcagtatttg ggatagatta  720
agtgaatctg agtctgtaaa taatagaatc tatgttgatg ttttaagtta ttctactttc  780
tttgatcgtc aaacagcaaa agccagaatt caggcattga ctccagagca agatatggct  840
ccgcctctca aaccagctct taatggaggg aagagaagaa agatagattc tttaatggga  900
catattgtac gtattggagg agctccgaga gtaggagggc tgacagttgt atttgatgac  960
ggcagtagcc atcgattagg tacaatatct ggtgagacgg catctatttc tctgaatggt  1020
agtcgaatta ccagtttgga agtatggggc aatggtgctg ttgatagagc cgtctttact  1080
ttgagtgatg gtcggttttt gttatttggc gatcctggaa catctcgata taggaaattt  1140
tatgttggtg atagtcacta tatttcaggg atatatttgt ccagtgatta caacccatta  1200
gcaggtcagg cagcaaatat tgctgtatct tatcagttga taaatgatga tgaaaaatag  1260

SEQ ID NO: 107         moltype = AA  length = 419
FEATURE                Location/Qualifiers
REGION                 1..419
                       note = The amino acid sequence of the PirB_ABE68879 PirB
                        protein.
source                 1..419
                       mol_type = protein
                       organism = Photorhabdus luminescens
```

```
SEQUENCE: 107
MHTENVLDIR TIVANEYVVK TSALEWDVTD IVKNAIIGGI SFIPSVGPAI SFLVGLFWPQ  60
SKENIWEGIV KQIERMIEES ALKTIKGILA GDIAYIQERM ATVADLLDKH PGSDEARSAF  120
NNLAENIDGY HKKFNNFSDD VNYQILPMFS TTVMMQITYW VAGLERRAEI GLSDIDIEKV  180
RGLIKKTVEQ ANSYINSIYD RELNDALNNS TADTVANNVM SVHGHCRLHG IEYISIWDRL  240
SESESVNNRI YVDVLSYSTF FDRQTAKARI QALTPEQDMA PPLKPALNGG KRRKIDSLMG  300
HIVRIGGAPR VGGLTVVFDD GSSHRLGTIS GETASISLNG SRITSLEVWG NGAVDRAVFT  360
LSDGRFLLFG DPGTSRYRKF YVGDSHYISG IYLSSDYNPL AGQAANIAVS YQLINDDEK   419

SEQ ID NO: 108          moltype = DNA  length = 1674
FEATURE                 Location/Qualifiers
misc_feature            1..1674
                        note = A nucleic acid sequence encoding a PirAB fusion
                         protein, TIC10434comprised of the PirA_ABE68878 and
                         PirB_ABE68879 coding sequencesin operable linkage and in
                         frame.
source                  1..1674
                        mol_type = other DNA
                        organism = synthetic construct
SEQUENCE: 108
atgaggaaaa taaatatgtc tagaataacc attgttgttg attcagatac acaaaaagca  60
gaagtttatt ctaattctcc tgtgccggta catagagatt taaatgcagt tggtcctttg  120
agtgatgtga ctatatcacc tcatgctagt gtggaagtat ttagaataga caccccaata  180
attccagaat ccagaagctc tctgagagtt gtaaatacag ggttagcaaa tagtgttacg  240
gctaaatttt actggtctca tagttttacc tctgaatggt ttgaagctgg atctatagat  300
gtaggattag gagaagataa ggtattaaac gtgcctagca gctcttttta ttatagtaaa  360
tttgttatct ataataacac ggatagagtg gcttatgtta cggcaaattt ggttatgcat  420
acagaaaatg ttttagacat cagaaccatt gtggctaatg aatatgtggt aaaaacgagt  480
gcattagagt gggatgttac ggatattgta aaaaatgcaa tcataggggg tatctctttt  540
ataccttcgg ttggtcctgc gatatctttt ttggtcggtt tattctggcc tcaatcgaaa  600
gaaaatatat gggaaggaat tgtcaaacaa attgagagga tgatagagga gtctgcgtta  660
aagacgatta aaggtatcct tgcgggtgat attgcctata tacaagagcg catggcaacc  720
gttgctgatc ttcttgataa gcatccagga tctgacgaag cgaggagcgc ctttaataac  780
ctggcagaaa atatagatgg ttatcacaaa aaatttaata atttttcgga tgatgttaac  840
tatcaaatat tacccatgtt ttctactacg gttatgatgc agataaccta ttgggttgct  900
ggtttagaga gaagagctga aattgggctt agtgatattg atattgaaaa agtccgagga  960
ttaatcaaaa agacggtaga acaagctaat agttatatta atagtatcta tgatagagag  1020
cttaatgatg ctcttaataa ctcgacggcg gacactgttg caaataatgt tatgtctgtt  1080
catggtcact gtcgtttaca tgggattgaa tatatcagta tttgggatag attaagtgaa  1140
tctgagtctg taaataatag aatctatgtt gatgttttaa gttattctac tttctttgat  1200
cgtcaaacag caaaagccag aattcaggca ttgactccag agcaagatat ggctccgcct  1260
ctcaaaccag ctcttaatgg agggaagaga agaaagatag attctttaat gggacatatt  1320
gtacgtattg gaggagctcc gagagtagga gggctgacag ttgtatttga tgacggcagt  1380
agccatcgat taggtacaat atctggtgag acggcatcta tttctctgaa tggtagtcga  1440
attaccagtt tggaagtatg gggcaatggt gctgttgata gagccgtctt tactttgagt  1500
gatggtcggt ttttgttatt tggcgatcct ggaacatctc gatataggaa attttatgtt  1560
ggtgatagtc actatatttc agggatatat ttgtccagtg attacaaccc attagcaggt  1620
caggcagcaa atattgctgt atcttatcag ttgataaatg atgatgaaaa atag        1674

SEQ ID NO: 109          moltype = AA  length = 557
FEATURE                 Location/Qualifiers
REGION                  1..557
                        note = The amino acid sequence of the TIC10434 PirAB fusion
                         protein.
source                  1..557
                        mol_type = protein
                        organism = synthetic construct
SEQUENCE: 109
MRKINMSRIT IVVDSDTQKA EVYSNSPVPV HRDLNAVGPL SDVTISPHAS VEVFRIDTPI  60
IPESRSSLRV VNTGLANSVT AKFYWSHSFT SEWFEAGSID VGLGEDKVLN VPSSSFYYSK  120
FVIYNNTDRV AYVTANLVMH TENVLDIRTI VANEYVVKTS ALEWDVTDIV KNAIIGGISF  180
IPSVGPAISF LVGLFWPQSK ENIWEGIVKQ IERMIEESAL KTIKGILAGD IAYIQERMAT  240
VADLLDKHPG SDEARSAFNN LAENIDGYHK KFNNFSDDVN YQILPMFSTT VMMQITYWVA  300
GLERRAEIGL SDIDIEKVRG LIKKTVEQAN SYINSIYDRE LNDALNNSTA DTVANNVMSV  360
HGHCRLHGIE YISIWDRLSE SESVNNRIYV DVLSYSTFFD RQTAKARIQA LTPEQDMAPP  420
LKPALNGGKR RKIDSLMGHI VRIGGAPRVG GLTVVFDDGS SHRLGTISGE TASISLNGSR  480
ITSLEVWGNG AVDRAVFTLS DGRFLLFGDP GTSRYRKFYV GDSHYISGIY LSSDYNPLAG  540
QAANIAVSYQ LINDDEK                                                557

SEQ ID NO: 110          moltype = DNA  length = 1668
FEATURE                 Location/Qualifiers
misc_feature            1..1668
                        note = A nucleic acid sequence encoding a PirAB fusion
                         protein, TIC11210comprised of the TIC7575 and TIC7665
                         coding sequences in operablelinkage and in frame.
source                  1..1668
                        mol_type = other DNA
                        organism = synthetic construct
SEQUENCE: 110
```

```
atgaatacaa tcaatataaa tataagtggc agtaccgtta cagtcataag caataacgat  60
tccaatccag aaccattaac ttataataca aacacaccag catcagaccc tcttacagcc  120
agtccttata gggatatgac aatagagcca cactcttcta ttgaagcaac aagaaccgat  180
acaccgatta ttcccgaaac tcgtcccaat tactatgtag ccaattctgg ccccgcatca  240
tcagttaggg ctgtttttta ttggtctcat tctttcacat cagaatggtt cgaatattcc  300
tctatcatag tgaaagccgg gaaagacgga atattacaat caccgaataa cgctttatat  360
tacagtaaag ttgtcattta taacgatacc gataaacgtg cctttgttac cggatataat  420
aagatgaata atagtccaat gaatgatcag ttatcaatag caccttattc aatttcgaca  480
cccaattatg aatgggatat gtcatcaatc ataaaagatg ccattatcgg tggcatagga  540
tttattcccg gaccaggctc tgcaatctct tttttattag ggctgttctg gcctcaacag  600
acagacaata cctgggatca aatcctccaa aaaatcgaac agatgataga agaagcgaat  660
ttaaaaacca ttaaaggtat attaaatgga gatatacaag aaattaaagg aaaaatggac  720
catgtgcaat atatgctaga gaattctcct ggcagccagg aaagccatga tgcttatatg  780
tttttagcaa ggtttttggt cagtattgat gaaaaattca aatctttcga tgatagaaca  840
aattatcaaa ttcttcccat gtatacgaac accattatgt tacaagcgcc ttattggaaa  900
atgggcctcg aaaagaaaga ggatatcggt ttaagcgata ttgaagttag cgaattaaaa  960
gaacttatcg ataaattata tactaaatca tatgattata tccataacac gtataatcgt  1020
gaatatgata atgcaatcaa tacgtcaacc gcagagagta tcaccaataa tttattgtct  1080
gtcagaggat attgtttatt acatggttgt gaatgtcttg aagttattgc gcatatacaa  1140
aacaatagcc ttgataaagg cttctaccct aaaacgatca gctattcgag tgttttcgat  1200
cgtcctacaa acaaaatgag gattcaggcg cttacagaag atgaccaaat gcaagaaccg  1260
ttcaaacctt ctttcgtcaa tggtcaatat aataaaataa aatcattgga gggttatgtc  1320
acaaggatcg gcaatgcccc ccgagtcggt ggaattaaaa tcacatttga aaacaacgca  1380
tcttatactc ttggtactgt gacttcagaa acaaccttta ttgaactcaa tgagagtgtt  1440
ataaccagca tagaagtgtg gggaaatggg gccgttgatg aggcattctt tacattgagt  1500
gacggtcgcc aaatgcggct tggtcaacgc tatgccagtc gctacagaaa atatgctgtc  1560
gatggtcatt atatctcagg attgtactta gccagtgatg aaccatccct tgctggtcaa  1620
gccgccggta ttgccgtttc atatcatatg attgttgata aacaatag             1668

SEQ ID NO: 111         moltype = AA  length = 555
FEATURE                Location/Qualifiers
REGION                 1..555
                       note = The amino acid sequence of the TIC11210 PirAB fusion
                        protein.
source                 1..555
                       mol_type = protein
                       organism = synthetic construct
SEQUENCE: 111
MNTININISG STVTVISNND SNPEPLTYNT NTPASDPLTA SPYRDMTIEP HSSIEATRTD  60
TPIIPETRPN YYVANSGPAS SVRAVFYWSH SFTSEWFEYS SIIVKAGKDG ILQSPNNALY  120
YSKVVIYNDT DKRAFVTGYN KMNNSPMNDQ LSIAPYSIST PNYEWDMSSI IKDAIIGGIG  180
FIPGPGSAIS FLLGLFWPQQ TDNTWDQILQ KIEQMIEEAN LKTIKGILNG DIQEIKGKMD  240
HVQYMLENSP GSQESHDAYM FLARFLVSID EKFKSFDDRT NYQILPMYTN TIMLQAPYWK  300
MGLEKKEDIG LSDIEVSELK ELIDKLYTKS YDYIHNTYNR EYDNAINTST AESITNNLLS  360
VRGYCLLHGC ECLEVIAHIQ NNSLDKGFYP KTISYSSVFD RPTNKMRIQA LTEDDQMQEP  420
FKPSFVNGQY NKIKSLEGYV TRIGNAPRVG GIKITFENNA SYTLGTVTSE TTFIELNESV  480
ITSIEVWGNG AVDEAFFTLS DGRQMRLGQR YASRYRKYAV DGHYISGLYL ASDEPSLAGQ  540
AAGIAVSYHM IVDKQ                                                  555

SEQ ID NO: 112         moltype = DNA  length = 1683
FEATURE                Location/Qualifiers
misc_feature           1..1683
                       note = A nucleic acid sequence encoding a PirAB fusion
                        protein, TIC11211comprised of the TIC7575 and TIC7667
                        coding sequences in operablelinkage and in frame.
source                 1..1683
                       mol_type = other DNA
                       organism = synthetic construct
SEQUENCE: 112
atgaatacaa tcaatataaa tataagtggc agtaccgtta cagtcataag caataacgat  60
tccaatccag aaccattaac ttataataca aacacaccag catcagaccc tcttacagcc  120
agtccttata gggatatgac aatagagcca cactcttcta ttgaagcaac aagaaccgat  180
acaccgatta ttcccgaaac tcgtcccaat tactatgtag ccaattctgg ccccgcatca  240
tcagttaggg ctgtttttta ttggtctcat tctttcacat cagaatggtt cgaatattcc  300
tctatcatag tgaaagccgg gaaagacgga atattacaat caccgaataa cgctttatat  360
tacagtaaag ttgtcattta taacgatacc gataaacgtg cctttgttac cggatataat  420
aagatgcata cagaaaatgt tttagacata agaaccattg tggctaatga atatgctgta  480
aaaacgagtg cattagagtg ggatgttact gatattgtaa aaaatgcaat catagggggga  540
atatccttta tcccttcggt tggtcccgct atatcttttt tagtcggttt attctggcct  600
caatcgaaag aaaatatatg ggaagggatt gtcaaacaaa ttgaaaggat gatagaggag  660
tctgcgttaa agacgattaa aggtatcctt gctggtgata ttgcatatat acaagaacga  720
atggcaaccg ttgctgatct tcttgataag catccaggat cagaagaagc gaggagtgct  780
tttaataacc tggcagaaaa tatagatggc tatcacaaaa agtttagtaa tttttcggat  840
gatgttaatt atcagatatt acccatgttt tctactacgg ttatgatgca gataacatat  900
tgggttgctg gtttagagag aaaagatgaa attgggctta gtaatattga tgttgaaaaa  960
gtccgaggat taattaaaaa gacggtagaa caggctaata gttatattaa caatatatat  1020
gatagagagc ttaatgatgc tcttaataac tcgacggctg acactgttgc aaataatgtt  1080
atgtctgttc atggtcactg tcgtttacat gggattgaat atatcagtat ttgggataaa  1140
ttaagtgaag ctgagtcggt aaataataaa atctatgttg atgttttaag ttattctact  1200
```

```
ttctttgacc gtcaaacagc aaaagccaga attcaggcat tgactccaga gaaagatatg  1260
actccacctc tcaaaccggc tcttaatgga ggaaaaagaa gaaagataga ttcgttaacg  1320
ggacatattg tgcgtattgg aggggctgcg agggtaggag ggctgacagt tgtatttgat  1380
gatggtaatc gccatcaatt aggtacaata tctggtgaga cgtcatctat ttctctgaat  1440
ggtagtcgaa ttaccagttt ggaagtatgg ggaaatggtg ctgttgatca agcggtcttt  1500
actttaaatg atggtcgttc attgtcattg ggctcgcctg gaacatctcg atataggaag  1560
ttttatgttg gtgaaagcca ctatattgca gggatatatt tgtccagtga ttacaaccca  1620
ttagctggtc aggcagcaaa tattgctgta tcttatcagt tgataaatga tgatgaaaaa  1680
tag                                                                1683
```

```
SEQ ID NO: 113          moltype = AA  length = 560
FEATURE                 Location/Qualifiers
REGION                  1..560
                        note = The amino acid sequence of the TIC11211 PirAB fusion
                         protein.
source                  1..560
                        mol_type = protein
                        organism = synthetic construct
SEQUENCE: 113
MNTININISG STVTVISNND SNPEPLTYNT NTPASDPLTA SPYRDMTIEP HSSIEATRTD  60
TPIIPETRPN YYVANSGPAS SVRAVFYWSH SFTSEWFEYS SIIVKAGKDG ILQSPNNALY  120
YSKVVIYNDT DKRAFVTGYN KMHTENVLDI RTIVANEYAV KTSALEWDVT DIVKNAIIGG  180
ISFIPSVGPA ISFLVGLFWP QSKENIWEGI VKQIERMIEE SALKTIKGIL AGDIAYIQER  240
MATVADLLDK HPGSEEARSA FNNLAENIDG YHKKFSNFSD DVNYQILPMF STTVMMQITY  300
WVAGLERKDE IGLSNIDVEK VRGLIKKTVE QANSYINNIY DRELNDALNN STADTVANNV  360
MSVHGHCRLH GIEYISIWDK LSEAESVNNK IYVDVLSYST FFDRQTAKAR IQALTPEKDM  420
TPPLKPALNG GKRRKIDSLT GHIVRIGGAA RVGGLTVVFD DGNRHQLGTI SGETSSISLN  480
GSRITSLEVW GNGAVDQAVF TLNDGRSLSL GSPGTSRYRK FYVGESHYIA GIYLSSDYNP  540
LAGQAANIAV SYQLINDDEK                                              560
```

```
SEQ ID NO: 114          moltype = DNA  length = 1668
FEATURE                 Location/Qualifiers
misc_feature            1..1668
                        note = A nucleic acid sequence encoding a PirAB fusion
                         protein, TIC11212comprised of the TIC7662 and TIC7665
                         coding sequences in operablelinkage and in frame.
source                  1..1668
                        mol_type = other DNA
                        organism = synthetic construct
SEQUENCE: 114
atgagtacaa tcaatatcaa tataagtagc agtaccgtta ccgtcatcac gaataacgga  60
gaaacgccag tcccactcac ttacaataca aatacacctg aatcagaacc tcttaccgtc  120
aatccttata gggatatgac aatagagcca cgctcttcta ttgaagcaac aaggattgat  180
acaccgatta ttcccgaaac acgccctaat tattatgtag ccaattcagg cccggcttca  240
tcagttaggg ccgtttttta ttggtcccat tctttcacat cacaatggtt cgaatattcc  300
tctatcatcg tcaaagccgg ggaagatggc atattagaat caccaagcaa ttctttatat  360
tacagcaaag tcgtcattta taatgatacc gataaacgcg cctttgtgac gggatataat  420
aagatgaata atagtccaat gaatgatcag ttatcaatag caccttattc aatttcgaca  480
cccaattatg aatgggatat gtcatcaatc ataaaagatg ccattatcgg tggcatagga  540
tttattcccg gaccaggctc tgcaatctct tttttattag ggctgttctg gcctcaacag  600
acagacaata cctgggatca aatcctccaa aaaatcgaac agatgataga agaagcgaat  660
ttaaaaacca ttaaaggtat attaaatgga gatatacaag aaattaaagg aaaaatggac  720
catgtgcaat atatgctaga gaattctcct ggcagccagg aaagccatga tgcttatatg  780
tttttagcaa ggtttttggt cagtattgat gaaaaattca aatctttcga tgatagaaca  840
aattatcaaa ttcttcccat gtatacgaac accattatgt tacaagcgcc ttattggaaa  900
atgggcctcg aaaagaaaga ggatatcggt ttaagcgata ttgaagttag cgaattaaaa  960
gaacttatcg ataaattata tactaaatca tatgattata tccataacac gtataatcgt  1020
gaatatgata atgcaatcaa tacgtcaacc gcagagagta tcaccaataa tttattgtct  1080
gtcagaggat attgtttatt acatggttgt gaatgtcttg aagttattgc gcatatacaa  1140
aacaatagcc ttgataaagg cttctaccct aaaacgatca gctattcgag tgttttcgat  1200
cgtcctacaa acaaaatgag gattcaggcg cttacagaag atgaccaaat gcaagaaccg  1260
ttcaaacctt ctttcgtcaa tggtcaatat aataaaataa aatcattgga gggttatgtc  1320
acaaggatcg gcaatgcccc ccgagtcggt ggaattaaaa tcacatttga aaacaacgca  1380
tcttatactc ttggtactgt gacttcagaa acaaccttta ttgaactcaa tgagagtgtt  1440
ataaccagca tagaagtgtg gggaaatggg gccgttgatg aggcattctt tacattgagt  1500
gacggtcgcc aaatgcggct tggtcaacgc tatgccagtc gctacagaaa atatgctgtc  1560
gatggtcatt atatctcagg attgtactta gccagtgatg aaccatccct tgctggtcaa  1620
gccgccggta ttgccgtttc atatcatatg attgttgata aacaatag               1668
```

```
SEQ ID NO: 115          moltype = AA  length = 555
FEATURE                 Location/Qualifiers
REGION                  1..555
                        note = The amino acid sequence of the TIC11212 PirAB fusion
                         protein.
source                  1..555
                        mol_type = protein
                        organism = synthetic construct
SEQUENCE: 115
MSTININISS STVTVITNNG ETPVPLTYNT NTPESEPLTV NPYRDMTIEP RSSIEATRID  60
```

```
TPIIPETRPN YYVANSGPAS SVRAVFYWSH SFTSQWFEYS SIIVKAGEDG ILESPSNSLY  120
YSKVVIYNDT DKRAFVTGYN KMNNSPMNDQ LSIAPYSIST PNYEWDMSSI IKDAIIGGIG  180
FIPGPGSAIS FLLGLFWPQQ TDNTWDQILQ KIEQMIEEAN LKTIKGILNG DIQEIKGKMD  240
HVQYMLENSP GSQESHDAYM FLARFLVSID EKFKSFDDRT NYQILPMYTN TIMLQAPYWK  300
MGLEKKEDIG LSDIEVSELK ELIDKLYTKS YDYIHNTYNR EYDNAINTST AESITNNLLS  360
VRGYCLLHGC ECLEVIAHIQ NNSLDKGFYP KTISYSSVFD RPTNKMRIQA LTEDDQMQEP  420
FKPSFVNGQY NKIKSLEGYV TRIGNAPRVG GIKITFENNA SYTLGTVTSE TTFIELNESV  480
ITSIEVWGNG AVDEAFFTLS DGRQMRLGQR YASRYRKYAV DGHYISGLYL ASDEPSLAGQ  540
AAGIAVSYHM IVDKQ                                                   555

SEQ ID NO: 116         moltype = DNA  length = 1701
FEATURE                Location/Qualifiers
misc_feature           1..1701
                       note = A nucleic acid sequence encoding a PirAB fusion
                        protein, TIC11301comprised of the TIC7575 and TIC7661
                        coding sequences in operablelinkage and in frame.
source                 1..1701
                       mol_type = other DNA
                       organism = synthetic construct
SEQUENCE: 116
atgaatacaa tcaatataaa tataagtggc agtaccgtta cagtcataag caataacgat  60
tccaatccag aaccattaac ttataataca aacacaccag catcagaccc tcttacagcc  120
agtccttata ggatatgac aatagagcca cactcttcta ttgaagcaac aagaaccgat  180
acaccgatta ttcccgaaac tcgtcccaat tactatgtag ccaattctgg ccccgcatca  240
tcagttaggg ctgtttttta ttggtctcat tctttcacat cagaatggtt cgaatattcc  300
tctatcatag tgaaagccgg gaaagacgga atattacaat caccgaataa cgctttatat  360
tacagtaaag ttgtcattta taacgatacc gataaacgtg cctttgttac cggatataat  420
aagatgaata ctacacctat tactgtatct acaaatgaaa catcgccttt aatgactgac  480
gtaatgccca tggatcttta tgcaatatcc acacctgatt atgaatggga catgtcgtca  540
atcataaagg atgctgttat tggtggcata ggatttattc caggtccggg cccggcaata  600
tccttcctgt tagggctatt ttggcctcag cagaaagaca atacttggga gcaaattctc  660
cagaaagtag agcagatgat agagaatgct gttctacaaa ctattaaagg aatacttaat  720
ggagaagttc aagagatcaa agggaaaatg gaacatgtag aatccatgct gaaaaactcg  780
cctggcagtc aggaaagtca tgatgcatat atgttcctgg cgagatatct ggttagtata  840
gatgaaaaat tcaaatcttt tgacaataga acaaattacc agcttctccc aatgtatact  900
aacactatta tgttacagat cccttattgg aaaatgggaa tagagaagaa aaaagatatt  960
gggctgacag atattgaagt taatgaatta aaagaactta tcgataaatt ggttgataag  1020
gccaaaaact atattcatac gatgtatact aatgaacata ataatgctgt aaacacatca  1080
acagcagaga gtgtcactaa taatttatta tctgtaagag gatattgttt attacacggt  1140
ttagaatgta ttgagttaat cgagcatata cagaataata gccttgagag tggtttctat  1200
cctaaaatta tcagttattc gactgcgttt gatcgtccta ctaacaaaat gagaattcag  1260
gctcttacag aagatgatgc aatgcaggag cctttcaaac catctttaat caatgggaaa  1320
tataataaaa tccaatcctt gactggatat gtacaaagaa ttgggaatgc acctagagtt  1380
ggtggtatca gaatcacatt taccaacggc tcatcttata cacttggtac agtgacctca  1440
gaaacgcatt caattaagct aaacgatagt gttatcgaaa gcttggaagt atgggggaat  1500
ggtgctgttg atgaggcgtt atttaagtta agtgatgggc gtttattgcg tattggtgag  1560
cgctacgcga aaaaatacag aaaatatgct gttgataatc actatattgc ggggatttac  1620
ttagccagcg atgagccttc acttgctggt caagccgcag gtattgccgt ttcatatcat  1680
atgatggctg acaaaaaata a                                            1701

SEQ ID NO: 117         moltype = AA  length = 566
FEATURE                Location/Qualifiers
REGION                 1..566
                       note = The amino acid sequence of the TIC11301 PirAB fusion
                        protein.
source                 1..566
                       mol_type = protein
                       organism = synthetic construct
SEQUENCE: 117
MNTININISG STVTVISNND SNPEPLTYNT NTPASDPLTA SPYRDMTIEP HSSIEATRTD  60
TPIIPETRPN YYVANSGPAS SVRAVFYWSH SFTSEWFEYS SIIVKAGKDG ILQSPNNALY  120
YSKVVIYNDT DKRAFVTGYN KMNTTPITVS TNETSPLMTD VMPMDLYAIS TPDYEWDMSS  180
IIKDAVIGGI GFIPGPGPAI SFLLGLFWPQ QKDNTWEQIL QKVEQMIENA VLQTIKGILN  240
GEVQEIKGKM EHVESMLKNS PGSQESHDAY MFLARYLVSI DEKFKSFDNR TNYQLLPMYT  300
NTIMLQIPYW KMGIEKKKDI GLTDIEVNEL KELIDKLVDK AKNYIHTMYT NEHNNAVNTS  360
TAESVTNNLL SVRGYCLLHG LECIELIEHI QNNSLESGFY PKIISYSTAF DRPTNKMRIQ  420
ALTEDDAMQE PFKPSLINGK YNKIQSLTGY VQRIGNAPRV GGIRITFTNG SSYTLGTVTS  480
ETHSIKLNDS VIESLEVWGN GAVDEALFKL SDGRLLRIGE RYAKKYRKYA VDNHYIAGIY  540
LASDEPSLAG QAAGIAVSYH MMADKK                                       566

SEQ ID NO: 118         moltype = DNA  length = 1701
FEATURE                Location/Qualifiers
misc_feature           1..1701
                       note = A nucleic acid sequence encoding a f PirAB usion
                        protein,TIC11302 comprised of the TIC7660 and TIC7576
                        coding sequences inoperable linkage and in frame.
source                 1..1701
                       mol_type = other DNA
                       organism = synthetic construct
```

SEQUENCE: 118
atgatcacaa taaatataaa tgtaaacggc aatgatgtta caggtacaaa taataatgaa 60
cctactccag tatcgacaac ttacggtcca aatacaccag catcagaacc ccctgtagtc 120
agtaattata gtgatataac aatagaaccg cattcttctg tgcaggcaac aagaattgat 180
acgcctgtta ttcctgaagc acgccccgat tactatgtag ccaactccgg ccctgcacca 240
tcagttaggg ctgtttttta ttggtctcat tctttcacat cagaatggtt cgaatcttcc 300
tctatcacag tgaaagcagg agaggacgga atattaaaag cacctggtaa ctctttatat 360
tacagcaaag tcgtcattta taatgatacg gataaacgag cctttgttac tggatataat 420
aaaatgaata tctcaccgat taatgtatct gaaaatgaaa cattacctga actcactgat 480
gttatgctta ttgtgcctta tacaacatct acccctgatt atgaatggga tatgtcatca 540
attataaagg atgcgattat tggcggcgta gggtttattc caggagcagg ctctgcaatg 600
tccttcctat tgggactatt ttggcctcaa cagaaagata atacatggga acagatcctc 660
caaaaagtag aacagatgat agagaatgcc gttctgcaaa ctattaaagg aatacttaat 720
ggagatatac aagaaatcaa ggggaaaatg gaacatgtgc aatacatgct ggaaacctcg 780
cctggcagtc aggaaagtca tgacgcatat atgttcctgg ctagatacct ggtgagtata 840
gatgaaaaat tcaagtcttt tgataataaa acaaactacc agatcctgcc gatgtacact 900
aacacggtta tgttacaaat cccttattgg aaaatgggaa tagagaagaa aaatgatatt 960
gggctgacag atattgaagt caatgagtta aaacagctta tcgataaatt ggtcgacaag 1020
gccaagagtt acatccatac gatgtatacg aatgaatata atgatgccat aaatacatca 1080
acagcatcga gtgtcactaa taatttactc tctgtaagag gatattgttt attacacggt 1140
ttagagtgta ttgagttaat tgaacatcta caaaacaata gcctcgaaag tggtttttat 1200
cctaaaacta tcagttattc aactgtattt gatcgtcaga ctaacaaaat gagaattcag 1260
gctcttacag aagacgatca aatgcaggaa ccctttaagc catctttaat caacggcaaa 1320
tacaataaaa tacaatcctt gcttggatat gtacaaagaa ttggaaatgc acctagagtg 1380
gggggtatta aaatcacctt tgccaacggt tcatcctata cacttggcac agtaacatca 1440
gaaacgagtt caattgaact caatgatagt gttatcgaaa gattggaagt atggggcaat 1500
ggcgctgttg atgaggcatt atttacgtta agtgatgggc gtcaactcag agtcggtgag 1560
cgctacgcga caaaatatag aaaatatgct gttgatggac actatattgc aggactgtac 1620
ttagctagcg atgaaccttc acttgctggt caagccgcag gtattgccgt ttcataccat 1680
atgttggatg ataaaaaata a 1701

SEQ ID NO: 119 moltype = AA length = 566
FEATURE Location/Qualifiers
REGION 1..566
note = The amino acid sequence of the TIC11302 f PirAB fusion protein.
source 1..566
mol_type = protein
organism = synthetic construct
SEQUENCE: 119
MITININVNG NDVTGTNNNE PTPVSTTYGP NTPASEPPVV SNYSDITIEP HSSVQATRID 60
TPVIPEARPD YYVANSGPAP SVRAVFYWSH SFTSEWFESS SITVKAGEDG ILKAPGNSLY 120
YSKVVIYNDT DKRAFVTGYN KMNISPINVS ENETLPELTD VMLIVPYTTS TPDYEWDMSS 180
IIKDAIIGGV GFIPGAGSAM SFLLGLFWPQ QKDNTWEQIL QKVEQMIENA VLQTIKGILN 240
GDIQEIKGKM EHVQYMLETS PGSQESHDAY MFLARYLVSI DEKFKSFDNK TNYQILPMYT 300
NTVMLQIPYW KMGIEKKNDI GLTDIEVNEL KQLIDKLVDK AKSYIHTMYT NEYNDAINTS 360
TASSVTNNLL SVRGYCLLHG LECIELIEHL QNNSLESGFY PKTISYSTVF DRQTNKMRIQ 420
ALTEDDQMQE PFKPSLINGK YNKIQSLLGY VQRIGNAPRV GGIKITFANG SSYTLGTVTS 480
ETSSIELNDS VIERLEVWGN GAVDEALFTL SDGRQLRVGE RYATKYRKYA VDGHYIAGLY 540
LASDEPSLAG QAAGIAVSYH MLDDKK 566

SEQ ID NO: 120 moltype = DNA length = 2097
FEATURE Location/Qualifiers
misc_feature 1..2097
note = A nucleic acid sequence encoding a PirAB fusion protein, TIC11440comprised of the TIC4771, TIC4771, and TIC4772 coding sequencesin operable linkage and in frame.
source 1..2097
mol_type = other DNA
organism = synthetic construct
SEQUENCE: 120
atgattacaa taaatataag tggtggtagt ataaaaatta gtaacaacat aggatcagaa 60
actgatatca aaaatacacc tttttcagaa cctctttcaa ttagtaatta taaggatatg 120
acaatagagc cacattcgtc tatccaagca acaagaactg atacaccaat tattcctgaa 180
acacgaccaa attattatgt agctaattcc ggccctgccg catcagtgag agctgttttt 240
tattggtctc attcttttac atcagaatgg ttcgaacatt catctatcat tgtaaaagca 300
ggagaagatg gaatattgaa ctcacctagc aattctgtat attacagtaa ggttgtcatt 360
tacaacgata cggataaacg ggcctttgtc acaggttatg acaaaatgat aaccattaac 420
atctcaggag gtagcataaa gattagtaat aacattggct cggaaactga tatcaagaac 480
acgccgtttt ctgaaccact ttcaattagt aattataaag atatgactat agaaccacac 540
tcgtctattc aggctacaag aacagataca ccaattatac ctgaaacacg acctaattac 600
tatgtagcca attccggacc tgcggcatca gtaagagctg tcttttactg gtcacattct 660
tttacgtcag agtggtttga acattcttca atcatagtaa aagcaggaga ggatggaatt 720
cttaactctc ctagcaactc tgtttattac agtaaagttg tgatatataa tgataccgat 780
aagagagctt tcgtgactgg atacgataag atgaataacg aacttatgaa cacaaatgaa 840
tcacaacctt cagagacatt atctttaatt aatgaatcta tattaacagc accttatgcc 900
gtttctaccc ctaattatga atgggatatg tcatcaataa taaaagatgc cattattgga 960
ggtataggat ttattcccgg gccgggttca gcaatatcgt ttttgctagg gctattttgg 1020
ccgcaacaaa cagacaatac ctgggagcaa attctccaaa aagtagaaca gatgatagag 1080

```
gaagcgaatt taaaaactat tcaaggaata ctgaacggag atatacaaga aataaaagga  1140
aagatggaac atgtggaata tatgctagaa acctcaccag gcactcaaga aagccatgac  1200
gcatatatgt tcttagcgag atatctggta agtatagatg aaaaattcaa atcttttgat  1260
aataaaacaa attatcaaat tcttccaatg tacaccaata cgcttatgtt acaggcacct  1320
tactggaaaa tgggtataga gaagaaaaat gatattttgc taacagatat agaagttaat  1380
gaattaaaac agcttatcga aaatctatat gccaaggcca atagctatat tcatgaagtg  1440
tatacccgtg aatacgataa tgcggtaaat acctcaacag caacaacgat taccaataat  1500
ttattgtctg taagagggta ttgtttatta catggattag agtgccttga agtccttgat  1560
catatacaaa ataataatct tgatcagagc ttctatccga aaactatcag ttattctact  1620
gtatttgatc gctcaacaaa caaaacaaga ctccaggctc ttaccgaaga cgagcaaatg  1680
gaagaaccac tcaaaccctc ttttattaat ggggaatata ataaaataaa atcactgatt  1740
ggatatgtac agagaattgg aaacgcccct agagttggag gtataaaaat tacatttact  1800
aatggatcat ctcatactct gggtacagtg acctcagaat caaactcaat tgaactaaat  1860
gatagtgtta taaccagtgt ggaagtatgg ggaaatggtg ctgttgatga ggcattcttt  1920
acattaagtg acggtcgtca atttaggctt ggtcaacgct atgccagtaa ctacagaaaa  1980
tatgctgttg atggccacta tatttcagga ttgtacttag ccagtgatga gccttcactt  2040
gctggtcaag ccgcaggtat tgcagtttca tatcatatat tggttgataa gaaataa     2097
```

```
SEQ ID NO: 121         moltype = AA  length = 698
FEATURE                Location/Qualifiers
REGION                 1..698
                       note = The amino acid sequence of the TIC11440 PirAB fusion
                        protein.
source                 1..698
                       mol_type = protein
                       organism = synthetic construct
SEQUENCE: 121
MITINISGGS IKISNNIGSE TDIKNTPFSE PLSISNYKDM TIEPHSSIQA TRTDTPIIPE  60
TRPNYYVANS GPAASVRAVF YWSHSFTSEW FEHSSIIVKA GEDGILNSPS NSVYYSKVVI  120
YNDTDKRAFV TGYDKMITIN ISGGSIKISN NIGSETDIKN TPFSEPLSIS NYKDMTIEPH  180
SSIQATRTDT PIIPETRPNY YVANSGPAAS VRAVFYWSHS FTSEWFEHSS IIVKAGEDGI  240
LNSPSNSVYY SKVVIYNDTD KRAFVTGYDK MNNELMNTNE SQPSETLSLI NESILTAPYA  300
VSTPNYEWDM SSIIKDAIIG GIGFIPGPGS AISFLLGLFW PQQTDNTWEQ ILQKVEQMIE  360
EANLKTIQGI LNGDIQEIKG KMEHVEYMLE TSPGTQESHD AYMFLARYLV SIDEKFKSFD  420
NKTNYQILPM YTNTLMLQAP YWKMGIEKKN DILLTDIEVN ELKQLIENLY AKANSYIHEV  480
YTREYDNAVN TSTATTITNN LLSVRGYCLL HGLECLEVLD HIQNNNLDQS FYPKTISYST  540
VFDRSTNKTR LQALTEDEQM EEPLKPSFIN GEYNKIKSLI GYVQRIGNAP RVGGIKITFT  600
NGSSHTLGTV TSESNSIELN DSVITSVEVW GNGAVDEAFF TLSDGRQFRL GQRYASNYRK  660
YAVDGHYISG LYLASDEPSL AGQAAGIAVS YHILVDKK                         698
```

```
SEQ ID NO: 122         moltype = DNA  length = 2124
FEATURE                Location/Qualifiers
misc_feature           1..2124
                       note = A nucleic acid sequence encoding a PirAB fusion
                        protein, TIC11441comprised of the TIC7575, TIC7575, and
                        TIC7576 coding sequencesin operable linkage and in frame.
source                 1..2124
                       mol_type = other DNA
                       organism = synthetic construct
SEQUENCE: 122
atgaatacaa tcaatataaa tataagtggc agtaccgtta cagtcataag caataacgat  60
tccaatccag aaccattaac ttataataca aacacaccag catcagaccc tcttacagcc  120
agtccttata gggatatgac aatagagcca cactcttcta ttgaagcaac aagaaccgat  180
acaccgatta ttcccgaaac tcgtcccaat tactatgtag ccaattctgg ccccgcatca  240
tcagttaggg ctgtttttta ttggtctcat tctttcacat cagaatggtt cgaatattcc  300
tctatcatag tgaaagccgg gaaagacgga atattacaat caccgaataa cgctttatat  360
tacagtaaag ttgtcattta taacgatacc gataaacgtg cctttgttac cggatataat  420
aagatgaaca ctataaacat caacatttcc ggaagcacgg taacggtgat ttctaacaat  480
gattcaaacc ctgagccatt aacatataac actaatacgc ctgcgagtga tccactaaca  540
gccagtccgt atagagatat gactatagag cctcattctt ctattgaggc aacgagaaca  600
gatacaccaa ttattccaga aactcgtccg aattactatg tcgccaattc tggtccagca  660
tcatcagtta gggctgtatt ctattggtct cattcattca catcagagtg gttcgaatat  720
tcatctatca tagtgaaagc aggcaaggac ggtatactac aaagcccaaa taacgcatta  780
tattactcga aggttgtcat ttacaatgat acggataaga gagctttcgt tactggatat  840
aacaaaatga atatctcacc gattaatgta tctgaaaatg aaacattacc tgaactcact  900
gatgttatgc ttattgtgcc ttatacaaca tctacccctg attatgaatg ggatatgtca  960
tcaattataa aggatgcgat tattggcggc gtagggttta ttccaggagc aggctctgca  1020
atgtccttcc tattgggact attttggcct caacagaaag ataatacatg ggaacagatc  1080
ctccaaaaag tagaacagat gatagagaat gccgttctgc aaactattaa aggaatactt  1140
aatggagata tacaagaaat caaggggaaa atggaacatg tgcaatacat gctggaaacc  1200
tcgcctggca gtcaggaaag tcatgacgca tatatgttcc tggctagata cctggtgagt  1260
atagatgaaa aattcaagtc ttttgataat aaaacaaact accagatcct gccgatgtac  1320
actaacacgg ttatgttaca aatcccttat tggaaaatgg gaatagagaa gaaaaatgat  1380
attgggctga cagatattga agtcaatgag ttaaaacagc ttatcgataa attggtcgac  1440
aaggccaaga gttacatcca tacgatgtat acgaatgaat ataatgatgc cataaataca  1500
tcaacagcat cgagtgtcac taataattta ctctctgtaa gaggatattg tttattacac  1560
ggtttagagt gtattgagtt aattgaacat ctacaaaaca atagcctcga aagtggtttt  1620
tatcctaaaa ctatcagtta ttcaactgta tttgatcgtc agactaacaa aatgagaatt  1680
caggctctta cagaagacga tcaaatgcag gaacccttta agccatcttt aatcaacggc  1740
```

```
aaatacaata aaatacaatc cttgcttgga tatgtacaaa gaattggaaa tgcacctaga  1800
gtggggggta ttaaaatcac ctttgccaac ggttcatcct atacacttgg cacagtaaca  1860
tcagaaacga gttcaattga actcaatgat agtgttatcg aaagattgga agtatggggc  1920
aatggcgctg ttgatgaggc attatttacg ttaagtgatg ggcgtcaact cagagtcggt  1980
gagcgctacg cgacaaaata tagaaaatat gctgttgatg gacactatat tgcaggactg  2040
tacttagcta gcgatgaacc ttcacttgct ggtcaagccg caggtattgc cgtttcatac  2100
catatgttgg atgataaaaa ataa                                          2124

SEQ ID NO: 123         moltype = AA  length = 707
FEATURE                Location/Qualifiers
REGION                 1..707
                       note = The amino acid sequence of the TIC11441 f PirAB
                        fusion protein.
source                 1..707
                       mol_type = protein
                       organism = synthetic construct
SEQUENCE: 123
MNTINININISG STVTVISNND SNPEPLTYNT NTPASDPLTA SPYRDMTIEP HSSIEATRTD  60
TPIIPETRPN YYVANSGPAS SVRAVFYWSH SFTSEWFEYS SIIVKAGKDG ILQSPNNALY  120
YSKVVIYNDT DKRAFVTGYN KMNTININIS GSTVTVISNN DSNPEPLTYN TNTPASDPLT  180
ASPYRDMTIE PHSSIEATRT DTPIIPETRP NYYVANSGPA SSVRAVFYWS HSFTSEWFEY  240
SSIIVKAGKD GILQSPNNAL YYSKVVIYND TDKRAFVTGY NKMNISPINV SENETLPELT  300
DVMLIVPYTT STPDYEWDMS SIIKDAIIGG VGFIPGAGSA MSFLLGLFWP QQKDNTWEQI  360
LQKVEQMIEN AVLQTIKGIL NGDIQEIKGK MEHVQYMLET SPGSQESHDA YMFLARYLVS  420
IDEKFKSFDN KTNYQILPMY TNTVMLQIPY WKMGIEKKND IGLTDIEVNE LKQLIDKLVD  480
KAKSYIHTMY TNEYNDAINT STASSVTNNL LSVRGYCLLH GLECIELIEH LQNNSLESGF  540
YPKTISYSTV FDRQTNKMRI QALTEDDQMQ EPFKPSLING KYNKIQSLLG YVQRIGNAPR  600
VGGIKITFAN GSSYTLGTVT SETSSIELND SVIERLEVWG NGAVDEALFT LSDGRQLRVG  660
ERYATKYRKY AVDGHYIAGL YLASDEPSLA GQAAGIAVSY HMLDDKK                 707

SEQ ID NO: 124         moltype = DNA  length = 2115
FEATURE                Location/Qualifiers
misc_feature           1..2115
                       note = A nucleic acid sequence encoding a PirAB fusion
                        protein, TIC11442comprised of the TIC7575, TIC4771, and
                        TIC4472 coding sequencesin operable linkage and in frame.
source                 1..2115
                       mol_type = other DNA
                       organism = synthetic construct
SEQUENCE: 124
atgaatacaa tcaatataaa tataagtggc agtaccgtta cagtcataag caataacgat  60
tccaatccag aaccattaac ttataataca aacacaccag catcagaccc tcttacagcc  120
agtccttata gggatatgac aatagagcca cactcttcta ttgaagcaac aagaaccgat  180
acaccgatta ttcccgaaac tcgtcccaat tactatgtag ccaattctgg ccccgcatca  240
tcagttaggg ctgtttttta ttggtctcat tctttcacat cagaatggtt cgaatattcc  300
tctatcatag tgaaagccgg gaaagacgga atattacaat caccgaataa cgctttatat  360
tacagtaaag ttgtcattta taacgatacc gataaacgtg cctttgttac cggatataat  420
aagatgatta caataaatat aagtggtggt agtataaaaa ttagtaacaa cataggatca  480
gaaactgata tcaaaaatac acctttttca gaacctcttt caattagtaa ttataaggat  540
atgacaatag agccacattc gtctatccaa gcaacaagaa ctgatacacc aattattcct  600
gaaacacgac caaattatta tgtagctaat tccggccctg ccgcatcagt gagagctgtt  660
ttttattggt ctcattcttt tacatcagaa tggttcgaac attcatctat cattgtaaaa  720
gcaggagaag atggaatatt gaactcacct agcaattctg tatattacag taaggttgtc  780
atttacaacg atacggataa acgggccttt gtcacaggtt atgacaaaat gaataacgaa  840
cttatgaaca caaatgaatc acaaccttca gagacattat ctttaattaa tgaatctata  900
ttaacagcac cttatgccgt ttctacccct aattatgaat gggatatgtc atcaataata  960
aaagatgcca ttattggagg tataggattt attcccgggc cgggttcagc aatatcgttt  1020
ttgctagggc tattttggcc gcaacaaaca gacaatacct gggagcaaat tctccaaaaa  1080
gtagaacaga tgatagagga agcgaattta aaaactattc aaggaatact gaacggagat  1140
atacaagaaa taaaaggaaa gatggaacat gtggaatata tgctagaaac ctcaccaggc  1200
actcaagaaa gccatgacgc atatatgttc ttagcgagat atctggtaag tatagatgaa  1260
aaattcaaat cttttgataa taaaacaaat tatcaaattc ttccaatgta caccaatacg  1320
cttatgttac aggcacctta ctggaaaatg ggtatagaga agaaaaatga tattttgcta  1380
acagatatag aagttaatga attaaaacag cttatcgaaa atctatatgc caaggccaat  1440
agctatattc atgaagtgta tacccgtgaa tacgataatg cggtaaatac ctcaacagca  1500
acaacgatta ccaataattt attgtctgta agagggtatt gtttattaca tggattagag  1560
tgccttgaag tccttgatca tatacaaaat aataatcttg atcagagctt ctatccgaaa  1620
actatcagtt attctactgt atttgatcgc tcaacaaaca aaacaagact ccaggctctt  1680
accgaagacg agcaaatgga agaaccactc aaaccctctt ttattaatgg ggaatataat  1740
aaaataaaat cactgattgg atatgtacag agaattggaa acgcccctag agttggaggt  1800
ataaaaatta catttactaa tggatcatct catactctgg gtacagtgac ctcagaatca  1860
aactcaattg aactaaatga tagtgttata accagtgtgg aagtatgggg aaatggtgct  1920
gttgatgagg cattctttac attaagtgac ggtcgtcaat ttaggcttgg tcaacgctat  1980
gccagtaact acagaaaata tgctgttgat ggccactata tttcaggatt gtacttagcc  2040
agtgatgagc cttcacttgc tggtcaagcc gcaggtattg cagtttcata tcatatattg  2100
gttgataaga aataa                                                    2115

SEQ ID NO: 125         moltype = AA  length = 704
FEATURE                Location/Qualifiers
```

```
REGION                  1..704
                        note = The amino acid sequence of the TIC11442 PirAB fusion
                         protein.
source                  1..704
                        mol_type = protein
                        organism = synthetic construct
SEQUENCE: 125
MNTININISG STVTVISNND SNPEPLTYNT NTPASDPLTA SPYRDMTIEP HSSIEATRTD  60
TPIIPETRPN YYVANSGPAS SVRAVFYWSH SFTSEWFEYS SIIVKAGKDG ILQSPNNALY  120
YSKVVIYNDT DKRAFVTGYN KMITINISGG SIKISNNIGS ETDIKNTPFS EPLSISNYKD  180
MTIEPHSSIQ ATRTDTPIIP ETRPNYYVAN SGPAASVRAV FYWSHSFTSE WFEHSSIIVK  240
AGEDGILNSP SNSVYYSKVV IYNDTDKRAF VTGYDKMNNE LMNTNESQPS ETLSLINESI  300
LTAPYAVSTP NYEWDMSSII KDAIIGGIGF IPGPGSAISF LLGLFWPQQT DNTWEQILQK  360
VEQMIEEANL KTIQGILNGD IQEIKGKMEH VEYMLETSPG TQESHDAYMF LARYLVSIDE  420
KFKSFDNKTN YQILPMYTNT LMLQAPYWKM GIEKKNDILL TDIEVNELKQ LIENLYAKAN  480
SYIHEVYTRE YDNAVNTSTA TTITNNLLSV RGYCLLHGLE CLEVLDHIQN NNLDQSFYPK  540
TISYSTVFDR STNKTRLQAL TEDEQMEEPL KPSFINGEYN KIKSLIGYVQ RIGNAPRVGG  600
IKITFTNGSS HTLGTVTSES NSIELNDSVI TSVEVWGNGA VDEAFFTLSD GRQFRLGQRY  660
ASNYRKYAVD GHYISGLYLA SDEPSLAGQA AGIAVSYHIL VDKK                  704

SEQ ID NO: 126          moltype = DNA  length = 2124
FEATURE                 Location/Qualifiers
misc_feature            1..2124
                        note = A nucleic acid sequence encoding a PirAB fusion
                         protein, TIC11443comprised of the TIC7660, TIC7575, and
                         TIC7576 coding sequencesin operable linkage and in frame.
source                  1..2124
                        mol_type = other DNA
                        organism = synthetic construct
SEQUENCE: 126
atgatcacaa taaatataaa tgtaaacggc aatgatgtta caggtacaaa taataatgaa  60
cctactccag tatcgacaac ttacggtcca aatacaccag catcagaacc ccctgtagtc  120
agtaattata gtgatataac aatagaaccg cattcttctg tgcaggcaac aagaattgat  180
acgcctgtta ttcctgaagc acgccccgat tactatgtag ccaactccgg ccctgcacca  240
tcagttaggg ctgtttttta ttggtctcat tctttcacat cagaatggtt cgaatcttcc  300
tctatcacag tgaaagcagg agaggacgga atattaaaag cacctggtaa ctctttatat  360
tacagcaaag tcgtcattta taatgatacg gataaacgag cctttgttac tggatataat  420
aaaatgaata caatcaatat aaatataagt ggcagtaccg ttacagtcat aagcaataac  480
gattccaatc cagaaccatt aacttataat acaaacacac cagcatcaga ccctcttaca  540
gccagtcctt atagggatat gacaatagag ccacactctt ctattgaagc aacaagaacc  600
gatacaccga ttattcccga aactcgtccc aattactatg tagccaattc tggccccgca  660
tcatcagtta gggctgtttt ttattggtct cattctttca catcagaatg gttcgaatat  720
tcctctatca tagtgaaagc cgggaaagac ggaatattac aatcaccgaa taacgcttta  780
tattacagta aagttgtcat ttataacgat accgataaac gtgcctttgt taccggatat  840
aataagatga atatctcacc gattaatgta tctgaaaatg aaacattacc tgaactcact  900
gatgttatgc ttattgtgcc ttatacaaca tctacccctg attatgaatg ggatatgtca  960
tcaattataa aggatgcgat tattggcggc gtagggttta ttccaggagc aggctctgca  1020
atgtccttcc tattgggact attttggcct caacagaaag ataatacatg ggaacagatc  1080
ctccaaaaag tagaacagat gatagagaat gccgttctgc aaactattaa aggaatactt  1140
aatggagata tacaagaaat caaggggaaa atggaacatg tgcaatacat gctggaaacc  1200
tcgcctggca gtcaggaaag tcatgacgca tatatgttcc tggctagata cctggtgagt  1260
atagatgaaa aattcaagtc ttttgataat aaaacaaact accagatcct gccgatgtac  1320
actaacacgg ttatgttaca aatcccttat tggaaaatgg gaatagagaa gaaaaatgat  1380
attgggctga cagatattga agtcaatgag ttaaaacagc ttatcgataa attggtcgac  1440
aaggccaaga gttacatcca tacgatgtat acgaatgaat ataatgatgc cataaataca  1500
tcaacagcat cgagtgtcac taataattta ctctctgtaa gaggatattg tttattacac  1560
ggtttagagt gtattgagtt aattgaacat ctacaaaaca atagcctcga aagtggtttt  1620
tatcctaaaa ctatcagtta ttcaactgta tttgatcgtc agactaacaa aatgagaatt  1680
caggctctta cagaagacga tcaaatgcag gaacccttta agccatcttt aatcaacggc  1740
aaatacaata aaatacaatc cttgcttgga tatgtacaaa gaattggaaa tgcacctaga  1800
gtggggggta ttaaaatcac ctttgccaac ggttcatcct atacacttgg cacagtaaca  1860
tcagaaacga gttcaattga actcaatgat agtgttatcg aaagattgga agtatggggc  1920
aatggcgctg ttgatgaggc attatttacg ttaagtgatg ggcgtcaact cagagtcggt  1980
gagcgctacg cgacaaaata tagaaaatat gctgttgatg gacactatat tgcaggactg  2040
tacttagcta gcgatgaacc ttcacttgct ggtcaagccg caggtattgc cgtttcatac  2100
catatgttgg atgataaaaa ataa                                        2124

SEQ ID NO: 127          moltype = AA  length = 707
FEATURE                 Location/Qualifiers
REGION                  1..707
                        note = The amino acid sequence of the TIC11443 PirAB fusion
                         protein.
source                  1..707
                        mol_type = protein
                        organism = synthetic construct
SEQUENCE: 127
MITININVNG NDVTGTNNNE PTPVSTTYGP NTPASEPPVV SNYSDITIEP HSSVQATRID  60
TPVIPEARPD YYVANSGPAP SVRAVFYWSH SFTSEWFESS SITVKAGEDG ILKAPGNSLY  120
YSKVVIYNDT DKRAFVTGYN KMNTININIS GSTVTVISNN DSNPEPLTYN TNTPASDPLT  180
```

```
ASPYRDMTIE PHSSIEATRT DTPIIPETRP NYYVANSGPA SSVRAVFYWS HSFTSEWFEY  240
SSIIVKAGKD GILQSPNNAL YYSKVVIYND TDKRAFVTGY NKMNISPINV SENETLPELT  300
DVMLIVPYTT STPDYEWDMS SIIKDAIIGG VGFIPGAGSA MSFLLGLFWP QQKDNTWEQI  360
LQKVEQMIEN AVLQTIKGIL NGDIQEIKGK MEHVQYMLET SPGSQESHDA YMFLARYLVS  420
IDEKFKSFDN KTNYQILPMY TNTVMLQIPY WKMGIEKKND IGLTDIEVNE LKQLIDKLVD  480
KAKSYIHTMY TNEYNDAINT STASSVTNNL LSVRGYCLLH GLECIELIEH LQNNSLESGF  540
YPKTISYSTV FDRQTNKMRI QALTEDDQMQ EPFKPSLING KYNKIQSLLG YVQRIGNAPR  600
VGGIKITFAN GSSYTLGTVT SETSSIELND SVIERLEVWG NGAVDEALFT LSDGRQLRVG  660
ERYATKYRKY AVDGHYIAGL YLASDEPSLA GQAAGIAVSY HMLDDKK                707

SEQ ID NO: 128          moltype = DNA  length = 2124
FEATURE                 Location/Qualifiers
misc_feature            1..2124
                        note = A nucleic acid sequence encoding a PirAB fusion
                         protein, TIC11444comprised of the TIC7660 and TIC7576
                         coding sequences in operablelinkage and in frame.
source                  1..2124
                        mol_type = other DNA
                        organism = synthetic construct
SEQUENCE: 128
atgaatacaa tcaatataaa tataagtggc agtaccgtta cagtcataag caataacgat  60
tccaatccag aaccattaac ttataataca aacacaccag catcagaccc tcttacagcc  120
agtccttata gggatatgac aatagagcca cactcttcta ttgaagcaac aagaaccgat  180
acaccgatta ttcccgaaac tcgtcccaat tactatgtag ccaattctgg ccccgcatca  240
tcagttaggg ctgtttttta ttggtctcat tctttcacat cagaatggtt cgaatattcc  300
tctatcatag tgaaagccgg gaaagacgga atattacaat caccgaataa cgctttatat  360
tacagtaaag ttgtcattta taacgatacc gataaacgtg cctttgttac cggatataat  420
aagatgatca caataaatat aaatgtaaac ggcaatgatg ttacaggtac aaataataat  480
gaacctactc cagtatcgac aacttacggt ccaaatacac cagcatcaga accccctgta  540
gtcagtaatt atagtgatat aacaatagaa ccgcattctt ctgtgcaggc aacaagaatt  600
gatacgcctg ttattcctga agcacgcccc gattactatg tagccaactc cggccctgca  660
ccatcagtta gggctgtttt ttattggtct cattctttca catcagaatg gttcgaatct  720
tcctctatca cagtgaaagc aggagaggac ggaatattaa aagcacctgg taactcttta  780
tattacagca aagtcgtcat ttataatgat acggataaac gagcctttgt tactggatat  840
aataaaatga atactacacc tattactgta tctacaaatg aaacatcgcc tttaatgact  900
gacgtaatgc ccatggatct ttatgcaata tccacacctg attatgaatg ggacatgtcg  960
tcaatcataa aggatgctgt tattggtggc ataggattta ttccaggtcc gggcccggca  1020
atatccttcc tgttagggct attttggcct cagcagaaag acaatacttg ggagcaaatt  1080
ctccagaaag tagagcagat gatagagaat gctgttctac aaactattaa aggaatactt  1140
aatggagaag ttcaagagat caaagggaaa atggaacatg tagaatccat gctgaaaaac  1200
tcgcctggca gtcaggaaag tcatgatgca tatatgttcc tggcgagata tctggttagt  1260
atagatgaaa aattcaaatc ttttgacaat agaacaaatt accagcttct cccaatgtat  1320
actaacacta ttatgttaca gatcccttat tggaaaatgg gaatagagaa gaaaaaagat  1380
attgggctga cagatattga agttaatgaa ttaaaagaac ttatcgataa attggttgat  1440
aaggccaaaa actatattca tacgatgtat actaatgaac ataataatgc tgtaaacaca  1500
tcaacagcag agagtgtcac taataattta ttatctgtaa gaggatattg tttattacac  1560
ggtttagaat gtattgagtt aatcgagcat atacagaata atagccttga gagtggtttc  1620
tatcctaaaa ttatcagtta ttcgactgcg tttgatcgtc ctactaacaa aatgagaatt  1680
caggctctta cagaagatga tgcaatgcag gagcctttca aaccatcttt aatcaatggg  1740
aaatataata aaatccaatc cttgactgga tatgtacaaa gaattgggaa tgcacctaga  1800
gttggtggta tcagaatcac atttaccaac ggctcatctt atacacttgg tacagtgacc  1860
tcagaaacgc attcaattaa gctaaacgat agtgttatcg aaagcttgga agtatggggg  1920
aatggtgctg ttgatgaggc gttatttaag ttaagtgatg ggcgtttatt gcgtattggt  1980
gagcgctacg cgaaaaaata cagaaaatat gctgttgata atcactatat tgcggggatt  2040
tacttagcca gcgatgagcc ttcacttgct ggtcaagccg caggtattgc cgtttcatat  2100
catatgatgg ctgacaaaaa ataa                                          2124

SEQ ID NO: 129          moltype = AA  length = 707
FEATURE                 Location/Qualifiers
REGION                  1..707
                        note = The amino acid sequence of the TIC11444 PirAB fusion
                         protein.
source                  1..707
                        mol_type = protein
                        organism = synthetic construct
SEQUENCE: 129
MNTININISG STVTVISNND SNPEPLTYNT NTPASDPLTA SPYRDMTIEP HSSIEATRTD  60
TPIIPETRPN YYVANSGPAS SVRAVFYWSH SFTSEWFEYS SIIVKAGKDG ILQSPNNALY  120
YSKVVIYNDT DKRAFVTGYN KMITININVN GNDVTGTNNN EPTPVSTTYG PNTPASEPPV  180
VSNYSDITIE PHSSVQATRI DTPVIPEARP DYYVANSGPA PSVRAVFYWS HSFTSEWFES  240
SSITVKAGED GILKAPGNSL YYSKVVIYND TDKRAFVTGY NKMNTTPITV STNETSPLMT  300
DVMPMDLYAI STPDYEWDMS SIIKDAVIGG IGFIPGPGPA ISFLLGLFWP QQKDNTWEQI  360
LQKVEQMIEN AVLQTIKGIL NGEVQEIKGK MEHVESMLKN SPGSQESHDA YMFLARYLVS  420
IDEKFKSFDN RTNYQLLPMY TNTIMLQIPY WKMGIEKKKD IGLTDIEVNE LKELIDKLVD  480
KAKNYIHTMY TNEHNNAVNT STAESVTNNL LSVRGYCLLH GLECIELIEH IQNNSLESGF  540
YPKIISYSTA FDRPTNKMRI QALTEDDAMQ EPFKPSLING KYNKIQSLTG YVQRIGNAPR  600
VGGIRITFTN GSSYTLGTVT SETHSIKLND SVIESLEVWG NGAVDEALFK LSDGRLLRIG  660
ERYAKKYRKY AVDNHYIAGI YLASDEPSLA GQAAGIAVSY HMMADKK                707
```

```
SEQ ID NO: 130         moltype = DNA  length = 2124
FEATURE                Location/Qualifiers
misc_feature           1..2124
                       note = A nucleic acid sequence encoding a PirAB fusion
                        protein, TIC11445comprised of the TIC7660, TIC7662, and
                        TIC7663 coding sequencesin operable linkage and in frame.
source                 1..2124
                       mol_type = other DNA
                       organism = synthetic construct
SEQUENCE: 130
atgatcacaa taaatataaa tgtaaacggc aatgatgtta caggtacaaa taataatgaa  60
cctactccag tatcgacaac ttacggtcca aatacaccag catcagaacc ccctgtagtc  120
agtaattata gtgatataac aatagaaccg cattcttctg tgcaggcaac aagaattgat  180
acgcctgtta ttcctgaagc acgccccgat tactatgtag ccaactccgg ccctgcacca  240
tcagttaggg ctgtttttta ttggtctcat tctttcacat cagaatggtt cgaatcttcc  300
tctatcacag tgaaagcagg agaggacgga atattaaaag cacctggtaa ctctttatat  360
tacagcaaag tcgtcattta taatgatacg gataaacgag cctttgttac tggatataat  420
aaaatgagta caatcaatat caatataagt agcagtaccg ttaccgtcat cacgaataac  480
ggagaaacgc cagtcccact cacttacaat acaaatacac ctgaatcaga acctcttacc  540
gtcaatcctt atagggatat gacaatagag ccacgctctt ctattgaagc aacaaggatt  600
gatacaccga ttattcccga aacacgccct aattattatg tagccaattc aggcccggct  660
tcatcagtta gggccgtttt ttattggtcc cattctttca catcacaatg gttcgaatat  720
tcctctatca tcgtcaaagc cggggaagat ggcatattag aatcaccaag caattcttta  780
tattacagca aagtcgtcat ttataatgat accgataaac gcgcctttgt gacgggatat  840
aataagatga ataccactct gattaatgta tctgaaaaag aaacattgcc tgtacaaact  900
gatatcatgc ttatcgcgcc ttattcagta tcgacccccg attatgaatg ggatatgtcc  960
tcactcatca aggatgccat tattggtggc gtagggttta ttcccgtcgt aggttccgca  1020
atgtccttcc tgctaggatt attttggccc caacagaaag ataatacttg ggagcaaatt  1080
ctccaaaaag tcgagcagat gatcgagaat gcccagctaa atacgattaa aggaatactt  1140
aatggcgata tacaagagat caaaggaaaa atggagcatg tacaatacat gttggaaacc  1200
tcgccgggca gtcaagaaag tcatgatgcc tatatgttcc tggccagata tctggtgagt  1260
atcgatgaga aatttaagtc ttttgataat aaaacaaact atcaaatttt gccgatgtat  1320
acgaacacgg ttatgttgca gatcccttat tggaaaatgg ggatcgagaa gaaaaatgat  1380
attgggctga ccgatattga agtcaatgag ttaaaacagc ttatcgacac attggttgac  1440
agagccagga actatattca tacgatgtat gaaagagaat atgataatgc catcaacacc  1500
tcaaccgcgg cgagcgtcac taataattta ttgtccgtca gaggatattg cctgttacac  1560
ggtttagagt gtattgaaac cattgaacat ctgcaaaata atagccttaa tagtggtttc  1620
tatcctaaaa ccattagtta ttcaacggta tttgatcgtc ccacgaacaa aacgagaatt  1680
caggctctga ccgaagatga ccaaatgcaa gagcctttca agccagcttt aattggcggt  1740
aagtacaata aaataaaatc attgcttggc tatgtacgaa gaattgggaa tgccccccaga  1800
gtggggggaa ttaaggtcac ctttaccaac ggatcatctt atacacttgg cacagtcaca  1860
tcagaaacgg actcaattga gctaaatgag agtgttatcg aaagattaga agtatggggc  1920
aatggtgctg ttgatgaggc attatttacg ttaagcgatg ggcgccaact caggatcggc  1980
gagcgctacg cgaaaaaata cagaaaatat gctgttgatg gacactatat ttcagggctg  2040
tacttagcca gcgatgaacc ttcccttgct ggtcaggccg caggtattgc cgtttcatac  2100
catatgcttg ctgataaaaa ataa                                        2124

SEQ ID NO: 131         moltype = AA  length = 707
FEATURE                Location/Qualifiers
REGION                 1..707
                       note = The amino acid sequence of the TIC11445 PirAB fusion
                        protein.
source                 1..707
                       mol_type = protein
                       organism = synthetic construct
SEQUENCE: 131
MITININVNG NDVTGTNNNE PTPVSTTYGP NTPASEPPVV SNYSDITIEP HSSVQATRID  60
TPVIPEARPD YYVANSGPAP SVRAVFYWSH SFTSEWFESS SITVKAGEDG ILKAPGNSLY  120
YSKVVIYNDT DKRAFVTGYN KMSTINININS SSTVTVITNN GETPVPLTYN TNTPESEPLT  180
VNPYRDMTIE PRSSIEATRI DTPIIPETRP NYYVANSGPA SSVRAVFYWS HSFTSQWFEY  240
SSIIVKAGED GILESPSNSL YYSKVVIYND TDKRAFVTGY NKMNTTLINV SEKETLPVQT  300
DIMLIAPYSV STPDYEWDMS SLIKDAIIGG VGFIPVVGSA MSFLLGLFWP QQKDNTWEQI  360
LQKVEQMIEN AQLNTIKGIL NGDIQEIKGK MEHVQYMLET SPGSQESHDA YMFLARYLVS  420
IDEKFKSFDN KTNYQILPMY TNTVMLQIPY WKMGIEKKND IGLTDIEVNE LKQLIDTLVD  480
RARNYIHTMY EREYDNAINT STAASVTNNL LSVRGYCLLH GLECIETIEH LQNNSLNSGF  540
YPKTISYSTV FDRPTNKTRI QALTEDDQMQ EPFKPALIGG KYNKIKSLLG YVRRIGNAPR  600
VGGIKVTFTN GSSYTLGTVT SETDSIELNE SVIERLEVWG NGAVDEALFT LSDGRQLRIG  660
ERYAKKYRKY AVDGHYISGL YLASDEPSLA GQAAGIAVSY HMLADKK               707

SEQ ID NO: 132         moltype = DNA  length = 2124
FEATURE                Location/Qualifiers
misc_feature           1..2124
                       note = A nucleic acid sequence encoding a fusion protein,
                        TIC11446comprised of the TIC7662, TIC7660, and TIC7661
                        coding sequencesin operable linkage and in frame.
source                 1..2124
                       mol_type = other DNA
                       organism = synthetic construct
SEQUENCE: 132
```

```
atgagtacaa tcaatatcaa tataagtagc agtaccgtta ccgtcatcac gaataacgga  60
gaaacgccag tcccactcac ttacaataca aatacacctg aatcagaacc tcttaccgtc  120
aatccttata gggatatgac aatagagcca cgctcttcta ttgaagcaac aaggattgat  180
acaccgatta ttcccgaaac acgccctaat tattatgtag ccaattcagg cccggcttca  240
tcagttaggg ccgtttttta ttggtcccat tctttcacat cacaatggtt cgaatattcc  300
tctatcatcg tcaaagccgg ggaagatggc atattagaat caccaagcaa ttctttatat  360
tacagcaaag tcgtcattta taatgatacc gataaacgcg cctttgtgac gggatataat  420
aagatgatca caataaatat aaatgtaaac ggcaatgatg ttacaggtac aaataataat  480
gaacctactc cagtatcgac aacttacggt ccaaatacac cagcatcaga accccctgta  540
gtcagtaatt atagtgatat aacaatagaa ccgcattctt ctgtgcaggc aacaagaatt  600
gatacgcctg ttattcctga agcacgcccc gattactatg tagccaactc cggccctgca  660
ccatcagtta gggctgtttt ttattggtct cattctttca catcagaatg gttcgaatct  720
tcctctatca cagtgaaagc aggagaggac ggaatattaa aagcacctgg taactcttta  780
tattacagca aagtcgtcat ttataatgat acggataaac gagcctttgt tactggatat  840
aataaaatga atactacacc tattactgta tctacaaatg aaacatcgcc tttaatgact  900
gacgtaatgc ccatggatct ttatgcaata tccacacctg attatgaatg ggacatgtcg  960
tcaatcataa aggatgctgt tattggtggc ataggattta ttccaggtcc gggcccggca  1020
atatccttcc tgttagggct attttggcct cagcagaaag acaatacttg ggagcaaatt  1080
ctccagaaag tagagcagat gatagagaat gctgttctac aaactattaa aggaatactt  1140
aatggagaag ttcaagagat caaagggaaa atggaacatg tagaatccat gctgaaaaac  1200
tcgcctggca gtcaggaaag tcatgatgca tatatgttcc tggcgagata tctggttagt  1260
atagatgaaa aattcaaatc ttttgacaat agaacaaatt accagcttct cccaatgtat  1320
actaacacta ttatgttaca gatcccttat tggaaaatgg gaatagagaa gaaaaaagat  1380
attgggctga cagatattga agttaatgaa ttaaaagaac ttatcgataa attggttgat  1440
aaggccaaaa actatattca tacgatgtat actaatgaac ataataatgc tgtaaacaca  1500
tcaacagcag agagtgtcac taataattta ttatctgtaa gaggatattg tttattacac  1560
ggtttagaat gtattgagtt aatcgagcat atacagaata atagccttga gagtggtttc  1620
tatcctaaaa ttatcagtta ttcgactgcg tttgatcgtc ctactaacaa aatgagaatt  1680
caggctctta cagaagatga tgcaatgcag gagcctttca aaccatcttt aatcaatggg  1740
aaatataata aaatccaatc cttgactgga tatgtacaaa gaattgggaa tgcacctaga  1800
gttggtggta tcagaatcac atttaccaac ggctcatctt atacacttgg tacagtgacc  1860
tcagaaacgc attcaattaa gctaaacgat agtgttatcg aaagcttgga agtatggggg  1920
aatggtgctg ttgatgaggc gttatttaag ttaagtgatg ggcgtttatt gcgtattggt  1980
gagcgctacg cgaaaaaata cagaaaatat gctgttgata atcactatat tgcggggatt  2040
tacttagcca gcgatgagcc ttcacttgct ggtcaagccg caggtattgc cgtttcatat  2100
catatgatgg ctgacaaaaa ataa                                        2124
```

```
SEQ ID NO: 133          moltype = AA  length = 707
FEATURE                 Location/Qualifiers
REGION                  1..707
                        note = The amino acid sequence of the TIC11446 PirAB fusion
                         protein.
source                  1..707
                        mol_type = protein
                        organism = synthetic construct
SEQUENCE: 133
MSTININISS STVTVITNNG ETPVPLTYNT NTPESEPLTV NPYRDMTIEP RSSIEATRID  60
TPIIPETRPN YYVANSGPAS SVRAVFYWSH SFTSQWFEYS SIIVKAGEDG ILESPSNSLY  120
YSKVVIYNDT DKRAFVTGYN KMITININVN GNDVTGTNNN EPTPVSTTYG PNTPASEPPV  180
VSNYSDITIE PHSSVQATRI DTPVIPEARP DYYVANSGPA PSVRAVFYWS HSFTSEWFES  240
SSITVKAGED GILKAPGNSL YYSKVVIYND TDKRAFVTGY NKMNTTPITV STNETSPLMT  300
DVMPMDLYAI STPDYEWDMS SIIKDAVIGG IGFIPGPGPA ISFLLGLFWP QQKDNTWEQI  360
LQKVEQMIEN AVLQTIKGIL NGEVQEIKGK MEHVESMLKN SPGSQESHDA YMFLARYLVS  420
IDEKFKSFDN RTNYQLLPMY TNTIMLQIPY WKMGIEKKKD IGLTDIEVNE LKELIDKLVD  480
KAKNYIHTMY TNEHNNAVNT STAESVTNNL LSVRGYCLLH GLECIELIEH IQNNSLESGF  540
YPKIISYSTA FDRPTNKMRI QALTEDDAMQ EPFKPSLING KYNKIQSLTG YVQRIGNAPR  600
VGGIRITFTN GSSYTLGTVT SETHSIKLND SVIESLEVWG NGAVDEALFK LSDGRLLRIG  660
ERYAKKYRKY AVDNHYIAGI YLASDEPSLA GQAAGIAVSY HMMADKK                707
```

```
SEQ ID NO: 134          moltype = DNA  length = 1305
FEATURE                 Location/Qualifiers
misc_feature            1..1305
                        note = A nucleic acid sequence obtained from Xenorhabdus
                         nematophilastrain MDI-0035777 encoding a TIC11505
                         pesticidal PirB proteinsequence.
source                  1..1305
                        mol_type = other DNA
                        organism = Xenorhabdus nematophila
SEQUENCE: 134
atgaataatg aaccgatgaa tactaatgaa tcacaagctt cagagatagt accctcaatg  60
aatgaatcta tattaaatga atctatatta gcagcacctt attcaatttc tacacctaat  120
tatgaatggg atatgtcatc aataataaaa gatgccatta ttggtggtat aggctttatt  180
cctggtccgg gttcagcaat atcatttttg ttagggttat tttggccaca acaaaccgac  240
aatacttggg agcaaattct ccaaaaagta gaacaaatga tcgagcaagc caatctcaaa  300
actattcaag gaatattgaa cggcgatata caagaaatta aaggcaaaat ggaacatgtg  360
caattcatgc tagaatcctc acctggcact caagaaagcc atgacgcata catgtttctg  420
gcgagatatc tggtcagtat agacgaaaaa ttcaagtctt ttgataacaa aacaaattat  480
caaattcttc ccatgtatac caatacgatt atgttacaag ccccttattg gaaaatgggt  540
atagagagaa aagatgagat aaaactaaca gatatagaag ttaatgaatt aaaagagctg  600
```

```
ataggaaaat tatctaccag cgccgataaa tatattcatg atgtctatac tcgtgaatat  660
gataatgcga tgaacacttc aacagcagca aatatcacca ataatttatt atctgtaaga  720
ggctattgtt tattacatgg tttagaatgt ctcgaagtca ttaaccatat acaaaataat  780
agccttgagc aaagttttta tcctaaaact atcagctact ccaccgtatt cgatcgccag  840
acaaataaaa caagggttca agccctgaca gaagacgatc aaatgcaaga gccattcaag  900
cctgctttaa ttaatgggaa gtacaacaaa ataaaatcat tgattgggta tgtacaaaga  960
atcggaaacg cacccagagt tggaggcatt aaagtcacat ttgcaaacga tgcatcttat  1020
accctcggta cagtaacttc agaagtaaac tcaattgaac tgaatgacag cgttataacc  1080
agcctggaag tatggggaaa tggcgctgtt gatgaggcat tctttacatt aagtgacgga  1140
cgtcaattta ggcttggcca acgctatgcc agtaactata gaaaatatgc tgtcgataac  1200
cactatattt caggattgta cttagccagt gatgaacctt cattggcagg ccaagcagca  1260
ggcattgcag tttcatacca tatgatagct gataaaaaat catag                 1305

SEQ ID NO: 135          moltype = AA  length = 434
FEATURE                 Location/Qualifiers
REGION                  1..434
                        note = The amino acid sequence of the TIC11505 PirB protein.
source                  1..434
                        mol_type = protein
                        organism = Xenorhabdus nematophila
SEQUENCE: 135
MNNEPMNTNE SQASEIVPSM NESILNESIL AAPYSISTPN YEWDMSSIIK DAIIGGIGFI  60
PGPGSAISFL LGLFWPQQTD NTWEQILQKV EQMIEQANLK TIQGILNGDI QEIKGKMEHV  120
QFMLESSPGT QESHDAYMFL ARYLVSIDEK FKSFDNKTNY QILPMYTNTI MLQAPYWKMG  180
IERKDEIKLT DIEVNELKEL IGKLSTSADK YIHDVYTREY DNAMNTSTAA NITNNLLSVR  240
GYCLLHGLEC LEVINHIQNN SLEQSFYPKT ISYSTVFDRQ TNKTRVQALT EDDQMQEPFK  300
PALINGKYNK IKSLIGYVQR IGNAPRVGGI KVTFANDASY TLGTVTSEVN SIELNDSVIT  360
SLEVWGNGAV DEAFFTLSDG RQFRLGQRYA SNYRKYAVDN HYISGLYLAS DEPSLAGQAA  420
GIAVSYHMIA DKKS                                                   434

SEQ ID NO: 136          moltype = DNA  length = 1731
FEATURE                 Location/Qualifiers
misc_feature            1..1731
                        note = A nucleic acid sequence encoding a PirAB fusion
                         protein, TIC11506comprised of the TIC10364 and TIC11505
                         coding sequences inoperable linkage and in frame.
source                  1..1731
                        mol_type = other DNA
                        organism = synthetic construct
SEQUENCE: 136
atgagcataa tcaatataaa tataagtggt agtagtgaca ttacaatcat aaacaatacc  60
ccatctaacc cagaaccact catttacaat acagacacac ccgcatcaga acctcttacc  120
gtcaatcctt atagggatat gacaatagag ccacactctt ctattgaggc aataagaatt  180
gatacgccaa ttattcccga aacccgcccc aattattacg tagccaattc tggccccgca  240
tcatcagtta gagccgtttt ttattggtct cactctttca catcagaatg gttcgaatat  300
tctgctatca cagtgaaagc cggggaagac ggcatattac aatcaccgag caactctgtg  360
tattacagca aggtcgtcat ttataacgaa accgataaac gcgcctttgt tactggatat  420
aataagatga ataatgaacc gatgaatact aatgaatcac aagcttcaga gatagtaccc  480
tcaatgaatg aatctatatt aaatgaatct atattagcag caccttattc aatttctaca  540
cctaattatg aatgggatat gtcatcaata ataaaagatg ccattattgg tggtataggc  600
tttattcctg gtccgggttc agcaatatca tttttgttag ggttattttg gccacaacaa  660
accgacaata cttgggagca aattctccaa aaagtagaac aaatgatcga gcaagccaat  720
ctcaaaacta ttcaaggaat attgaacggc gatatacaag aaattaaagg caaaatggaa  780
catgtgcaat tcatgctaga atcctcacct ggcactcaag aaagccatga cgcatacatg  840
tttctggcga gatatctggt cagtatagac gaaaaattca agtcttttga taacaaaaca  900
aattatcaaa ttcttcccat gtataccaat acgattatgt tacaagcccc ttattggaaa  960
atgggtatag agagaaaaga tgagataaaa ctaacagata tagaagttaa tgaattaaaa  1020
gagctgatag gaaaattatc taccagcgcc gataaatata ttcatgatgt ctatactcgt  1080
gaatatgata atgcgatgaa cacttcaaca gcagcaaata tcaccaataa tttattatct  1140
gtaagaggct attgtttatt acatggttta gaatgtctcg aagtcattaa ccatatacaa  1200
aataatagcc ttgagcaaag tttttatcct aaaactatca gctactccac cgtattcgat  1260
cgccagacaa ataaaacaag ggttcaagcc ctgacagaag acgatcaaat gcaagagcca  1320
ttcaagcctg ctttaattaa tgggaagtac aacaaaataa aatcattgat tgggtatgta  1380
caaagaatcg gaaacgcacc cagagttgga ggcattaaag tcacatttgc aaacgatgca  1440
tcttataccc tcggtacagt aacttcagaa gtaaactcaa ttgaactgaa tgacagcgtt  1500
ataaccagcc tggaagtatg gggaaatggc gctgttgatg aggcattctt tacattaagt  1560
gacggacgtc aatttaggct tggccaacgc tatgccagta actatagaaa atatgctgtc  1620
gataaccact atatttcagg attgtactta gccagtgatg aaccttcatt ggcaggccaa  1680
gcagcaggca ttgcagtttc ataccatatg atagctgata aaaaatcata g           1731

SEQ ID NO: 137          moltype = AA  length = 576
FEATURE                 Location/Qualifiers
REGION                  1..576
                        note = The amino acid sequence of the TIC11506 PirAB fusion
                         protein.
source                  1..576
                        mol_type = protein
                        organism = synthetic construct
SEQUENCE: 137
```

```
MSIININISG SSDITIINNT PSNPEPLIYN TDTPASEPLT VNPYRDMTIE PHSSIEAIRI  60
DTPIIPETRP NYYVANSGPA SSVRAVFYWS HSFTSEWFEY SAITVKAGED GILQSPSNSV  120
YYSKVVIYNE TDKRAFVTGY NKMNNEPMNT NESQASEIVP SMNESILNES ILAAPYSIST  180
PNYEWDMSSI IKDAIIGGIG FIPGPGSAIS FLLGLFWPQQ TDNTWEQILQ KVEQMIEQAN  240
LKTIQGILNG DIQEIKGKME HVQFMLESSP GTQESHDAYM FLARYLVSID EKFKSFDNKT  300
NYQILPMYTN TIMLQAPYWK MGIERKDEIK LTDIEVNELK ELIGKLSTSA DKYIHDVYTR  360
EYDNAMNTST AANITNNLLS VRGYCLLHGL ECLEVINHIQ NNSLEQSFYP KTISYSTVFD  420
RQTNKTRVQA LTEDDQMQEP FKPALINGKY NKIKSLIGYV QRIGNAPRVG GIKVTFANDA  480
SYTLGTVTSE VNSIELNDSV ITSLEVWGNG AVDEAFFTLS DGRQFRLGQR YASNYRKYAV  540
DNHYISGLYL ASDEPSLAGQ AAGIAVSYHM IADKKS                          576
```

```
SEQ ID NO: 138          moltype = DNA  length = 1290
FEATURE                 Location/Qualifiers
misc_feature            1..1290
                        note = A nucleic acid sequence obtained from Xenorhabdus
                         bovienii strainMDI-0035808 encoding a TIC11510 pesticidal
                         PirB protein sequence.
source                  1..1290
                        mol_type = other DNA
                        organism = Xenorhabdus bovienii
SEQUENCE: 138
atgaataatg aaccgatgaa tactaatgaa tcacaagctt cagagatagt accctcaatg  60
aatgaatcta tattagcagc accttattca atttctacac ctaattatga atgggatatg  120
tcatcaataa taaaagatgc cattattggt ggtataggct ttattcctgg tccgggctca  180
gcaatatcat ttttgttagg gttattttgg ccacaacaaa ccgacaatac ttgggagcaa  240
attctccaaa aagtagaaca aatgatcgag caagccaatc tcaaaactat tcaaggaata  300
ttgaacggcg atatacaaga aattaaaggc aaaatggaac atgtgcaatt catgctagaa  360
tcctcatctg gcactcaaga aagccatgac gcatacatgt ttctggcgag atatctggtc  420
agtatagacg aaaaattcaa gtcttttgat aacaaaacaa attatcaaat tcttcccatg  480
tataccaata cgattatgtt acaagcccct tattggaaaa tgggtataga gagaaaagat  540
gagatcaaac taacagatat agaagttaat gaattaaaag agctgatagg aaaattatct  600
accagcgccg ataaatatat tcatgatgtc tatactcgtg aatatgataa tgcgatgaac  660
acttcaacag cagcaaatat caccaataat ttattatctg taagaggcta ttgtttatta  720
catggtttag aatgtctcga agtcattaac catatacaaa ataatagcct tgagcaaagt  780
ttttatccta aaactatcag ctactccacc gtattcgatc gccagacaaa taaaacaagg  840
gttcaagccc tgacagaaga cgatcaaatg caagagccat tcaagcctgc tttagttaat  900
gggaagtaca acaaaataaa atcattgatt gggtatgtac aaagaatcgg aaacgcaccc  960
agagttggag gcattaaagt cacatttgca aacgatgcat cttataccct cggtacagta  1020
acttcagaag taaactcaat tgaactgaat gacagcgtta taaccagcct ggaagtatgg  1080
ggaaatggcg ctattgatga ggcattcttt acattaagtg acggacgtca atttaggctt  1140
ggccaacgct atgccagtaa ctatagaaaa tatgctgtcg ataaccacta tatttcagga  1200
ttgtacttag ccagtgatga accttcattg gcaggtcaag cagcaggcat tgcagtttca  1260
taccatatga tagctgataa aaaatcatag                                 1290
```

```
SEQ ID NO: 139          moltype = AA  length = 429
FEATURE                 Location/Qualifiers
REGION                  1..429
                        note = The amino acid sequence of the TIC11510 PirB protein.
source                  1..429
                        mol_type = protein
                        organism = Xenorhabdus bovienii
SEQUENCE: 139
MNNEPMNTNE SQASEIVPSM NESILAAPYS ISTPNYEWDM SSIIKDAIIG GIGFIPGPGS  60
AISFLLGLFW PQQTDNTWEQ ILQKVEQMIE QANLKTIQGI LNGDIQEIKG KMEHVQFMLE  120
SSSGTQESHD AYMFLARYLV SIDEKFKSFD NKTNYQILPM YTNTIMLQAP YWKMGIERKD  180
EIKLTDIEVN ELKELIGKLS TSADKYIHDV YTREYDNAMN TSTAANITNN LLSVRGYCLL  240
HGLECLEVIN HIQNNSLEQS FYPKTISYST VFDRQTNKTR VQALTEDDQM QEPFKPALVN  300
GKYNKIKSLI GYVQRIGNAP RVGGIKVTFA NDASYTLGTV TSEVNSIELN DSVITSLEVW  360
GNGAIDEAFF TLSDGRQFRL GQRYASNYRK YAVDNHYISG LYLASDEPSL AGQAAGIAVS  420
YHMIADKKS                                                        429
```

```
SEQ ID NO: 140          moltype = DNA  length = 1716
FEATURE                 Location/Qualifiers
misc_feature            1..1716
                        note = A nucleic acid sequence encoding a PirAB fusion
                         protein, TIC11512comprised of the TIC10364 and TIC11510
                         coding sequences inoperable linkage and in frame.
source                  1..1716
                        mol_type = other DNA
                        organism = synthetic construct
SEQUENCE: 140
atgagcataa tcaatataaa tataagtggt agtagtgaca ttacaatcat aaacaatacc  60
ccatctaacc cagaaccact catttacaat acagacacac ccgcatcaga acctcttacc  120
gtcaatcctt atagggatat gacaatagag ccacactctt ctattgaggc aataagaatt  180
gatacgccaa ttattcccga aacccgcccc aattattacg tagccaattc tggccccgca  240
tcatcagtta gagccgtttt ttattggtct cactctttca catcagaatg gttcgaatat  300
tctgctatca cagtgaaagc cggggaagac ggcatattac aatcaccgag caactctgtg  360
tattacagca aggtcgtcat ttataacgaa accgataaac gcgcctttgt tactggatat  420
aataagatga ataatgaacc gatgaatact aatgaatcac aagcttcaga gatagtaccc  480
```

```
tcaatgaatg aatctatatt agcagcacct tattcaattt ctacacctaa ttatgaatgg  540
gatatgtcat caataataaa agatgccatt attggtggta taggctttat tcctggtccg  600
ggctcagcaa tatcattttt gttagggtta ttttggccac aacaaaccga caatacttgg  660
gagcaaattc tccaaaaagt agaacaaatg atcgagcaag ccaatctcaa aactattcaa  720
ggaatattga acggcgatat acaagaaatt aaaggcaaaa tggaacatgt gcaattcatg  780
ctagaatcct catctggcac tcaagaaagc catgacgcat acatgtttct ggcgagatat  840
ctggtcagta tagacgaaaa attcaagtct tttgataaca aaacaaatta tcaaattctt  900
cccatgtata ccaatacgat tatgttacaa gccccttatt ggaaaatggg tatagagaga  960
aaagatgaga tcaaactaac agatatagaa gttaatgaat taaaagagct gataggaaaa  1020
ttatctacca gcgccgataa atatattcat gatgtctata ctcgtgaata tgataatgcg  1080
atgaacactt caacagcagc aaatatcacc aataatttat tatctgtaag aggctattgt  1140
ttattacatg gtttagaatg tctcgaagtc attaaccata tacaaaataa tagccttgag  1200
caaagttttt atcctaaaac tatcagctac tccaccgtat tcgatcgcca gacaaataaa  1260
acaagggttc aagccctgac agaagacgat caaatgcaag agccattcaa gcctgcttta  1320
gttaatggga agtacaacaa aataaaatca ttgattgggt atgtacaaag aatcggaaac  1380
gcacccagag ttggaggcat taaagtcaca tttgcaaacg atgcatctta taccctcggt  1440
acagtaactt cagaagtaaa ctcaattgaa ctgaatgaca gcgttataac cagcctggaa  1500
gtatggggaa atggcgctat tgatgaggca ttctttacat taagtgacgg acgtcaattt  1560
aggcttggcc aacgctatgc cagtaactat agaaaatatg ctgtcgataa ccactatatt  1620
tcaggattgt acttagccag tgatgaacct tcattggcag gtcaagcagc aggcattgca  1680
gtttcatacc atatgatagc tgataaaaaa tcatag                             1716
```

```
SEQ ID NO: 141          moltype = AA  length = 571
FEATURE                 Location/Qualifiers
REGION                  1..571
                        note = The amino acid sequence of the TIC11512 PirAB fusion
                         protein.
source                  1..571
                        mol_type = protein
                        organism = synthetic construct
SEQUENCE: 141
MSIININISG SSDITIINNT PSNPEPLIYN TDTPASEPLT VNPYRDMTIE PHSSIEAIRI  60
DTPIIPETRP NYYVANSGPA SSVRAVFYWS HSFTSEWFEY SAITVKAGED GILQSPSNSV  120
YYSKVVIYNE TDKRAFVTGY NKMNNEPMNT NESQASEIVP SMNESILAAP YSISTPNYEW  180
DMSSIIKDAI IGGIGFIPGP GSAISFLLGL FWPQQTDNTW EQILQKVEQM IEQANLKTIQ  240
GILNGDIQEI KGKMEHVQFM LESSSGTQES HDAYMFLARY LVSIDEKFKS FDNKTNYQIL  300
PMYTNTIMLQ APYWKMGIER KDEIKLTDIE VNELKELIGK LSTSADKYIH DVYTREYDNA  360
MNTSTAANIT NNLLSVRGYC LLHGLECLEV INHIQNNSLE QSFYPKTISY STVFDRQTNK  420
TRVQALTEDD QMQEPFKPAL VNGKYNKIKS LIGYVQRIGN APRVGGIKVT FANDASYTLG  480
TVTSEVNSIE LNDSVITSLE VWGNGAIDEA FFTLSDGRQF RLGQRYASNY RKYAVDNHYI  540
SGLYLASDEP SLAGQAAGIA VSYHMIADKK S                                571
```

```
SEQ ID NO: 142          moltype = DNA  length = 1290
FEATURE                 Location/Qualifiers
misc_feature            1..1290
                        note = A nucleic acid sequence obtained from Xenorhabdus
                         nematophilastrain AN6/1 encoding a TIC11511 pesticidal
                         PirB proteinsequence.
source                  1..1290
                        mol_type = other DNA
                        organism = Xenorhabdus nematophila
SEQUENCE: 142
atgaataatg aaccgatgaa tactaatgaa tcacaagctt cagagatagt accctcaatg  60
aatgaatcta tattagcagc accttattca atttctacac ctaattatga atgggatatg  120
tcatcaataa taaaagatgc cattattggt ggtataggct ttattcctgg tccgggctca  180
gcaatatcat ttttgttagg gttattttgg ccacaacaaa ccgacaatac ttgggagcaa  240
attctccaaa aagtagaaca aatgatcgag caagccaatc tcaaaactat tcaaggaata  300
ttgaacggcg atatacaaga aattaaaggc aaaatggaac atgtgcaatt catgctagaa  360
tcctcacctg gcactcaaga aagccatgac gcatacatgt ttctggcgag atatctggtc  420
agtatagacg aaaaattcaa gtcttttgat aacaaaacaa attatcaaat tcttcccatg  480
tataccaata cgattatgtt acaagcccct tattggaaaa tgggtataga gagaaaagat  540
gagataaaac taacagatat agaagttaat gaattaaaag agctgatagg aaaattatct  600
accagcgccg ataaatatat tcatgatgtc tatactcgtg aatatgataa tgcgatgaac  660
acttcaacag cagcaaatat caccaataat ttattatctg taagaggcta ttgtttatta  720
catggtttag aatgtctcga agtcattaac catatacaaa ataatagcct tgagcaaagt  780
ttttatccta aaactatcag ctactccacc gtattcgatc gccagacaaa taaaacaagg  840
gttcaagccc tgacagaaga cgatcaaatg caagagccat tcaagcctgc tttaattaat  900
gggaagtaca acaaaataaa atcattgatt gggtatgtac aaagaatcgg aaacgcaccc  960
agagttggag gcattaaagt cacatttgca aacgatgcat cttataccct cggtacagta  1020
acttcagaag taaactcaat tgaactgaat gacagcgtta taaccagcct ggaagtatgg  1080
ggaaatggcg ctattgatga ggcattcttt acattaagtg acggacgtca atttaggctt  1140
ggccaacgct atgccagtaa ctatagaaaa tatgctgtcg ataaccacta tatttcagga  1200
ttgtacttag ccagtgatga accttcattg gcaggccaag cagcaggcat tgcagtttca  1260
taccatatga tagctgataa aaaatcatag                                  1290
```

```
SEQ ID NO: 143          moltype = AA  length = 429
FEATURE                 Location/Qualifiers
REGION                  1..429
                        note = The amino acid sequence of the TIC11511 PirB protein.
```

```
source                  1..429
                        mol_type = protein
                        organism = Xenorhabdus nematophila
SEQUENCE: 143
MNNEPMNTNE SQASEIVPSM NESILAAPYS ISTPNYEWDM SSIIKDAIIG GIGFIPGPGS  60
AISFLLGLFW PQQTDNTWEQ ILQKVEQMIE QANLKTIQGI LNGDIQEIKG KMEHVQFMLE  120
SSPGTQESHD AYMFLARYLV SIDEKFKSFD NKTNYQILPM YTNTIMLQAP YWKMGIERKD  180
EIKLTDIEVN ELKELIGKLS TSADKYIHDV YTREYDNAMN TSTAANITNN LLSVRGYCLL  240
HGLECLEVIN HIQNNSLEQS FYPKTISYST VFDRQTNKTR VQALTEDDQM QEPFKPALIN  300
GKYNKIKSLI GYVQRIGNAP RVGGIKVTFA NDASYTLGTV TSEVNSIELN DSVITSLEVW  360
GNGAIDEAFF TLSDGRQFRL GQRYASNYRK YAVDNHYISG LYLASDEPSL AGQAAGIAVS  420
YHMIADKKS                                                         429

SEQ ID NO: 144          moltype = DNA  length = 1716
FEATURE                 Location/Qualifiers
misc_feature            1..1716
                        note = A nucleic acid sequence encoding a PirAB fusion
                         protein, TIC11513comprised of the TIC10364 and TIC11511
                         coding sequences inoperable linkage and in frame.
source                  1..1716
                        mol_type = other DNA
                        organism = synthetic construct
SEQUENCE: 144
atgagcataa tcaatataaa tataagtggt agtagtgaca ttacaatcat aaacaatacc  60
ccatctaacc cagaaccact catttacaat acagacacac ccgcatcaga acctcttacc  120
gtcaatcctt atagggatat gacaatagag ccacactctt ctattgaggc aataagaatt  180
gatacgccaa ttattcccga aacccgcccc aattattacg tagccaattc tggccccgca  240
tcatcagtta gagccgtttt ttattggtct cactctttca catcagaatg gttcgaatat  300
tctgctatca cagtgaaagc cggggaagac ggcatattac aatcaccgag caactctgtg  360
tattacagca aggtcgtcat ttataacgaa accgataaac gcgcctttgt tactggatat  420
aataagatga ataatgaacc gatgaatact aatgaatcac aagcttcaga gatagtaccc  480
tcaatgaatg aatctatatt agcagcacct tattcaattt ctacacctaa ttatgaatgg  540
gatatgtcat caataataaa agatgccatt attggtggta taggctttat tcctggtccg  600
ggctcagcaa tatcattttt gttagggtta ttttggccac aacaaaccga caatacttgg  660
gagcaaattc tccaaaaagt agaacaaatg atcgagcaag ccaatctcaa aactattcaa  720
ggaatattga acggcgatat acaagaaatt aaaggcaaaa tggaacatgt gcaattcatg  780
ctagaatcct cacctggcac tcaagaaagc catgacgcat acatgtttct ggcgagatat  840
ctggtcagta tagacgaaaa attcaagtct tttgataaca aaacaaatta tcaaattctt  900
cccatgtata ccaatacgat tatgttacaa gccccttatt ggaaaatggg tatagagaga  960
aaagatgaga taaaactaac agatatagaa gttaatgaat taaaagagct gataggaaaa  1020
ttatctacca gcgccgataa atatattcat gatgtctata ctcgtgaata tgataatgcg  1080
atgaacactt caacagcagc aaatatcacc aataatttat tatctgtaag aggctattgt  1140
ttattacatg gtttagaatg tctcgaagtc attaaccata tacaaaataa tagccttgag  1200
caaagttttt atcctaaaac tatcagctac tccaccgtat tcgatcgcca gacaaataaa  1260
acaagggttc aagccctgac agaagacgat caaatgcaag agccattcaa gcctgcttta  1320
attaatggga agtacaacaa aataaaatca ttgattgggt atgtacaaag aatcggaaac  1380
gcacccagag ttggaggcat taaagtcaca tttgcaaacg atgcatctta taccctcggt  1440
acagtaactt cagaagtaaa ctcaattgaa ctgaatgaca gcgttataac cagcctggaa  1500
gtatggggaa atggcgctat tgatgaggca ttctttacat taagtgacgg acgtcaattt  1560
aggcttggcc aacgctatgc cagtaactat agaaaatatg ctgtcgataa ccactatatt  1620
tcaggattgt acttagccag tgatgaacct tcattggcag gccaagcagc aggcattgca  1680
gtttcatacc atatgatagc tgataaaaaa tcatag                           1716

SEQ ID NO: 145          moltype = AA  length = 571
FEATURE                 Location/Qualifiers
REGION                  1..571
                        note = The amino acid sequence of the TIC11513 PirAB fusion
                         protein.
source                  1..571
                        mol_type = protein
                        organism = synthetic construct
SEQUENCE: 145
MSIININISG SSDITIINNT PSNPEPLIYN TDTPASEPLT VNPYRDMTIE PHSSIEAIRI  60
DTPIIPETRP NYYVANSGPA SSVRAVFYWS HSFTSEWFEY SAITVKAGED GILQSPSNSV  120
YYSKVVIYNE TDKRAFVTGY NKMNNEPMNT NESQASEIVP SMNESILAAP YSISTPNYEW  180
DMSSIIKDAI IGGIGFIPGP GSAISFLLGL FWPQQTDNTW EQILQKVEQM IEQANLKTIQ  240
GILNGDIQEI KGKMEHVQFM LESSPGTQES HDAYMFLARY LVSIDEKFKS FDNKTNYQIL  300
PMYTNTIMLQ APYWKMGIER KDEIKLTDIE VNELKELIGK LSTSADKYIH DVYTREYDNA  360
MNTSTAANIT NNLLSVRGYC LLHGLECLEV INHIQNNSLE QSFYPKTISY STVFDRQTNK  420
TRVQALTEDD QMQEPFKPAL INGKYNKIKS LIGYVQRIGN APRVGGIKVT FANDASYTLG  480
TVTSEVNSIE LNDSVITSLE VWGNGAIDEA FFTLSDGRQF RLGQRYASNY RKYAVDNHYI  540
SGLYLASDEP SLAGQAAGIA VSYHMIADKK S                                571

SEQ ID NO: 146          moltype = DNA  length = 1689
FEATURE                 Location/Qualifiers
misc_feature            1..1689
                        note = a synthetic coding sequence used for expression in
                         plant cellsencoding a TIC10376PL PirAB fusion protein with
                         an additionalalanine codon inserted after the initiating
```

```
                         methionine codon.
source                  1..1689
                        mol_type = other DNA
                        organism = synthetic construct
SEQUENCE: 146
atggctccgg tgaaccagat cgggctccac aacgagaagg tcaagaacat gcggaagatc  60
accgtggaca atgacgtggt gggccacgac accgagatca acagcgtcgt gagcagcacg  120
gccgagaaga tccggcagca gttcggcgtg aaagtcgatc ccaattcgtc ccaggagaag  180
ttctacatcg ccacgcccat catcccggag tcccgcaaga acatcgtggt caccaacgag  240
ggcctggcgg acgtcatcac cgccaagtac tattggagcc acagcttcac cagcgaatac  300
tttgaggaca actcggtgga cgtcaaggtg ggcgagagca aagtgctggt cgctccgagc  360
aaccctctct actacagcaa ggtcgtcatc ttcaacaaca ccaagtcggt ggccttcgtc  420
acggtccgcg agaagatgag cgacatcgtg aagtacaacg acgtcagcgc gcccatcccg  480
tacgcggttt acagtaacgc cgtgtacgcc ttcgagtggg actcgtcggc gatcctcaag  540
caagcagtgg tgaagggctt gtcctacgtg ccgcacgtcg ggaagtacct ctcgtacatc  600
gtcggattct tctggaagga caaggagaag gacatctggc aagaggtggt gggcaaggtg  660
cagcagttgg tagaggactc gatcctcaag gcggtgaagg gcatcctgtc cggcaacatc  720
aacgagctaa aggagaagat gaatgaggtg atccgctccc ttgagaagaa tttgggaacc  780
caagaggccc gcgacgacta catgcacctg gcccgcagca tggtgggcaa ggaggcaagc  840
cttatcttcc acgagaacaa gaccaacttc cacatcctgc cgatgtactc tacgctcgcc  900
ctcatgcaga tcatgtactg gacggtgggc atcgaacgcc gcaaggaaat tggtctgagc  960
gacatcgagg tcgagaacct ccggagctac atcaagaagc tcgtcagcga cgcggagcac  1020
cacgtgaacc gggtgtacaa gctggagctg gactccgtgg tcagcgactc ggacgtgaac  1080
cgggtggcgg acaacatcat gtacgtccac ggctactgcc agattcacgg cctggagtac  1140
atggacatca tcaagaacat acagtctcgt ggcaacaaca tcaccggctt ctaccctagg  1200
actatctcgt actctacatt ctttggctcg ccgaccagcg acgcgcggat tctggccctg  1260
cggccggaga aggacatgcc cgagcctttc aagcccaagt tcctgaacga gcggttcaac  1320
aagatcgcgt cggtcaaggg ctacatcgtc cggatcggag gtgccaagag ggtcggcggc  1380
ctggagatca cgttcgagaa cgggtcgaag taccagcaag ggcaagcgac caacgagcac  1440
gagatcgtga acctcaaggg caaccttatc aagaccctgg aggtgtgggg aaacggtgcc  1500
atcgacgagg ccaagttcac gctgacgaac ggcgacgtcc tcaccatcgg gcagcgcaac  1560
agcagcaact accggaagtt ctccctggac ggccactaca tctgcggcgt gttcatcgcc  1620
aacgaccgct cgggcctcgc gggacaagcc gcgaacatcg ccgtctccta ccatcagctc  1680
gtcgagtga                                                          1689

SEQ ID NO: 147          moltype = AA  length = 562
FEATURE                 Location/Qualifiers
REGION                  1..562
                        note = The amino acid sequence of the TIC10376PL PirAB
                         fusion protein.
source                  1..562
                        mol_type = protein
                        organism = synthetic construct
SEQUENCE: 147
MAPVNQIGLH NEKVKNMRKI TVDNDVVGHD TEINSVVSST AEKIRQQFGV KVDPNSSQEK  60
FYIATPIIPE SRKNIVVTNE GLADVITAKY YWSHSFTSEY FEDNSVDVKV GESKVLVAPS  120
NPLYYSKVVI FNNTKSVAFV TVREKMSDIV KYNDVSAPIP YAVYSNAVYA FEWDSSAILK  180
QAVVKGLSYV PHVGKYLSYI VGFFWKDKEK DIWQEVVGKV QQLVEDSILK AVKGILSGNI  240
NELKEKMNEV IRSLEKNLGT QEARDDYMHL ARSMVGKEAS LIFHENKTNF HILPMYSTLA  300
LMQIMYWTVG IERRKEIGLS DIEVENLRSY IKKLVSDAEH HVNRVYKLEL DSVVSDSDVN  360
RVADNIMYVH GYCQIHGLEY MDIIKNIQSR GNNITGFYPR TISYSTFFGS PTSDARILAL  420
RPEKDMPEPF KPKFLNERFN KIASVKGYIV RIGGAKRVGG LEITFENGSK YQQGQATNEH  480
EIVNLKGNLI KTLEVWGNGA IDEAKFTLTN GDVLTIGQRN SSNYRKFSLD GHYICGVFIA  540
NDRSGLAGQA ANIAVSYHQL VE                                           562

SEQ ID NO: 148          moltype = DNA  length = 1710
FEATURE                 Location/Qualifiers
misc_feature            1..1710
                        note = A synthetic coding sequence used for expression in
                         plant cellsencoding a TIC10378PL PirAB fusion protein with
                         an additionalalanine codon inserted after the initiating
                         methionine codon.
source                  1..1710
                        mol_type = other DNA
                        organism = synthetic construct
SEQUENCE: 148
atggctatca cgatcaacat caacaccaac ggcgtgaacg gcatcaccat caccaacagc  60
aacaacgagc cgacgcccgt aagcacgacc tacggtccca acactccggc gagcgagccg  120
ctcaccgtca gcaactactc ggacatcacc atcgagccgc acagctccgt ccaggccacg  180
cgcatcgaca cgccgatcat cccggagacc cggccggact actacgtcgc taactccggg  240
cccgcgccga ccgtccgcgc cgtgttctac tggtcgcaca gcttcacgtc cgagtggttc  300
gagtccagct ccataacggt gaaggcgggc gaggatggta tcctcaaagc gcccggaaac  360
tcgctctact acagcaaggt ggtcatctac aatgacaccg acaagcgcgc cttcgtgacc  420
ggctacaaca agatgaacac gacgccgatc accgtgtcgg agaacgagac gtcgcctctc  480
ctcaccgacg tcatgccgat ggacctgtac gcggtgtcca cacccgacta cgagtgggac  540
atgtcctcca tcatcaagga cgccatcatc ggcggcatcg gcttcattcc cggtcccggc  600
cctgctctgt cgttcttgct cggactgttc tggccgcagc agaaggacaa cacttgggag  660
caaatccttc agaaggtgga gcagatgatc gagaacgcgg tgctccagac gatcaagggc  720
atcctgaacg gcgagatcca ggagatcaag ggcaagatgg agcacgtgga gtccatgctc  780
```

```
aagaatagcc ctggtagcca agagtcccac gacgcctaca tgttcctagc ccgttacctc  840
gtttccatcg acgagaaatt caagtccttc gacaaccgca cgaactacca gatcctcccg  900
atgtacacca ataccatcat gctccagatt ccctactgga agatgggcat cgagaagaag  960
aaggacattg gcctgacgga catcgaggtc aacgaactta aagagctgat cgacaagctc  1020
gtcgggaagg ccaagaatta catccacaca atgtacacta atgagtacaa cgacgcgatc  1080
aacacgagca cggctgggtc ggttaccaac aacctgctct ccgtgcgcgg gtactgcttg  1140
ctgcacgggc tagagtgcat tgagctgatc gagcacatcc agaacaatag cctggagagc  1200
gggttctacc ctaagaccat ctcgtactcc acggtgttcg accgccctac gaacaagatg  1260
cggatacagg cgctgaccga ggacgacgcg atgcaagaac cgttcaagcc gagcctgatt  1320
aacggcaagt acaacaagat ccagtcgatt atcgggtacg tccagcggat cgggaacgct  1380
ccgcgcgtcg gcgggattaa gatcaccttc acaaacggta gcagttacac gctcgggact  1440
gtcacgtccg agacaaatag tatcgagttg aacgacagcg tgatcgagtc cctggaggtg  1500
tggggcaacg gcgcggtgga cgaggcgctg tttaagctgt cggatggccg tctgctgcga  1560
ataggcgagc ggtacgccaa gaaataccgc aagtacgccg tggaccacca ttacatcgcc  1620
gggatctacc tcgccagcga tgaaccctcg cttgcgggac aggcggccgg gatcgcggtg  1680
tcgtatcaca tgatggccga caagaaatga                                  1710

SEQ ID NO: 149         moltype = AA  length = 569
FEATURE                Location/Qualifiers
REGION                 1..569
                       note = The amino acid sequence of the TIC10378PL PirAB
                        fusion protein.
source                 1..569
                       mol_type = protein
                       organism = synthetic construct
SEQUENCE: 149
MAITININTN GVNGITITNS NNEPTPVSTT YGPNTPASEP LTVSNYSDIT IEPHSSVQAT  60
RIDTPIIPET RPDYYVANSG PAPTVRAVFY WSHSFTSEWF ESSSITVKAG EDGILKAPGN  120
SLYYSKVVIY NDTDKRAFVT GYNKMNTTPI TVSENETSPL LTDVMPMDLY AVSTPDYEWD  180
MSSIIKDAII GGIGFIPGPG PALSFLLGLF WPQQKDNTWE QILQKVEQMI ENAVLQTIKG  240
ILNGEIQEIK GKMEHVESML KNSPGSQESH DAYMFLARYL VSIDEKFKSF DNRTNYQILP  300
MYTNTIMLQI PYWKMGIEKK KDIGLTDIEV NELKELIDKL VGKAKNYIHT MYTNEYNDAI  360
NTSTAGSVTN NLLSVRGYCL LHGLECIELI EHIQNNSLES GFYPKTISYS TVFDRPTNKM  420
RIQALTEDDA MQEPFKPSLI NGKYNKIQSI IGYVQRIGNA PRVGGIKITF TNGSSYTLGT  480
VTSETNSIEL NDSVIESLEV WGNGAVDEAL FKLSDGRLLR IGERYAKKYR KYAVDHHYIA  540
GIYLASDEPS LAGQAAGIAV SYHMMADKK                                   569

SEQ ID NO: 150         moltype = DNA  length = 1707
FEATURE                Location/Qualifiers
misc_feature           1..1707
                       note = A synthetic coding sequence used for expression in
                        plant cellsencoding a TIC10380PL PirAB fusion protein with
                        an additionalalanine codon inserted after the initiating
                        methionine codon.
source                 1..1707
                       mol_type = other DNA
                       organism = synthetic construct
SEQUENCE: 150
atggctatca ccatcaacat cagcggcggg tccgtgacga tcaacaacac ctacaacatc  60
acttccgaga gcggcatcca gaacacgcca gcgtcggagc ctctcaccgt catcccgtac  120
cgtgacatga ccatcgagcc tcacagcagc attgaggcca cccgcaccga cacgccgatc  180
atcccggaga cgcggcccaa ctactacatc gctaactcgg gcccggcctc cgaggtgcgc  240
gcggtgttct actggtcgca ctcgttcacg tcgcagtggt tcgagtcgtc cagcataatc  300
gtcaaggcgg gcgaggacgg catcctccag tcgccgtcga acagtctgta ctactcgaag  360
gtggtcatct acaatgacac cgacaagcgc gcgttcgtca ccggctacaa caagatgaac  420
aacacctcca tcaacatcaa tgagaacgag acgctgccgc ttgaagtcat cccgtccatg  480
cccgagccca tgctgatcgt cccgtatgcc acgagcacgc cggattacga gtgggacgcc  540
agcgggatca tcaaggatgc catcatcggc gggatcgggt tcataccggg ccctggccca  600
gcgatctcct tcctgctggg cttgttctgg ccgcaacaag ctgacaacac ctgggagcag  660
atcctccaga aggtcgagca gatgatcgag gacgcagtgc taaagaccat ccagggcatc  720
ctgaacggtg acatccagga gatcaagggc aagatggagc acgtgcagta catgctggag  780
acatcgcccg gcagccagga gtcccgtgag gcgtacatgt tcctcgcccg ctacctcgtc  840
agcattgacg agaagttcaa gtccttcgac aacaagacca attaccagat cctgcccatg  900
tacacgaata ctctcatgct ccaagtgcca tactggaaga tgggcatcga gaagcagaag  960
gacatcggcc tctccgacat cgaagtcaac gagcttaaac agctaatcga caagctctac  1020
accaaagcta attcgtacat acacgaaaca tacacacggc agtacaacga cgcgataaac  1080
accagcacgg cagccaacat caccaacaac ctgttcagcg tgcgcggcta ctgcttgctg  1140
cacgggctgg agtgcctgga gatgattgag catcttcaga agaatagcct tgaatcgggt  1200
ttctacccta agaccataag ctacagcaca gtctttgacc gtcagacgcc caagatgcgg  1260
atacaagccc tgaccgagga cgatcagatg caagagccgc tcaaaccctc gctgataaac  1320
ggcaagtaca accagatcaa gagcctcacc ggatacgtcc ggcggatcgg caacgctccg  1380
cgcgtcggcg gaatgacgat caccttcgcc aatggcgcgt cctacaccct cgggacggtc  1440
acctccgaga ccaccagtat cgagctgaac ggctccgtga tcgagtccct ggaggtgtgg  1500
ggcgacggcg cggtggacga ggcgctcttc accttaagcg acaagcgcct gttccgtatc  1560
ggcgagcgct atgcgcgcaa gtacaagaag tatgccgtgg acagccacta catcgctggg  1620
ctctacctgg cctcggacga gccatcgttg gccgggcaag ctgcgggcat tgccgtcagc  1680
taccacatgc tcgacgacaa gaaatga                                     1707

SEQ ID NO: 151         moltype = AA  length = 568
```

```
FEATURE                Location/Qualifiers
REGION                 1..568
                       note = The amino acid sequence of the TIC10380PL PirAB
                        fusion protein.
source                 1..568
                       mol_type = protein
                       organism = synthetic construct
SEQUENCE: 151
MAITINISGG SVTINNTYNI TSESGIQNTP ASEPLTVIPY RDMTIEPHSS IEATRTDTPI  60
IPETRPNYYI ANSGPASEVR AVFYWSHSFT SQWFESSSII VKAGEDGILQ SPSNSLYYSK  120
VVIYNDTDKR AFVTGYNKMN NTSININENE TLPLEVIPSM PEPMLIVPYA TSTPDYEWDA  180
SGIIKDAIIG GIGFIPGPGP AISFLLGLFW PQQADNTWEQ ILQKVEQMIE DAVLKTIQGI  240
LNGDIQEIKG KMEHVQYMLE TSPGSQESRE AYMFLARYLV SIDEKFKSFD NKTNYQILPM  300
YTNTLMLQVP YWKMGIEKQK DIGLSDIEVN ELKQLIDKLY TKANSYIHET YTRQYNDAIN  360
TSTAANITNN LFSVRGYCLL HGLECLEMIE HLQKNSLESG FYPKTISYST VFDRQTPKMR  420
IQALTEDDQM QEPLKPSLIN GKYNQIKSLT GYVRRIGNAP RVGGMTITFA NGASYTLGTV  480
TSETTSIELN GSVIESLEVW GDGAVDEALF TLSDKRLFRI GERYARKYKK YAVDSHYIAG  540
LYLASDEPSL AGQAAGIAVS YHMLDDKK                                    568

SEQ ID NO: 152         moltype = DNA  length = 1707
FEATURE                Location/Qualifiers
misc_feature           1..1707
                       note = A synthetic coding sequence used for expression in
                        plant cellsencoding a TIC10381PL PirAB fusion protein with
                        an additionalalanine codon inserted after the initiating
                        methionine codon.
source                 1..1707
                       mol_type = other DNA
                       organism = synthetic construct
SEQUENCE: 152
atggcttcaa tcatcaacat caacattagc gggtcgtcgg acattactat cattaacaac  60
acgccgagca acccggagcc gctgatctac aacactgaca ctccggcctc cgagccgctc  120
accgtcaacc cttaccggga catgaccatc gagccgcaca gcagcatcga ggccattcga  180
atcgacacac ccatcatccc ggagacgcgg cccaactatt acgtggccaa ctcgggcccg  240
gcctcgtccg tccgggcggt gttctactgg tcgcactcct tcacgtccga gtggttcgag  300
tacagcgcca tcacggtcaa ggcgggcgaa gacggtatcc tccaatcgcc ctcgaacagc  360
gtgtactatt caaaggtcgt catctacaac gagacggata agcgcgcgtt cgtcaccggc  420
tacaacaaga tgaacaccac gccgatcaac gtgagcgaga acgacaccct acccgtgctc  480
accgacgtga tgttgatcgt gccctacaca acctccacgc cggactacga gtgggacatg  540
agtagcatca tcaaggacgc catcatcggc ggcgtgggct tcattcccgg cgtcgggtcg  600
gcgatgtcgt tcctgctggg cttgttctgg ccgcaacaga aggacaacac ctgggagcag  660
atccttcaga aggttgagca gatgatcgag aacgcggcac tccagaccat caagggcatc  720
ctgaacggcg acatccagga gatcaagggc aagatggagc acgtgcagta catgctggaa  780
acgtcgcccg gctctcagga atcccacgac gcctacatgt tcctggccag atacctcgtc  840
tctatcgacg agcgcttcaa gtccttcgac aacaagacga attaccagat cctgccgatg  900
tacacaaata ccgtgatgct acaaattccc tactggaaga tgggcatcga gaagaagaat  960
gacatcgggc tgacggacat cgaggtgaac gagctaaagc agctaatcga caccctggtg  1020
gaccgcgcaa ggaactacat tcacacaatg tacactaacg agtacaacaa cgccatcaac  1080
acttctactg ccgaatccgt gaccaacaac ctcctctccg tacgcggtta ctgcctcctg  1140
cacggcctag agtgcattga gctgatcgag cacctccaga acaattcgtt agagtccggc  1200
tttaacccga agaccatcag ctacagcacc gtcttcgacc ggccgaccaa caagacccgc  1260
atccaggccc tcacggagga cgaccaaatg caagagccgt tcaagccgag cctgatcgac  1320
gggaagtaca acaagatcaa gtcgctgctt ggctacgtcc gcagaatcgg gaacgcaccg  1380
cgcgtcggcg gcatacagat caccttcgcc aacgactcca gctacaccct gggcaccgta  1440
acatccgaga cgtcatccat cgagctgaac gacagcgtta tcgagcggct ggaggtgtgg  1500
ggcaacggcg cggtggatga ggccctgttc acgctgagcg acggccgcca gctccgcgtc  1560
ggcgagcggt acgccacgaa gtatcggaag tacgcggtgg atgggcacta catcgctggc  1620
ttgtacctcg cgtccgacga gcccagcctc gcgggccagg cggctgggat cgccgtatcg  1680
taccacatgc tcgcggacaa gaagtga                                     1707

SEQ ID NO: 153         moltype = AA  length = 568
FEATURE                Location/Qualifiers
REGION                 1..568
                       note = The amino acid sequence of the TIC10381PL PirAB
                        fusion protein.
source                 1..568
                       mol_type = protein
                       organism = synthetic construct
SEQUENCE: 153
MASIININIS GSSDITIINN TPSNPEPLIY NTDTPASEPL TVNPYRDMTI EPHSSIEAIR  60
IDTPIIPETR PNYYVANSGP ASSVRAVFYW SHSFTSEWFE YSAITVKAGE DGILQSPSNS  120
VYYSKVVIYN ETDKRAFVTG YNKMNTTPIN VSENDTLPVL TDVMLIVPYT TSTPDYEWDM  180
SSIIKDAIIG GVGFIPGVGS AMSFLLGLFW PQQKDNTWEQ ILQKVEQMIE NAALQTIKGI  240
LNGDIQEIKG KMEHVQYMLE TSPGSQESHD AYMFLARYLV SIDERFKSFD NKTNYQILPM  300
YTNTVMLQIP YWKMGIEKKN DIGLTDIEVN ELKQLIDTLV DRARNYIHTM YTNEYNNAIN  360
TSTAESVTNN LLSVRGYCLL HGLECIELIE HLQNNSLESG FNPKTISYST VFDRPTNKTR  420
IQALTEDDQM QEPFKPSLID GKYNKIKSLL GYVRRIGNAP RVGGIQITFA NDSSYTLGTV  480
TSETSSIELN DSVIERLEVW GNGAVDEALF TLSDGRQLRV GERYATKYRK YAVDGHYIAG  540
LYLASDEPSL AGQAAGIAVS YHMLADKK                                    568
```

```
SEQ ID NO: 154          moltype = DNA  length = 1701
FEATURE                 Location/Qualifiers
misc_feature            1..1701
                        note = A synthetic coding sequence used for expression in
                         plant cellsencoding a TIC11103 PirAB fusion protein
                         comprised of the TIC7661and TIC7660 coding sequences
                         operably linked.
source                  1..1701
                        mol_type = other DNA
                        organism = synthetic construct
SEQUENCE: 154
atgaacacca ctccgattac tgtaagcact aacgaaacat cgcctctcat gacggacgtg  60
atgccgatgg acctgtacgc catctcgacg ccagactacg agtgggacat gagttccatc  120
atcaaggacg ccgtaattgg cggcatcggg ttcatccctg ggcccggccc ggccatctcc  180
ttcctgctgg gcctgttctg gccgcagcag aaggacaaca catgggagca gatactccag  240
aaggtcgagc aaatgattga gaatgccgtg ttgcagacga tcaagggaat cctaaacggc  300
gaagtacagg agatcaaggg caagatggag cacgtcgagt ctatgctcaa gaactcgcca  360
ggctctcagg agtcacacga cgcctacatg ttcctggctc gttacctcgt ttcaattgac  420
gagaagttca agagcttcga caaccgcacc aactaccaac tgttgccgat gtacaccaat  480
acgattatgc tccagatacc ttattggaag atgggcatcg agaagaagaa ggacattggc  540
ctgaccgaca ttgaagtcaa cgagcttaag gagctgatcg acaagctggt ggacaaggcc  600
aagaactaca tccacacaat gtacacgaac gagcacaaca acgccgtgaa caccagcact  660
gccgagtccg tcacgaacaa tctcctcagc gtgcgcggct actgcctgtt acacgggctg  720
gagtgcattg agctaatcga gcacatccag aacaactccc tggagagcgg gttctacccg  780
aagatcatca gctacagcac cgctttcgac cgcccgacaa acaagatgcg tatccaagcg  840
ctcacggagg acgacgcgat gcaagagccg tttaaaccgt cgctcattaa cggcaagtac  900
aacaagatcc agagcctcac gggctacgtg cagcggatcg gcaacgcgcc gcgcgtcggc  960
ggcatccgca tcacgttcac caacgggtcg tcctacacgc tcgggacggt gacctccgag  1020
acgcacagca tcaagctgaa cgactccgtg atcgagtcgt tagaggtctg ggaaacggt  1080
gccgtggacg aggccctgtt caagctgtcc gacgggcggc tcctccgcat cggcgagcgg  1140
tacgccaaga agtaccgcaa gtacgcggtg gacaaccact acatcgcggg catctaccta  1200
gcgagcgacg agccgtccct ggcgggtcaa gccgccggga tcgccgtgag ctatcacatg  1260
atggcggaca agaaaatgat tacgatcaac atcaacgtga acggcaacga cgtgacgggc  1320
accaacaaca atgagcccac tccagtcagc acgacgtacg gcccgaacac tccggcctcg  1380
gagccaccgg tcgtctcgaa ctactccgac atcaccattg agccgcacag ctcggtccag  1440
gccacgcgga tcgacacgcc ggtgatcccg gaggcccggc cggactacta cgtggcgaac  1500
tcgggccctg cgccgtccgt gcgggccgtg ttctactggt cgcactcgtt cacctccgag  1560
tggttcgagt cgtccagcat caccgtgaag gcgggcgagg acggaatcct caaggctcca  1620
gggaacagcc tgtactacag caaggtcgtc atctacaacg acacagacaa gcgggccttc  1680
gttaccgggt acaacaagtg a                                            1701

SEQ ID NO: 155          moltype = AA  length = 566
FEATURE                 Location/Qualifiers
REGION                  1..566
                        note = The amino acid sequence of the TIC11103 PirAB fusion
                         protein.
source                  1..566
                        mol_type = protein
                        organism = synthetic construct
SEQUENCE: 155
MNTTPITVST NETSPLMTDV MPMDLYAIST PDYEWDMSSI IKDAVIGGIG FIPGPGPAIS  60
FLLGLFWPQQ KDNTWEQILQ KVEQMIENAV LQTIKGILNG EVQEIKGKME HVESMLKNSP  120
GSQESHDAYM FLARYLVSID EKFKSFDNRT NYQLLPMYTN TIMLQIPYWK MGIEKKKDIG  180
LTDIEVNELK ELIDKLVDKA KNYIHTMYTN EHNNAVNTST AESVTNNLLS VRGYCLLHGL  240
ECIELIEHIQ NNSLESGFYP KIISYSTAFD RPTNKMRIQA LTEDDAMQEP FKPSLINGKY  300
NKIQSLTGYV QRIGNAPRVG GIRITFTNGS SYTLGTVTSE THSIKLNDSV IESLEVWGNG  360
AVDEALFKLS DGRLLRIGER YAKKYRKYAV DNHYIAGIYL ASDEPSLAGQ AAGIAVSYHM  420
MADKKMITIN INVNGNDVTG TNNNEPTPVS TTYGPNTPAS EPPVVSNYSD ITIEPHSSVQ  480
ATRIDTPVIP EARPDYYVAN SGPAPSVRAV FYWSHSFTSE WFESSSITVK AGEDGILKAP  540
GNSLYYSKVV IYNDTDKRAF VTGYNK                                       566

SEQ ID NO: 156          moltype = DNA  length = 1701
FEATURE                 Location/Qualifiers
misc_feature            1..1701
                        note = A synthetic coding sequence used for expression in
                         plant cellsencoding a TIC11104 PirAB fusion protein
                         comprised of the TIC7663and TIC7662 coding sequences
                         operably linked.
source                  1..1701
                        mol_type = other DNA
                        organism = synthetic construct
SEQUENCE: 156
atgaacacca ccctcatcaa cgtaagtgag aaggagacgc tgccggtgca gaccgacatc  60
atgctgatcg cgccgtactc cgtgtccacg ccggactacg agtgggacat gtcatcgctc  120
atcaaggacg cgatcatcgg cggcgtcgga ttcatccctg tcgtcggctc ggccatgtcc  180
ttcctcctcg gcctgttctg gccgcagcag aaggacaaca cttgggaaca aatactgcag  240
aaggtcgagc agatgatcga gaacgcgcag ctcaacacga ttaagggcat tctgaacggc  300
gacatccagg agattaaggg caagatggag cacgtgcagt acatgcttga gacaagtcca  360
```

```
gggagtcagg agtcacacga cgcctacatg ttcttagccc gctacctagt gagcatcgac  420
gagaagttca agtcgttcga caacaagaca aactaccaaa tcttgccaat gtacacgaat  480
accgtcatgc tacagatccc atactggaag atgggaattg agaagaagaa cgacattggc  540
ttgacggaca tcgaagtcaa cgagcttaaa cagcttatcg acactctggt ggaccgcgcg  600
cgcaactaca tccacaccat gtacgagcga gagtacgaca acgccatcaa cacctcaacc  660
gctgcctcgg tgaccaacaa cctgctctcc gtgcgcgggt actgcctcct gcacgggctg  720
gagtgcatcg agactatcga gcaccttcag aacaacagcc tcaacagtgg gttctacccg  780
aagaccatca gctacagcac tgtcttcgac cggcccacga acaagacccg catccaggct  840
ctgacggaag acgaccaaat gcaagagccg ttcaagcccg cgctgatcgg cggcaagtac  900
aacaagatca agtccctgtt gggctacgtg cgaaggatcg gcaacgctcc acggtcggc  960
ggcatcaagg tgacgttcac caatgggtcg agctacacgc tcgggacggt cacgtcggaa  1020
accgactcca tcgaactgaa cgagtcggtc atcgagcggc tggaggtgtg gggcaacgga  1080
gccgtggacg aggccctctt taccctgagc gatggccgcc agctccgcat cggcgagcgg  1140
tacgccaaga aataccggaa gtacgcggtg gatgggcact acatcagcgg cctctacctc  1200
gcgtcggacg agccctccct cgccggtcaa gcagccggga tcgcggtgtc ctaccacatg  1260
ctcgcagaca agaagatgtc caccatcaac atcaacatct cctccagcac ggtcactgtg  1320
attacaaaca atggcgagac gcccgtcccg ctcacctaca acaccaacac gccggagtcg  1380
gagccgctga cggtcaaccc gtaccgcgac atgaccatcg agccgcgctc ctccattgag  1440
gcgacccgca tcgacacgcc gatcatcccg gagacgagac cgaactacta tgtggcgaac  1500
tccggcccgg ccagcagcgt ccgggcggta ttctactggt cgcacagctt cacctcgcaa  1560
tggttcgagt attcgtcgat catcgtgaag gcgggtgagg acggcatact ggagtcgccg  1620
tcgaacagcc tctactacag caaggtggtg atctacaacg acacggacaa gagggcattc  1680
gtcacgggct acaacaagtg a                                          1701

SEQ ID NO: 157          moltype = AA  length = 566
FEATURE                 Location/Qualifiers
REGION                  1..566
                        note = The amino acid sequence of the TIC11104 PirAB fusion
                         protein.
source                  1..566
                        mol_type = protein
                        organism = synthetic construct
SEQUENCE: 157
MNTTLINVSE KETLPVQTDI MLIAPYSVST PDYEWDMSSL IKDAIIGGVG FIPVVGSAMS  60
FLLGLFWPQQ KDNTWEQILQ KVEQMIENAQ LNTIKGILNG DIQEIKGKME HVQYMLETSP  120
GSQESHDAYM FLARYLVSID EKFKSFDNKT NYQILPMYTN TVMLQIPYWK MGIEKKNDIG  180
LTDIEVNELK QLIDTLVDRA RNYIHTMYER EYDNAINTST AASVTNNLLS VRGYCLLHGL  240
ECIETIEHLQ NNSLNSGFYP KTISYSTVFD RPTNKTRIQA LTEDDQMQEP FKPALIGGKY  300
NKIKSLLGYV RRIGNAPRVG GIKVTFTNGS SYTLGTVTSE TDSIELNESV IERLEVWGNG  360
AVDEALFTLS DGRQLRIGER YAKKYRKYAV DGHYISGLYL ASDEPSLAGQ AAGIAVSYHM  420
LADKKMSTIN INISSSTVTV ITNNGETPVP LTYNTNTPES EPLTVNPYRD MTIEPRSSIE  480
ATRIDTPIIP ETRPNYYVAN SGPASSVRAV FYWSHSFTSQ WFEYSSIIVK AGEDGILESP  540
SNSLYYSKVV IYNDTDKRAF VTGYNK                                     566

SEQ ID NO: 158          moltype = DNA  length = 1701
FEATURE                 Location/Qualifiers
misc_feature            1..1701
                        note = A synthetic coding sequence used for expression in
                         plant cellsencoding a TIC11302 PirAB fusion protein.
source                  1..1701
                        mol_type = other DNA
                        organism = synthetic construct
SEQUENCE: 158
atgattacga tcaacatcaa cgtgaacggc aacgacgtga cgggcaccaa caacaatgag  60
cccactccag tcagcacgac gtacggcccg aacactccgg cctcggagcc accggtcgtc  120
tcgaactact ccgacatcac cattgagccg cacagctcgg tccaggccac gcggatcgac  180
acgccggtga tcccggaggc ccggccggac tactacgtgg cgaactcggg ccctgcgccg  240
tccgtgcggg ccgtgttcta ctggtcgcac tcgttcacct ccgagtggtt cgagtcgtcc  300
agcatcaccg tgaaggcggg cgaggacgga atcctcaagg ctccagggaa cagcctgtac  360
tacagcaagg tcgtcatcta caacgacaca gacaagcggg ccttcgttac cgggtacaac  420
aagatgaaca tcagcccgat caacgtctcg gagaacgaga cgctcccgga gctgaccgac  480
gtgatgctga tcgtcccata cacgaccagc acgccggatt acgagtggga catgtcgtcg  540
atcattaagg atgcgatcat cggaggcgtt ggcttcatcc ctggcgcggg ctcggccatg  600
agcttcctgc tcggcctgtt ctggccgcag cagaaggata acacttggga gcagatactt  660
cagaaggtgg aacagatgat cgagaacgcg gtcctccaaa cgatcaaggg catcctcaac  720
ggcgacatcc aggagattaa gggaaagatg gagcacgttc agtacatgct cgaaaccagc  780
cctgggagcc aggagagcca cgacgcctac atgttcttgg cacgttacct cgtctcgatt  840
gacgagaagt tcaagtcctt cgacaacaag acaaactacc agatcttgcc aatgtacacc  900
aatacggtta tgttacagat tccgtactgg aagatgggca tcgagaagaa gaatgacatc  960
ggcttgaccg acatcgaggt caatgagctt aagcaactta tcgacaagct ggtggacaag  1020
gccaagtcct acatccacac aatgtacacc aacgagtaca acgacgcgat caacaccagc  1080
accgcctcaa gcgtcacaaa caacctcctg tccgtgcgcg gttactgcct tctgcacggc  1140
ctggagtgca tcgaacttat tgagcatctc cagaacaaca gcctggagtc cggcttctac  1200
ccgaagacga tcagctactc cacggtcttc gaccggcaga ccaacaagat gcggatacaa  1260
gcgctcactg aggacgacca gatgcaagaa cccttcaagc cctcgctcat caacgggaag  1320
tacaacaaga tccagagcct cctcggctac gtccagcgca tcggcaacgc gccgcgcgtc  1380
ggcgggatca agatcacgtt cgccaacggg tctagttaca cgctgggcac cgtgaccagc  1440
gagacctcca gtattgagct taacgactcg gtgatcgagc ggctggaggt gtggggcaac  1500
ggcgcggtgg acgaggcgct gttcaccctc tcggacgggc ggcagctccg ggtcggcgag  1560
```

-continued

```
cggtacgcga ccaagtaccg taagtacgcc gtggacggcc actacatcgc cggtctgtac  1620
ctcgccagtg acgagcccag cctagcgggc caggcggctg gcatcgccgt gtcgtaccac  1680
atgctcgacg acaagaagtg a                                            1701

SEQ ID NO: 159         moltype = DNA  length = 24
FEATURE                Location/Qualifiers
misc_feature           1..24
                       note = A synthetic coding sequence encoding a Histidine tag
                        that isoperably linked to coding sequences expressed in
                        Escherichia coliand used for protein purification.
source                 1..24
                       mol_type = other DNA
                       organism = synthetic construct
SEQUENCE: 159
caccaccatc acgctcacca tcac                                         24

SEQ ID NO: 160         moltype = AA  length = 8
FEATURE                Location/Qualifiers
REGION                 1..8
                       note = The amino acid sequence of the Histidine tag.
source                 1..8
                       mol_type = protein
                       organism = synthetic construct
SEQUENCE: 160
HHHHAHHH                                                           8
```

What is claimed is:

1. A recombinant nucleic acid molecule comprising a heterologous promoter operably linked to a polynucleotide segment encoding a pesticidal protein or pesticidal fragment thereof, wherein said pesticidal protein comprises the amino acid sequence of SEQ ID NO:14 and the amino acid sequence of SEQ ID NO:10, wherein the amino acid sequence of SEQ ID NO:14 and the amino acid sequence of SEQ ID NO:10 are contiguous.

2. A construct comprising the recombinant nucleic acid molecule of claim 1, wherein said construct is selected from the group consisting of a plasmid, phagemid, bacmid, cosmid, and a bacterial or yeast artificial chromosome.

3. A host cell comprising the recombinant nucleic acid molecule of claim 1, wherein said host cell is selected from the group consisting of a bacterial and a plant cell.

4. The host cell of claim 3, wherein the host cell is from a genus of bacteria selected from the group consisting of: *Agrobacterium, Rhizobium, Bacillus, Brevibacillus, Escherichia, Pseudomonas, Klebsiella, Pantoea*, and *Erwinia.*

5. The host cell of claim 4, wherein the *Bacillus* species is *Bacillus cereus* or *Bacillus thuringiensis*, said *Brevibacillus* is *Brevibacillus laterosperus*, or said *Escherichia* is *Escherichia coli.*

6. The host cell of claim 3, wherein said plant cell is a dicotyledonous or a monocotyledonous plant cell.

7. The host cell of claim 6, wherein said plant host cell is selected from the group consisting of: alfalfa, banana, barley, bean, broccoli, cabbage, *Brassica*, carrot, cassava, castor, cauliflower, celery, chickpea, Chinese cabbage, citrus, coconut, coffee, corn, clover, cotton, cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell.

8. The recombinant nucleic acid molecule of claim 1, wherein said pesticidal protein exhibits activity against a Coleopteran insect.

9. The recombinant nucleic acid molecule of claim 1, wherein said pesticidal protein exhibits activity against Corn Rootworm or Corn Borer.

10. The recombinant nucleic acid molecule of claim 1, wherein said pesticidal protein exhibits activity against an insect species of the order of Lepidoptera.

11. The recombinant nucleic acid molecule of claim 10, wherein said insect is Black Cutworm, Corn Earworm, Diamondback Moth, European Corn Borer, Fall Armyworm, Southern Armyworm, Soybean Looper, Southwestern Corn Borer, Tobacco Budworm, Velvetbean Caterpillar, Sugarcane Borer, Lesser Cornstalk Borer, Black Armyworm, Beet Armyworm, Old World Bollworm, Oriental leaf Worm, or Pink Bollworm.

12. The recombinant nucleic acid molecule of claim 1, wherein said pesticidal protein exhibits activity against an insect species in the order of Hemiptera.

13. The recombinant nucleic acid molecule of claim 12, wherein said insect is Southern Green Stinkbug, Neotropical Brown Stinkbug, Redbanded Stink Bug, Black-Spined Green-Belly Stink Bug species, Brown-Winged Stink Bug, Brown Stink Bug, Green Stink Bug, Brown Marmorated Stink Bug Western Tarnished Plant Bug, or Tarnished Plant Bug.

14. A plant or part thereof comprising the recombinant nucleic acid molecule of claim 1.

15. The plant or part thereof of claim 14, wherein said plant is a monocot plant or a dicot plant.

16. The plant or part thereof of claim 14, wherein the plant is selected from the group consisting of: alfalfa, banana, barley, bean, broccoli, cabbage, *Brassica*, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeon pea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

17. A seed of the plant of claim 14, wherein said seed comprises said recombinant nucleic acid molecule.

18. An insect inhibitory composition comprising the recombinant nucleic acid molecule of claim 1 and the pesticidal protein encoded by the polynucleotide segment.

19. The insect inhibitory composition of claim 18, further comprising a nucleotide sequence encoding at least one other pesticidal agent that is different from said pesticidal protein.

20. The insect inhibitory composition of claim 19, wherein said at least one other pesticidal agent is selected from the group consisting of an insect inhibitory protein, an insect inhibitory dsRNA molecule, and an ancillary protein.

21. The insect inhibitory composition of claim 19, wherein said at least one other pesticidal agent exhibits activity against one or more pest species of the orders Lepidoptera, Coleoptera, or Hemiptera.

22. The insect inhibitory composition of claim 21, wherein said at least one other pesticidal agent is selected from the group consisting of Cry1A, Cry1Ab, Cry1Ac, Cry1A.105, Cry1Ae, Cry1B, Cry1C, Cry1C variants, Cry1D, Cry1E, Cry1F, Cry1A/F chimeras, Cry1G, Cry1H, Cry1I, Cry1J, Cry1K, Cry1L, Cry2A, Cry2Ab, Cry2Ae, Cry3, Cry3A variants, Cry3B, Cry4B, Cry6, Cry7, Cry8, Cry9, Cry15, Cry34, Cry35, Cry43A, Cry43B, Cry51Aa1, ET29, ET33, ET34, ET35, ET66, ET70, TIC400, TIC407, TIC417, TIC431, TIC800, TIC807, TIC834, TIC853, TIC900, TIC901, TIC1201, TIC1415, TIC2160, TIC3131, TIC836, TIC860, TIC867, TIC869, TIC1100, VIP3A, VIP3B, VIP3Ab, AXMI-88, AXMI-97, AXMI-102, AXMI-112, AXMI-117, AXMI-100, AXMI-115, AXMI-113, AXMI-005, AXMI134, AXMI-150, AXMI-171, AXMI-184, AXMI-196, AXMI-204, AXMI-207, AXMI-209, AXMI-205, AXMI-218, AXMI-220, AXMI-221z, AXMI-222z, AXMI-223z, AXMI-224z, AXMI-225z, AXMI-238, AXMI-270, AXMI-279, AXMI-345, AXMI-335, AXMI-R1 AXMI-R1 variants, IP3, IP3 variants, DIG-3, DIG-5, DIG-10, DIG-657 DIG-11, Cry71Aa1, Cry72Aa1, PHI-4 variants, PIP-72 variants, PIP-45 variants, PIP-64 variants, PIP-74 variants, PIP-75 variants, PIP-77 variants, Axmi422, Dig-305, Axmi440, PIP-47 variants, Axmi281, BT-009, BT-0012, BT-0013, BT-0023, BT0067, BT-0044, BT-0051, BT-0068, BT-0128, DIG-17, DIG-90, DIG-79, Cry1JP578V, Cry1JPS1, and Cry1 JPS1P578V.

23. The insect inhibitory composition of claim 18, further defined as comprising a plant cell that expresses said recombinant nucleic acid molecule.

24. A commodity product produced from the plant or part thereof of claim 14, wherein the commodity product comprises a detectable amount of said recombinant nucleic acid molecule or a pesticidal protein encoded thereby.

25. The commodity product of claim 24, selected from the group consisting of commodity corn bagged by a grain handler, corn flakes, corn cakes, corn flour, corn meal, corn syrup, corn oil, corn silage, corn starch, corn cereal, whole or processed cotton seed, cotton oil, lint, seeds processed for feed or food, plant parts processed for feed or food, fiber, paper, biomasses, fuel products derived from cotton oil or pellets derived from cotton gin waste, whole or processed soybean seed, soybean oil, soybean protein, soybean meal, soybean flour, soybean flakes, soybean bran, soybean milk, soybean cheese, soybean wine, animal feed comprising soybean, paper comprising soybean, cream comprising soybean, soybean biomass, and fuel products produced using soybean plants and soybean plant parts.

26. A method of producing seed, said method comprising:

a. planting at least a first seed according to claim 17, b. growing a plant from the seed; and c. harvesting seed from the plant, wherein said harvested seed comprises said recombinant nucleic acid molecule.

27. A plant resistant to insect infestation, wherein the cells of said plant comprise the recombinant nucleic acid molecule of claim 1.

28. A method for controlling a Coleopteran, Lepidopteran, or Hemipteran species pest or pest infestation, said method comprising: contacting the pest with a transgenic plant cell expressing an insecticidally effective amount of a pesticidal protein, the pesticidal protein comprising the amino acid sequence of SEQ ID NO:14 and the amino acid sequence of SEQ ID NO:10, wherein the amino acid sequence of SEQ ID NO:14 and the amino acid sequence of SEQ ID NO:10 are contiguous.

29. The recombinant nucleic acid molecule of claim 1, wherein the pesticidal protein comprises the amino acid sequence of SEQ ID NO: 119.

30. The recombinant nucleic acid molecule of claim 1, wherein the polynucleotide segment comprises the nucleotide sequence of SEQ ID NO:118 or SEQ ID NO:158.

* * * * *